US009114175B2

(12) United States Patent
Gegg et al.

(10) Patent No.: US 9,114,175 B2
(45) Date of Patent: Aug. 25, 2015

(54) MODIFIED FC MOLECULES

(75) Inventors: Colin V. Gegg, Camarillo, CA (US); Kenneth W. Walker, Newbury Park, CA (US); Leslie P. Miranda, Thousand Oaks, CA (US); Fei Xiong, Wayne, CA (US)

(73) Assignee: AMGEN INC., Thousand Oaks, CA (US)

( * ) Notice: Subject to any disclaimer, the term of this patent is extended or adjusted under 35 U.S.C. 154(b) by 0 days.

(21) Appl. No.: 13/171,233

(22) Filed: Jun. 28, 2011

(65) Prior Publication Data

US 2012/0009205 A1 Jan. 12, 2012

Related U.S. Application Data

(62) Division of application No. 11/502,761, filed on Aug. 10, 2006, now Pat. No. 8,008,453.

(60) Provisional application No. 60/707,842, filed on Aug. 12, 2005.

(51) Int. Cl.
*C07K 16/00* (2006.01)
*A61K 47/48* (2006.01)
*A61K 38/00* (2006.01)

(52) U.S. Cl.
CPC ..... *A61K 47/48215* (2013.01); *A61K 47/48369* (2013.01); *C07K 2317/40* (2013.01); *C07K 2317/52* (2013.01)

(58) Field of Classification Search
None
See application file for complete search history.

(56) References Cited

U.S. PATENT DOCUMENTS

| | | | |
|---|---|---|---|
| 3,691,016 A | 9/1972 | Patel | |
| 3,817,837 A | 6/1974 | Rubenstein et al. | |
| 3,850,752 A | 11/1974 | Schuurs et al. | |
| 3,939,350 A | 2/1976 | Kronick et al. | |
| 3,941,763 A | 3/1976 | Sarantakis | |
| 3,969,287 A | 7/1976 | Jaworek et al. | |
| 3,996,345 A | 12/1976 | Ullman et al. | |
| 4,083,368 A | 4/1978 | Freezer | |
| 4,087,778 A | 5/1978 | Merz et al. | |
| 4,179,337 A | 12/1979 | Davis et al. | |
| 4,195,128 A | 3/1980 | Hildebrand et al. | |
| 4,227,437 A | 10/1980 | Inloes | |
| 4,229,537 A | 10/1980 | Hodgins et al. | |
| 4,247,642 A | 1/1981 | Hirohara | |
| 4,301,144 A | 11/1981 | Iwashita et al. | |
| 4,330,440 A | 5/1982 | Ayers et al. | |
| 4,351,337 A | 9/1982 | Sidman et al. | |
| 4,496,689 A | 1/1985 | Mitra et al. | |
| 4,640,835 A | 2/1987 | Shimizu et al. | |
| 4,670,417 A | 6/1987 | Iwasaki et al. | |
| 4,719,192 A | 1/1988 | Schneider et al. | |
| 4,847,325 A | 7/1989 | Shadle et al. | |
| 4,849,224 A | 7/1989 | Chang et al. | |
| 4,906,169 A | 3/1990 | Chien et al. | |
| 4,911,916 A | 3/1990 | Cleary | |
| 4,925,673 A | 5/1990 | Steiner et al. | |
| 4,925,677 A | 5/1990 | Feijen | |
| 4,983,395 A | 1/1991 | Chang et al. | |
| 4,994,439 A | 2/1991 | Longenecker et al. | |
| 5,013,556 A | 5/1991 | Woodle et al. | |
| 5,023,084 A | 6/1991 | Chien et al. | |
| 5,098,833 A | 3/1992 | Lasky et al. | |
| 5,116,964 A | 5/1992 | Capon et al. | |
| 5,166,322 A | 11/1992 | Shaw et al. | |
| 5,206,344 A | 4/1993 | Katre et al. | |
| 5,216,131 A | 6/1993 | Lasky et al. | |
| 5,223,409 A | 6/1993 | Ladner et al. | |
| 5,225,538 A | 7/1993 | Capon et al. | |
| 5,252,714 A | 10/1993 | Harris et al. | |
| 5,284,656 A | 2/1994 | Platz et al. | |
| 5,336,603 A | 8/1994 | Capon et al. | |
| 5,338,665 A | 8/1994 | Schatz et al. | |
| 5,346,701 A | 9/1994 | Heiber et al. | |
| 5,428,130 A | 6/1995 | Capon et al. | |
| 5,432,018 A | 7/1995 | Dower et al. | |
| 5,446,090 A | 8/1995 | Harris | |
| 5,455,165 A | 10/1995 | Capon et al. | |
| 5,460,820 A | 10/1995 | Ebert et al. | |
| 5,480,981 A | 1/1996 | Goodwin et al. | |

(Continued)

FOREIGN PATENT DOCUMENTS

| | | |
|---|---|---|
| AU | 64763/98 | 7/1998 |
| EP | 0 315 062 A2 | 5/1989 |

(Continued)

OTHER PUBLICATIONS

U.S. Appl. No. 60/641,144, filed Jan. 5, 2005, Ruker et al.

(Continued)

*Primary Examiner* — Yunsoo Kim
(74) *Attorney, Agent, or Firm* — Angela L. Purcell

(57) ABSTRACT

Disclosed is a process for preparing a pharmacologically active compound, in which at least one internal conjugation site of an Fc domain sequence is selected that is amenable to conjugation of an additional functional moiety by a defined conjugation chemistry through the side chain of an amino acid residue at the conjugation site. An appropriate amino acid residue for conjugation may be present in a native Fc domain at the conjugation site or may be added by insertion (i.e., between amino acids in the native Fc domain) or by replacement (i.e., removing amino acids and substituting different amino acids). In the latter case, the number of amino acids added need not correspond to the number of amino acids removed from the previously existing Fc domain. This technology may be used to produce useful compositions of matter and pharmaceutical compositions containing them. A DNA encoding the inventive composition of matter, an expression vector containing the DNA, and a host cell containing the expression vector are also disclosed.

21 Claims, 8 Drawing Sheets

(56) References Cited

U.S. PATENT DOCUMENTS

| | | | |
|---|---|---|---|
| 5,498,530 A | 3/1996 | Schatz et al. |
| 5,514,582 A | 5/1996 | Capon et al. |
| 5,516,523 A | 5/1996 | Heiber et al. |
| 5,605,702 A | 2/1997 | Teillaud et al. |
| 5,608,035 A | 3/1997 | Yanofsky et al. |
| 5,643,575 A | 7/1997 | Martinez et al. |
| 5,662,925 A | 9/1997 | Ebert et al. |
| 5,714,142 A | 2/1998 | Blaney et al. |
| 5,714,147 A | 2/1998 | Capon et al. |
| 5,726,290 A | 3/1998 | Bodary et al. |
| 5,733,731 A | 3/1998 | Schatz et al. |
| 5,739,277 A | 4/1998 | Presta et al. |
| 5,767,234 A | 6/1998 | Yanofsky et al. |
| 5,773,569 A | 6/1998 | Wrighton et al. |
| 5,783,208 A | 7/1998 | Venkateshwaran et al. |
| 5,786,331 A | 7/1998 | Barrett et al. |
| 5,792,451 A | 8/1998 | Sarubbi et al. |
| 5,800,096 A | 9/1998 | Barrow |
| 5,808,029 A | 9/1998 | Bruckhous et al. |
| 5,840,844 A | 11/1998 | Lasky et al. |
| 5,843,725 A | 12/1998 | Sledzlewski et al. |
| 5,849,452 A | 12/1998 | Takenaka et al. |
| 5,869,451 A | 2/1999 | Dower et al. |
| 5,869,452 A | 2/1999 | Ng et al. |
| 5,877,151 A | 3/1999 | Pereira |
| 5,877,289 A | 3/1999 | Thorpe et al. |
| 5,880,096 A | 3/1999 | Barret et al. |
| 5,880,103 A | 3/1999 | Urban et al. |
| 5,886,150 A | 3/1999 | Duchesne et al. |
| 5,888,763 A | 3/1999 | Hanafusa et al. |
| 5,919,455 A | 7/1999 | Greenwald et al. |
| 5,922,545 A | 7/1999 | Matheakis et al. |
| 5,932,462 A | 8/1999 | Harris et al. |
| 5,932,546 A | 8/1999 | Barrett et al. |
| 5,945,507 A | 8/1999 | Montelaro et al. |
| 5,985,599 A | 11/1999 | McKenzie et al. |
| 5,990,237 A | 11/1999 | Bentley et al. |
| 6,004,555 A | 12/1999 | Thorpe et al. |
| 6,077,680 A | 6/2000 | Kem et al. |
| 6,108,026 A | 8/2000 | Corbett |
| 6,117,655 A | 9/2000 | Capon et al. |
| 6,132,729 A | 10/2000 | Thorpe et al. |
| 6,132,730 A | 10/2000 | Thorpe et al. |
| 6,133,426 A | 10/2000 | Gonzalez et al. |
| 6,156,321 A | 12/2000 | Thorpe et al. |
| 6,245,740 B1 | 6/2001 | Goldenberg et al. |
| 6,273,086 B1 | 8/2001 | Ohki et al. |
| 6,291,212 B1 | 9/2001 | Sledziewski et al. |
| 6,291,646 B1 | 9/2001 | Sledziewski et al. |
| 6,300,099 B1 | 10/2001 | Sledziewski et al. |
| 6,323,323 B1 | 11/2001 | Sledziewski et al. |
| 6,342,225 B1 | 1/2002 | Jones et al. |
| 6,406,697 B1 | 6/2002 | Capon et al. |
| 6,420,339 B1 | 7/2002 | Gegg et al. |
| 6,451,986 B1 | 9/2002 | Pettit |
| 6,548,644 B1 | 4/2003 | Pettit |
| 6,602,498 B2 | 8/2003 | Shen |
| 6,660,843 B1 | 12/2003 | Feige et al. |
| 6,818,418 B1 | 11/2004 | Lipovsek et al. |
| 6,892,728 B2 | 5/2005 | Helgesson et al. |
| 6,919,426 B2 | 7/2005 | Boone et al. |
| 6,926,898 B2 | 8/2005 | Rosen et al. |
| 6,932,962 B1 | 8/2005 | Bäckström et al. |
| 7,045,337 B2 | 5/2006 | Schultz et al. |
| 7,138,370 B2 | 11/2006 | Oliner et al. |
| 7,259,137 B2 * | 8/2007 | Min et al. ............... 424/278.1 |
| 7,442,778 B2 | 10/2008 | Gegg et al. |
| 7,645,861 B2 | 1/2010 | Gegg et al. |
| 7,655,764 B2 | 2/2010 | Gegg et al. |
| 7,655,765 B2 | 2/2010 | Gegg et al. |
| 7,662,931 B2 | 2/2010 | Gegg et al. |
| 7,750,127 B2 | 7/2010 | Gegg et al. |
| 7,750,128 B2 | 7/2010 | Gegg et al. |
| 8,008,453 B2 * | 8/2011 | Gegg et al. ............. 530/391.7 |
| 2003/0069395 A1 | 4/2003 | Sato et al. |
| 2003/0143220 A1 | 7/2003 | Capon et al. |
| 2003/0176352 A1 | 9/2003 | Min et al. |
| 2003/0195156 A1 | 10/2003 | Min et al. |
| 2003/0229023 A1 | 12/2003 | Oliner et al. |
| 2003/0236192 A1 | 12/2003 | Dasch et al. |
| 2003/0236193 A1 | 12/2003 | Oliner et al. |
| 2004/0087778 A1 | 5/2004 | Feige et al. |
| 2004/0121959 A1 | 6/2004 | Boone et al. |
| 2004/0181033 A1 | 9/2004 | Han et al. |
| 2006/0140934 A1 | 6/2006 | Gegg et al. |

FOREIGN PATENT DOCUMENTS

| | | |
|---|---|---|
| EP | 0 315 456 A2 | 5/1989 |
| EP | 0 668 353 A1 | 4/1990 |
| EP | 0 668 354 A1 | 4/1990 |
| EP | 0 473 084 B1 | 8/1991 |
| EP | 0 714 912 A2 | 6/1996 |
| EP | 0 325 224 B1 | 7/1996 |
| EP | 0 469 074 B1 | 7/1996 |
| EP | 0 911 393 A1 | 4/1999 |
| EP | 0 585 287 B1 | 10/1999 |
| EP | 0 958 829 A1 | 11/1999 |
| EP | 1 029 870 A2 | 8/2000 |
| EP | 0 526 452 B1 | 2/2001 |
| EP | 0 575 545 B1 | 5/2003 |
| EP | 0 770 624 B1 | 5/2003 |
| EP | 0 988 056 B1 | 7/2003 |
| EP | 1 752 471 A1 | 1/2006 |
| EP | 1 772 465 A1 | 1/2006 |
| WO | WO 89/09622 | 10/1989 |
| WO | WO 91/08298 | 6/1991 |
| WO | WO 94/04689 | 3/1994 |
| WO | WO 94/07921 | 4/1994 |
| WO | WO 95/09917 | 4/1995 |
| WO | WO 95/14714 | 6/1995 |
| WO | WO 95/18858 | 7/1995 |
| WO | WO 95/21919 | 8/1995 |
| WO | WO 95/21920 | 8/1995 |
| WO | WO 95/26746 | 10/1995 |
| WO | WO 96/05309 | 2/1996 |
| WO | WO 96/11214 | 4/1996 |
| WO | WO 96/11953 | 4/1996 |
| WO | 96/14339 A1 | 5/1996 |
| WO | WO 96/17942 | 6/1996 |
| WO | WO 96/18412 | 6/1996 |
| WO | WO 96/23899 | 8/1996 |
| WO | WO 96/30057 | 10/1996 |
| WO | WO 96/32478 | 10/1996 |
| WO | WO 96/40772 | 12/1996 |
| WO | WO 96/40987 | 12/1996 |
| WO | WO 97/00270 | 1/1997 |
| WO | WO 97/08203 | 3/1997 |
| WO | WO 97/08553 | 3/1997 |
| WO | WO 97/23614 | 7/1997 |
| WO | WO 97/28828 | 8/1997 |
| WO | WO 97/31019 | 8/1997 |
| WO | WO 97/34631 | 9/1997 |
| WO | WO 97/35969 | 10/1997 |
| WO | WO 97/40070 | 10/1997 |
| WO | WO 97/41220 | 11/1997 |
| WO | WO 97/44453 | 11/1997 |
| WO | WO 98/09985 | 3/1998 |
| WO | WO 98/10795 | 3/1998 |
| WO | WO 98/15833 | 4/1998 |
| WO | WO 98/24477 | 6/1998 |
| WO | WO 98/28427 | 7/1998 |
| WO | WO 98/31820 | 7/1998 |
| WO | WO 98/33812 | 8/1998 |
| WO | WO 98/46257 | 10/1998 |
| WO | WO 98/53842 | 12/1998 |
| WO | WO 98/55620 | 12/1998 |
| WO | WO 99/02711 | 1/1999 |
| WO | WO 99/05302 | 2/1999 |
| WO | WO 99/14244 | 3/1999 |
| WO | WO 99/17789 | 4/1999 |
| WO | WO 99/18243 | 4/1999 |
| WO | WO 99/18781 | 4/1999 |
| WO | WO 99/24055 | 5/1999 |

(56) References Cited

FOREIGN PATENT DOCUMENTS

| | | |
|---|---|---|
| WO | WO 99/24462 | 5/1999 |
| WO | WO 99/24782 | 5/1999 |
| WO | WO 99/38008 | 7/1999 |
| WO | WO 99/38526 | 8/1999 |
| WO | WO 99/42592 | 8/1999 |
| WO | WO 99/45944 | 9/1999 |
| WO | WO 99/46283 | 9/1999 |
| WO | WO 99/47151 | 9/1999 |
| WO | WO 99/50282 | 10/1999 |
| WO | WO 99/51254 | 10/1999 |
| WO | WO 99/51720 | 10/1999 |
| WO | WO 99/51732 | 10/1999 |
| WO | WO 99/51748 | 10/1999 |
| WO | WO 99/60013 | 11/1999 |
| WO | WO 99/61476 | 12/1999 |
| WO | WO 99/62539 | 12/1999 |
| WO | WO 00/01402 | 1/2000 |
| WO | WO 00/04048 | 1/2000 |
| WO | WO 00/09560 | 2/2000 |
| WO | WO 00/11027 | 3/2000 |
| WO | WO 00/11028 | 3/2000 |
| WO | WO 00/12727 | 3/2000 |
| WO | WO 00/17226 | 3/2000 |
| WO | WO 00/17358 | 3/2000 |
| WO | WO 00/17370 | 3/2000 |
| WO | WO 00/17648 | 3/2000 |
| WO | WO 00/18895 | 4/2000 |
| WO | WO 00/23585 | 4/2000 |
| WO | WO 00/24770 | 5/2000 |
| WO | WO 00/24782 A2 | 5/2000 |
| WO | WO 00/38651 | 7/2000 |
| WO | WO 00/38652 | 7/2000 |
| WO | WO 01/02440 A1 | 1/2001 |
| WO | WO 01/04296 A1 | 1/2001 |
| WO | WO 01/83525 A2 | 11/2001 |
| WO | WO 02/11801 A1 | 2/2002 |
| WO | WO 02/32925 A2 | 4/2002 |
| WO | WO 02/32925 A3 | 4/2002 |
| WO | WO 02/092620 A2 | 11/2002 |
| WO | WO 02/092620 A3 | 11/2002 |
| WO | WO 03/031589 A2 | 4/2003 |
| WO | WO 03/057134 A2 | 7/2003 |
| WO | WO 2004/002417 A2 | 1/2004 |
| WO | WO 2004/002424 A2 | 1/2004 |
| WO | WO 2004/010989 A1 | 2/2004 |
| WO | WO 2004/017918 A2 | 3/2004 |
| WO | WO 2004/017918 A3 | 3/2004 |
| WO | WO 2004/026329 A1 | 4/2004 |
| WO | WO 2004/058988 A2 | 7/2004 |
| WO | WO 2004/092215 A2 | 10/2004 |
| WO | WO 2004/099249 A2 | 11/2004 |
| WO | WO 2004/110472 A2 | 12/2004 |
| WO | WO 2005/018572 A2 | 3/2005 |
| WO | WO 2005/047334 A1 | 5/2005 |
| WO | WO 2005/047337 A1 | 5/2005 |
| WO | WO 2005/089807 A2 | 9/2005 |
| WO | WO 2006/002850 A2 | 1/2006 |
| WO | WO 2006/072620 A1 | 1/2006 |
| WO | 2006/034488 A2 | 3/2006 |
| WO | WO 2006/036834 A2 | 4/2006 |
| WO | WO 2006/042151 A2 | 4/2006 |

OTHER PUBLICATIONS

Abuchowski and Davis, "Soluble Polymer-Enzyme Adducts", *Enzymes as Drugs*, Chap. 13, pp. 367-383 (1981).
Adey & Kay, Identification of Calmodulin-Binding Peptide Consensus Sequences from a Phage-Displayed Random Peptide Library, *Gene* 169: 133-134(1996).
Adey & Kay, "Isolation of Peptides From Phage-Displayed Random Peptide Libraries That Interact With the Talin-Binding Domain of Vinculin", *Biochem. J.* 324: 523-528 (1997).
Adjei & Garren, Pulmonary Delivery of Peptide Drugs: Effect of Particle Size on Bioavailability of Leuprolide Acetate in Healthy Male Volunteers, *Pharma. Res.* 7: 556-569 (1990).
Adjei, et al., "Bioavailability of Leuprolide Following Intratracheal Administration to Beagle Dogs", *Internatl. J. Pharmaceutics*, 63: 135-144 (1990).
Agard, et al., "A Strain-Promoted [3 + 2] Azide-Alyne Cycloaddition for Covalent Modification of Biomolecules in Living Systems", *J. Am. Chem. Soc.* 126: 15046-15047 (2004).
Ahern, et al., "Special Report: The Peptide-Oligonucleotide Partnership", *The Scientist* 4(19): 24-25 (1990).
Akerstrom, "Protein G: A Powerful Tool for Binding and Detection of Monoclonal and Polyclonal Antibodies", *J. Immunol.* 135(4): 2589-2592 (1985).
Akeson, et al., "AF12198, a Novel Low Molecular Weight Antagonist, Selectively Binds the Human Type I Interleukin (IL)-1 Receptor and Blocks in vivo Responses to IL-1", *J. Biol Chem.* 271: 30517-20523 (1996).
Alberts, et al., "Synthesis of a Novel Hematopoietic Peptide SK&F 107647", *Thirteenth Am. Pep. Symp.*, 67-369 (1993).
Altschul, et al., "Basic Local Alignment Search Tool", *J. Mol. Biol.*, 215: 401-410 (1990).
Asai, et al., "Anti-Bodies in Cell Biology", Methods in cell Biology, vol. 37, *Academic Press, Inc., New York* (1993) (Table of Contents Provided Only).
Ball, et al., "Cell Cycle Arrest and Inhibition of Cdk4 Activity by Small Peptides Based on the Carboxy-Terminal Domain of $p21^{WAF1}$", *Current Biology* 7(1): 71-80 (1997).
Barna, et al., "Combination Therapy with a Synthetic Peptide of C-Reactive Protein and Interleukin 2: Augmented Survival and Eradication of Pulmonary Metastases", *Cancer Immunol. Immunotherapy* 38: 38-42 (1994).
Barrett, A., et al., Ed., Handbook of Proteolytic Enzymes, *Academic Press* (1998) (Table of Contents Provided Only).
Bhatnagar, et al., "Structure-Activity Relationships of Novel Hematoregulatory Pepticides", *J. Med. Chem.* 39: 3814-3819 (1996).
Bodanszky, M., Ed., *Principles of Peptide Synthesis*, $2^{nd}$ Ed, Springer Laboratory, Springer-Verlag (1994) (Table of Contents Provided Only).
Bodanszky, M. and A. Bodanszky, Eds., *The Practice of Peptide Synthesis*, $2^{nd}$ Revised Ed, Springer-Verlag (1994) (Table of Contents Provided Only).
Bogdanovich, et al. "Functional Improvement of Dystrophic Muscle by Myostatin Blockade", *Nature* 420: 418 (2002).
Boghaert, et al., "Antibody-Targeted Chemotherapy with the Calicheamicin Conjugate hu3S193-N-Acetylγ Calicheamicin Dimethyl Hydrazide Targets Lewis$^y$ and Eliminates Lewis$^y$-Positive Human Carcinoma Cells and Xenografts," *Clin. Cancer Research*, 10: 4538-4549 (2004).
Bong, et al., "Chemoselective Pd(0)-Catalyzed Peptide Coupling in Water", *Organic Ltrs.* 3(16): 2509-2511 (2001).
Böttger, et al., Molecular Characterization of the hdm2-p53 Interaction, *J. Mol. Biol.* 269: 744-759 (1997).
Böttger, et al., "Identification of novel mdm2 binding peptides by phage display", *Oncogene* 13: 2141-2147 (1996).
Bowie, et al., "A Method to Identify Protein Sequences That Fold into a Known Three-Dimensional Structure" *Science* 253: 164-170 (1991).
Braquet, et al., "Effect of Endothelin-1 on Blood Pressure and Bronchopulmonary System of the Guinea Pig", *J.Cardio. Pharm.* 13: S143-S146 (1989).
Brenner, et al., "Population Statistics of Protein Structures: Lessons from Structural Classifications", *Current Op. Struct. Biol.* 7(3): 369-376.
Brocks, et al., "A TNF Receptor Antagonistic scFv, which is not Secreted in Mammalian Cells, is Expressed as a Soluble Mono- and Bivalent scFv Derivative in Insect Cells", *Immunotechnology* 3(3): 173-184 (1997).
Burstein, et al., "Thymic Humoral Factor γ2: Purification and Amino Acid Sequence of an Immunoregulatory Peptide from Calf Thymus", *Biochemistry* 27: 4066-4071 (1988).
Capon et al., "Designing CD4 Immunoadhesins for AIDS Therapy", *Nature* 337: 525-531 (1989).
Carillo, et al., "The Multiple Sequence Alignment Problem in Biology", *SIAM J. Applied Math* 48: 1073-1082 (1988).

(56) References Cited

OTHER PUBLICATIONS

Chamow, S. M., et al., "Immunoadhesins: Principles and Applications", *Tibtech* 14: 52-60 (1996).

Chan and Kim, et al., "HIV Entry and Its Inhibition" *Cell* 93: 681-684 (1998).

Chan, W. C. and White, P. D., Eds., *Fmoc Solid Phase Peptide Synthesis: A Practical Approach*, Oxford University Press (2000) (Table of Contents Provided Only).

Chaubert, et al., "Simultaneous Double Immunoenzymatic Labeling: A New Procedure for the Histopathlogic Routine", *Mod. Pathol.* 10: 585 (1997).

Chen, et al., "Site-Specific Labeling of Cell surface Proteins with Biophysical Probes Using Biotin Ligase", *Nature Methods*, 2(2): 99-104 (2005).

Chirinos-Rojas, et al., "A Peptidomimetic Antagonist of TNF-α-Mediated Cytotoxicity Identified from a Phage-Displayed Random Peptide Library", *Journal of Immunology* 161: 5621-5626 (1998).

Chou, et al. "Conformational Parameters for Amino Acids in Helical, α-Sheet, and Random Coil Regions Calculated from Proteins", *Biochemistry* 13(2): 211-222 (1974).

Chou, et al., "Prediction of the β-Turns", *J. Biophys.* 26: 367-384 (1979).

Chou, et al., "Prediction of the Secondary Structure of Proteins From Their Amino Acid Sequence", *Adv. Enzymol. Related. Areas Mol. Biol.* 47: 45-148 (1978).

Chou, et al., "Empirical Predictions of Protein Conformation", *Ann. Rev. Biochem.* 47: 251-276 (1979).

Clackson, et al., "A Hot Spot of Binding Energy in a Hormone-Receptor Interface", *Science* 267: 383-336 (1995).

Cooper, et al., "Purification and Characterization of a peptide from Anyloid-Rich Pancreases of Type 2 Diabetic Patients", *PNAS* 84: 8628-8632 (1987).

Cortese, et al., "Selection of Biologically Active Peptides by Phage Display of Random Peptide Libraries", *Current Opinion in Biotechnology* 7: 616-621 (1996).

Couet, et al., "Identification of Peptide and Protein Ligands for the Caveolin-Scaffolding Domain", *The Journal of Biological Chemistry* 272(10): 6525-6533 (1997).

Couet, et al., "Interaction of a Receptor Tyosine Kinase, EGF-R, with Caveolins", *The Journal of Biological Chemistry* 272(48): 30429-30438 (1997).

Creighton, "Proteins: Structures and Molecular Principles", W. H. Freeman & Co., New York, pp. 70-86 (1983).

Cuthbertson, et al., "Design of Low Molecular Weight Hematoregulatory Agents from the Structure-Activity Relationship of a Dimeric Pentapeptide", *J. Med. Chem.* 40: 2876-2882 (1997).

Cwirla, et al., "Peptide Agonist of the Thrombopoietin Receptor as Potent as the Natural Cytokine", *Science* 276: 1696-1699 (1997).

Davis, et al., "Preparation and Characterization of Antibodies with Specificity for the Amino-Terminal Tetrapeptide Sequence of the Platelet-Derived Connective Tissue", *Biochem Intl.* 10: 395-404 (1985).

Dayhoff, et al., Atlas of Protein Sequence and Structure, *Natl. Biomed. Research Foundation*, 5(3) (1978) (Table of Contents Provided Only).

Debs, et al., "Lung-Specific Delivery of Cytokines Induces Sustained Pulmonary and Systemic Immunomodulation in Rats", *J. Immunol.* 140: 3482-3488, (1988).

Dedman, et al., "Selection of Targeted Biological Modifiers from a Bacteriophage Library of Random Peptides", *J. Biol. Chem.* 268(31): 23025-23030 (1993).

del Rio-Portilla, et al., MR solution Structure of Cn12, a Novel Peptide from the mexican Scorpion *Centruroides noxius* With a Typical β-Toxin Sequence but with α-like Physiological Activity *Eur. J. Biochem.* 271: 2504-2515 (2004).

DeVasher, et al., "Aqueous-Phase, Palladium-Catalyzed Cross-Coupling of Aryl Bromides Under Mild Conditions, Using Water-Soluble, Sterically Demanding Alkylphosphines", *J. Org. Chem.* 69: 7919-7927 (2004).

Devereux, et al., "A Comprehensive Set of Sequence Analysis Programs for the VAX", *Nucleid Acids Research.*, 12: 387-395 (1984).

Devlin, et al., "Random Peptide Libraries: A Source of Specific Protein Binding Molecules", *Science* 249: 404-406 (1990).

DiBowski, et al., "Bioconjugation of Peptides by Palladium-Catalyzed C—C Cross-Coupling in Water", *Angew. Chem. Int. Ed.*, 37: No. 476-478 (1998).

Duncan, et al. "Localization of the Binding Site for the Human High-Affinity Fc Receptor on IgG", *Nature* 332: 563-564 (1988).

Dysan & Murray, "Selection of Peptide Inhibitors of Interactions Involved in Complex Protein Assemblies: Association of the Core and Surface Antigens of Hepatitis B Virus", *Proc. Natl. Acad. Sci. USA* 92: 2194-2198 (1995).

Earnshaw, et al., "Mammalian Caspases: Structure, Activation, Substrates, and Functions During Apoptosis", *Annu. Rev. Biochem.* 68: 383-424 (1999).

Ellison, et al., "The Nucleotide Sequence of a Human Immunoglobulin $C\gamma_1$ Gene", *Nucleic Acids Res.* 10: 4071-4079 (1982).

Engel, et al., "Insertion of Carrier Proteins Into Hydrophilic Loops of the *Escherichia coli* Lactose Permease", *Biochimica et Biophysica Acta* 1564: 38-46 (2002).

Erickson, et al., *The Proteins*, "Solid-Phase Peptide Synthesis", ($3^{rd}$ ed.), vol. II, pp. 257-527 (1976).

Fahraeus, et al., "Inhibition of pRb Phosphorylation and Cell-Cycle Progression by a 20-Residue Peptide Derived from $p16CDKN2/INK4A$", *Current Biology.* 6: 84-91 (1996).

Fairbrother, et al., "Novel Peptides Selected to Find Vascular Endothelial Growth Factor Target the Receptor-Binding Site", *Biochemestry* 37: 17754-17764 (1998).

Felix, A.M., "Pegylated Peptides IV: Enhanced Biological Activity of Site-Directed Pegylated GRF Analogs", *Int. J. Peptide Protein Res.* 46: 253-264.

Finn, et al., *The Proteins*, "The Synthesis of Peptides by Solution Methods with Emphasis on Peptide Hormones", ($3^{rd}$ ed.), vol. II, pp. 105-253 (1976).

Fisher, et al., "Treatment of Septic Shock with the Tumor Necrosis Factor Receptor : Fc Fusion Protein", *N. England J.; Med.* 334(26): 1697-1702 (1996).

Francis, Gillian E., "Protein Modification and Fusion Proteins", *Royal Free Hospital School of Medicine* 3: 4-10 (1992).

Fukumoto, et al., "Peptide Mimics of the CTLAA4-Bindining Domain Stimulate T-Cell Proliferation", *Nature Biotechnology* 16: 267-270 (1998).

Gan, et al., "Echistatin", *J. Biol. Chem.* 263: 19827-19832 (1988).

Gennaro, A. R., *Remington's Pharmaceutical Sciences*, $18^{th}$ Ed., Mack Publishing Co., Easton, PA, Part 8: 1435-1712 (1990).

Ghetie, et al., "Increasing the Serum Persistence of an IgG Fragment by Random Mutagenesis", *Nature Biotechnology* 15: 637-640 (1997).

Gibbs, et al., "Farnesyltransferase Inhibitors: Ras Research Yields a Potential Cancer Therapeutic", *Cell* 77: 175-178 (1994).

Gibbs, et al., "Pharmaceutical Research in Molecular Oncology", *Cell* 79: 193-198 (1994).

Golub, E. S. and Green D. R., eds., *Immunology-A Synthesis*, Sinauer Associates, Sunderland, Mass.; $2^{nd}$ Edition, "The Structure of Immunoglobulins", Chapter 3, pp. 42-52; "The Constant Region", Chapter 6, pp. 92-107; "Amino Acid Abbreviations", Appendix 1, p. 716 (1991).

Gonzalez-Cadavid, et al., "Organization of the Human Myostatin Gene and Expression in Healthy Men and HIV-Infected Men with Muscle Wasting" *Proc. Natl. Acad. Sci.* 95:14938-14943 (1998).

Goodson, et al., "Site-Directed Pegylation of Recombinant Interleukin-2 at its Glycosylation Site", *Biotechnology* 8: 343-346 (1990).

Goodson, et al., "High—Affinity Urokinase Receptor Antagonists Identified with Bacteriophase Peptide Display", *Proc. Natl. Acad. Sci.* 91: 7129-7133 (1994).

Graf and Kastin, "Delta-Sleep-Inducing Peptide (DSIP): An Update", *Peptides* 7: 1165-1187 (1986).

Grant, G. A., Ed., *Synthetic Peptides: A User's Guide*, W. H. Freeman & Co., 1992 (Table of Contents Provided Only).

(56) References Cited

OTHER PUBLICATIONS

Greene, et al., *Protective Groups in Organic Synthesis*, 3rd Ed., John Wiley & Sons, Inc. (Table of Contents Provided Only).
Greenwald, et al., "Poly(ethylene glycol) Conjugated Drugs and Prodrugs: A Comprehensive Review", *Critical Reviews™ in Therapeutic Drug Carrier Systems*, 17(2): 101-161 (2000).
Gribskov, M. and Devereux, *Sequence Analysis Primer*, Stockton Press, New York (1991) (Table of Contents Provided Only).
Gribskov, et al., "Profile Analysis", *Meth. Enzym.* 183: 146-159 (1990).
Gribskov, et al., "Profile Analysis: Detection of Distantly Related Proteins", *Proc. Nat. Acad. Sci.* 84(13): 4355-4358 (1987).
Griffin, A.M., and Griffin, H.G., *Computer Analysis of Sequence Data, Part 1*, Humana Press, New Jersey (1994) (Table of Contents Provided Only).
Halaby, et al., "The Immunoglobulin Fold Family Sequence Analysis and 3D Structure Comparisons", *Protein Engineering*, 12(7): 563-571 (1999).
Hamrick, et al., "Bone Mineral Content and Density in the Humerus of Adult Myostatin-Deficient Mice", *Calcif. Tissue Int.* 71(1): 63-68 (2002).
Harris et al., "Structure of Immunoglobulin", RCSB, Protein Data Bank (An Information Portal to Biological Macromolecular Structures), Release Date: Apr. 15, 1998, Search conducted at www.rcsb.org/pdb.
Harvill, et al., "An IgG3-IL2 Fusion Protein Activates Complement, Binds FcγRI, Generates LAK Activity and Shows Enhanced Binding to the High Affinity IL-2R", *Immunotech* 1: 95-105 (1995).
Harwig, et al., "Neutrophi Defenses: Purification, Characterization, and Antimicrobial Testing", *Methods Enzymology* 236: 160-172 (1994).
Hendrickson, et al., "Incorporation of Nonnatural Amino Acids into Proteins", *Annu. Rev. Biochem.*, 73: 147-176 (2004).
Henikoff, et al., "Amino Acid Substitution Matrices from Protein Blocks", *Proc. Natl. Acad. Sci. USA* 89: 10915-10919 (1992).
Herman, et al., Poly(Ethylene Glycol) with Reactive Endgroups: I. Modification of Proteins, *J. of Bioactive and Compatible Polymers*, 10(2): 145-187 (1995).
Herz, et al., "Molecular Approaches to Receptors as Targets for Drug Discovery", *J. of Receptor & Signal Transduction Research*, 17(5): 671-776 (1997).
Holm, et al., "Protein Folds and Families: Sequence and Structure Alignments", *Nucleic Acids Research.*, 27(1): 244-247 (1999).
Hong, et al., "Protein Ligands of the Human Adenovirus Type 2 Outer Capsid Identified by Biopanning of a Phage-Displayed Peptide Library on Separate Domains of Wild-Type and Mutant Penton Capsomers", *The EMBO Journal* 14: 4714-4727 (1995).
Hubbard, et al., "Anti-Neutrophil-Elastase Defenses of the Lower Respiratory Tract in α1-Antitrypsin Deficiency Directly Augmented with an Aerosol of α1-Antitrypsin", *Annals of Internal Medicine* 3(3): 206-212 (1989).
Hughes, David, "Therapeutic Antibodies Make a Comeback", *Drug Discovery Today* 3(10): 439-442 (1998).
Inagaki-Ohara, et al., "Effects of a Nonapeptide Thymic Hormone on Intestinal Intraepithelial Lymphocytes in Mice Following Administration of 5-Fluorouracil", *Cellular Immunol.*, 17: 30-40 (1996).
Inglot, Anna, D., "Classification of Cytokines According to the Receptor Code", *Archivum Immunologiae et Therapine Experimentalis*, 45: 353-357 (1997).
Ishikawa, et al., "Actions of the Novel Oral Antidiabetic Agent HQL-975 in Insulin-Resistant Non-insulin-dependent Diabetes Mellitus Model Animals", *Diabetes Research and Clinical Practice*, 41: 101-111 (1998).
IUPAC-IUB Joint Commission on biochemical Nomenclature (JCBN), "Nomenclature and Symbolism for Amino Acids and Peptides", *Biochem J.*, 219: 345-373 (1984).
Jaravine, et al., "Three Dimensional Structure of Toxin OSK1 from *Orthochirus scrobiculosus* Scorpion Venom", *Biochemistry* 36: 1223-1232 (1997).
Jefferies, D., "Selection of Novel Ligands from Phage Display Libraries: An Alternative Approach to Drug and Vaccine Discovery?", *Parasitology Today* 14(5): 202-206 (1988).
Jefferis, et al., "Recognition Sites on Human IgG for Fcy Receptors: the Role of Glycosylation", *Immunology Letters* 44: 111-117 (1995).
Jefferis, et al., Molecular Definition of Interaction Sites on Human IgG Fc Receptors (huFcγ R), *Molecular Immunology* 27(12): 1237-1240 (1990).
Johnson, et al., Identification of a 13 Amino Acid Peptide Mimetic of Erythropoietin and Description of Amino Acids, Critical for the Mimetic Activity of EMP1, *Biochemistry* 37(11): 3699-3710 (1998).
(JCBN) Joint Commission on Biochemical Nomenclature, "Nomenclature and Symbolism for Amino Acids and Peptides", *Biochem. J.*, 219: 345-373 (1984).
Jones, et al., "Stromal Expression of Jagged 1 Promotes Colony Formation by Fetal Hematopoietic Progenitor Cells", *Blood* 92(5): 1505-1511 (1998).
Jones, D., "Progress in Protein Structure Prediction", *Curr. Opin. Struct. Biol.* 7(3): 377-387 (1997).
Junghans, R. P., "Finally! The Branbell Receptor (FcRB)", *Immunologic Research* 16(1): 29-57 (1997).
Kalman, et al., "ShK-Dap$^{22}$, a Potent Kv1.3-specific Immunosuppressive Polypeptide" *J. Biol. Chem.* 273(49): 32697-32707 (1998).
Kay, et al., "From Peptides to Drugs via Phage Display", *Drug Discovery Today* 3: 370-378 (1998).
Keil, B., *Specificity of Proteolysis*, Springer-Verlag Berlin-Heidelberg—New York (1992) (Table of Contents Provided Only).
Kho, et al., "A Tagging-via-Substrate Technology for Detection and Proteomics of Farnesylated Proteins", *Proc. Nat'l. Acad. Science*, 101: 12479-12484 (2004).
King, et al., "Modulation of Bone Marrow Stromal Cell Production of Colony Stimulating Activity by the Synthetic Peptide", *Exp. Hematol* 19: 481 (1991).
King, et al., "Hematoregulatory Peptide, SK&F Induced Stromal Cell Production of KC Enhances CFU-GM Growth and Effector Cell Function", *Blood* 86(1): 309a (1995).
Kitamura, et al., "Adrenomedullin: A Novel Hypotensive Peptide Isolated From Human Pheochromocytoma", *BBRC*, 192: 553-560 (1993).
Kluczyk, et al., "Immunomodulatory Activity of Oligopeptides Related to Interleukin 1 Receptor Antagonist Sequence", *Archivum Immunologiac et Therapiae Experimentalis* 45: 427-433 (1997).
Kocienski, *Protecting Groups*, G. T. Verlag Stuttgart, New York (1994) (Table of Contents Provided Only).
Koivunen, et al., "Tumor Targeting with a Selective Gelatinase Inhibitor", *Nat. Biotech.* 17: 768-774 (1999).
Kottke, et al., "Tablet Dosage Forms", *Modern Pharmaceutics*, 4th Ed., Chap. 10, 287-333 (1979).
Kraft, et al., "Definition of an Unexpected Ligand Recognition Motif for αvβ6 Integrin", *Journal of Biological Chemistry* 274(4): 1979-1985 (1999).
Krapp et al., "Crystal Structure of the Human IGG1 Fc-Fragment, Glycoform (MN2F) 2", RCSB, Protein Data Bank (An Information Portal to Biological Macromolecular Structures), Release Date: Jan. 23, 2003, Search conducted at: www.rcsb.org/pdb.
Kreeger, Karen Young, "Immunological Applications Top List of Peptide-Synthesis Services", *The Scientist* 10(13): 19-20 (1998).
Kuai, et al., "Plasminogen Activator Inhibitor-1 Fused With Erythropoietin (EPO) Mimetic Peptide (EMP) Enhances the EPO Activity of EMP", *J. Peptide Research* 56: 59-61 (2000).
Kyte, et al., "A Simple Method for Displaying the Hydropathic Character of a Protein", *J. Mol Biol.*, 157: 105-131 (1982).
Laerum, et al., "The Dimer of Hemoregulatory Peptide (HP5B) Stimulates Mouse and Human Myelpoiesis in Vitro", *Exp. Hemat.* 16: 274-280 (1988).
Lalani, et al., "Myostatin and Insulin-Like Growth Factor-I and -II Expression in the Muscle of Rats Exposed to the Microgravity Environment of the NeuroLab Space Shuttle Flight", *J. Endocrin* 167(3): 417-428 (2000).
Lehmann-Horn, et al., "Voltage-Gated Ion Channels and Hereditary Disease", *Physiol. Reviews*, 79(4): 1317-1372 (1999).

(56) References Cited

OTHER PUBLICATIONS

Lesk, A. M., Computational Molecular Biology—Sources and Methods for Sequence Analysis, *Oxford University Press* (1988) (Table of Contents Provided Only).
Lewin, B., Genes V., *Oxford University Press*, p. 11 (1994).
Lin, et al., "Myostatin Knockout in Mice Increases Myogenesis and Decreases Adipogenesis" *Biochem Biophys. Res. Commun.* 291(3): 701-706 (2002).
Link,et al., "Non-Canonical Amino Acids in Protein Engineering", *Cur. Opin. Biotech.* 14(5): 603-609 (2003).
Link, et al., "Presentation and Detection of Azide Functionality in Bacterial Cell Surface Proteins", *J. Am. Chem. Soc.*, 126: 10598-10602 (2004).
Linse, et al., "A Region of Vitamin K-Dependent Protein S That binds to C4b Binding Protein (C4BP) Identified Using Bacteriophage Peptide Display Libraries", *The Journal Biological Chemistry* 272(23): 14658-14665 (1997).
Linsley, et al., "CTLA-4 is a Second Receptor for the B Cell Activation Antigen B7",*J. Exp. Med.* 174: 561-569 (1991).
Livnah, et al., "Functional Mimicry of a Protein Hormone by a Peptide Agonist: The EPO Receptor Complex at 2.8 Å", *Science* 273: 464-471 (1996).
Loetscher, et al., "Efficacy of a Chimeric TNFR-1gG Fusion Protein to Inhibit TNF Activity in Animal Models of Septic Shock", *Int'l. Congress Series 2: Elsevier Science Publishers* pp. 455-462 (1993).
Lowman, H. B., "Bacteriophage Display and Discovery of Peptide Leads for Drug Development", *Annu. Rev. Biophys. Biomol. Struct.* 26: 401-424(1997).
Lu, et al., "Pegylated Peptides, III. Solid-Phase Synthesis with Pegylating Reagents of Varying Molecular Weight: Synthesis of Multiply Peglylated Peptides", *Reactive Polymers*, 22: 221-229 (1994).
Lundergan, et al., "Angiotensin-II Increases Cyctoplasmic Calcium, Cell Number and Total DNA or Human Periodontal Ligamental Cells In Vitro", *J. Periodontal Res.* 34(4): 223-288 (1999).
Mahal, et al, "Engineering Chemical Reactivity on Cell Surfaces Through Oligosaccharide Biosysnthesis", *Science*, 276: 1125-1128 (1997).
Mariuzza, Roy A. and Winter, Greg; "Secretion of a Homodimeric V.C.T-cell Receptor-Immunoglobulin Chimeric Protein" *The J. Biol. Chem.* 13: 7310-7316 (1989).
Marshall, K., "Solid Oral Dosage Forms", *Modern Pharmaceutics*, Chapter 10: 359-427 (1979).
Martens, et al., "Peptides Which Bind to E-Selectin and Block Neutrophil Adhesion", *The Journal of Biological Chemistry* 270(36): 21129-21136 (1995).
Martin et al., "Non-FCRN Binding Fc Fragment of Rat IGG2A", RCSB, Protein Data Bank (An Information Portal to Biological Macromolecular Structures), Release Date: Feb. 14, 2001, Search conducted at www.rcsb.org/pdb.
Maurer, et al. "Autodisplay: One-Component System for Efficient Surface Display and Release of Soluble Recombinant Proteins from *Escherichia coli*", *Journal of Bacteriology* 179(3): 794-780 (1997).
McGregor, Duncan, "Selection of Proteins and Peptides from Libraries Displayed on Filamentous Bacteriophage", *Molecular Biotechnology* 6: 155-162 (1996).
Means, et al., *Chemical Modification of Proteins*, "Selected Techniques for the Modification of Protein Side Chains" Holden Day, Inc., 214-230 (1971).
Merrifield, R.B., "Solid-Phase Peptide Synthesis", *Chem. Polypeptides* 335-361 (1973).
Merrifield, R.B., "Solid-Phase Peptide Synthesis. I. The Synthesis of a Tetrapeptide", *J. Am. Chem. Soc.* 85: 2149-2154 (1963).
Miura, Y, Kirito, K. and Komatsu, N., "Regulation of Both Erythroid and Megakaryocytic Differentiation of a Human Leukemia Cell Line, UT-7," *Acta Haematologica*, 99: 180-184 (1998).
Moodie, et al., "The 3Rs of life: Ras, Raf and Growth Regulation", *TIG* 10(2): 44-48 (1994).

Moonga, et al., Effects of Peptide Fragments of Protein Kinase C on Isolated Rat Osteoclasts, *Experimental Physiology* 83: 717-725 (1998).
Morikis, et al., "Solution Structure of Compstatin, a Potent Complement Inhibitor", *Protein Science* 7: 619-627 (1998).
Morpurgo, et al., "Preparation and Characteriziation of Poly(ethylene glycol) Vinyl Sulfone", *Bioconjugate Chem.* 7: 363-368 (1996).
Moult, J., "The Current State of the Art in Protein Structure Prediction", *Curr. Op. in Biotech.* 7(4): 422-427 (1996).
Nachman, et al., "Pseudodipeptide Analogs of the Pyrokinin/PBAN (FXPRLa) Insect Neuropeptide Family Containing Carbocyclic Pro-Mimetic Conformational Components", *Regulatory Peptides* 57: 359-370 (1995).
Naranda, et al., "Activation of Erythropoietin Receptor in the Absence of Hormone by a Peptide that Binds to a Domain Different from the Hormone Binding Site", *Proc. Natl. Acad, Sci. USA* 96: 7569-7574 (1999).
Needleman, et al., "A General Method Applicable to the Search for Similarities in the Amino Acid Sequence of Two Proteins", *J. Mol. Biol.* 48: 443-453 (1970).
Newmark, et al., "Preparation and Properties of Adducts of Streptokinase and Streptokinase-Plasmin Complex with Polyethlene Glycol and Pluronic Polyol F38", *J. Appl. Biochem* 4: 185-189 (1982).
Niemeyer, et al., "Ion Channels in Health and Disease", *EMBO Reports* 2(7): 568-573 (2001).
Nishi, et al., "Tight-Binding Inhibitory Sequences Against $pp60^{c-src}$ Identified Using a Random 15-Amino-Acid Peptide Library", *FEBS* 399: 237-240 (1996).
Park, et al., "Rationally Designed Anti-HER2/neu Peptide Mimetic Disables $P185^{HER2/neu}$ Tyrosine Kinases In Vitro and In Vivo", *Nat. Biotechnol.* 18: 194-198 (2000).
Pasquaimi, et al., "Organ Targeting In Vivo Using Phage Display Peptide Libraries", Nature 380: 364-366 (1996).
Paukovitis, et al., Structural Investigations on a Peptide Regulating Hemopoiesis In Vitro and In Vivo *Hoppe-Seylers Z. Physio. Chem.* 365: 303-311 (1984).
Pawson, et al., "SH2 and SH3 Domains", *Current Biology*, 3: 434-442 (1993).
Pennington, et al., "Role of Disulfide Bonds in the Structure and Potassium Channel Blocking Activity of ShK Toxin", *Biochemistry* 38: 14549-14558 (1999).
Picksley, et al., "Immunochemical Analysis of the Interaction of p53 with MDM2;—Fine Mapping of the MDM2 Binding Site on p53 Using Synthetic Peptides", *Oncogene* 9: 2523-2529 (1994).
Pierce, et al., "Identification of Cyclized Calmodulin Antagonists From a Phage Display Random Peptide Library", *Molec. Diversity* 1: 259-265 (1995).
Piette, et al., "Mdm2: Keeping p53 Under Control", *Oncogene* 15: 1001-1010 (1997).
Powis, Garth, "Signaling Targets for Anticancer Drug Development", *TIPS* 12: 188-194 (1991).
Prescher, et al., "Chemical Remodeling of Cell Surfaces in Living Animals", *Nature* 430: 873-877 (2004)
Prescher, et al., "Chemistry in Living Systems", *Nature Chem. Biol.*, 1(1): 13-21 (2005).
Prochnicka-Chalufour, "Solution of Discrepin, a New K+ Channel Blocking Peptide from the α-KTx15 Subfamily", *Biochemistry* 45: 1795-1804 (2006).
Ptacek, L. J. and Fu, Y., "Channels and Disease—Past, Present, and Future", Neurol. Review 61: 1663-1668 (2004).
Rickles, et al., "Identification of Src, Fyn, Lyn, PI3K and AbI SH3 Domain Ligands Using Phagel Display Libraries", *The EMBO Journal* 13(23): 5598-5604 (1994).
Roberts & Szostak, "RNA-Peptide Fusions for the In Vitro Selection of Peptides and Proteins", *Proc. Natl. Acad. Sci. USA*, 94: 12297-12303 (1997).
Rodriguez-Viciana, et al., "Phosphatidylinositol-3-OH Kinase as a Direct Target of Ras", *Nature* 370: 527-532 (1994).
Sahu, et al., "Inhibition of Human Complement by a C3-Binding Peptide Isolated from a Phage-Displayed Random Peptide Library", *The Journal of Immunology* 57(2): 884-891 (1996).

(56) References Cited

OTHER PUBLICATIONS

Sandler & Karo, "Polyoxyalkylation of Hydroxy Compounds", *Polymer Synthesis*, vol. 3, Chap. 5, 138-161 (1998)
Sarmay, et al., "Mapping and Comparison of the Interaction Sites on the Fc Region of IgG Responsible for Triggering Antibody Dependent Cellular Cytotoxicity (ADCC) Through Different Types of Human Fcγ Receptor", *Molecular Immunology* 29(5): 633-639 (1993).
Schechter I. & Berger A., "On the Active Site of Proteases. III. Mapping the Active Site of Papain; Specific Peptide Inhibitors of Papain," *Biochem. & Biophys. Res. Comm.*, 32(5): 898-902 (1968).
Schechter I. & Berger A., "On the Size of the Active Site in Proteases. I. Papain," *Biochem. & Biophys. Res. Comm.*, 27(2): 157-162 (1967).
Scott, et al., "Searching for Peptide Ligands with an Epitope Library", *Science* 249: 386-390 (1990).
Sharma, et al., "Myostatin, a Transforming Growth Factor-β Superfamily Member, Is Expressed in Heart Muscle and Is Upregulated in Carciomyocytes After Infarct", *J. Cell Physiol.* 180(1): 1-9 (1999).
Shinmei, et al., "Quantitation of Chondroitin 4-Sulfate and Chondroitin 6-Sulfate in Pathologic Joint Fluid", *Arthritis Rheum.* 35: 1304-1308 (1992).
Siemion, et al., "The Evidence on the Possible Interleukin-1α Tuftsin Competition", *Archivium Immunologiae et Therapiae Experimentalis* 39: 605-611 (1991).
Silberberg, Anderson's Pathology, "Diseases of Joints," Kissane (ed.), Ch. 42, II: 1828 (1985).
Sippl, et al., "Threading Thrills and Threats", *Structure* 4(1): 15-19 (1996).
Smith, et al., "Pulmonary Deposition and Clearance of Aerosolized Alpha-l-Proteinase Inhibitor Administered to Dogs and to Sheep" *J. Clin. Invest.* .84: 1145-1146 (1989).
Smith, et al., "Isolation of Glucagon Antagonists by Random Molecular Mutagenesis and Screening", *Mol. Pharmacol*, 43: 741-748 (1993).
Smith, D.W., Ed., Biocomputing: Informatics and Genome Projects, *Academic Press*, New York (1993) (Table of Contents Provided Only).
Sparks, et al., Distinct Ligand Preferences of Src Homology 3 Domains from Src, Yes, Abl, Cortactin, p53bp2, PLCγ, Crk, and Grb2, *Proc. Natl. Acad. Sci. USA* 93: 1540-1544 (1996).
Sparks, et al., "Identification and Characterization of Src SH3 Ligands from Phage-Displayed Random Peptide Libraries", *The Journal Biological Chemistry* 269(39): 23853-23856 (1994).
Speers, et al., "Activity-Based Protein Profiling in Vivo Using a Copper (I)-Catalyzed Azide-Alkyne [3 + 2] Cycloaddition", *J. Am. Chem. Soc.*, 125: 4686-4687 (2003).
Speers, et al., "Profiling Enzyme Activities In Vivo Using Click Chemistry Methods", *Chem. & Biol.*, 11: 535-546 (2004).
Staufer, et al., "Inhibition of Lyn Function in Mast Cell Activation by SH3 Domain Binding Peptides", *Biochemestry* 36: 9388-9394 (1997).
Stewart and Young, Solid Phase Peptide Synthesis, *W.H. Freeman and Co.* (1969) (Table of Contents Provided Only).
Suzuki and Yoshino, "The Relationship Between Amino Acid Sequences of Sperm-Activiating Peptides and the Taxonomy of Echinoids", *Comp. Biochem. Physiol. B*. 102(4): 679-690 (1992).
Tai, Mei-Sheng, et al., "A Bifunctional Fusion Protein Containing Fc-Binding Fragment B of Staphylococcal Protein A Amino Terminal to Antidigoxin Single-Chain Fv†", *Biochemistry* 29: 8024-8030 (1990).
Takasaki, et al., "Structure-Based Design and Characterization of Exocyclic Peptidomimetics that Inhibit TNFα Binding to its Receptor", *Nature Biotechnology* 15: 1266-1270 (1997).
Thonar, et al., "Body Fluid Markers of Cartilage Changes in Osteoarthritis", *Rheumatoid Disease Clinics of North America*, 19(3): 635-657 (1993).
Turk, et al., "Determination of Protease Cleavage Site Motifs Using Mixture-Based Oriented Peptide Libraries", *Nature Biotech*. 19: 661-667 (2001).
Van Zee, et al., "Protection Against Lethal *Escherichia coli* Bacteremia in Baboons (*Papio anubis*) by Pretreatment with a 55-kDa TNF Receptor (CD120a)-Ig Fusion Protein, Ro 45/2081", *J. Immunol.* 156(6): 2221-2230 (1996).
Von Heinje, G., *Sequence Analysis in Molecular Biology*, Academic Press (1987) (Table of Contents Provided Only).
Wells, et al., "Rapid Evolution of Peptide and Protein Binding Properties In Vivo", *Current Opinion of Biotechnology* 3: 355-362 (1992).
Western, et al., "Efficient One-Step Suzuki Arylation of Unprotected Halonucleosides, Using Water-Soluble Palladium Catalysts", *J. Org. Chem.* 68: 6767-6774 (2003).
Whitty, et al., "Small Molecule Cytokine Mimetics", *Chemistry & Biology* 6: R107-R118 (1996).
Wieczorek, et al., "The Immunomodulatory Activity of Tetra- and Tripeptides of Tuftsin-Kentsin Group", *Peptides* 15(2): 215-221 (1994).
Williams, G. T. and Neuberger, M. S.; "Production of Antibody-Tagged Enzymes by Myeloma Cells: Application to DNA Polymerase I Klenow Fragmont", *Gene* 43: 319-324 (1986).
Wilson, et al., "Phage Display: Applications, Innovations, and Issues in Phage and Host Biology", *Can. J. Microbiol*. 44: 313-329 (1998).
Wright, et al., "The Importance of Loop Length in the Folding of an Immunoglobulin Domain", *Protein Engin. Design & Selection* 17: 443-453 (2004).
Wrighton, et al., "Small Peptides as Potent Mimetics of the Protein Hormone Erythropoietin", *Science* 273: 458-463 (1996).
Wrighton, et al., "Increased Potency of an Erythropoietin Peptide Mimetic through Covalent Dimerization", Nature Biotechnology 15: 1261-1265 (1997).
Yanofsky, et al., "High Affinity Type I Interleukin 1 Receptor Antagonists Discovered by Screening Recombinant Peptide Libraries", *Proc. Natl. Acad. Sci.* 93: 7381-7386 (1996).
Yarasheski, et al., "Serum Myostatin-Immunoreactive Protein is Increased in 60-92 Year Women and Men with Muscled Wasting," *J. Nutr. Aging*, 6(5): 343-348 (2002).
Yen, et al., "Obesity, Diabetes, and Neoplasia in Yellow A $^{vy}$/– Mice: Ectopic Expression of the *Agouti* Gene", *FASEB J.* 8: 479 (1994).
Yoshida, et al., "The Activity of Synthetic Analogs of Serum Thymic Factor (FTS) to Convert Mouse Pre-T Cells into Thy-1 Positive Cells", *Int. I. Immunopharmac* 6(2): 141-146 (1984).
Yu, et al., "Structural Basis for the Binding of Proline-Rich Peptides to SH3 Domains", *Cell* 76(5): 933-945 (1994).
Zachwieja, et al., "Plasma Myostatin-Immunoreactive Protein is Increased After Prolonged Bed Rest with Low-Dow T, Administration", *J. Gravit Physiol*. 6(2): 11 (1999).
Zalipsky, S. and Lee, C.; "Use of Functionalized Poly(Ethylene Glycol)s for Modification of Polypeptides", *Adv. Drug Devel. Rev.* 16: 157-182 (1995).
Zhang, et al., "A New Strategy for the Site-Specific Modification of Proteins in Vivo", *Biochemistry* 42: 6735-6746 (2003).
Zheng, et al., "Administration of Noncytolytic IL-10/Fc in Murine Models of Lipopolsaccharide-Induced Septic Shock and Allogeneic Islet Transplantation", *J. Immunol.* 154: 5590-5600 (1995).
Zimmers, et al., "Induction of Cachexia in Mice by Systemically Administered Myostatin", *Science* 296: 1486-1488 (2002).
Shopes, B, "A genetically engineered human IgG mutant with enhanced cytolytic activity", *J of Immunology*, 148(9): 2918-2922 (1992).

\* cited by examiner

FIG. 1

Human Fc:

```
  1 DKTHTCPPCP APELLGGPSV FLFPPKPKDT LMISRTPEVT CVVVDVSHED PEVKFNWYVD
 61 GVEVHNAKTK PREEQYNSTY RVVSVLTVLH QDWLNGKEYK CKVSNKALPA PIEKTISKAK
121 GQPREPQVYT LPPSRDELTK NQVSLTCLVK GFYPSDIAVE WESNGQPENN YKTTPPVLDS
181 DGSFFLYSKL TVDKSRWQQG NVFSCSVMHE ALHNHYTQKS LSLSPGK
```

FIG. 2

IgG1 Fc
human Fc alone

```
  1 MDKTHTCPPC PAPELLGGPS VFLFPPKPKD TLMISRTPEV TCVVVDVSHE
 51 DPEVKFNWYV DGVEVHNAKT KPREEQYNST YRVVSVLTVL HQDWLNGKEY
101 KCKVSNKALP APIEKTISKA KGQPREPQVY TLPPSRDELT KNQVSLTCLV
151 KGFYPSDIAV EWESNGQPEN NYKTTPPVLD SDGSFFLYSK LTVDKSRWQQ
201 GNVFSCSVMH EALHNHYTQK SLSLSPGK*
```

FIG. 3

IgG1 Fc
human Fc alone

```
  1  MDKTHTCPPC PAPELLGGPS VFLFPPKPKD TLMISRTPEV TCVVVDVSHE
 51  DPEVKFNWYV DGVEVHNAKT KPREEQYNST YRVVSVLTVL HQDWLNGKEY
101  KCKVSNKALP APIEKTISKA KGQPREPQVY TLPPSRDELT KNQVSLTCLV
151  KGFYPSDIAV EWESNGQPEN NYKTTPPVLD SDGSFFLYSK LTVDKSRWQQ
201  GNVFSCSVMH EALHNHYTQK SLSLSPGK*
```

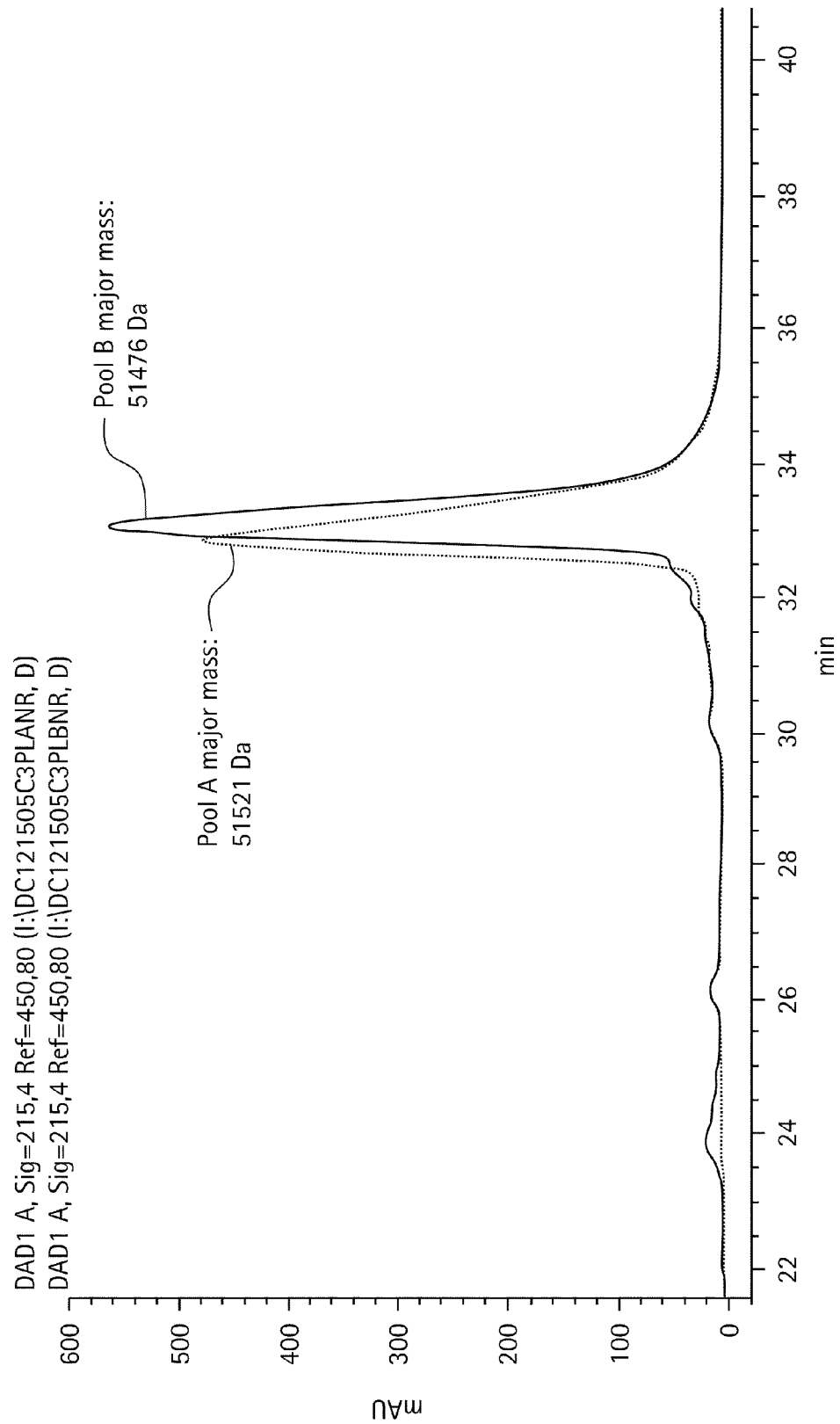

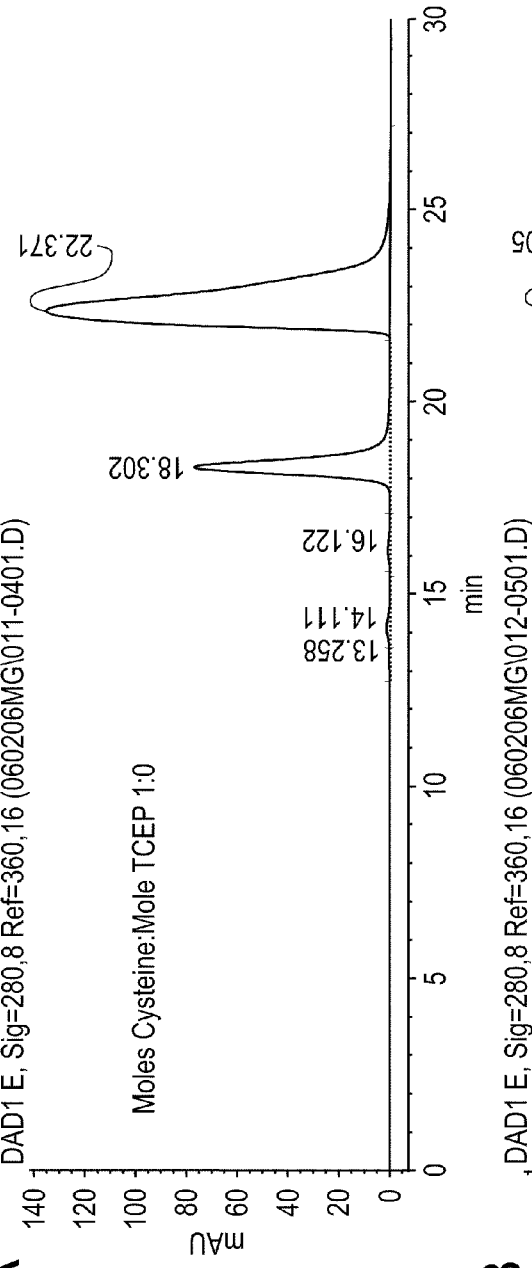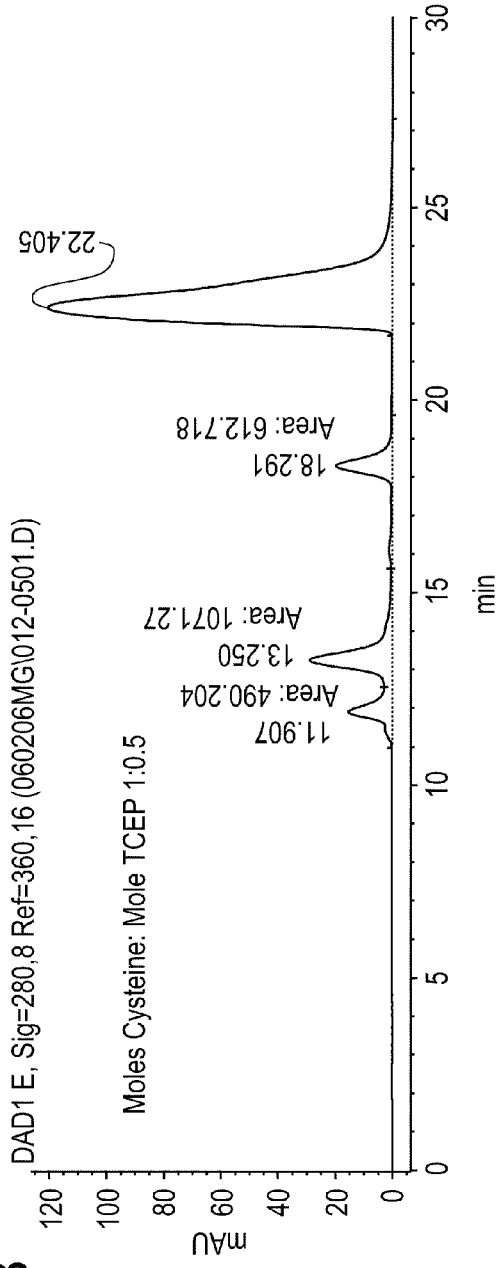

MODIFIED FC MOLECULES

This application is a division of U.S. Nonprovisional Application No. 11/502,761, filed Aug. 10, 2006, which issued as U.S. Pat. No. 8,008,453 on Aug. 30, 2011 and claims the benefit of U.S. Provisional Application No. 60/707,842, filed Aug. 12, 2005, both of which applications are hereby incorporated by reference.

This application incorporates by reference all subject matter contained in this text file, which is identified by the name of the file, A-1037USSeqList081006ST25.txt created on Aug. 10, 2006, the size of which file is 229 KB.

Throughout this application various publications are referenced within parentheses or brackets. The disclosures of these publications in their entireties are hereby incorporated by reference in this application in order to more fully describe the state of the art to which this invention pertains.

BACKGROUND OF THE INVENTION

1. Field of Art

The present invention relates to the biochemical arts, particularly to conjugates with immunoglobulin Fc domains.

2. Discussion of Related Art

The immunoglobulin Fc domain has found widespread use as a carrier protein for a variety of therapeutic and diagnostic molecules. Antibodies comprise two functionally independent parts, a variable domain known as "Fab", which binds antigen, and a constant domain known as "Fc", which links to such effector functions as complement activation and attack by phagocytic cells. An Fc has a long serum half-life, whereas a Fab is short-lived. (Capon et al. (1989), Nature 337: 525-31). When constructed together with a therapeutic protein or peptide, an Fc domain can provide longer half-life, or can incorporate such functions as Fc receptor binding, protein A binding, complement fixation and perhaps even placental transfer. Id.

Numerous fusions of proteins and peptides have been engineered at either the amino- or carboxy-termini. Also, a variety of enzymes and synthetic reporter molecules have been chemically conjugated to the side chains of non-terminal amino acids as well as the derivatized carbohydrate moieties of the Fc domain. Further, several polymers, such as polyethylene glycol (PEG) have been conjugated to the Fc domain for the purpose of improved half-life in vivo and reduced immunogenicity.

The success of the drug Enbrel® (etanercept) brought to fruition the promise of therapeutic agents modified with the constant domain of an antibody. Table 1 summarizes several examples of the use of Fc fusion proteins known in the art.

TABLE 1

Fc fusion with therapeutic proteins

| Form of Fc | Fusion partner | Therapeutic implications | Reference |
|---|---|---|---|
| IgG1 | N-terminus of CD30-L | Hodgkin's disease; anaplastic lymphoma; T-cell leukemia | U.S. Pat. No. 5,480,981 |
| Murine Fcγ2a | IL-10 | Anti-inflammatory; transplant rejection | Zheng et al., (1995), J. Immunol. 154: 5590-600 |
| IgG1 | TNF receptor | Septic shock | Fisher et al. (1996), N. Engl. J. Med. 334: 1697-1702; Van Zee, K. et al. (1996), J. Immunol. 156: 2221-30 |
| IgG, IgA, IgM, or IgE (excluding the first domain) | TNF receptor | Inflammation, autoimmune disorders | U.S. Pat. No. 5,808,029, issued Sep. 15, 1998 |
| IgG1 | CD4 receptor | AIDS | Capon et al. (1989), Nature 337: 525-31 |
| IgG1, IgG3 | N-terminus of IL-2 | Anti-cancer, antiviral | Harvill et al. (1995), Immunotech. 1: 95-105 |
| IgG1 | C-terminus of OPG | osteoarthritis; bone density | WO 97/23614, published Jul. 3, 1997 |
| IgG1 | N-terminus of leptin | Anti-obesity | WO 98/28427, filed Dec. 11, 1997 |
| Human Ig C1 | CTLA-4 | Autoimmune disorders | Linsley (1991), J. Exp. Med. 174: 561-9 |

A more recent development is fusion of randomly generated peptides with the Fc domain. See U.S. Pat. No. 6,660,843, issued Dec. 9, 2003 to Feige et al. (incorporated by reference in its entirety). Such molecules have come to be known as "peptibodies." They include one or more peptides linked to the N-terminus, C-terminus, amino acid side chains, or to more than one of these sites. Peptibody technology enables design of therapeutic agents that incorporate peptides that target one or more ligands or receptors, tumor-homing peptides, membrane-transporting peptides, and the like. Peptibody technology has proven useful in design of a number of such molecules, including linear and disulfide-constrained peptides, "tandem peptide multimers" (i.e., more than one peptide on a single chain of an Fc domain). See, for example, U.S. Pat. No. 6,660,843; U.S. Pat. App. No. 2003/0195156 A1, published Oct. 16, 2003 (corresponding to WO 02/092620, published Nov. 21, 2002); U.S. Pat. App. No. 2003/0176352, published Sep. 18, 2003 (corresponding to WO 03/031589, published Apr. 17, 2003); U.S. Ser. No. 09/422,838, filed Oct. 22, 1999 (corresponding to WO 00/24770, published May 4, 2000); U.S. Pat. App. No. 2003/0229023, published Dec. 11, 2003; WO 03/057134, published Jul. 17, 2003; U.S. Pat. App. No. 2003/0236193, published Dec. 25, 2003 (corresponding to PCT/US04/010989, filed Apr. 8, 2004); U.S. Ser. No. 10/666,480, filed Sep. 18, 2003 (corresponding to WO 04/026329, published Apr. 1, 2004), U.S. Patent App. No. 2006/0140934, published Jun. 29, 2006 (corresponding to WO 2006/036834, published Apr. 4, 2006), each of which is hereby incorporated by reference in its entirety. The art would benefit from further technology enabling such rational design of polypeptide therapeutic agents.

Conventional approaches for chemical conjugation to the immunoglobulin Fc domain include random coupling to naturally occurring primary amines such as lysine and the amino-terminus or carboxylic acids such as glutamic acid, aspartic acid and the carboxy terminus. Alternatively, semi-selective site-specific coupling may be achieved through N-terminal conjugation under appropriate conditions, or derivatized carbohydrates as found on Fc proteins isolated from eukaryotic sources, or by partial reduction and coupling of native cysteine residues. (E.g., Kim et al., A pharmaceutical composition comprising an immunoglobulin Fc region as a carrier, WO 2005/047337). While each of these approaches has been applied successfully, they typically suffer from varying degrees of conjugate heterogeneity, relatively low yields and sometimes, significant losses in functional activity are also observed. The art would benefit from a process for selective, site-specific conjugation to the immunoglobulin Fc domain without significant loss in functional activity.

SUMMARY OF THE INVENTION

The present invention concerns compositions of matter and a process for making them. The inventive composition of matter, which is a pharmacologically active compound, comprises a monomeric or multimeric Fc domain having at least one additional functional moiety that is covalently bound (or conjugated), either directly or through a linker, to one or more specifically selected conjugation site(s) in the Fc domain through the side chain of an amino acid residue at the conjugation site(s). Such an internal conjugation site may be already present in a native Fc domain sequence or can be added by insertion (i.e., between amino acids in the native Fc domain) or by replacement (i.e., removing amino acid residue(s) and substituting different canonical and/or non-canonical amino acid residue(s)) in the native Fc domain sequence in order to create or "engineer" the conjugation site. In the latter case, the number of amino acid residues added need not correspond to the number of amino acid residues removed from the previously existing Fc domain sequence.

This inventive process of preparing a pharmacologically active compound comprising an Fc domain includes:

a. selecting at least one internal conjugation site of an Fc domain sequence, said conjugation site being amenable to conjugation of an additional moiety by a defined coupling chemistry through the side chain of an amino acid residue at the conjugation site; and b. conjugating a predetermined functional moiety to the selected conjugation site by employing the defined conjugation chemistry.

In some embodiments, the functional moiety is a half-life extending moiety and/or a pharmacologically active moiety, which can be, for example, a polypeptide, a peptide, a peptidomimetic, or a non-peptide organic moiety. In other embodiments the additional functional moiety is a moiety detectably labeled with a radioisotope, an enzyme (e.g., a peroxidase or a kinase), a biotinyl moiety, a fluorophore, or a chromophore. Alternatively, the additional functional moiety is an immobilized substrate, such as but not limited to, a plate surface, a bead, a particle, a microparticle, a nanoparticle, a chip, a liposome, a matrix, or the like, provided that in a chain of additional functional moieties, the immobilized substrate is the additional moiety most distal from the Fc domain, and there can be no more than one immobilized substrate in the chain.

The inventive process can be employed to modify an Fc domain that is already linked through an N- or C-terminus or side chain to a polypeptide (e.g., a soluble fragment of TNF-R2, as in etanercept) or to a peptide (e.g., as described in U.S. Pat. App. Nos. 2003/0195156 A1, 2003/0176352, 2003/0229023, and 2003/0236193; WO 00/24770; WO 04/026329). The process described throughout can also be employed to modify an Fc domain that is part of an antibody (e.g., adalimumab, epratuzumab, infliximab, Herceptin®, and the like). In this way, different molecules can be produced that have additional functionalities, such as a binding domain to a different epitope, an additional binding domain to the precursor molecule's existing epitope, or an additional half-life extending moiety.

The compounds of this invention may be prepared by standard synthetic methods, recombinant DNA techniques, or any other methods of preparing peptides and fusion proteins with reference to the disclosure of this specification.

The compounds of this invention may be used for therapeutic or prophylactic purposes by formulating them by methods known for other proteinacious molecules and administering an effective amount to a patient, such as a human (or other mammal) in need thereof. Other related aspects are also included in the current invention.

Numerous additional aspects and advantages of the present invention will become apparent upon consideration of the figures and detailed description of the invention.

BRIEF DESCRIPTION OF THE FIGURES

FIG. 1 shows a preferred subset (highlighted) of amino acid residue positions for modification as conjugation site(s) from the superset of solvent-exposed surface residues (see Table 2) in a human IgG1 Fc domain sequence (SEQ ID NO:600). Underlined residues are not present in crystal structure 1FC1, and many of these residues are good candidates for modification (e.g., insertion or substitution of amino acid residues) for creation of a conjugation site in accordance with the present invention, particularly the following amino acid residues from the aminoterminal fragment (first eighteen amino acid residues): DKTHTC . . . C . . A . . E . . . GG, i.e., through a side chain in the subsequence at positions 1 through 6 of SEQ ID NO:600, at position 9 of SEQ ID NO:600, at position 11 of SEQ ID NO:600, at position 13 of SEQ ID NO:600, at position 16 of SEQ ID NO:600, at position 17 of SEQ ID NO:600, and the following amino acids from the carboxy terminal fragment: .GK, i.e., a non-terminal site at position 226 of SEQ ID NO:600, or position 227 of SEQ ID NO:600.

FIG. 2 shows (SEQ ID NO:599), the sequence of human IgG1 Fc monomer with predicted loop region sequences in boldface; the N-terminal methionine is added for expression from *E. coli* and is not otherwise present in the native IgG1 sequence (reference sequence SEQ ID NO:600). Amino acid residues useful as preferred sites for insertion or substitution of amino acid residues for creation of a conjugation site in accordance with the present invention are underlined.

FIG. 3 shows (SEQ ID NO:599), the sequence of human IgG1 Fc monomer with predicted loop region sequences in boldface. Amino acid residue positions useful as conjugation sites in accordance with the present invention also include the underlined. Preferred surface exposed conjugation sites selected from FIG. 1 are indicated by highlighting here.

A: Ser 196, which is the most solvent-exposed and is in a rigid helix.

B: Gln 143, which is a deep polar pocket and is from the same strand as Cys 148.

C: Leu 139, which is an Fc-loop region, and is near the C-terminus in a polar pocket.

D: Ser 145, which is from the same strand as cys 148 and is in a polar pocket on a β-sheet surface in a cleft between subunits.

Figure 5:
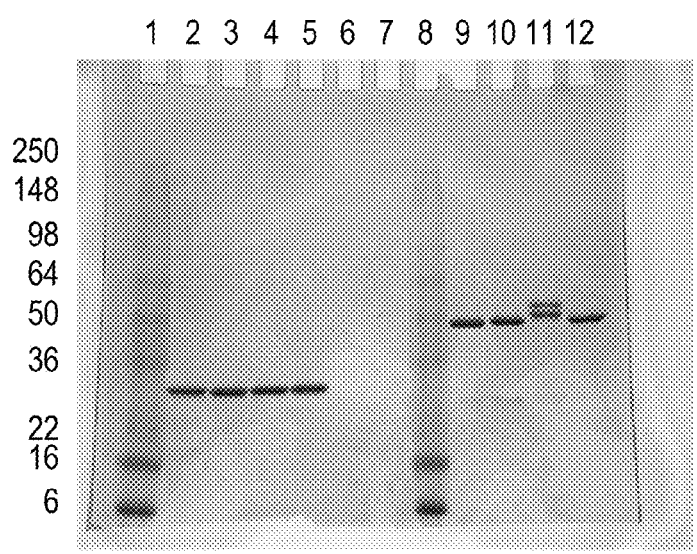

FIG. 5 shows SDS-PAGE gel analysis (4-20% Tris:Glycine polyacrylamide gel for 1.5 hours at 125V, 35 mA, 0.1% SDS)

of purified huFc-cysteine analogs described in Example 2. Lanes: 1,8 contained MW markers, lanes 2, 9 contained clone 13300 Fc(Q143C), lanes 3, 10 contained clone 13322 Fc(L139C), lanes 4, 11 contained clone 13323 Fc(S145C) and lanes 5, 12 contained clone 13324 Fc(S196C). Lanes 2-6 were reduced and lanes 9-12 were non-reduced.

Figure 6:
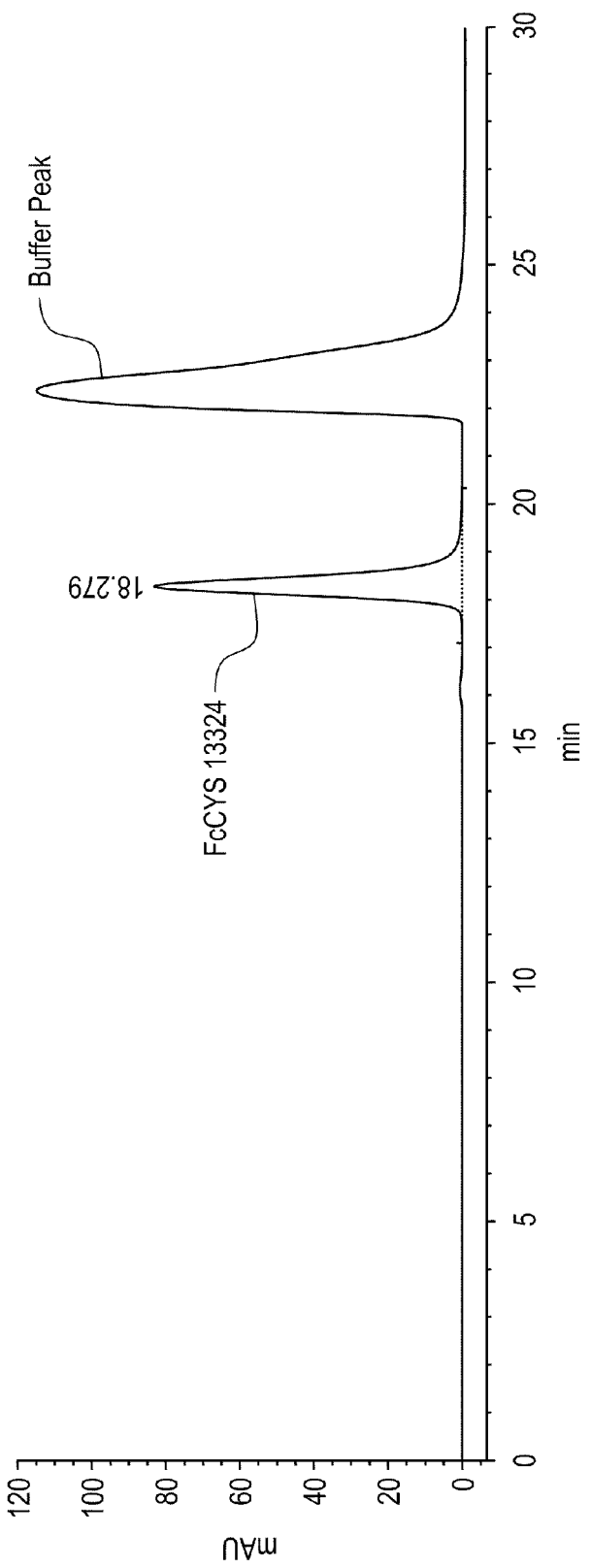

FIG. 6 shows purity by SEC-HPLC analyses of clone 13324 huFc(S196C) as described in Example 2. Samples (20 μg) were eluted in 100 mM sodium phosphate, 150 mM NaCl, pH 6.9 on a TSK G3000SW×1 column, 7.8 mm ID×30 cm, 5 μm bead size) at 0.5 ml/min.

FIG. 7 shows purity and mass determination by LC-MS of clone 13324 huFc(S196C) as described in Example 2. Samples (20 μg) were eluted in 0.1% TFA with a linear 0-90% acetonitrile gradient from a Zorbax 300SB-C18 column, 2.1 mm×150 cm.

Figure 8A:
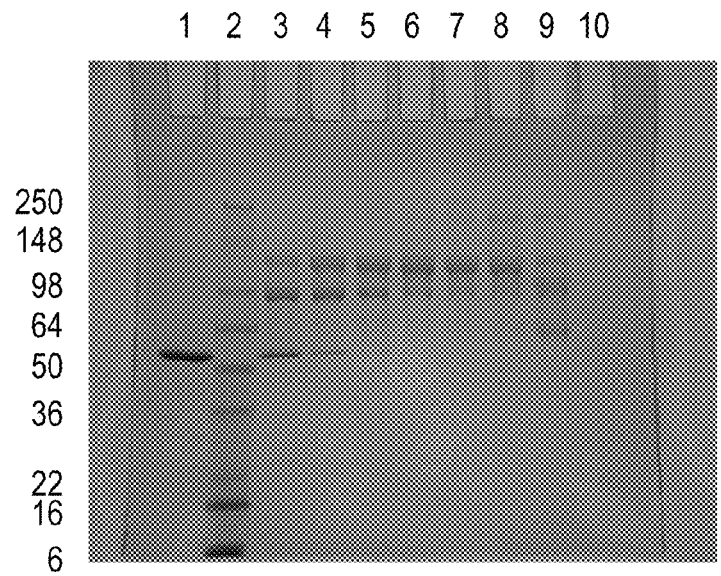

FIG. 8A shows non-reduced SDS-PAGE analysis of huFc (S196C) analog PEGylated after varying degrees of TCEP reduction, as described in Example 3. Molar stoichiometries of engineered Cysteine: TCEP were: 1:0 in lane 1, 1:0.5 in lane 3, 1:0.75 in lane 4, 1:1 in lane 5, 1:1.25 in lane 6, 1:1.5 in lane 7, 1:2 in lane 8 and 1:5 in lane 9. MW markers were in lane 2. 2 μg of non-reduced protein were loaded to each lane and run in 4-20% Tris-Glycine polyacrylamide gel with 0.1% SDS at 125 V, 35 mA and 5 W, for 1.5 hours.

Figure 8B:
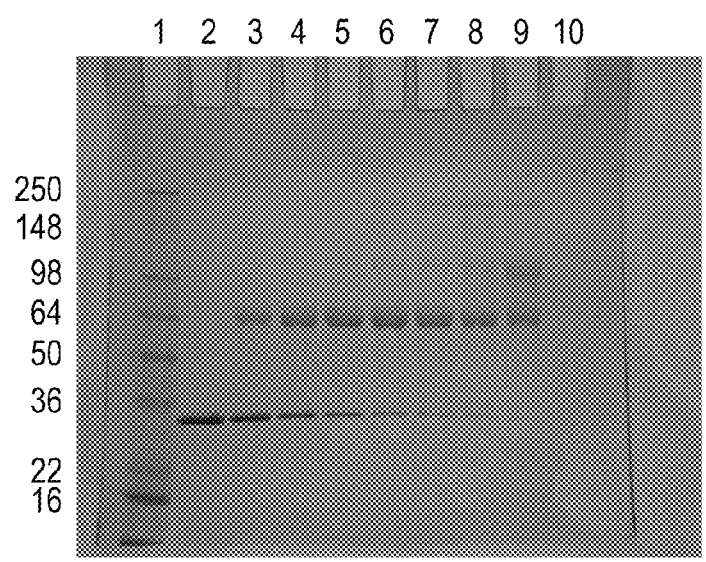

FIG. 8B shows reduced SDS-PAGE analysis of huFc (S196C) analog PEGylated after varying degrees of TCEP reduction, as described in Example 3. Molar stoichiometries of engineered Cysteine: TCEP were: 1:0 in lane 2, 1:0.5 in lane 3, 1:0.75 in lane 4, 1:1 in lane 5, 1:1.25 in lane 6, 1:1.5 in lane 7, 1:2 in lane 8 and 1:5 in lane 9. MW markers were in lane 1. 2 μg of reduced protein were loaded to each lane and run in 4-20% Tris-Glycine polyacrylamide gel with 0.1% SDS at 125 V, 35 mA and 5 W, for 1.5 hours.

FIG. 9A-B shows SEC-HPLC analyses of huFc (S196C) analog PEGylated after varying degrees of TCEP reduction, as described in Example 3. 20 μg protein were loaded to TSK 3000SW×1 column (7.8 mm×30 cm, 5 micron) and eluted in 100 mM sodium phosphate, 150 mM NaCl, pH 6.9.

DETAILED DESCRIPTION OF EXEMPLARY EMBODIMENTS OF THE INVENTION

Definition of Terms

The terms used throughout this specification are defined as follows, unless otherwise limited in specific instances. As used in the specification and the appended claims, the singular forms "a", "an", and "the" include plural referents unless the context clearly dictates otherwise. Unless specified otherwise, the left-hand end of single-stranded polynucleotide sequences is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the RNA transcript are referred to as "downstream sequences".

When used in connection with an amino acid sequence, the term "comprising" means that a compound may include additional amino acid residues on either or both of the N- or C-termini of the given sequence.

A conjugation site being "amenable to conjugation" means that the side chain of the amino acid residue at the selected conjugation site will react with the additional functional moiety of interest (or with a linker covalently attached to the additional functional moiety), under the defined chemical conditions, resulting in covalent binding of the additional functional moiety (directly or via the linker) to the side chain as a major reaction product.

"Antibody" or "antibody peptide(s)" refer to an intact antibody, or a binding fragment thereof that competes with the intact antibody for specific binding and includes chimeric, humanized, fully human, and bispecific antibodies. In certain embodiments, binding fragments are produced by recombinant DNA techniques. In additional embodiments, binding fragments are produced by enzymatic or chemical cleavage of intact antibodies. Binding fragments include, but are not limited to, Fab, Fab', F(ab')$_2$, Fv, and single-chain antibodies.

The inventive composition comprises a Fc domain having at least one additional functional moiety covalently bound to the Fc domain. The term "Fc domain" encompasses native Fc and Fc variant molecules and sequences as defined herein below. As with Fc variants and native Fc's, the term "Fc domain" includes molecules in monomeric or multimeric form, whether digested from whole antibody or produced by other means. In one embodiment, the Fc domain is a human native Fc domain. In other embodiments, the "Fc domain" can be a Fc variant, an analog, a mutant, a truncation, or a derivative of human Fc or of an alternative mammalian Fc polypeptide.

The term "native Fc" refers to a molecule or sequence comprising the amino acid sequence of a non-antigen-binding fragment resulting from digestion of whole antibody, whether in monomeric or multimeric form, at which a peptide may be added or conjugated by being covalently bound, directly or indirectly through a linker, to a loop region of the Fc domain. The original immunoglobulin source of the native Fc is preferably of human origin (although non-human mammalian native Fc is included in "native Fc" and can also be useful in some embodiments), and may be any of the immunoglobulins, although IgG1 and IgG2 are preferred. The native Fc may optionally comprise an amino terminal methionine residue. By way of example, SEQ ID NO:600 is the native human IgG1 sequence (used, in some cases, as a reference sequence herein), and Fc variant SEQ ID NO:599 (also used in some cases as a reference sequence herein) is the same sequence with an amino terminal methionine residue. Native Fcs are made up of monomeric polypeptides that may be linked into dimeric or multimeric forms by covalent (i.e., disulfide bonds) and non-covalent association. The number of intermolecular disulfide bonds between monomeric subunits of native Fc molecules ranges from 1 to 4 depending on class (e.g., IgG, IgA, IgE) or subclass (e.g., IgG1, IgG2, IgG3, IgA1, IgGA2). One example of a native Fc is a disulfide-bonded dimer resulting from papain digestion of an IgG (see Ellison et al. (1982), *Nucleic Acids Res.* 10: 4071-9). The term "native Fc" as used herein is generic to the monomeric, dimeric, and multimeric forms.

Statements or claims concerning amino acid residue positions cited herein relative to one particular "reference sequence" (i.e., SEQ ID NO:600 or SEQ ID NO:599) apply equally to the corresponding position in the other reference sequence, or in a different native Fc sequence, Fc variant sequence, or other modified Fc domain sequence, in an alignment of the two (i.e., comparing the recited reference sequence and the second Fc domain sequence of interest), e.g., position 2 in SEQ ID NO:599 corresponds to position 1 in SEQ ID NO:600, etc.

The term "Fc variant" refers to a molecule or sequence that is modified from a native Fc but still comprises a binding site for the salvage receptor, FcRn. International applications WO 97/34631 (published 25 Sep. 1997) and WO 96/32478 describe exemplary Fc variants, as well as interaction with the salvage receptor, and are hereby incorporated by reference. Thus, the term "Fc variant" comprises a molecule or sequence that is humanized from a non-human native Fc. Furthermore, a native Fc comprises sites that may be removed because they provide structural features or biological activity that are not required for molecules of the present invention. Thus, the term "Fc variant" comprises a molecule or sequence that lacks one or more native Fc sites or residues that affect or are involved in (1) disulfide bond formation, (2) incompatibility with a selected host cell (3) N-terminal heterogeneity upon expression in a selected host cell, (4) glycosylation, (5) interaction with complement, (6) binding to an Fc receptor other than a salvage receptor, or (7) antibody-dependent cellular cytotoxicity (ADCC). Fc variants are described in further detail hereinafter.

The term "internal" conjugation site means that conjugation of the at least one additional moiety, or moieties, is non-terminal, i.e., not through the α-amino site or the a-carboxy site of the Fc domain, although there optionally can also be additional moieties conjugated terminally at the N-terminal and/or C-terminal of the Fc domain.

The term "loop" region or "Fc-loop" region refers to a primary sequence of amino acid residues which connects two regions comprising secondary structure, such as an α-helix or a β-sheet, in the immediate N-terminal and C-terminal directions of primary structure from the loop region. Examples include, but are not limited to, CH2 or CH3 loop regions. One of skill in the art understands that a loop region, while not itself comprising secondary structure, may influence or contribute to secondary or higher order protein structure.

The term "multimer" as applied to Fc domains or molecules comprising Fc domains refers to molecules having two or more Fc domain polypeptide chains associated covalently, noncovalently, or by both covalent and non-covalent interactions. IgG molecules typically form dimers; IgM, pentamers; IgD, dimers; and IgA, monomers, dimers, trimers, or tetramers. Multimers may be formed by exploiting the sequence and resulting activity of the native Ig source of the Fc or by derivatizing (as defined below) such a native Fc.

The term "dimer" as applied to Fc domains or molecules comprising Fc domains refers to molecules having two polypeptide chains associated covalently or non-covalently. Exemplary dimers within the scope of this invention are as shown in U.S. Pat. No. 6,660,843, FIG. 2, which is hereby incorporated by reference. "Dimers" include homodimers and heterodimers.

The terms "derivatizing" and "derivative" or "derivatized" comprise processes and resulting compounds respectively in which (1) the compound has a cyclic portion; for example, cross-linking between cysteinyl residues within the compound; (2) the compound is cross-linked or has a cross-linking site; for example, the compound has a cysteinyl residue and thus forms cross-linked dimers in culture or in vivo; (3) one or more peptidyl linkage is replaced by a non-peptidyl linkage; (4) the N-terminus is replaced by —NRR$^1$, NRC(O)R$^1$, —NRC(O)OR$^1$, —NRS(O)$_2$R$^1$, —NHC(O)NHR, a succinimide group, or substituted or unsubstituted benzyloxycarbonyl-NH—, wherein R and R$^1$ and the ring substituents are as defined hereinafter; (5) the C-terminus is replaced by —C(O)R$^2$ or —NR$^3$R$^4$ wherein R$^2$, R$^3$ and R$^4$ are as defined hereinafter; and (6) compounds in which individual amino acid moieties are modified through treatment with agents capable of reacting with selected side chains or terminal residues. Derivatives are further described hereinafter.

The term "half-life extending moiety refers to a pharmaceutically acceptable moiety, domain, or "vehicle" covalently linked or conjugated to the Fc domain and/or a pharmaceutically active moiety, that prevents or mitigates in vivo proteolytic degradation or other activity-diminishing chemical modification of the pharmaceutically active moiety, increases half-life or other pharmacokinetic properties such as but not limited to increasing the rate of absorption, reduces toxicity, improves solubility, increases biological activity and/or target selectivity of the pharmaceutically active moiety with respect to a target of interest, increases manufacturability, and/or reduces immunogenicity of the pharmaceutically active moiety (e.g., a peptide or non-peptide moiety), compared to an unconjugated form of the pharmaceutically active moiety. Polyethylene glycol (PEG) is an example of a useful half-life extending moiety. Other examples of the half-life extending moiety, in accordance with the invention, include a copolymer of ethylene glycol, a copolymer of propylene glycol, a carboxymethylcellulose, a polyvinyl pyrrolidone, a poly-1,3-dioxolane, a poly-1,3,6-trioxane, an ethylene maleic anhydride copolymer, a polyaminoacid (e.g., polylysine), a dextran n-vinyl pyrrolidone, a poly n-vinyl pyrrolidone, a propylene glycol homopolymer, a propylene oxide polymer, an ethylene oxide polymer, a polyoxyethylated polyol, a polyvinyl alcohol, a linear or branched glycosylated chain, a polyacetal, a long chain fatty acid, a long chain hydrophobic aliphatic group, an immunoglobulin $F_c$ domain (see, e.g., Feige et al., Modified peptides as therapeutic agents, U.S. Pat. No. 6,660,843), an albumin (e.g., human serum albumin; see, e.g., Rosen et al., Albumin fusion proteins, U.S. Pat. No. 6,926,898 and US 2005/0054051; Bridon et al., Protection of endogenous therapeutic peptides from peptidase activity through conjugation to blood components, U.S. Pat. No. 6,887,470), a transthyretin (TTR; see, e.g., Walker et al., Use of transthyretin peptide/protein fusions to increase the serum half-life of pharmacologically active peptides/proteins, US 2003/0195154 A1; 2003/0191056 A1), or a thyroxine-binding globulin (TBG).

Other embodiments of the useful half-life extending moiety, in accordance with the invention, include peptide ligands or small (non-peptide organic) molecule ligands that have binding affinity for a long half-life serum protein under physiological conditions of temperature, pH, and ionic strength. Examples include an albumin-binding peptide or small molecule ligand, a transthyretin-binding peptide or small molecule ligand, a thyroxine-binding globulin-binding peptide or small molecule ligand, an antibody-binding peptide or small molecule ligand, or another peptide or small molecule that has an affinity for a long half-life serum protein. (See, e.g., Blaney et al., Method and compositions for increasing the serum half-life of pharmacologically active agents by binding to transthyretin-selective ligands, U.S. Pat. No. 5,714,142; Sato et al., Serum albumin binding moieties, US 2003/0069395 A1; Jones et al., Pharmaceutical active conjugates, U.S. Pat. No. 6,342,225). A "long half-life serum protein" is one of the hundreds of different proteins dissolved in mammalian blood plasma, including so-called "carrier proteins" (such as albumin, transferrin and haptoglobin), fibrinogen and other blood coagulation factors, complement components, immunoglobulins, enzyme inhibitors, precursors of substances such as angiotensin and bradykinin and many other types of proteins. The invention encompasses the use of any single species of pharmaceutically acceptable half-life extending moiety, such as, but not limited to, those described herein, or the use of a combination of two or more different half-life extending moieties.

The term "polypeptide" refers to molecules of greater than 40 amino acids, whether existing in nature or not, provided that such molecules are not membrane-bound. Exemplary polypeptides include interleukin (IL)-1ra, leptin, soluble tumor necrosis factor (TNF) receptors type 1 and type 2 (sTNF-R1, sTNF-R2), keratinocyte growth factor (KGF), erythropoietin (EPO), thrombopoietin (TPO), granulocyte colony-stimulating factor (G-CSF), darbepoietin, glial cell line-derived neurotrophic factor (GDNF), Fab fragments and the like. "Polypeptide" and "protein" are used interchangeably herein.

The term "peptide" refers to molecules of 2 to 40 amino acid residues in length, with molecules of 3 to 40 amino acid residues or 6 to 40 amino acid residues in length preferred. Exemplary peptides may be randomly generated by any of the methods cited above, carried in a peptide library (e.g., a phage display library), or derived by digestion of proteins. "Peptides" include cyclic peptides.

In further describing peptides or polypeptides herein, a one-letter abbreviation system is frequently applied to designate the identities of the twenty "canonical" amino acid residues generally incorporated into naturally occurring peptides and proteins (Table 1A). Such one-letter abbreviations are entirely interchangeable in meaning with three-letter abbreviations, or non-abbreviated amino acid names. Within the one-letter abbreviation system used herein, an uppercase letter indicates a L-amino acid, and a lower case letter indicates a D-amino acid, unless otherwise noted herein. For example, the abbreviation "R" designates L-arginine and the abbreviation "r" designates D-arginine.

TABLE 1A

One-letter abbreviations for the canonical amino acids. Three-letter abbreviations are in parentheses.

| | |
|---|---|
| Alanine (Ala) | A |
| Glutamine (Gln) | Q |
| Leucine (Leu) | L |
| Serine (Ser) | S |
| Arginine (Arg) | R |
| Glutamic Acid (Glu) | E |
| Lysine (Lys) | K |
| Threonine (Thr) | T |
| Asparagine (Asn) | N |
| Glycine (Gly) | G |
| Methionine (Met) | M |
| Tryptophan (Trp) | W |
| Aspartic Acid (Asp) | D |
| Histidine (His) | H |
| Phenylalanine (Phe) | F |
| Tyrosine (Tyr) | Y |
| Cysteine (Cys) | C |
| Isoleucine (Ile) | I |
| Proline (Pro) | P |
| Valine (Val) | V |

An amino acid substitution in an amino acid sequence is typically designated herein with a one-letter abbreviation for the amino acid residue in a particular position, followed by the numerical amino acid position relative to the native peptide or polypeptide sequence of interest, which is then followed by the one-letter symbol for the amino acid residue substituted in. For example, "T30D" symbolizes a substitution of a threonine residue by an aspartate residue at amino acid position 30, relative to a hypothetical native peptide or polypeptide sequence. By way of further example, "R18 hR" or "R18Cit" indicates a substitution of an arginine residue by a homoarginine or a citrulline residue, respectively, at amino acid position 18, relative to the hypothetical native peptide or polypeptide. An amino acid position within the amino acid sequence of any particular polypeptide or peptide (or peptide analog) described herein may differ from its position relative to the native sequence, i.e., as determined in an alignment of the N-terminal or C-terminal end of the peptide's amino acid sequence with the N-terminal or C-terminal end, as appropriate, of the native polypeptide or peptide sequence.

The term "non-canonical amino acid residue" refers to amino acid residues in D- or L-form that are not among the 20 canonical amino acids generally incorporated into naturally occurring proteins. Non-canonical amino acids include naturally rare (in peptides or proteins) amino acid residues or unnatural amino acid residues. Example of non-canonical amino acids include, without limitation, β-amino acids, homoamino acids, cyclic amino acids, α-, α-disubstituted amino acids, N-alkyl amino acids, and amino acids with derivatized side chains. Other examples include (in the L-form or D-form): citrulline (Cit), homocitrulline (hCit), N-methylcitrulline (NMeCit), N-methylhomocitrulline (NMeHoCit), ornithine (Orn or O), N-Methylornithine (NMeOrn), sarcosine (Sar), homolysine (hK or Hlys), homoarginine (hR or hArg), homoglutamine (hQ), N-methylarginine (NMeR), N-methylleucine (NMeL), N-methylhomolysine (NMeHoK), N-methylglutamine (NMeQ), norleucine (Nle), norvaline (Nva), 1,2,3,4-tetrahydroisoquinoline (Tic), nitrophenylalanine (nitrophe), aminophenylalanine (aminophe), benzylphenylalanine (benzylphe), γ-carboxyglutamic acid (γ-carboxyglu), hydroxyproline (hydroxypro), p-carboxyl-phenylalanine (Cpa), α-aminoadipic acid (Aad), acetylarginine (acetylarg), α, β-diaminopropionoic acid (Dpr), α, γ-diaminobutyric acid (Dab), diaminopropionic acid (Dap), β-(1-Naphthyl)-alanine (1Na1), β-(2-Naphthyl)-alanine (2Na1), cyclohexylalanine (Cha), 4-methyl-phenylalanine (MePhe), β,β-diphenyl-alanine (BiPhA), aminobutyric acid (Abu), 4-phenyl-phenylalanine (4Bip), α-aminoisobutyric acid (Aib), beta-alanine, beta-aminopropionic acid, piperidinic acid, aminocaprioic acid, aminoheptanoic acid, aminopimelic acid, desmosine, diaminopimelic acid, N-ethylglycine, N-ethylaspargine, hyroxylysine, allo-hydroxylysine, isodesmosine, allo-isoleucine, N-methylglycine, N-methylisoleucine, N-methylvaline, 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, ω-methylarginine, and other similar amino acids, and derivatized forms of any of these as described herein.

Nomenclature and Symbolism for Amino Acids and Peptides by the UPAC-IUB Joint Commission on Biochemical Nomenclature (JCBN) have been published in the following documents: Biochem. J., 1984, 219, 345-373; Eur. J. Biochem., 1984, 138, 9-37; 1985, 152, 1; 1993, 213, 2; Internat. J. Pept. Prot. Res., 1984, 24, following p 84; J. Biol. Chem., 1985, 260,14-42; Pure Appl. Chem., 1984, 56, 595-624; Amino Acids and Peptides, 1985, 16, 387-410; Biochemical Nomenclature and Related Documents, 2nd edition, Portland Press, 1992, pages 39-69. The term "protease" is synonymous with "peptidase". Proteases comprise two groups of enzymes: the endopeptidases which cleave peptide bonds at points within the protein, and the exopeptidases, which remove one or more amino acids from either N- or C-terminus respectively. The term "proteinase" is also used as a synonym for endopeptidase. The four mechanistic classes of proteinases are: serine proteinases, cysteine proteinases, aspartic proteinases, and metallo-proteinases. In addition to these four mechanistic classes, there is a section of the enzyme nomenclature which is allocated for proteases of unidentified catalytic mechanism. This indicates that the catalytic mechanism has not been identified.

Cleavage subsite nomenclature is commonly adopted from a scheme created by Schechter and Berger (Schechter I. & Berger A., On the size of the active site in proteases. I. Papain, Biochemical and Biophysical Research Communication, 27:157 (1967); Schechter I. & Berger A., On the active site of proteases. 3. Mapping the active site of papain; specific inhibitor peptides of papain, Biochemical and Biophysical Research Communication, 32:898 (1968)). According to this model, amino acid residues in a substrate undergoing cleavage are designated P1, P2, P3, P4 etc. in the N-terminal direction from the cleaved bond. Likewise, the residues in the C-terminal direction are designated P1', P2', P3', P4'. etc.

The skilled artisan is aware of a variety of tools for identifying protease binding or protease cleavage sites of interest. For example, the PeptideCutter software tool is available through the ExPASy (Expert Protein Analysis System) proteomics server of the Swiss Institute of Bioinformatics (SIB; expasy.org/tools/peptidecutter). PeptideCutter searches a protein sequence from the SWISS-PROT and/or TrEMBL databases or a user-entered protein sequence for protease cleavage sites. Single proteases and chemicals, a selection or the whole list of proteases and chemicals can be used. Different forms of output of the results are available: tables of cleavage sites either grouped alphabetically according to enzyme names or sequentially according to the amino acid number. A third option for output is a map of cleavage sites. The sequence and the cleavage sites mapped onto it are grouped in blocks, the size of which can be chosen by the user. Other tools are also known for determining protease cleavage sites. (E.g., Turk, B. et al., Determination of protease cleavage site motifs using mixture-based oriented peptide libraries, Nature Biotechnology, 19:661-667 (2001); Barrett A. et al., Handbook of proteolytic enzymes, Academic Press (1998)).

The serine proteinases include the chymotrypsin family, which includes mammalian protease enzymes such as chymotrypsin, trypsin or elastase or kallikrein. The serine proteinases exhibit different substrate specificities, which are related to amino acid substitutions in the various enzyme subsites interacting with the substrate residues. Some enzymes have an extended interaction site with the substrate whereas others have a specificity restricted to the P1 substrate residue.

Trypsin preferentially cleaves at R or K in position P1. A statistical study carried out by Keil (1992) described the negative influences of residues surrounding the Arg- and Lys-bonds (i.e. the positions P2 and P1', respectively) during trypsin cleavage. (Keil, B., Specificity of proteolysis, Springer-Verlag Berlin-Heidelberg-N.Y., 335 (1992)). A proline residue in position P1' normally exerts a strong negative influence on trypsin cleavage. Similarly, the positioning of R and K in P1' results in an inhibition, as well as negatively charged residues in positions P2 and P1'.

Chymotrypsin preferentially cleaves at a W, Y or F in position P1 (high specificity) and to a lesser extent at L, M or H residue in position P1. (Keil, 1992). Exceptions to these rules are the following: When W is found in position P1, the cleavage is blocked when M or P are found in position P1' at the same time. Furthermore, a proline residue in position P1' nearly fully blocks the cleavage independent of the amino acids found in position P1. When an M residue is found in position P1, the cleavage is blocked by the presence of a Y residue in position P1'. Finally, when H is located in position P1, the presence of a D, M or W residue also blocks the cleavage.

Membrane metallo-endopeptidase (NEP; neutral endopeptidase, kidney-brush-border neutral proteinase, enkephalinase, EC 3.4.24.11) cleaves peptides at the amino side of hydrophobic amino acid residues. (Connelly, J C et al., Neutral Endopeptidase 24.11 in Human Neutrophils: Cleavage of Chemotactic Peptide, PNAS, 82(24):8737-8741 (1985)).

Thrombin preferentially cleaves at an R residue in position P1. (Keil, 1992). The natural substrate of thrombin is fibrinogen. Optimum cleavage sites are when an R residue is in position P1 and Gly is in position P2 and position P1'. Likewise, when hydrophobic amino acid residues are found in position P4 and position P3, a proline residue in position P2, an R residue in position P1, and non-acidic amino acid residues in position P1' and position P2'. A very important residue for its natural substrate fibrinogen is a D residue in P10.

Caspases are a family of cysteine proteases bearing an active site with a conserved amino acid sequence and which cleave peptides specifically following D residues. (Earnshaw W C et al., Mammalian caspases: Structure, activation, substrates, and functions during apoptosis, Annual Review of Biochemistry, 68:383-424 (1999)).

The Arg-C proteinase preferentially cleaves at an R residue in position P1. The cleavage behavior seems to be only moderately affected by residues in position P1'. (Keil, 1992). The Asp-N endopeptidase cleaves specifically bonds with a D residue in position P1'. (Keil, 1992).

The foregoing is merely exemplary and by no means an exhaustive treatment of knowledge available to the skilled artisan concerning protease binding and/or cleavage sites that the skilled artisan may be interested in eliminating in practicing the invention.

The term "randomized" as used to refer to peptide sequences refers to random sequences (e.g., selected by phage display methods) and sequences in which one or more residues of a naturally occurring molecule is replaced by an amino acid residue not appearing in that position in the naturally occurring molecule. Exemplary methods for identifying peptide sequences include phage display, *E. coli* display, ribosome display, yeast-based screening, RNA-peptide screening, chemical screening, rational design, protein structural analysis, and the like.

A peptidomimetic can include a small peptide-like chain that contains one or more amide bond isosteres and can contain both natural and unnatural amino acids. Such peptide-like peptidomimetics typically arise from modification of an existing polypeptide or peptide in order to alter the molecule's properties. For example, they may arise from modifications to change the molecule's stability or biological activity. These modifications involve changes to the peptide that will not occur naturally (such as incorporation of unnatural amino acids). Alternatively, peptidomimetics include non-peptide small molecules having peptide-like biochemical or pharmacological activity and/or chemical structure, such as, but not limited to, steric structure. An example of such a peptidomimetic compound is BIBN 4096 BS.

The term "pharmacologically active" means that a substance so described is determined to have activity that affects a medical parameter (e.g., blood pressure, blood cell count, cholesterol level) or disease state (e.g., cancer, autoimmune disorders, neurological disorders, chronic pain). Thus, pharmacologically active peptides or polypeptides comprise agonistic or mimetic and antagonistic peptides as defined below.

The terms "-mimetic peptide" and "-agonist peptide" refer, respectively, to a peptide or polypeptide having biological activity comparable to a protein (e.g., EPO, TPO, G-CSF) of interest or to a peptide or polypeptide that interacts as an agonist with a particular protein of interest. These terms further include peptides or polypeptides that indirectly mimic the activity of a protein of interest, such as by potentiating the effects of the natural ligand of the protein of interest; see, for example, the EPO-mimetic peptides listed in Table 5 hereof and in U.S. Pat. No. 6,660,843, which is hereby incorporated by reference. Thus, the term "EPO-mimetic peptide" comprises any peptides or polypeptides that can be identified or derived as described in Wrighton et al. (1996), Science 273: 458-63, Naranda et al. (1999), Proc. Natl. Acad. Sci. USA 96: 7569-74, or any other reference in Table 5 identified as having EPO-mimetic subject matter. Those of ordinary skill in the art appreciate that each of these references enables one to select different peptides or polypeptides than actually disclosed therein by following the disclosed procedures with different peptide libraries.

The term "-antagonist peptide" or "inhibitor peptide" refers to a peptide that blocks or in some way interferes with the biological activity of the associated protein of interest, or has biological activity comparable to a known antagonist or inhibitor of the associated protein of interest. Thus, the term "BAFF-antagonist peptide" comprises peptides that can be identified or derived as described in U.S. Pat. Appln. No. 2003/0195156 A1, which is incorporated herein by reference and those peptides appearing in Table 10. Those of ordinary skill in the art appreciate that the foregoing reference enables one to select different peptides than actually disclosed therein by following the disclosed procedures with different peptide libraries.

In the inventive composition of composition matter, the monomeric or multimeric Fc domain has at least one additional functional moiety that is covalently bound (or conjugated) to one or more "specifically selected" conjugation site(s) in the Fc domain. The term "specifically selected" with respect to conjugation site means that the major product or derivative of the conjugation chemistry (or chemical reaction) employed is through the side chain of an amino acid residue at the specifically selected conjugation site in the Fc domain. Minor reaction products can also result from the conjugation reaction, but these can be purified out, if desired or appropriate. "Toxin peptides" include peptides and polypeptides having the same amino acid sequence of a naturally occurring pharmacologically active peptide or polypeptide that can be isolated from a venom, and also include modified peptide analogs of such naturally occurring molecules. (See, e.g., Kalman et al., ShK-Dap22, a potent Kv1.3-specific immunosuppressive polypeptide, J. Biol. Chem. 273(49):32697-707 (1998); Kem et al., U.S. Pat. No. 6,077,680; Mouhat et al., OsK1 derivatives, WO 2006/002850 A2; Chandy et al., Analogs of SHK toxin and their uses in selective inhibition of Kv1.3 potassium channels, WO 2006/042151). Snakes, scorpions, spiders, bees, snails and sea anemone are a few examples of organisms that produce venom that can serve as a rich source of small bioactive toxin peptides or "toxins" that potently and selectively target ion channels and receptors.

The toxin peptides are usually between about 20 and about 80 amino acids in length, contain 2-5 disulfide linkages and form a very compact structure. Toxin peptides (e.g., from the venom of scorpions, sea anemones and cone snails) have been isolated and characterized for their impact on ion channels. Such peptides appear to have evolved from a relatively small number of structural frameworks that are particularly well suited to addressing the critical issues of potency and stability. The majority of scorpion and Conus toxin peptides, for example, contain 10-40 amino acids and up to five disulfide bonds, forming extremely compact and constrained structure (microproteins) often resistant to proteolysis. The conotoxin and scorpion toxin peptides can be divided into a number of superfamilies based on their disulfide connections and peptide folds. The solution structure of many of these has been determined by NMR spectroscopy, illustrating their compact structure and verifying conservation of their family fold. (E.g., Tudor et al., Ionisation behaviour and solution properties of the potassium-channel blocker ShK toxin, Eur. J. Biochem. 251(1-2):133-41 (1998); Pennington et al., Role of disulfide bonds in the structure and potassium channel blocking activity of ShK toxin, Biochem. 38(44): 14549-58 (1999); Jaravine et al., Three-dimensional structure of toxin OSK1 from Orthochirus scrobiculosus scorpion venom, Biochem. 36(6):1223-32 (1997); del Rio-Portillo et al.; NMR solution structure of Cn12, a novel peptide from the Mexican scorpion Centruroides noxius with a typical beta-toxin sequence but with alpha-like physiological activity, Eur. J. Biochem. 271 (12): 2504-16 (2004); Prochnicka-Chalufour et al., Solution structure of discrepin, a new K+-channel blocking peptide from the alpha-KTx15 subfamily, Biochem. 45(6):1795-1804 (2006)). Examples of pharmacologically active toxin peptides for which the practice of the present invention can be useful include, but are not limited to ShK, OSK1, charybdotoxin (ChTx), kaliotoxin1 KTX1), or maurotoxin, or toxin peptide analogs of any of these, modified from the native sequences at one or more amino acid residues. Other examples are known in the art, or can be found in U.S. patent application Ser. No. 11/406,454 (titled: Toxin Peptide Therapeutic Agents), filed on Apr. 17, 2006, which is incorporated by reference in its entirety.

The term "TPO-mimetic peptide" comprises peptides that can be identified or derived as described in Cwirla et al. (1997), Science 276: 1696-9, U.S. Pat. Nos. 5,869,451 and 5,932,946, which are incorporated by reference; U.S. Pat. App. No. 2003/0176352, published Sep. 18, 2003, which is incorporated by reference; WO 03/031589, published Apr. 17, 2003; WO 00/24770, published May 4, 2000; and any peptides appearing in Table 6. Those of ordinary skill in the art appreciate that each of these references enables one to select different peptides than actually disclosed therein by following the disclosed procedures with different peptide libraries.

The term "ang-2-binding peptide" comprises peptides that can be identified or derived as described in U.S. Pat. App. No. 2003/0229023, published Dec. 11, 2003; WO 03/057134, published Jul. 17, 2003; U.S. 2003/0236193, published Dec. 25, 2003 (each of which is incorporated herein by reference); and any peptides appearing in Table 7. Those of ordinary skill in the art appreciate that each of these references enables one to select different peptides than actually disclosed therein by following the disclosed procedures with different peptide libraries.

The term "NGF-binding peptide" comprises peptides that can be identified or derived as described in WO 04/026329, published Apr. 1, 2004 and any peptides identified in Table 8. Those of ordinary skill in the art appreciate that this reference enables one to select different peptides than actually disclosed therein by following the disclosed procedures with different peptide libraries.

The term "myostatin-binding peptide" comprises peptides that can be identified or derived as described in U.S. Ser. No. 10/742,379, filed Dec. 19, 2003, which is incorporated herein by reference, and peptides appearing in Table 9. Those of ordinary skill in the art appreciate that each of these references enables one to select different peptides than actually disclosed therein by following the disclosed procedures with different peptide libraries.

"PEGylated peptide" is meant a peptide or protein having a polyethylene glycol (PEG) moiety covalently bound to an amino acid residue of the peptide itself or to a peptidyl or non-peptidyl linker (including but not limited to aromatic linkers) that is covalently bound to a residue of the peptide.

By "polyethylene glycol" or "PEG" is meant a polyalkylene glycol compound or a derivative thereof, with or without coupling agents or derivatization with coupling or activating moieties (e.g., with aldehyde, hydroxysuccinimidyl, hydrazide, thiol, triflate, tresylate, azirdine, oxirane, orthopyridyl disulphide, vinylsulfone, iodoacetamide or a maleimide moiety). In accordance with the present invention, useful PEG includes substantially linear, straight chain PEG, branched PEG, or dendritic PEG. (See, e.g., Merrill, U.S. Pat. No. 5,171,264; Harris et al., Multiarmed, monofunctional, polymer for coupling to molecules and surfaces, U.S. Pat. No. 5,932,462; Shen, N-maleimidyl polymer derivatives, U.S. Pat. No. 6,602,498).

Additionally, physiologically acceptable salts of the compounds of this invention are also encompassed herein. By "physiologically acceptable salts" is meant any salts that are known or later discovered to be pharmaceutically acceptable. Some examples are: acetate; trifluoroacetate; hydrohalides, such as hydrochloride and hydrobromide; sulfate; citrate; maleate; tartrate; glycolate; gluconate; succinate; mesylate; besylate; and oxalate salts.

General Methodology

The present invention relates to a process for preparing a pharmacologically active compound involving selecting at least one internal conjugation site of an Fc domain sequence. The conjugation site must be amenable to conjugation of an additional functional moiety by a defined conjugation chemistry through the side chain of an amino acid residue at the conjugation site. Achieving highly selective, site-specific conjugation to Fc, in accordance with the present invention, requires consideration of a diverse variety of design criteria. First, the conjugation partner, i.e., the additional functional moiety (or moieties) of interest, and a preferred conjugation or coupling chemistry must be defined or predetermined. Functional moieties such as, but not limited to, proteins, peptides, polymers or other non-peptide organic moieties (e.g., "small molecules"), can be conjugated or coupled to the selected conjugation site through an assortment of different conjugation chemistries known in the art. For example, a maleimide-activated conjugation partner targeting an accessible cysteine thiol on the Fc domain is one embodiment, but numerous conjugation or coupling chemistries targeting the side chains of either canonical or non-canonical, e.g., unnatural amino acids in the Fc domain sequence, can be employed in accordance with the present invention.

Chemistries for the chemoselective conjugation, in accordance with the present invention, to specifically derivatized peptides, polymers, small molecules, or other agents to engineer proteins displaying novel and specifically reactive side chain functionality include: copper(I)-catalyzed azide-alkyne [3+2] dipolar cycloadditions, Staudinger ligation, other acyl transfers processes (S→N; X→N), oximations, hydrazone bonding formation and other suitable organic chemistry reactions such as cross-couplings using water-soluble palladium catalysts. (E.g., Bong et al., Chemoselective Pd(0)-catalyzed peptide coupling in water, Organic Letters 3(16):2509-11 (2001); Dibowski et al., Bioconjugation of peptides by palladium-catalyzed C—C cross-coupling in water, Angew. Chem. Int. Ed. 37(4):476-78 (1998); DeVasher et al., Aqueous-phase, palladium-catalyzed cross-coupling of aryl bromides under mild conditions, using water-soluble, sterically demanding alkylphosphines, J. Org. Chem. 69:7919-27 (2004); Shaugnessy et al., J. Org. Chem., 2003, 68, 6767-6774; Prescher, J A and Bertozzi C R, Chemistry in living system, Nature Chemical Biology 1(1); 13-21 (2005)). Some useful conjugation chemistries are illustrated in Table 1B below.

Table 1B. Some useful conjugation chemistries. Citations: 17=Link et al., Presentation and detection of azide functionality in bacterial cell surface proteins, J. Am. Chem. Soc. 126:10598-602 (2004); 19=Chen et al., Site-specific labeling of cell surface proteins with biophysical probes using biotin ligase, Nat. Methods 2:99-104 (2005); 20=Zhang et al., A new strategy for the site-specific modification of proteins in vivo, Biochemistry 42:6735-46 (2003); 22=Mahal et al., Engineering chemical reactivity on cell surfaces through oligosaccharide biosynthesis, Science 276:1125-28 (1997); 25=Kho et al., A tagging-via-substrate technology for detection and proteomics of farnesylated proteins, Proc. Natl. Acad. Sci. USA 101:12479-484 (2004); 26=Speers et al., Activity-based protein profiling in vivo using a copper(I)-catalyzed azide-alkyne [3+2] cycloaddition, J. Am. Chem. Soc. 125:4686-87 (2003); 29=Speers et al., Profiling enzyme activities in vivo using click chemistry, methods, Chem. Biol. 11:535-46 (2004); 30=Prescher et al., Chemical remodeling of cell surfaces in living animals, Nature 430:873-77 (2004); 34=Agard et al., A strain-promoted [3+2] azide-alkyne cycloaddition for covalent modification of biomolecules in living systems, J. Am. Chem. Soc. 126:15046-47 (2004).

TABLE 1B

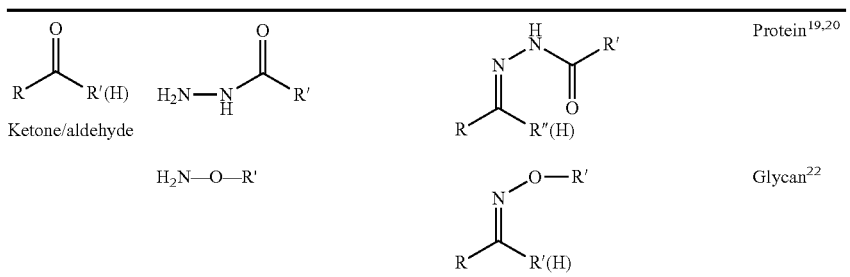

TABLE 1B-continued

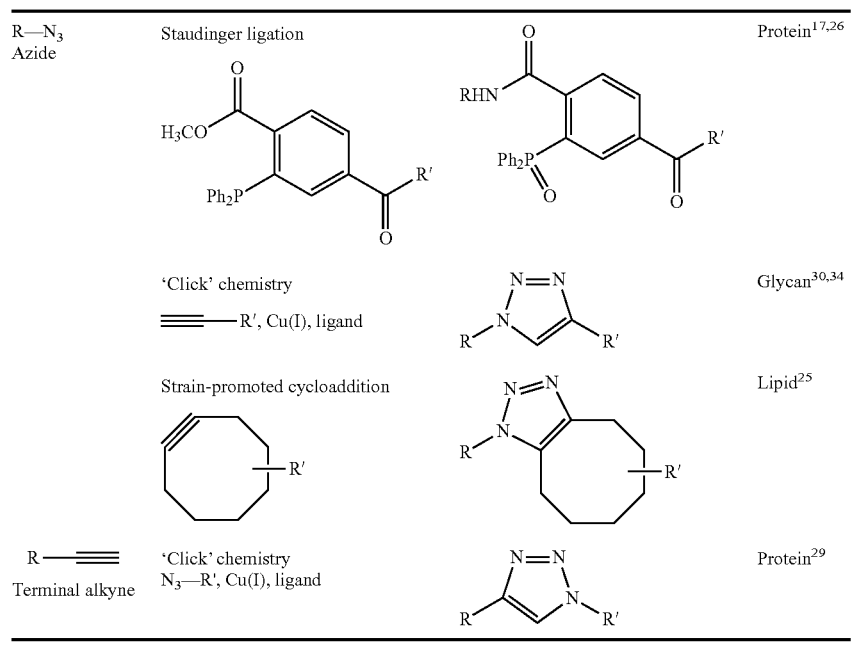

As mentioned above, the conjugation (or covalent binding) to the Fc domain is through the side chain of an amino acid residue at the conjugation site, for example, but not limited to, a cysteinyl residue. The amino acid residue, for example, a cysteinyl residue, at the internal conjugation site that is selected can be one that occupies the same amino acid residue position in a native Fc domain sequence, or the amino acid residue can be engineered into the Fc domain sequence by substitution or insertion. Such amino acid residues can have either L or D stereochemistry (except for Gly, which is neither L nor D) and the polypeptides, peptides and compositions of the present invention can comprise a combination of stereochemistries. However, the L stereochemistry is preferred. The invention also provides reverse molecules wherein the amino terminal to carboxy terminal sequence of the amino acids is reversed. For example, the reverse of a molecule having the normal sequence $X_1$-$X_2$-$X_3$ would be $X_3$-$X_2$-$X_1$. The invention also provides retro-reverse molecules wherein, as above, the amino terminal to carboxy terminal sequence of amino acids is reversed and residues that are normally "L" enantiomers are altered to the "D" stereoisomer form.

Stereoisomers (e.g., D-amino acids) of the twenty canonical amino acids, and other non-canonical amino acids, described herein, such as unnatural amino acids, can also be suitable components for polypeptide or peptide portions of certain embodiments of the inventive composition of matter.

Other examples of unnatural amino acid residues that can be particularly useful as the conjugation site in some embodiments of the inventive processes and compositions of matter include: azido-containing amino acid residues, e.g., azidohomoalanine, p-azido-phenylalanine; keto-containing amino acid residues, e.g., p-acetyl-phenylalanine; alkyne-containing amino acid residues, e.g., p-ethynylphenylalanine, homopropargylglycine, p-(prop-2-ynyl)-tyrosine; alkene-containing amino acid residues e.g., homoallylglycine; aryl halide-containing amino acid residues e.g. p-iodophenylalanine, p-bromophenylalanine; and 1,2-aminothiol containing amino acid residues.

The non-canonical amino acid residues can be incorporated by amino acid substitution or insertion. Non-canonical amino acid residues can be incorporated into the peptide by chemical peptide synthesis rather than by synthesis in biological systems, such as recombinantly expressing cells, or alternatively the skilled artisan can employ known techniques of protein engineering that use recombinantly expressing cells. (See, e.g., Link et al., Non-canonical amino acids in protein engineering, Current Opinion in Biotechnology, 14(6):603-609 (2003); Schultz et al., In vivo incorporation of unnatural amino acids, U.S. Pat. No. 7,045,337).

The selection of the placement of the conjugation site in the overall Fc sequence is another important facet of selecting an internal conjugation site in accordance with the present invention. Any of the exposed amino acid residues on the Fc surface, or either of the Fc CH2 or CH3 loop regions or subdomains can be potentially useful conjugation sites (FIG. 1) and can be mutated to cysteine or some other reactive amino acid for site-selective coupling, if not already present at the selected conjugation site of the Fc domain sequence. However, this approach does not take into account potential steric constraints that may perturb the activity of the fusion partner or limit the reactivity of the engineered mutation. For example, a cysteine engineered to be fully solvent-exposed may become oxidized during purification, leaving little or no reactive thiol for conjugation. Furthermore, the mutation introduced for conjugation, be it cysteine or any other amino acid, should not destabilize the Fc structure or interfere with expression or recovery yields of the Fc analog. Finally, in the case of an intact Fc domain, selected conjugation sites should be allosteric to the Fc dimer interface, if present. Also, some therapeutic applications may further benefit by maintaining conjugation sites distal to the Fc receptor (FcRn) interface.

In this invention a detailed topographical survey of the immunoglobulin Fc surface structure is described, which identifies solvent exposed amino acids representing potentially suitable conjugation sites for chemically coupling proteins, peptides, polymers or other small molecules (FIG. 1). In this analysis, not all the hydrophilic, solvent-exposed residues were deemed suitable for conjugation. In fact, only 36 residues of a possible 115 were selected based on their juxtaposition with the FcRn binding and dimer interfaces as well as other localized steric constraints. The list of potential conjugation sites was further refined using the available Fc domain crystal structures, their receptors and numerous Fc sequence alignments to map all of the putative Fc structural loop regions (FIG. 2, boldface). Specific residues that are most suitable for substitution within these loop region were identified by homology modeling and solvent accessibility (FIG. 2, underlined). Finally, each of these potential conjugation sites were ranked based on their juxtaposition relative to the FcRn and dimer interface, inter-species and isotype homologies and the sites' proximity and involvement in key elements of Fc secondary structure (Table 2). This approach using structure-based homology modeling to identify Fc loop regions and to predict insertion-tolerant mutation sites has been previously validated using therapeutic peptide insertions as described in Amgen patent application U.S. Prov. Appln. No. 60/612,680 filed Sep. 24, 2004. (See, WO 2006/036834) Based on that work, the most preferred mutation sites are Thr140, Asn78 and Glu50 (FIG. 2; amino acid residue positions cited relate to reference sequence SEQ ID NO:599).

To compare the preferred conjugation sites selected from the solvent exposed surface residues highlighted in FIG. 1, with the boldfaced putative loop regions and the underlined preferred conjugation sites within those loops (FIG. 2), the two sequences were aligned and mapped to the human IgG1 Fc domain as shown in FIG. 3. Here emerges a very consistent agreement between the surface exposure model and the loop model for selecting potential conjugation sites. Clearly, these examples demonstrate that through a detailed structural analysis and comparison of immunoglobulin Fc domains it is possible to identify an experimentally manageable number of potential conjugation sites that are not readily obvious from simple hydrophobic maps of the sequence.

Figure 4:
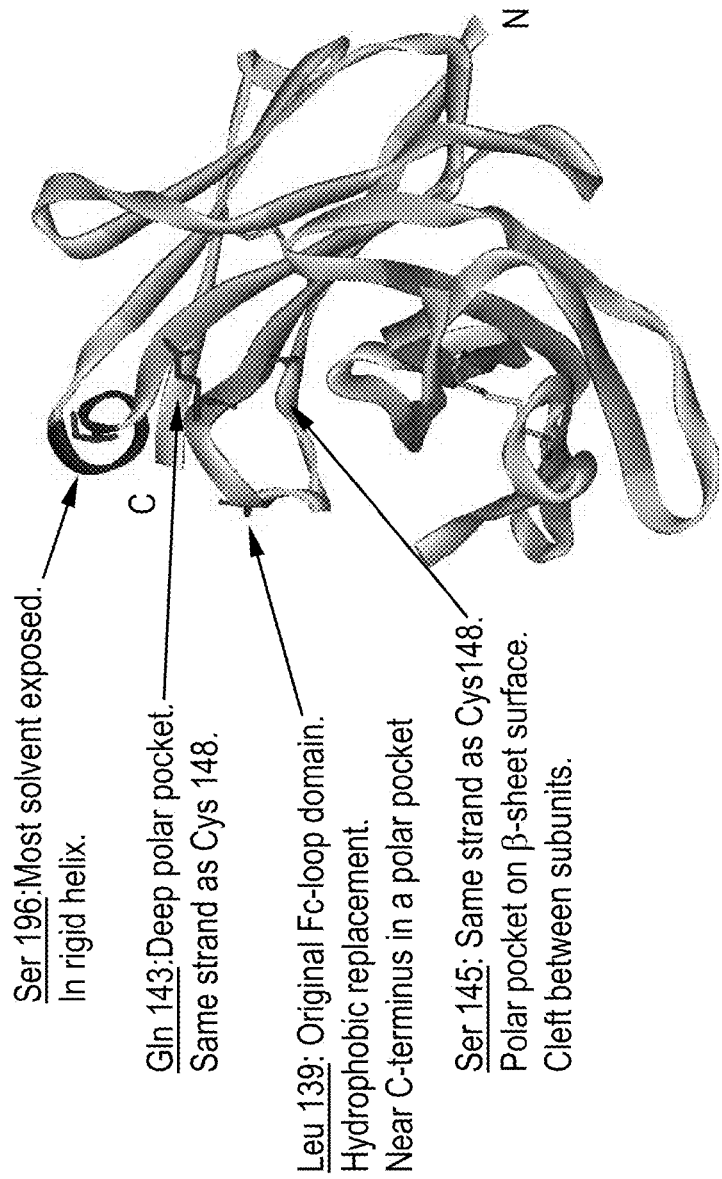
FIG. 4 shows proposed cysteine mutation sites mapped to Fc structure. The amino acid residues identified by arrows are designated positions relative to reference sequence SEQ ID NO:599, as follows.

Another subset of preferred mutations for coupling specifically addresses the use of cysteine analogs wherein the free thiol functionality must be preserved for efficient conjugation. This strategy presumes that cysteine mutations should be engineered into comparatively rigid elements of secondary structure, as opposed to loop regions, and the cysteine thiol should be juxtaposed within a pocket on the protein surface, providing minimal solvent exposure, to help protect it from oxidation. This strategy has been effectively demonstrated in U.S. Pat. No. 6,420,339. Under this approach, the most preferred residues for cysteine mutation are, but not limited to, Ser196, Gln143, Leu139 and Ser145 of the human Fc sequence (FIG. 4), with the positions recited being relative to reference sequence SEQ ID NO: 599.

The inventors further envision as part of this invention that none of these potential conjugation sites require a full-length immunoglobulin Fc domain to provide suitable substrates for coupling proteins, peptides, polymers, or other small molecules. In fact, any truncation of Fc that still includes a potential conjugation site recognized by this invention can be used for conjugation. For example, a CH2 subdomain or CH3 subdomain of an Fc greater than about 9 kD can be a useful "Fc domain" in accordance with the invention. Thus, this invention includes isolated Fc truncations, such as the CH2 or CH3 loop regions or subdomains. Further, given the highly conserved three-dimensional structure of the "immunoglobulin fold" equivalent conjugation sites can be readily deduced in other Ig Fc isotypes, truncations and subdomains, by sequence alignment and are therefore included in this invention.

Table 2 shows human Fc surface residues (using Protein Database file 1FC1 as the data source) (S239 from the PDB file corresponds to S19 of reference sequence SEQ ID NO:600 and S20 of reference sequence SEQ ID NO:599; K246 corresponds to K26 of SEQ ID NO:600 and K27 of SEQ ID NO:599, etc.).

TABLE 2

Human Fc surface residues, wherein 239S (i.e., S239) corresponds to S20 of reference sequence SEQ ID NO: 599.

| 239S | 289T | 333E | 382E* | 419Q+ |
|---|---|---|---|---|
| 246K | 290K | 334K | 383S | 420G+ |
| 248K* | 292R | 335T | 384N | 421N+ |
| 249D | 293E | 337S | 385G* | 424S |
| 254S* | 294Q | 338K | 386Q* | 430E |
| 255R* | 295Q+ | 339A | 388E | 431A |
| 256T* | 296Y | 340K+ | 389N+ | 433H* |
| 258E | 297N+ | 341G+ | 390N | 434N* |
| 260T | 298S+ | 342Q+ | 391Y | 435H* |
| 265D+ | 299T | 344R | 392K+ | 436Y* |
| 267S+ | 300Y | 345E | 393T | 437T |
| 268H+ | 307T* | 347Q | 394T# | 438Q* |
| 269E+ | 310H* | 350T | 399D# | 439K |
| 270D | 311Q* | 354S | 400S+ | 440S |
| 272E+ | 312N | 355R+ | 401N | 442S+ |
| 274K+ | 315D | 356E+ | 402G+ | |
| 276N | 316G | 359T+ | 403S | |
| 278Y | 317K | 360K+ | 407Y# | |
| 280D+ | 318E+ | 361N+ | 409K# | |
| 281G+ | 320K | 362Q+ | 411T | |
| 283Q | 322K | 371G | 413D+ | |
| 285H | 324S | 373Y | 414K+ | |
| 286N | 326K+ | 375S | 415S+ | |
| 287A | 327A | 376D | 416R+ | |
| 288K* | 330A+ | 380E | 418Q+ | |

*indicates likely FcRn interacting residues based on rat structures (not good candidates);
indicates dimer interaction domains (not good candidates);
+indicates best candidates for modification.

Table 3 below shows prioritized sites for mutation or modification in the predicted loop regions of human IgG1 Fc domain. Amino acid residue positions are numbered here in relation to reference sequence SEQ ID NO: 599.

TABLE 3

Prioritized sites for mutation or modification in the predicted loop regions of human IgG1 Fc domain.

| Domain | Loop | Insertion |
|---|---|---|
| CH2 | $D_{46}$-$E_{53}$ | $H_{49}/E_{50}$ - $1^{st}$ |
| | | $E_{50}/D_{51}$ - $2^{nd}$ |
| CH2 | $E_{74}$-$T_{80}$ | $Y_{77}/N_{78}$ - $1^{st}$ |
| | | $N_{78}/S_{79}$ - $2^{nd}$ |
| CH2-CH3 linker | $N_{106}$-$P_{127}$ | $K_{107}/A_{108}$ - $1^{st}$ |
| | | $N_{106}/K_{107}$ - $2^{nd}$ |
| CH3 | $D_{137}$-$K_{141}$ | $L_{139}/T_{140}$ - $1^{st}$ |
| | | $E_{138}/L_{139}$ - $2^{nd}$ |
| CH3 | $N_{165}$-$N_{177}$ | $E_{169}/N_{170}$ - $1^{st}$ |
| | | $N_{170}/N_{171}$ - $2^{nd}$ |
| CH3 | $T_{175}$-$S_{184}$ | $S_{181}/D_{182}$ - $1^{st}$ |
| | | $V_{178}/L_{179}$ - $2^{nd}$ |
| CH3 | $K_{195}$-$V_{203}$ | $G_{201}/N_{202}$ - $1^{st}$ |
| | | $N_{202}/V_{203}$ - $2^{nd}$ |
| CH3 | NA | $Q_{167}/P_{168}$ |
| CH3 | NA | $G_{183}/S_{184}$ |

In summary, this specification details a systematic approach to the identification of useful conjugation sites on the surface of immunoglobulin Fc and includes all the mutation sites described herein. The identification of specific conjugation sites derives from the application of structural and sequence data to a detailed set of structure/function criteria developed by these inventors.

Structure of Inventive Compounds

Fc Domains. This inventive composition requires the presence of at least one Fc domain monomer, but multimeric Fc embodiments (e.g., Fc domain dimers, trimers, tetramers, pentamers, etc.) are also preferred. Both native Fcs and Fc variants are suitable Fc domains for use within the scope of this invention, as are Fc domains comprised in antibodies. A native Fc may be extensively modified to form an Fc variant in accordance with this invention, provided binding to the salvage receptor is maintained; see, for example WO 97/34631 and WO 96/32478. In some useful embodiments, one can remove one or more sites of a native Fc that provide structural features or functional activity not required by a molecule of this invention, such as a fusion molecule. One may remove these sites by, for example, substituting or deleting amino acid residues, inserting residues into the site, or truncating portions containing the site. The inserted or substituted residues may also be altered amino acids, such as peptidomimetics or D-amino acids. Fc variants may be desirable for a number of reasons, several of which are described below.

Exemplary Fc variants include molecules and sequences in which:

1. Sites involved in disulfide bond formation are removed. Such removal may avoid reaction with other cysteine-containing proteins present in the host cell used to produce the molecules of the invention. For this purpose, the cysteine-containing segment at the N-terminus may be truncated or cysteine residues may be deleted or substituted with other amino acids (e.g., alanyl, seryl). For example, one may truncate the N-terminal segment (truncations up to about the first 20-amino acid residues of reference sequence SEQ ID NO: 599 or SEQ ID NO:600) or delete or substitute the cysteine residues at positions 7 and 10 of SEQ ID NO: 599 (positions 6 and 9 of SEQ ID NO:600). Even when cysteine residues are removed, the single chain Fc domains can still form a dimeric Fc domain that is held together non-covalently.
2. A native Fc is modified to make it more compatible with a selected host cell. For example, one may remove the PA sequence near the N-terminus of a typical native Fc, which may be recognized by a digestive enzyme in *E. coli* such as proline iminopeptidase. One may also add an N-terminal methionine residue, especially when the molecule is expressed recombinantly in a bacterial cell such as *E. coli*. The Fc domain of reference sequence SEQ ID NO: 599 (FIG. 2) is one such Fc variant, in which a methionine has been added to the N-terminal of SEQ ID NO: 600.
3. A portion of the N-terminus of a native Fc is removed to prevent N-terminal heterogeneity when expressed in a selected host cell. For this purpose, one may delete any or all of the first 20 amino acid residues at the N-terminus, particularly those corresponding to positions 1, 2, 3, 4 and 5 of reference sequence SEQ ID NO: 600.
4. One or more glycosylation sites are removed. Residues that are typically glycosylated (e.g., asparagine) may confer cytolytic response. Such residues may be deleted or substituted with unglycosylated residues (e.g., alanine)
5. Sites involved in interaction with complement, such as the C1q binding site, are removed. For example, one may delete or substitute the EKK sequence of human IgG1. Complement recruitment may not be advantageous for the molecules of this invention and so may be avoided with such an Fc variant.
6. Sites are removed that affect binding to Fc receptors other than a salvage receptor. A native Fc may have sites for interaction with certain white blood cells that are not required for the fusion molecules of the present invention and so may be removed.
7. The ADCC site is removed. ADCC sites are known in the art; see, for example, *Molec. Immunol.* 29 (5): 633-9 (1992) with regard to ADCC sites in IgG1. These sites, as well, are not required for the fusion molecules of the present invention and so may be removed.
8. When the native Fc is derived from a non-human antibody, the native Fc may be humanized. Typically, to humanize a native Fc, one will substitute selected residues in the non-human native Fc with residues that are normally found in human native Fc. Techniques for antibody humanization are well known in the art.

Preferred Fc variants include the following. In reference sequence SEQ ID NO: 599 (FIG. 2) the leucine at position 15 may be substituted with glutamate; the glutamate at position 99, with alanine; and the lysines at positions 101 and 103, with alanines. In addition, one or more tyrosine residues can be replaced by phenylalanine residues.

In some preferred embodiments, the Fc domain is an IgG1 Fc domain comprising an amino acid sequence SEQ ID NO: 603:

Glu Pro Lys Ser Cys Asp Lys Thr His Thr Cys Pro Pro Cys Pro Ala Pro Glu Leu Leu Gly Gly Pro Ser Val Phe Leu Phe Pro Pro Lys Pro Lys Asp Thr Leu Met Ile Ser Arg Thr Pro Glu Val Thr Cys Val Val Val Asp Val Ser His Glu Asp Pro Glu Val Lys Phe Asn Trp Tyr Val Asp Gly Val Glu Val His Asn Ala Lys Thr Lys Pro Arg Glu Glu Gln Tyr Asn Ser Thr Tyr Arg Val Val Ser Val Leu Thr Val Leu His Gln Asp Tip Leu Asn Gly Lys Glu Tyr Lys Cys Lys Val Ser Asn Lys Ala Leu Pro Ala Pro Ile Glu Lys Thr Ile Ser Lys Ala Lys Gly Gln Pro Arg Glu Pro Gln Val Tyr Thr Leu Pro Pro Ser Arg Asp Glu Leu Thr Lys Asn Gln Val Ser Leu Thr Cys Leu Val Lys Gly Phe Tyr Pro Ser Asp Ile Ala Val Glu Tip Glu Ser Asn Gly Gln Pro Glu Asn Asn Tyr Lys Thr Thr Pro Pro Val Leu Asp Ser Asp Gly Ser Phe Phe Leu Tyr Ser Lys Leu Thr Val Asp Lys Ser Arg Trp Gln Gln Gly Asn Val Phe Ser Cys Ser Val Met His Glu Ala Leu His Asn His Tyr Thr Gln Lys Ser Leu Ser Leu Ser Pro Gly Lys// (SEQ ID NO: 603); and the one or more specifically selected conjugation site(s) is selected from an amino acid residue position contained in a loop region that comprises an amino acid sequence selected from the group consisting of Pro Pro //SEQ ID NO: 601, Asp Val Ser His Glu Asp Pro Glu//SEQ ID NO: 602, Val His Asn Ala//SEQ ID NO: 604, Glu Glu Gln Tyr Asn Ser Thr//SEQ ID NO: 605, Val Leu His Gln Asp Trp Leu Asn Gly Lys Glu//SEQ ID NO: 606, Asn Lys Ala Leu Pro Ala Pro Ile Glu Lys Thr Ile Ser Lys Ala Lys Gly Gln Pro Arg Glu Pro//SEQ ID NO: 607, Asp Glu Leu Thr Lys//SEQ ID NO: 608, Asn Gly Gln Pro Glu Asn Asn//SEQ ID NO: 609, Thr Thr Pro Pro Val Leu Asp Ser Asp Gly Ser//SEQ ID NO: 610, and Lys Ser Arg Trp Gln Gln Gly Asn Val //SEQ ID NO: 611.

In the compositions of matter prepared in accordance with this invention, at least one additional functional moiety is covalently bound to a monomeric or multimeric Fc domain through a specifically selected conjugation site involving an amino acid residue side chain selected as described herein. Optionally, other moieties, such as a polypeptide, peptide, peptidomimetic or non-peptide organic moiety can be attached to the Fc domain through the Fc domain's N-terminus (i.e., via the α-amino site) or C-terminus (i.e., via the α-carboxy site).

Certain embodiments of the molecules of this invention may be described by the following formula I:

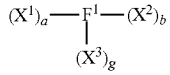
(I)

wherein:
- $F^1$ is a monomer of the monomeric or multimeric Fc domain;
- $X^1$ is covalently bound to the N-terminus of $F^1$ through the α-amino site of $F^1$;
- $X^2$ is covalently bound to the C-terminus of $F^1$ through the α-carboxy site of $F^1$;
- $X^3$ is covalently bound to the one or more specifically selected conjugation site(s) in $F^1$ selected from the group consisting of underlined residue positions in FIG. 1, boldface residue positions in FIG. 2, highlighted residue positions in FIG. 3, underlined residue positions in FIG. 3, and a cysteine residue added to the Fc domain by substitution at an Fc site selected from the group consisting of Leu139, Gln143, Ser145, and Ser196, or, if g>1, any combination of these members;
- $X^1$, $X^2$, and $X^3$ are each independently selected from -$(L^1)_c$-$P^0$, -$(L^1)_c$-$P^1$, -$(L^1)_c$-$P^1$-$(L^2)_d$-$P^2$, -$(L^1)_c$-$P^1$-$(L^2)_d$-$P^2$-$(L^3)_e$-$P^3$, and -$(L^1)_c$-$P^1$-$(L^2)_d$-$P^2$-$(L^3)_e$-$P^3$-$(L^4)_f$-$P^4$;
- $P^0$, $P^1$, $P^3$, and $P^4$ are each independently selected from the group consisting of:
  i) a pharmaceutically acceptable polymer or dextran;
  ii) a pharmacologically active polypeptide, peptide, peptidomimetic, or non-peptide organic moiety;
  iii) a radioisotope, an enzyme, a biotinyl moiety, a fluorophore, or a chromophore; and
  iv) an immobilized substrate, provided that in a chain comprising more than one additional functional moieties, the immobilized substrate is the moiety most distal from $F^1$, and there can be no more than one immobilized substrate in the chain;
- $L^1$, $L^2$, $L^3$, and $L^4$ are each independently linkers;
- a, b, c, d, e, and f are each independently 0 or 1; and g is 1, 2, 3, or 4.

Those of ordinary skill in the art will appreciate that more than one additional functional moieties ($X^3$) can be attached to the Fc domain, and that the multiple $X^3$ substituents may be the same or different; for example, comprising same or different $P^1$ functional moiety (i.e., a $P^1$ in a given formula may be the same or different from any other $P^1$, $P^2$, $P^3$, or $P^4$), different linkers attached to the same peptide sequence, and so on. Likewise, $X^1$ and $X^2$ may be the same, different, or absent (i.e., a and/or b=0), and the integers c through f may be different for $X^1$, $X^2$, and $X^3$.

Thus, compounds of Formula I encompass, but are not limited to, exemplary embodiments of the inventive compounds of the following formulae (II)-(XXVIII):

(II)

and multimers thereof, wherein a=1, b=0, $F^1$ is attached at the C-terminus of a polypeptide or peptide comprised in $X^1$, and $X^3$ is attached through a specifically selected internal conjugation site in $F^1$;

(III)

and multimers thereof, wherein a=0, b=1, $F^1$ is attached at the N-terminus of a polypeptide or peptide comprised in $X^2$, and $X^3$ is attached through a specifically selected internal conjugation site in $F^1$;

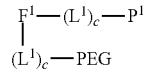
(IV)

and multimers thereof, wherein a=0, b=1, $F^1$ is attached through the N-terminus of a polypeptide or peptide $P^1$ comprised in -$(L^1)_c$-$P^1$ and -$(L^1)_c$-PEG is attached through a specifically selected internal conjugation site in $F^1$;

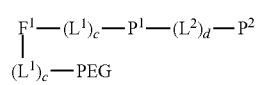
(V)

and multimers thereof, wherein a=0, b=1, $F^1$ is attached through the N-terminus of a polypeptide or peptide $P^1$ comprised in -$(L^1)_c$-$P^1$-$(L^2)_d$-$P^2$ and -$(L^1)_c$-PEG is attached through a specifically selected internal conjugation site in $F^1$;

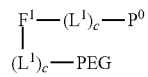
(VI)

and multimers thereof, wherein a=0, b=1, $F^1$ is attached through the N-terminus of a polypeptide or peptide $P^0$ comprised in -$(L^1)_c$-$P^0$ and -$(L^1)_c$-PEG is attached through a specifically selected internal conjugation site in $F^1$;

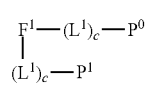
(VII)

and multimers thereof, wherein a=0, b=1, $F^1$ is attached through the N-terminus of a polypeptide or peptide $P^0$ comprised in -$(L^1)_c$-$P^0$ and -$(L^1)_c$-$P^1$ is attached through a specifically selected internal conjugation site in $F^1$;

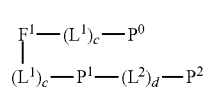
(VIII)

and multimers thereof, wherein a=0, b=1, $F^1$ is attached through the N-terminus of a polypeptide or peptide $P^0$ comprised in -$(L^1)_c$-$P^0$ and -$(L^1)_c$-$P^1$-$(L^2)_d$-$P^2$ is attached through a specifically selected internal conjugation site in $F^1$;

(IX)

and multimers thereof, wherein a=0, b=1, g=2, $F^1$ is attached through the N-terminus of a polypeptide or peptide $P^0$ comprised in -$(L^1)_c$-$P^0$, and -$(L^1)_c$-PEG and -$(L^1)_c$-$P^1$ are each independently attached through specifically selected internal conjugation sites in $F^1$;

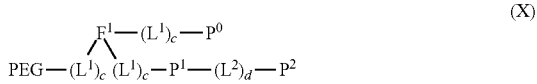
(X)

and multimers thereof, wherein a=0, b=1, g=2, $F^1$ is attached through the N-terminus of a polypeptide or peptide $P^0$ comprised in -$(L^1)_c$-$P^0$ and -$(L^1)_c$-PEG and -$(L^1)_c$-$P^1$-$(L^2)_d$-$P^2$ are each independently attached through specifically selected internal conjugation sites in $F^1$;

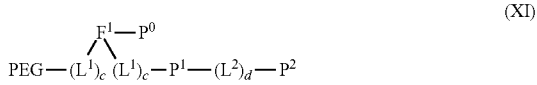
(XI)

and multimers thereof, wherein a=0, b=1, $F^1$ is attached at the N-terminus of a polypeptide or peptide -$P^0$, and -$(L^1)_c$-PEG and -$(L^1)_c$-$P^2$-$(L^2)_d$-$P^2$ are each independently attached through specifically selected internal conjugation sites in $F^1$.

(XII)

and multimers thereof, wherein a=1, b=0, $F^1$ is attached through the C-terminus of a polypeptide or peptide $P^1$ comprised in -$(L^1)_c$-$P^1$ and -$(L^1)_c$-PEG is attached through a specifically selected internal conjugation site in $F^1$;

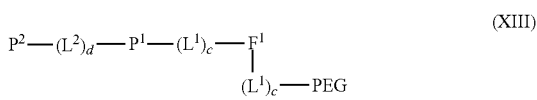
(XIII)

and multimers thereof, wherein a=1, b=0, $F^1$ is attached through the C-terminus of a polypeptide or peptide $P^1$ comprised in -$(L^1)_c$-$P^1$-$(L^2)_d$-$P^2$ and -$(L^1)_c$-PEG is attached through a specifically selected internal conjugation site in $F^1$;

(XIV)

and multimers thereof, wherein a=1, b=0, $F^1$ is attached through the C-terminus of a polypeptide or peptide $P^0$ comprised in -$(L^1)_c$-$P^0$ and -$(L^1)_c$-PEG is attached through a specifically selected internal conjugation site in $F^1$;

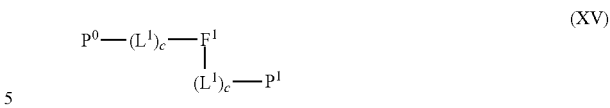
(XV)

and multimers thereof, wherein a=1, b=0, $F^1$ is attached through the C-terminus of a polypeptide or peptide $P^0$ comprised in -$(L^1)_c$-$P^0$ and $(L^1)_c$-$P^1$ is attached through a specifically selected internal conjugation site in $F^1$;

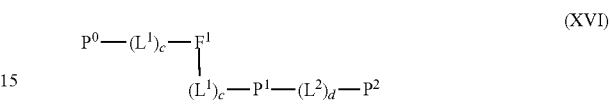
(XVI)

and multimers thereof, wherein a=1, b=0, $F^1$ is attached through the C-terminus of a polypeptide or peptide $P^0$ comprised in -$(L^1)_c$-$P^0$, and -$(L^1)_c$-$P^1$-$(L^2)_d$-$P^2$ is attached through a specifically selected internal conjugation site in $F^1$;

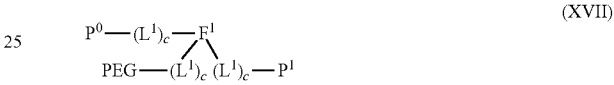
(XVII)

and multimers thereof, wherein a=1, b=0, g=2, $F^1$ is attached through the C-terminus of a polypeptide or peptide $P^0$ comprised in -$(L^1)_c$-$P^0$ and $(L^1)_c$-PEG and $(L^1)_c$-$P^1$ are each independently attached through specifically selected internal conjugation sites in $F^1$;

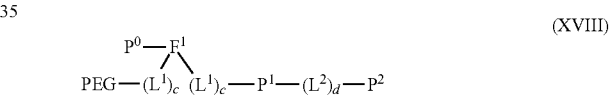
(XVIII)

and multimers thereof, wherein a=1, b=0, g=2, $F^1$ is attached at the C-terminus of a polypeptide or peptide -$P^0$ and -$(L^1)_c$-PEG and -$(L^1)_c$-$P^1$-$(L^2)_d$-$P^2$ are each independently attached through specifically selected internal conjugation sites in $F^1$;

(XIX)

and multimers thereof, wherein a=1, b=0, g=2, $F^1$ is attached through the C-terminus of a polypeptide or peptide $P^1$ comprised in -$(L^1)_c$-$P^1$, and -$(L^1)_c$-PEG and -$(L^1)_c$-$P^2$-$(L^2)_d$-$P^2$ are each independently attached through specifically selected internal conjugation sites in $F^1$;

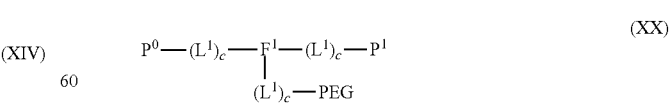
(XX)

and multimers thereof, wherein a=1, b=1, $P^0$-$(L^1)_c$-$F^1$-$(L^1)_c$-$P^1$ is attached as written from the N-terminus of a polypeptide or peptide $P^0$ to the C-terminus of a polypeptide or peptide $P^1$ and -$(L^1)_c$-PEG is attached through a specifically selected internal conjugation site in $F^1$;

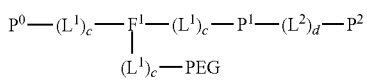
(XXI)

and multimers thereof, wherein a=1, b=1, c=1, $P^0$-$(L^1)_c$-$F^1$-$(L^1)_c$-$P^1$-$(L^2)_d$-$P^2$ is attached as written from the N-terminus of a polypeptide or peptide $P^0$ to the C-terminus of a polypeptide or peptide $P^1$ (if $P^1$ but not $P^2$ is a polypeptide or peptide) or $P^2$ (if both $P^1$ and $P^2$ are a polypeptide or peptide) and -$(L^1)_c$-PEG is attached through a specifically selected internal conjugation site in $F^1$;

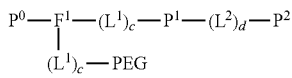
(XXII)

and multimers thereof, wherein a=1, b=1, $P^0$-$F^1$-$(L^1)_c$-$P^1$-$(L^2)_d$-$P^2$ is attached as written from the N-terminus of a polypeptide or peptide $P^0$ to the C-terminus of a polypeptide or peptide $P^1$ (if $P^1$ but not $P^2$ is a polypeptide or peptide) or $P^2$ (if both $P^1$ and $P^2$ are a polypeptide or peptide), and -$(L^1)_c$-PEG is attached through a specifically selected internal conjugation site in $F^1$;

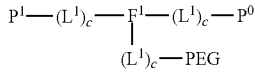
(XXIII)

and multimers thereof, wherein a=1, b=1, c=1, $P^1$-$(L^1)_c$-$F^1$-$(L^1)_c$-$P^0$ is attached as written from the N-terminus of a polypeptide or peptide $P^1$ to the C-terminus of a polypeptide or peptide $P^0$ and -$(L^1)_c$-PEG is attached through a specifically selected internal conjugation site in $F^1$;

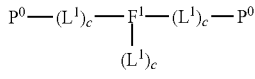
(XXIV)

and multimers thereof, wherein a=1, b=1, c=1, $P^1$-$(L^1)_c$-$F^1$-$(L^1)_c$-$P^0$ is attached as written from the N-terminus of a polypeptide or peptide $P^1$ to the C-terminus of a polypeptide or peptide $P^0$ and $(L^1)_c$-$P^1$ is attached through a specifically selected internal conjugation site in $F^1$;

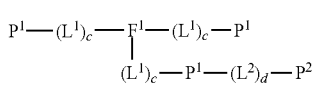
(XXV)

and multimers thereof, wherein a=1, b=1, c=1, $P^1$-$(L^1)_c$-$F^1$-$(L^1)_c$-$P^0$ is attached as written from the N-terminus of a polypeptide or peptide $P^1$ to the C-terminus of a polypeptide or peptide $P^0$, and -$(L^1)_c$-$P^1$-$(L^2)_d$-$P^2$ is attached through a specifically selected internal conjugation site in $F^1$;

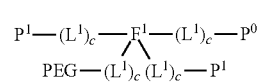
(XXVI)

and multimers thereof, wherein a=1, b=1, c=1, $P^1$-$(L^1)_c$-$F^1$-$(L^1)_c$-$P^0$ is attached as written from the N-terminus of a polypeptide or peptide $P^1$ to the C-terminus of a polypeptide or peptide $P^0$ and -$(L^1)_c$-PEG and -$(L^1)_c$-$P^1$ are each independently attached through specifically selected internal conjugation sites in $F^1$;

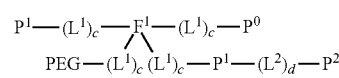
(XXVII)

and multimers thereof, wherein a=1, b=1, c=1, $P^1$-$(L^1)_c$-$F^1$-$(L^1)_c$-$P^0$ is attached as written from the N-terminus of a polypeptide or peptide $P^1$ to the C-terminus of a polypeptide or peptide $P^0$, and -$(L^1)_c$-PEG and -$(L^1)_c$-$P^1$-$(L^2)_d$-$P^2$ are each independently attached through specifically selected internal conjugation sites in $F^1$; and

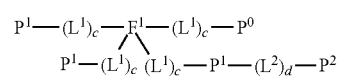
(XXVIII)

and multimers thereof, wherein a=1, b=1, c=1, $P^1$-$(L^1)_c$-$F^1$-$(L^1)_c$-$P^0$ is attached as written from the N-terminus of a polypeptide or peptide $P^1$ to the C-terminus of a polypeptide or peptide $P^0$, and the second -$(L^1)_c$-$P^1$ and $(L^1)_c$-$P^2$-$(L^2)_d$-$P^2$ are each independently attached through specifically selected internal conjugation sites in $F^1$.

In another embodiment of the present invention, the composition of matter is an antibody modified, which comprises at least one additional functional moiety ($X^3$) covalently bound to the Fc domain of the antibody through one or more specifically selected conjugation site(s) in the Fc domain. The conjugation site, or sites, are selected from: underlined residue positions in FIG. 1, boldface residue positions in FIG. 2, highlighted residue positions in FIG. 3, underlined residue positions in FIG. 3, or a cysteine residue added to the Fc domain by substitution at an Fc site selected from the group consisting of Leu139, Gln143, Ser145, and Ser196, or, if there is more than one $X^3$, any combination of these members. $X^3$ is selected from -$(L^1)_c$-$P^0$, -$(L^1)_c$-$P^1$, -$(L^1)_c$-$P^1$-$(L^2)_d$-$P^2$, -$(L^1)_c$-$P^1$-$(L^2)_d$-$P^2$-$(L^3)_e$-$P^3$, and -$(L^1)_c$-$P^1$-$(L^2)_d$-$P^2$-$(L^3)_e$-$P^3$-$(L^4)_f$-$P^4$;

$P^0$, $P^1$, $P^2$, $P^3$, and $P^4$ are each independently selected from the group consisting of:
  i) a pharmaceutically acceptable polymer or dextran;
  ii) a pharmacologically active polypeptide, peptide, peptidomimetic, or non-peptide organic moiety;
  iii) a radioisotope, an enzyme, a biotinyl moiety, a fluorophore, or a chromophore; and
  iv) an immobilized substrate, provided that in a chain comprising more than one additional functional moieties, the immobilized substrate is the moiety most distal from the Fc domain, and there can be no more than one immobilized substrate in the chain;

$L^1$, $L^2$, $L^3$, and $L^4$ are each independently linkers;
c, d, e, and f are each independently 0 or 1.

Additional functional moiety or moieties ($X^3$)

Some embodiments of the additional functional moiety, or moieties, (i.e., $P^0$, $P^1$, $P^2$, $P^3$, $P^4$), that can be conjugated to the Fc domain, in accordance with the present invention, will now be exemplified in greater detail.

Polypeptides or peptides. One or more additional functional moieties is conjugated to the Fc domain molecules of this invention. Such additional functional moieties can include a polypeptide, a peptide, an antibody, antibody fragment, (or a non-peptide organic molecule "small molecules", e.g., a peptidomimetic compound) capable of binding to a salvage receptor. For example, one can use as a functional moiety a polypeptide as described in U.S. Pat. No. 5,739,277, issued Apr. 14, 1998 to Presta et al. Peptides of interest can also be selected by phage display for binding to the FcRn salvage receptor. Such salvage receptor-binding compounds are also included within the meaning of "functional moiety" in this invention. Such functional moieties can be selected, for example, for increased half-life (e.g., by avoiding sequences recognized by proteases) and decreased immunogenicity (e.g., by favoring non-immunogenic sequences, as discovered in antibody humanization).

In other embodiments, a variety of other peptides or polypeptides can be used as the additional functional moiety in conjunction with the present invention. Exemplary polypeptides that can be used include those mentioned as fusion partners in Table 1 hereinabove. Preferred polypeptides have therapeutic utility and include the human proteins anakinra, sTNF-R2, sTNF-R1, CTLA4, OPG, GDNF, PTH fragments, glucagons fragments, GLP-1, and the like. Accordingly, a preferred polypeptide sequence is the sTNF-R2 sequence below:

(SEQ ID NO: 617)
QICNVVAIPGNASMDAVCTSTSPTRSMAPGAVHLPQPVSTRSQHTQPTPE

PSTAPSTSFLLPMGPSPPAEGSTGDFALPVGLIVGVTALGLLIIGVVNCV

IMTQVKKKPLCLQREAKVPHLPADKARGTQGPEQQHLLITAPSSSSSSLE

SSASALDRRAPTRNQPQAPGVEASGAGEARASTGSSDSSPGGHGTQVNVT

CIVNVCSSSDHSSQCSSQASSTMGDTDSSPSESPKDEQVPFSKEECAFRS

QLETPETLLGSTEEKPLPLGVPDAGMKPS//

In accordance with the present invention, one may modify Fc fusion proteins comprising such polypeptides by adding an additional functional moiety such as PEG through a selected site in the Fc domain. In this way, for example, a PEGylated derivative of etanercept is within the scope of this invention in which the PEG molecule is attached through a selected site in the Fc domain of etanercept. Such a molecule can be described by formula XIV above in which $P^0$-$(L^1)_c$-$F^1$ encodes etanercept (wherein $P^0$ is SEQ ID NO: 618:

1 Leu-Pro-Ala-Gln-Val-Ala-Phe-Thr-Pro-Tyr-
11 Ala-Pro-Glu-Pro-Gly-Ser-Thr-Cys-Arg-Leu-
21 Arg-Glu-Tyr-Tyr-Asp-Gln-Thr-Ala-Gln-Met-
31 Cys-Cys-Ser-Lys-Cys-Ser-Pro-Gly-Gln-His-
41 Ala-Lys-Val-Phe-Cys-Thr-Lys-Thr-Ser-Asp-
51 Thr-Val-Cys-Asp-Ser-Cys-Glu-Asp-Ser-Thr-
61 Tyr-Thr-Gln-Leu-Trp-Asn-Trp-Val-Pro-Glu-
71 Cys-Leu-Ser-Cys-Gly-Ser-Arg-Cys-Ser-Ser-
81 Asp-Gln-Val-Glu-Thr-Gln-Ala-Cys-Thr-Arg-
91 Glu-Gln-Asn-Arg-Ile-Cys-Thr-Cys-Arg-Pro-
101 Gly-Trp-Tyr-Cys-Ala-Leu-Ser-Lys-Gln-Glu-
111 Gly-Cys-Arg-Leu-Cys-Ala-Pro-Leu-Arg-Lys-
121 Cys-Arg-Pro-Gly-Phe-Gly-Val-Ala-Arg-Pro-
131 Gly-Thr-Glu-Thr-Ser-Asp-Val-Val-Cys-Lys-
141 Pro-Cys-Ala-Pro-Gly-Thr-Phe-Ser-Asn-Thr-
151 Thr-Ser-S er-Thr-Asp-Ile-Cys-Arg-Pro-His-
161 Gln-Ile-Cys-Asn-Val-Val-Ala-Ile-Pro-Gly-
171 Asn-Ala-Ser-Met-Asp-Ala-Val-Cys-Thr-Ser-
181 Thr-Ser-Pro-Thr-Arg-Ser-Met-Ala-Pro-Gly-
191 Ala-Val-His-Leu-Pro-Gln-Pro-Val-Ser-Thr-
201 Arg-Ser-Gln-His-Thr-Gln-Pro-Thr-Pro-Glu-
211 Pro-Ser-Thr-Ala-Pro-Ser-Thr-Ser-Phe-Leu-
221 Leu-Pro-Met-Gly-Pro-Ser-Pro-Pro-Ala-Glu-
231 Gly-Ser-Thr-Gly-Asp-Glu-Pro-Lys-Ser-Cys-
241 Asp-Lys-Thr-His-Thr-Cys-Pro-Pro-Cys-Pro-
251 Ala-Pro-Glu-Leu-Leu-Gly-Gly-Pro-Ser-Val-
261 Phe-Leu-Phe-Pro-Pro-Lys-Pro-Lys-Asp-Thr-
271 Leu-M et-Ile-Ser-Arg-Thr-Pro-Glu-Val-Thr-
281 Cys-Val-Val-Val-Asp-Val-Ser-His-Glu-Asp-
291 Pro-Glu-Val-Lys-Phe-Asn-Trp-Tyr-Val-Asp-
301 Gly-Val-Glu-Val-His-Asn-Ala-Lys-Thr-Lys-
311 Pro-Arg-Glu-Glu-Gln-Tyr-Asn-Ser-Thr-Tyr-
321 Arg-Val-Val-Ser-Val-Leu-Thr-Val-Leu-His-
331 Gln-Asp-Trp-Leu-Asn-Gly-Lys-Glu-Tyr-Lys-
341 Cys-Lys-Val-Ser-Asn-Lys-Ala-Leu-Pro-Ala-
351 Pro-Ile-Glu-Lys-Thr-Ile-Ser-Lys-Ala-Lys-
361 Gly-Gln-Pro-Arg-Glu-Pro-Gln-Val-Tyr-Thr-
371 Leu-Pro-Pro-Ser-Arg-Glu-Glu-Met-Thr-Lys-
381 Asn-Gln-Val-Ser-Leu-Thr-Cys-Leu-Val-Lys-
391 Gly-Phe-Tyr-Pro-Ser-Asp-Ile-Ala-Val-Glu-
401 Trp-Glu-Ser-Asn-Gly-Gln-Pro-Glu-Asn-Asn-
411 Tyr-Lys-Thr-Thr-Pro-Pro-Val-Leu-Asp-Ser-
421 Asp-Gly-Ser-Phe-Phe-Leu-Tyr-Ser-Lys-Leu-
431 Thr-Val-Asp-Lys-S er-Arg-Trp-Gln-Gln-Gly-
441 Asn-Val-Phe-Ser-Cys-Ser-Val-Met-His-Glu-
451 Ala-Leu-His-Asn-His-Tyr-Thr-Gln-Lys-Ser-
461 Leu-Ser-Leu-Ser-Pro-Gly-Lys// SEQ ID NO: 618, and c is 0) or a molecule based on the etanercept sequence with one or more modified residues to enable linkage to the $(L^1)_c$-PEG substituent.

Also in accordance with this invention, a peptide or additional polypeptide functional moiety can be linked through a selected site in the Fc domain. Alternatively, the polypeptide-Fc fusion protein can be linked to a peptide or tandem dimer, trimer, or tetramer (i.e., -$(L^1)_c$-$P^1$, -$(L^1)_c$-$P^1$, -$(L^2)_d$-$P^2$, -$(L^1)_c$-$P^1$-$(L^2)_d$-$P^2$-$(L^3)_e$-$P^3$, and -$(L^1)_c$-$P^1$-$(L^2)_d$-$P^2$-$(L^3)_e$-$P^3$-$(L^4)_f$-$P^4$. The peptides can be linked through a selected internal Fc site or at an available N- or C-terminus of the fusion protein. In this way, this invention encompasses an etanercept derivative comprising, for example, a BAFF-binding peptide dimer (see Table 10 hereinafter), a PEG moiety, or both. In such a molecule for example, the structure can follow formula XXI above wherein $P^0$ is SEQ ID NO: 617, $P^1$ and $P^2$ are BAFF-binding peptides such as LPGCKWDLLIKQWVCDPL (SEQ ID NO: 514).

Any number of peptides or polypeptides can be used in conjunction with the present invention. In some embodiments, the peptides or polypeptides bind to angiopoietin-2 (ang-2), myostatin, nerve growth factor (NGF), tumor necrosis factor (TNF), B cell activating factor (BAFF, also referred to as TALL-1) or mimic the activity of EPO, TPO, or G-CSF. Targeting peptides are also of interest, including tumor-homing peptides, membrane-transporting peptides, and the like. All of these classes of peptides or polypeptides can be discovered by methods described in the references cited in this specification and other references.

As mentioned above, phage display is useful in generating peptides for use in the present invention. It has been stated that affinity selection from libraries of random peptides can be used to identify peptide ligands for any site of any gene product. Dedman et al. (1993), *J. Biol. Chem.* 268: 23025-30. Phage display is particularly well suited for identifying peptides that bind to such proteins of interest as cell surface receptors or any proteins having linear epitopes. Wilson et al. (1998), *Can. J. Microbiol.* 44: 313-29; Kay et al. (1998), *Drug Disc. Today* 3: 370-8. Such proteins are extensively reviewed in Herz et al. (1997), *J. Receptor & Signal Transduction Res.* 17(5): 671-776, which is hereby incorporated by reference. Such proteins of interest are preferred for use in this invention.

A particularly preferred group of peptides are those that bind to cytokine receptors. Cytokines have recently been classified according to their receptor code. See Inglot (1997), *Archivum Immunologiae et Therapiae Experimentalis* 45: 353-7, which is hereby incorporated by reference. Among these receptors, most preferred are the CKRs (family I in Table 4). The receptor classification appears in Table 4.

TABLE 4

| Cytokine Receptors Classified by Receptor Code | | | | |
|---|---|---|---|---|
| Cytokines (ligands) | | Receptor Type | | |
| Family | Subfamily | family | | subfamily |
| I. Hematopoietic cytokines | 1. IL-2, IL-4, IL-7, IL-9, IL-13, IL-15<br>2. IL-3, IL-5, GM-CSF<br>3. IL-6, IL-11, IL-12, LIF, OSM, CNTF, Leptin (OB)<br>4. G-CSF, EPO, TPO, PRL, GH<br>5. IL-17, HVS-IL-17 | I. Cytokine R (CKR) | 1. shared γCr, IL-9R, IL-4R<br>2. shared GP 140 βR<br>3. 3.shared RP 130, IL-6 R, Leptin R<br>4. "single chain" R, GCSF-R, TPO-R, GH-R<br>5. other R$^a$ | |
| II. IL-10 ligands | IL-10, BCRF-1, HSV-IL-10 | II. IL-10 R | | |
| III. Interferons | 1. IFN-α1, α2, α4, m, t, IFN-β$^b$<br>2. IFN-γ | III. Interferon R | 1. IFNAR<br>2. IFNGR | |
| IV. IL-1 and IL-1 like ligands | 1. IL-1α, IL-1β, IL-1Ra<br>2. IL-18, IL-18BP | IV. IL-1R | 1. IL-1R, IL-1RAcP<br>2. IL-18R, IL-18RAcP | |
| V. TNF family | 1. TNF-α, TNF-β (LT), FASL, CD40 L, CD30L, CD27 L, OX40L, OPGL, TRAIL, APRIL, AGP-3, BLys, TL5, Ntn-2, KAY, Neutrokine-α | 3. NGF/TNF R$^c$ | TNF-RI, AGP-3R, DR4, DR5, OX40, OPG, TACI, CD40, FAS, ODR | |
| VI. Chemokines | 1. α chemokines: IL-8, GRO α, β, γ, IF-10, PF-4, SDF-1<br>2. β chemokines: MIP1α, MIP1β, MCP-1, 2, 3, 4, RANTES, eotaxin<br>3. γ chemokines: lymphotactin | 4. Chemokine R | 1. CXCR<br>2. CCR<br>3. CR<br>4. DARC$^d$ | |
| VII. Growth factors | 1.1 SCF, M-CSF, PDGF-AA, AB, BB, KDR, FLT-1, FLT-3L, VEGF, SSV-PDGF, HGF, SF<br>1.2 FGFα, FGFβ<br>1.3 EGF, TGF-α, VV-F19 (EGF-like)<br>1.4 IGF-I, IGF-II, Insulin<br>1.5 NGF, BDNF, NT-3, NT-4$^e$<br>2. TGF-β1, β2, β3 | VII. RKF | 1. TK subfamily<br>1.1 IgTK III R, VEGF-RI, VEGF-RII<br>1.2 IgTK IV R<br>1.3 Cysteine-rich TK-I<br>1.4 Cysteine rich TK-II, IGF-RI<br>1.5 Cysteine knot TK V<br>2. Serine-threonine kinase | |

TABLE 4-continued

Cytokine Receptors Classified by Receptor Code

| Cytokines (ligands) | | Receptor Type | |
|---|---|---|---|
| Family | Subfamily | family | subfamily |
| | | | subfamily (STKS)[6] |

[2]Other IFN type I subtypes remain unassigned. Hematopoietic cytokines, IL-10 ligands and interferons do not possess functional intrinsic protein kinases. The signaling molecules for the cytokines are JAK's, STATs and related non-receptor molecules. IL-14, IL-16 and IL-18 have been cloned but according to the receptor code they remain unassigned.
[3]TNF receptors use multiple, distinct intracellular molecules for signal transduction including "death domain" of FAS R and 55 kDa TNF- R that participates in their cytotoxic effects. NGF/TNF R can bind both NGF and related factors as well as TNF ligands. Chemokine receptors are seven transmembrane (7TM, serpentine) domain receptors. They are G protein-coupled.
[4]The Duffy blood group antigen (DARC) is an erythrocyte receptor that can bind several different chemokines. IL-1R belongs to the immunoglobulin superfamily but their signal transduction events characteristics remain unclear.
[5]The neurotrophic cytokines can associate with NGF/TNF receptors also.
[6]STKS may encompass many other TGF-β-related factors that remain unassigned. The protein kinases are intrinsic part of the intracellular domain of receptor kinase family (RKF). The enzymes participate in the signals transmission via the receptors.

Particular proteins of interest as targets for peptide generation in the present invention include, but are not limited to, the following:
αVβ3
αVβ1
Ang-2
BAFF/TALL-1
B7
B7RP1
CRP1
Calcitonin
CD28
CETP
cMet
Complement factor B
C4b
CTLA4
Glucagon
Glucagon Receptor
LIPG
MPL
myostatin
splice variants of molecules preferentially expressed on tumor
cells; e.g., CD44, CD30
unglycosylated variants of mucin and Lewis Y surface glycoproteins
CD19, CD20, CD33, CD45
prostate specific membrane antigen and prostate specific cell antigen
matrix metalloproteinases (MMPs), both secreted and membrane-bound (e.g., MMP-9)
Cathepsins
angiopoietin-2
TIE-2 receptor
heparanase
urokinase plasminogen activator (UPA), UPA receptor
parathyroid hormone (PTH), parathyroid hormone-related protein (PTHrP), PTH-RI, PTH-RII
Her2
Her3
Insulin Exemplary peptides for this invention appear in Tables 4 through 20 of U.S. Pat. No. 6,660,843, which are hereby incorporated by reference. Additional preferred peptides appear in U.S. 2003/0229023, published Dec. 11, 2003; WO 03/057134, published Jul. 17, 2003; U.S. 2003/0236193, published Dec. 25, 2003; WO 00/24770, published May 4, 2000; U.S. 2003/0176352, published Sep. 18, 2003; WO 03/031589, published Apr. 17, 2003; U.S. Ser. No. 10/666,480, filed Sep. 18, 2003; WO 04/026329, published Apr. 1, 2004; U.S. Ser. No. 10/742,379, filed Dec. 19, 2003; PCT/US03/40781, filed Dec. 19, 2003, each of which are hereby incorporated by reference. Such peptides may be prepared by methods disclosed in the art.

The amino acid sequences of some preferred peptides and polypeptides appear in Tables 5-10 below. Single letter amino acid abbreviations are used. Any of these peptides may be linked in tandem (i.e., sequentially), with or without linkers. Any peptide containing a cysteinyl residue may be cross-linked with another Cys-containing peptide or protein. Any peptide having more than one Cys residue may form an intrapeptide disulfide bond, as well. Any of these peptides may be derivatized as described herein. All peptides are linked through peptide bonds unless otherwise noted.

TABLE 5

EPO-mimetic peptide sequences

| SEQUENCE | SEQ ID NO: |
|---|---|
| YXCXXGPXTWXCXP, wherein X is any amino acid | 1 |
| GGTYSCHFGPLTWVCKPQGG | 2 |
| GGDYHCRMGPLTWVCKPLGG | 3 |
| GGVYACRMGPITWVCSPLGG | 4 |
| VGNYMCHFGPITWVCRPGGG | 5 |
| GGLYLCRFGPVTWDCGYKGG | 6 |
| GGTYSCHFGPLTWVCKPQGGSSK | 7 |
| GGTYSCHGPLTWVCKPQGG | 8 |
| VGNYMAHMGPITWVCRPGG | 9 |
| GGPHHVYACRMGPLTWIC | 10 |
| GGTYSCHFGPLTWVCKPQ | 11 |
| GGLYACHMGPMTWVCQPLRG | 12 |
| TIAQYICYMGPETWECRPSPKA | 13 |
| YSCHFGPLTWVCK | 14 |
| YCHFGPLTWVC | 15 |
| GGLYLCRFGPVTWDCGYKGG | 16 |

TABLE 5-continued

EPO-mimetic peptide sequences

| SEQUENCE | SEQ ID NO: |
|---|---|
| GGTYSCHFGPLTWVCKPQGG | 17 |
| GGDYHCRMGPLTWVCKPLGG | 18 |
| VGNYMCHFGPITWVCRPGGG | 19 |
| GGVYACRMGPITWVCSPLGG | 20 |
| VGNYMAHMGPITWVCRPGG | 21 |
| GGTYSCHFGPLTWVCKPQ | 22 |
| GGLYACHMGPMTWVCQPLRG | 23 |
| TIAQYICYMGPETWECRPSPKA | 24 |
| YSCHFGPLTWVCK | 25 |
| YCHFGPLTWVC | 26 |
| SCHFGPLTWVCK | 27 |

TABLE 6

TPO-mimetic peptide sequences

| SEQUENCE | SEQ ID NO: |
|---|---|
| IEGPTLRQWLAARA | 28 |
| IEGPTLRQWLAAKA | 29 |
| IEGPTLREWLAARA | 30 |
| TLREWL | 31 |
| GRVRDQVAGW | 32 |
| GRVKDQIAQL | 33 |
| GVRDQVSWAL | 34 |
| ESVREQVMKY | 35 |
| SVRSQISASL | 36 |
| GVRETVYRHM | 37 |
| GVREVIVHML | 38 |
| GRVRDQIWAAL | 39 |
| AGVRDQILIWL | 40 |
| GRVRDQIMLSL | 41 |
| CTLRQWLQGC | 42 |
| CTLQEFLEGC | 43 |
| CTRTEWLHGC | 44 |
| CTLREWLHGGFC | 45 |
| CTLREWVFAGLC | 46 |
| CTLRQWLILLGMC | 47 |
| CTLAEFLASGVEQC | 48 |
| CSLQEFLSHGGYVC | 49 |
| CTLREFLDPTTAVC | 50 |

TABLE 6-continued

TPO-mimetic peptide sequences

| SEQUENCE | SEQ ID NO: |
|---|---|
| CTLKEWLVSHEVWC | 51 |
| REGPTLRQWM | 52 |
| EGPTLRQWLA | 53 |
| ERGPFWAKAC | 54 |
| REGPRCVMWM | 55 |
| CGTEGPTLSTWLDC | 56 |
| CEQDGPTLLEWLKC | 57 |
| CELVGPSLMSWLTC | 58 |
| CLTGPFVTQWLYEC | 59 |
| CRAGPTLLEWLTLC | 60 |
| CADGPTLREWISFC | 61 |
| GGCTLREWLHGGFCGG | 62 |
| GGCADGPTLREWISFCGG | 63 |
| GNADGPTLRQWLEGRRPKN | 64 |
| LAIEGPTLRQWLHGNGRDT | 65 |
| HGRVGPTLREWKTQVATKK | 66 |
| TIKGPTLRQWLKSREHTS | 67 |
| ISDGPTLKEWLSVTRGAS | 68 |
| SIEGPTLREWLTSRTPHS | 69 |
| GAREGPTLRQWLEWVRVG | 70 |
| RDLDGPTLRQWLPLPSVQ | 71 |
| ALRDGPTLKQWLEYRRQA | 72 |
| ARQEGPTLKEWLFWVRMG | 73 |
| EALLGPTLREWLAWRRAQ | 74 |
| MARDGPTLREWLRTYRMM | 75 |
| WMPEGPTLKQWLFHGRGQ | 76 |
| HIREGPTLRQWLVALRMV | 77 |
| QLGHGPTLRQWLSWYRGM | 78 |
| ELRQGPTLHEWLQHLASK | 79 |
| VGIEGPTLRQWLAQRLNP | 80 |
| WSRDGPTLREWLAWRAVG | 81 |
| AVPQGPTLKQWLLWRRCA | 82 |
| RIREGPTLKEWLAQRRGF | 83 |
| RFAEGPTLREWLEQRKLV | 84 |
| DRFQGPTLREWLAAIRSV | 85 |
| AGREGPTLREWLNMRVWQ | 86 |
| ALQEGPTLRQWLGWGQWG | 87 |
| YCDEGPTLKQWLVCLGLQ | 88 |

TABLE 6-continued

TPO-mimetic peptide sequences

| SEQUENCE | SEQ ID NO: |
|---|---|
| WCKEGPTLREWLRWGFLC | 89 |
| CSSGGPTLREWLQCRRMQ | 90 |
| CSWGGPTLKQWLQCVRAK | 91 |
| CQLGGPTLREWLACRLGA | 92 |
| CWEGGPTLKEWLQCLVER | 93 |
| CRGGGPTLHQWLSCFRWQ | 94 |
| CRDGGPTLRQWLACLQQK | 95 |
| ELRSGPTLKEWLVWRLAQ | 96 |
| GCRSGPTLREWLACREVQ | 97 |
| TCEQGPTLRQWLLCRQGR | 98 |
| QGYCDEGPTLKQWLVCLGLQHS | 99 |

TABLE 7

Ang-2 binding peptide sequences

| SEQUENCE | SEQ ID NO. |
|---|---|
| WDPWT | 100 |
| WDPWTC | 101 |
| CXWDPWT (wherein X is an acidic or neutral polar amino acid residue) | 102 |
| CXWDPWTC (wherein X is an acidic or neutral polar amino acid residue) | 103 |
| PIRQEECDWDPWTCEHMWEV | 104 |
| TNIQEECEWDPWTCDHMPGK | 105 |
| WYEQDACEWDPWTCEHMAEV | 106 |
| NRLQEVCEWDPWTCEHMENV | 107 |
| AATQEECEWDPWTCEHMPRS | 108 |
| LRHQEGCEWDPWTCEHMFDW | 109 |
| VPRQKDCEWDPWTCEHMYVG | 110 |
| SISHEECEWDPWTCEHMQVG | 111 |
| WAAQEECEWDPWTCEHMGRM | 112 |
| TWPQDKCEWDPWTCEHMGST | 113 |
| GHSQEECGWDPWTCEHMGTS | 114 |
| QHWQEECEWDPWTCDHMPSK | 115 |
| NVRQEKCEWDPWTCEHMPVR | 116 |
| KSGQVECNWDPWTCEHMPRN | 117 |
| VKTQEHCDWDPWTCEHMREW | 118 |
| AWGQEGCDWDPWTCEHMLPM | 119 |
| PVNQEDCEWDPWTCEHMPPM | 120 |

TABLE 7-continued

Ang-2 binding peptide sequences

| SEQUENCE | SEQ ID NO. |
|---|---|
| RAPQEDCEWDPWTCAHMDIK | 121 |
| HGQNMECEWDPWTCEHMFRY | 122 |
| PRLQEECVWDPWTCEHMPLR | 123 |
| RTTQEKCEWDPWTCEHMESQ | 124 |
| QTSQEDCVWDPWTCDHMVSS | 125 |
| QVIGRPCEWDPWTCEHLEGL | 126 |
| WAQQEECAWDPWTCDHMVGL | 127 |
| LPGQEDCEWDPWTCEHMVRS | 128 |
| PMNQVECDWDPWTCEHMPRS | 129 |
| FGWSHGCEWDPWTCEHMGST | 130 |
| KSTQDDCDWDPWTCEHMVGP | 131 |
| GPRISTCQWDPWTCEHMDQL | 132 |
| STIGDMCEWDPWTCAHMQVD | 133 |
| VLGGQGCEWDPWTCRLLQGW | 134 |
| VLGGQGCQWDPWTCSHLEDG | 135 |
| TTIGSMCEWDPWTCAHMQGG | 136 |
| TKGKSVCQWDPWTCSHMQSG | 137 |
| TTIGSMCQWDPWTCAHMQGG | 138 |
| WVNEVVCEWDPWTCNHWDTP | 139 |
| VVQVGMCQWDPWTCKHMRLQ | 140 |
| AVGSQTCEWDPWTCAHLVEV | 141 |
| QGMKMFCEWDPWTCAHIVYR | 142 |
| TTIGSMCQWDPWTCEHMQGG | 143 |
| TSQRVGCEWDPWTCQHLTYT | 144 |
| QWSWPPCEWDPWTCQTVWPS | 145 |
| GTSPSFCQWDPWTCSHMVQG | 146 |
| QEECEWDPWTCEHM | 147 |
| QNYKPLDELDATLYEHFIFHYT | 148 |
| LNFTPLDELEQTLYEQWTLQQS | 149 |
| TKFNPLDELEQTLYEQWTLQHQ | 150 |
| VKFKPLDALEQTLYEHWMFQQA | 151 |
| VKYKPLDELDEILYEQQTFQER | 152 |
| TNFMPMDDLEQRLYEQFILQQG | 153 |
| SKFKPLDELEQTLYEQWTLQHA | 154 |
| QKFQPLDELEQTLYEQFMLQQA | 155 |
| QNFKPMDELEDTLYKQFLFQHS | 156 |
| YKFTPLDDLEQTLYEQWTLQHV | 157 |
| QEYEPLDELDETLYNQWMFHQR | 158 |

TABLE 7-continued

Ang-2 binding peptide sequences

| SEQUENCE | SEQ ID NO. |
|---|---|
| SNFMPLDELEQTLYEQFMLQHQ | 159 |
| QKYQPLDELDKTLYDQFMLQQG | 160 |
| QKFQPLDELEETLYKQWTLQQR | 161 |
| VKYKPLDELDEWLYHQFTLHHQ | 162 |
| QKFMPLDELDEILYEQFMQQS | 163 |
| QTFQPLDDEEYLYEQWIRRYH | 164 |
| EDYMPLDALDAQLYEQFILLHG | 165 |
| HTFQPLDELEETLYYQWLYDQL | 166 |
| YKFNPMDELEQTLYEEFLFQHA | 167 |
| TNYKPLDELDATLYEHWILQHS | 168 |
| QKFKPLDELEQTLYEQWTLQQR | 169 |
| TKFQPLDELDQTLYEQWTLQQR | 170 |
| TNFQPLDELDQTLYEQWTLQQR | 171 |
| KFNPLDELEETLYEQFTFQQ | 172 |
| AGGMRPYDGMLGWPNYDVQA | 173 |
| QTWDDPCMHILGPVTWRRCI | 174 |
| APGQRPYDGMLGWPTYQRIV | 175 |
| SGQLRPCEEIFGCGTQNLAL | 176 |
| FGDKRPLECMFGGPIQLCPR | 177 |
| GQDLRPCEDMFGCGTKDWYG | 178 |
| KRPCEEIFGGCTYQ | 179 |
| GFEYCDGMEDPFTFGCDKQT | 180 |
| KLEYCDGMEDPFTQGCDNQS | 181 |
| LQEWCEGVEDPFTFGCEKQR | 182 |
| AQDYCEGMEDPFTFGCEMQK | 183 |
| LLDYCEGVQDPFTFGCENLD | 184 |
| HQEYCEGMEDPFTFGCEYQG | 185 |
| MLDYCEGMDDPFTFGCDKQM | 186 |
| LQDYCEGVEDPFTFGCENQR | 187 |
| LQDYCEGVEDPFTFGCEKQR | 188 |
| FDYCEGVEDPFTFGCDNH | 189 |

TABLE 8

NGF-Binding Peptide Sequences

| SEQUENCE | SEQ ID NO. |
|---|---|
| TGYTEYTEEWPMGFGYQWSF | 190 |
| TDWLSDFPFYEQYFGLMPPG | 191 |
| FMRFPNPWKLVEPPQGWYYG | 192 |

TABLE 8-continued

NGF-Binding Peptide Sequences

| SEQUENCE | SEQ ID NO. |
|---|---|
| VVKAPHFEFLAPPHFHEFPF | 193 |
| FSYIWIDETPSNIDRYMLWL | 194 |
| VNFPKVPEDVEPWPWSLKLY | 195 |
| TWHPKTYEEFALPFFVPEAP | 196 |
| WHFGTPYIQQQPGVYWLQAP | 197 |
| VWNYGPFFMNFPDSTYFLHE | 198 |
| WRIHSKPLDYSHVWFFPADF | 199 |
| FWDGNQPPDILVDWPWNPPV | 200 |
| FYSLEWLKDHSEFFQTVTEW | 201 |
| QFMELLKFFNSPGDSSHHFL | 202 |
| TNVDWISNNWEHMKSFFTED | 203 |
| PNEKPYQMQSWFPPDWPVPY | 204 |
| WSHTEWVPQVWWKPPNHFYV | 205 |
| WGEWINDAQVHMHEGFISES | 206 |
| VPWEHDHDLWEIISQDWHIA | 207 |
| VLHLQDPRGWSNFPPGVLEL | 208 |
| IHGCWFTEEGCVWQ | 209 |
| YMQCQFARDGCPQW | 210 |
| KLQCQYSESGCPTI | 211 |
| FLQCEISGGACPAP | 212 |
| KLQCEFSTSGCPDL | 213 |
| KLQCEFSTQGCPDL | 214 |
| KLQCEFSTSGCPWL | 215 |
| IQGCWFTEEGCPWQ | 216 |
| SFDCDNPWGHVLQSCFGF | 217 |
| SFDCDNPWGHKLQSCFGF | 218 |

TABLE 9

Myostatin binding peptide or polypeptide sequences

| SEQUENCE | SEQ ID NO: |
|---|---|
| KDKCKMWHWMCKPP | 616 |
| KDLCAMWHWMCKPP | 219 |
| KDLCKMWKWMCKPP | 220 |
| KDLCKMWHWMCKPK | 221 |
| WYPCYEFHFWCYDL | 222 |
| WYPCYEGHFWCYDL | 223 |
| IFGCKWWDVQCYQF | 224 |

TABLE 9-continued

| Myostatin binding peptide or polypeptide sequences | |
|---|---|
| SEQUENCE | SEQ ID NO: |
| IFGCKWWDVDCYQF | 225 |
| ADWCVSPNWFCMVM | 226 |
| HKFCPWWALFCWDF | 227 |
| KDLCKMWHWMCKPP | 228 |
| IDKCAIWGWMCPPL | 229 |
| WYPCGEFGMWCLNV | 230 |
| WFTCLWNCDNE | 231 |
| HTPCPWFAPLCVEW | 232 |
| KEWCWRWKWMCKPE | 233 |
| FETCPSWAYFCLDI | 234 |
| AYKCEANDWGCWWL | 235 |
| NSWCEDQWHRCWWL | 236 |
| WSACYAGHFWCYDL | 237 |
| ANWCVSPNWFCMVM | 238 |
| WTECYQQEFWCWNL | 239 |
| ENTCERWKWMCPPK | 240 |
| WLPCHQEGFWCMNF | 241 |
| STMCSQWHWMCNPF | 242 |
| IFGCHWWDVDCYQF | 243 |
| IYGCKWWDIQCYDI | 244 |
| PDWCIDPDWWCKFW | 245 |
| QGHCTRWPWMCPPY | 246 |
| WQECYREGFWCLQT | 247 |
| WFDCYGPGFKCWSP | 248 |
| GVRCPKGHLWCLYP | 249 |
| HWACGYWPWSCKWV | 250 |
| GPACHSPWWWCVFG | 251 |
| TTWCISPMWFCSQQ | 252 |
| HKFCPPWAIFCWDF | 253 |
| PDWCVSPRWYCNMW | 254 |
| VWKCHWFGMDCEPT | 255 |
| KKHCQIWTWMCAPK | 256 |
| WFQCGSTLFWCYNL | 257 |
| WSPCYDHYFYCYTI | 258 |
| SWMCGFFKEVCMWV | 259 |
| EMLCMIHPVFCNPH | 260 |
| LKTCNLWPWMCPPL | 261 |

TABLE 9-continued

| Myostatin binding peptide or polypeptide sequences | |
|---|---|
| SEQUENCE | SEQ ID NO: |
| VVGCKWYEAWCYNK | 262 |
| PIHCTQWAWMCPPT | 263 |
| DSNCPWYFLSCVIF | 264 |
| HIWCNLAMMKCVEM | 265 |
| NLQCIYFLGKCIYF | 266 |
| AWRCMWFSDVCTPG | 267 |
| WFRCFLDADWCTSV | 268 |
| EKICQMWSWMCAPP | 269 |
| WFYCHLNKSECTEP | 270 |
| FWRCAIGIDKCKRV | 271 |
| NLGCKWYEVWCFTY | 272 |
| IDLCNMWDGMCYPP | 273 |
| EMPCNIWGWMCPPV | 274 |
| WFRCVLTGIVDWSECFGL | 275 |
| GFSCTFGLDEFYVDCSPF | 276 |
| LPWCHDQVNADWGFCMLW | 277 |
| YPTCSEKFWIYGQTCVLW | 278 |
| LGPCPIHHGPWPQYCVYW | 279 |
| PFPCETHQISWLGHCLSF | 280 |
| HWGCEDLMWSWHPLCRRP | 281 |
| LPLCDADMMPTIGFCVAY | 282 |
| SHWCETTFWMNYAKCVHA | 283 |
| LPKCTHVPFDQGGFCLWY | 284 |
| FSSCWSPVSRQDMFCVFY | 285 |
| SHKCEYSGWLQPLCYRP | 286 |
| PWWCQDNYVQHMLHCDSP | 287 |
| WFRCMLMNSFDAFQCVSY | 288 |
| PDACRDQPWYMFMGCMLG | 289 |
| FLACFVEFELCFDS | 290 |
| SAYCIITESDPYVLCVPL | 291 |
| PSICESYSTMWLPMCQHN | 292 |
| WLDCHDDSWAWTKMCRSH | 293 |
| YLNCVMMNTSPFVECVFN | 294 |
| YPWCDGFMIQQGITCMFY | 295 |
| FDYCTWLNGFKDWKCWSR | 296 |
| LPLCNLKEISHVQACVLF | 297 |
| SPECAFARWLGIEQCQRD | 298 |
| YPQCFNLHLLEWTECDWF | 299 |

TABLE 9-continued

Myostatin binding peptide or polypeptide sequences

| SEQUENCE | SEQ ID NO: |
|---|---|
| RWRCEIYDSEFLPKCWFF | 300 |
| LVGCDNVWHRCKLF | 301 |
| AGWCHVWGEMFGMGCSAL | 302 |
| HHECEWMARWMSLDCVGL | 303 |
| FPMCGIAGMKDFDFCVWY | 304 |
| RDDCTFWPEWLWKLCERP | 305 |
| YNFCSYLFGVSKEACQLP | 306 |
| AHWCEQGPWRYGNICMAY | 307 |
| NLVCGKISAWGDEACARA | 308 |
| HNVCTIMGPSMKWFCWND | 309 |
| NDLCAMWGWRNTIWCQNS | 310 |
| PPFCQNDNDMLQSLCKLL | 311 |
| WYDCNVPNELLSGLCRLF | 312 |
| YGDCDQNHWMWPFTCLSL | 313 |
| GWMCHFDLHDWGATCQPD | 314 |
| YFHCMFGGHEFEVHCESF | 315 |
| AYWCWHGQCVRF | 316 |
| SEHWTFTDWDGNEWWVRPF | 317 |
| MEMLDSLFELLKDMVPISKA | 318 |
| SPPEEALMEWLGWQYGKFT | 319 |
| SPENLLNDLYILMTKQEWYG | 320 |
| FHWEEGIPFHVVTPYSYDRM | 321 |
| KRLLEQFMNDLAELVSGHS | 322 |
| DTRDALFQEFYEFVRSRLVI | 323 |
| RMSAAPRPLTYRDIMDQYWH | 324 |
| NDKAHFFEMFMFDVHNFVES | 325 |
| QTQAQKIDGLWELLQSIRNQ | 326 |
| MLSEFEEFLGNLVHRQEA | 327 |
| YTPKMGSEWTSFWHNRIHYL | 328 |
| LNDTLLRELKMVLNSLSDMK | 329 |
| FDVERDLMRWLEGFMQSAAT | 330 |
| HHGWNYLRKGSAPQWFEAWV | 331 |
| VESLHQLQMWLDQKLASGPH | 332 |
| RATLLKDFWQLVEGYGDN | 333 |
| EELLREFYRFVSAFDY | 334 |
| GLLDEFSHFIAEQFYQMPGG | 335 |
| YREMSMLEGLLDVLERLQHY | 336 |
| HNSSQMLLSELIMLVGSMMQ | 337 |
| WREHFLNSDYIRDKLIAIDG | 338 |
| QFPFYVFDDLPAQLEYWIA | 339 |
| EFFHWLHNHRSEVNHWLDMN | 340 |
| EALFQNFFRDVLTLSEREY | 341 |
| QYWEQQWMTYFRENGLHVQY | 342 |
| NQRMMLEDLWRIMTPMFGRS | 343 |
| FLDELKAELSRHYALDDLDE | 344 |
| GKLIEGLLNELMQLETFMPD | 345 |
| ILLLDEYKKDWKSWF | 346 |
| QGHCTRWPWMCPPYGSGSATGGSGSTAS SGSGSATGQGHCTRWPWMCPPY | 347 |
| WYPCYEGHFWCYDLGSGSTASSGSGSAT GWYPCYEGHFWCYDL | 348 |
| HTPCPWFAPLCVEWGSGSATGGSGSTAS SGSGSATGHTPCPWFAPLCVEW | 349 |
| PDWCIDPDWWCKFWGSGSATGGSGSTA SSGSGSATGPDWCIDPDWWCKFW | 350 |
| ANWCVSPNWFCMVMGSGSATGGSGSTA SSGSGSATGANWCVSPNWFCMVM | 351 |
| PDWCIDPDWWCKFWGSGSATGGSGSTA SSGSGSATGPDWCIDPDWWCKFW | 352 |
| HWACGYWPWSCKWVGSGSATGGSGST ASSGSGSATGHWACGYWPWSCKWV | 353 |
| KKHCQIWTWMCAPKGSGSATGGSGSTAS SGSGSATGQGHCTRWPWMCPPY | 354 |
| QGHCTRWPWMCPPYGSGSATGGSGSTAS SGSGSATGKKHCQIWTWMCAPK | 355 |
| KKHCQIWTWMCAPKGSGSATGGSGSTAS SGSGSATGQGHCTRWPWMCPPY | 356 |
| KKHCQIWTWMCAPKGGGGGGGGQGHC TRWPWMCPPY | 357 |
| QGHCTRWPWMCPPYGGGGGGKKHCQI WTWMCAPK | 358 |
| VALHGQCTRWPWMCPPQREG | 359 |
| YPEQGLCTRWPWMCPPQTLA | 360 |
| GLNQGHCTRWPWMCPPQDSN | 361 |
| MITQGQCTRWPWMCPPQPSG | 362 |
| AGAQEHCTRWPWMCAPNDWI | 363 |
| GVNQGQCTRWRWMCPPNGWE | 364 |
| LADHGQCIRWPWMCPPEGWE | 365 |
| ILEQAQCTRWPWMCPPQRGG | 366 |
| TQTHAQCTRWPWMCPPQWEG | 367 |
| VVTQGHCTLWPWMCPPQRWR | 368 |

TABLE 9-continued

Myostatin binding peptide or polypeptide sequences

| SEQUENCE | SEQ ID NO: |
|---|---|
| IYPHDQCTRWPWMCPPQPYP | 369 |
| SYWQGQCTRWPWMCPPQWRG | 370 |
| MWQQGHCTRWPWMCPPQGWG | 371 |
| EFTQWHCTRWPWMCPPQRSQ | 372 |
| LDDQWQCTRWPWMCPPQGFS | 373 |
| YQTQGLCTRWPWMCPPQSQR | 374 |
| ESNQGQCTRWPWMCPPQGGW | 375 |
| WTDRGPCTRWPWMCPPQANG | 376 |
| VGTQGQCTRWPWMCPPYETG | 377 |
| PYEQGKCTRWPWMCPPYEVE | 378 |
| SEYQGLCTRWPWMCPPQGWK | 379 |
| TFSQGHCTRWPWMCPPQGWG | 380 |
| PGAHDHCTRWPWMCPPQSRY | 381 |
| VAEEWHCRRWPWMCPPQDWR | 382 |
| VGTQGHCTRWPWMCPPQPAG | 383 |
| EEDQAHCRSWPWMCPPQGWV | 384 |
| ADTQGHCTRWPWMCPPQHWF | 385 |
| SGPQGHCTRWPWMCAPQGWF | 386 |
| TLVQGHCTRWPWMCPPQRWV | 387 |
| GMAHGKCTRWAWMCPPQSWK | 388 |
| ELYHGQCTRWPWMCPPQSWA | 389 |
| VADHGHCTRWPWMCPPQGWG | 390 |
| PESQGHCTRWPWMCPPQGWG | 391 |
| IPAHGHCTRWPWMCPPQRWR | 392 |
| FTVHGHCTRWPWMCPPYGWV | 393 |
| PDFPGHCTRWRWMCPPQGWE | 394 |
| QLWQGPCTQWPWMCPPKGRY | 395 |
| HANDGHCTRWQWMCPPQWGG | 396 |
| ETDHGLCTRWPWMCPPYGAR | 397 |
| GTWQGLCTRWPWMCPPQGWQ | 398 |
| VATQGQCTRWPWMCPPQGWG | 399 |
| VATQGQCTRWPWMCPPQRWG | 400 |
| QREWYPCYGGHLWCYDLHKA | 401 |
| ISAWYSCYAGHFWCWDLKQK | 402 |
| WTGWYQCYGGHLWCYDLRRK | 403 |
| KTFWYPCYDGHFWCYNLKSS | 404 |
| ESRWYPCYEGHLWCFDLTET | 405 |
| MEMLDSLFELLKDMVPISKA | 406 |
| RMEMLESLLELLKEIVPMSKAG | 407 |
| RMEMLESLLELLKEIVPMSKAR | 408 |
| RMEMLESLLELLKDIVPMSKPS | 409 |
| GMEMLESLFELLQEIVPMSKAP | 410 |
| RMEMLESLLELLKDIVPISNPP | 411 |
| RIEMLESLLELLQEIVPISKAE | 412 |
| RMEMLQSLLELLKDIVPMSNAR | 413 |
| RMEMLESLLELLKEIVPTSNGT | 414 |
| RMEMLESLFELLKEIVPMSKAG | 415 |
| RMEMLGSLLELLKEIVPMSKAR | 416 |
| QMELLDSLFELLKEIVPKSQPA | 417 |
| RMEMLDSLLELLKEIVPMSNAR | 418 |
| RMEMLESLLELLHEIVPMSQAG | 419 |
| QMEMLESLLQLLKEIVPMSKAS | 420 |
| RMEMLDSLLELLKDMVPMTTGA | 421 |
| RIEMLESLLELLKDMVPMANAS | 422 |
| RMEMLESLLQLLNEIVPMSRAR | 423 |
| RMEMLESLFDLLKELVPMSKGV | 424 |
| RIEMLESLLELLKDIVPIQKAR | 425 |
| RMELLESLFELLKDMVPMSDSS | 426 |
| RMEMLESLLEVLQEIVPRAKGA | 427 |
| RMEMLDSLLQLLNEIVPMSHAR | 428 |
| RMEMLESLLELLKDIVPMSNAG | 429 |
| RMEMLQSLFELLKGMVPISKAG | 430 |
| RMEMLESLLELLKEIVPNSTAA | 431 |
| RMEMLQSLLELLKEIVPISKAG | 432 |
| RIEMLDSLLELLNELVPMSKAR | 433 |
| HHGWNYLRKGSAPQWFEAWV | 434 |
| QVESLQQLLMWLDQKLASGPQG | 435 |
| RMELLESLFELLKEMVPRSKAV | 436 |
| QAVSLQHLLMWLDQKLASGPQH | 437 |
| DEDSLQQLLMWLDQKLASGPQL | 438 |
| PVASLQQLLIWLDQKLAQGPHA | 439 |
| EVDELQQLLNWLDHKLASGPLQ | 440 |
| DVESLEQLLMWLDHQLASGPHG | 441 |
| QVDSLQQVLLWLEHKLALGPQV | 442 |
| GDESLQHLLMWLEQKLALGPHG | 443 |

TABLE 9-continued

| Myostatin binding peptide or polypeptide sequences | |
|---|---|
| SEQUENCE | SEQ ID NO: |
| QIEMLESLLDLLRDMVPMSNAF | 444 |
| EVDSLQQLLMWLDQKLASGPQA | 445 |
| EDESLQQLLIYLDKMLSSGPQV | 446 |
| AMDQLHQLLIWLDHKLASGPQA | 447 |
| RIEMLESLLELLDEIALIPKAW | 448 |
| EVVSLQHLLMWLEHKLASGPDG | 449 |
| GGESLQQLLMWLDQQLASGPQR | 450 |
| GVESLQQLLIFLDHMLVSGPHD | 451 |
| NVESLEHLMMWLERLLASGPYA | 452 |
| QVDSLQQLLIWLDHQLASGPKR | 453 |
| EVESLQQLLMWLEHKLAQGPQG | 454 |
| EVDSLQQLLMWLDQKLASGPHA | 455 |
| EVDSLQQLLMWLDQQLASGPQK | 456 |
| GVEQLPQLLMWLEQKLASGPQR | 457 |
| GEDSLQQLLMWLDQQLAAGPQV | 458 |
| ADDSLQQLLMWLDRKLASGPHV | 459 |
| PVDSLQQLLIWLDQKLASGPQG | 460 |
| RATLLKDFWQLVEGYGDN | 461 |
| DWRATLLKEFWQLVEGLGDNLV | 462 |
| QSRATLLKEFWQLVEGLGDKQA | 463 |
| DGRATLLTEFWQLVQGLGQKEA | 464 |
| LARATLLKEFWQLVEGLGEKVV | 465 |
| GSRDTLLKEFWQLVVGLGDMQT | 466 |
| DARATLLKEFWQLVDAYGDRMV | 467 |
| NDRAQLLRDFWQLVDGLGVKSW | 468 |
| GVRETLLYELWYLLKGLGANQG | 469 |
| QARATLLKEFCQLVGCQGDKLS | 470 |
| QERATLLKEFWQLVAGLGQNMR | 471 |
| SGRATLLKEFWQLVQGLGEYRW | 472 |
| TMRATLLKEFWLFVDGQREMQW | 473 |
| GERATLLNDFWQLVDGQGDNTG | 474 |
| DERETLLKEFWQLVHGWGDNVA | 475 |
| GGRATLLKELWQLLEGQGANLV | 476 |
| TARATLLNELVQLVKGYGDKLV | 477 |
| GMRATLLQEFWQLVGGQGDNWM | 478 |
| STRATLLNDLWQLMKGWAEDRG | 479 |
| SERATLLKELWQLVGGWGDNFG | 480 |
| VGRATLLKEFWQLVEGLVGQSR | 481 |
| EIRATLLKEFWQLVDEWREQPN | 482 |
| QLRATLLKEFLQLVHGLGETDS | 483 |
| TQRATLLKEFWQLIEGLGGKHV | 484 |
| HYRATLLKEFWQLVDGLREQGV | 485 |
| QSRVTLLREFWQLVESYRPIVN | 486 |
| LSRATLLNEFWQFVDGQRDKRM | 487 |
| WDRATLLNDFWHLMEELSQKPG | 488 |
| QERATLLKEFWRMVEGLGKNRG | 489 |
| NERATLLREFWQLVGGYGVNQR | 490 |
| YREMSMLEGLLDVLERLQHY | 491 |
| HQRDMSMLWELLDVLDGLRQYS | 492 |
| TQRDMSMLDGLLEVLDQLRQQR | 493 |
| TSRDMSLLWELLEELDRLGHQR | 494 |
| MQHDMSMLYGLVELLESLGHQI | 495 |
| WNRDMRMLESLFEVLDGLRQQV | 496 |
| GYRDMSMLEGLLAVLDRLGPQL | 497 |
| TQRDMSMLEGLLEVLDRLGQQR | 498 |
| WYRDMSMLEGLLEVLDRLGQQR | 499 |
| HNSSQMLLSELIMLVGSMMQ | 500 |
| TQNSRQMLLSDFMMLVGSMIQG | 501 |
| MQTSRHILLSEFMMLVGSIMHG | 502 |
| HDNSRQMLLSDLLHLVGTMIQG | 503 |
| MENSRQNLLRELIMLVGNMSHQ | 504 |
| QDTSRHMLLREFMMLVGEMIQG | 505 |
| DQNSRQMLLSDLMILVGSMIQG | 506 |
| EFFHWLHNHRSEVNHWLDMN | 507 |
| NVFFQWVQKHGRVVYQWLDINV | 508 |
| FDFLQWLQNHRSEVEHWLVMDV | 509 |

TABLE 10

| BAFF binding peptide sequences | |
|---|---|
| SEQUENCE | SEQ ID NO: |
| PGTCFPFPWECTHA | 510 |
| WGACWPFPWECFKE | 511 |
| VPFCDLLTKHCFEA | 512 |
| GSRCKYKWDVLTKQCFHH | 513 |

TABLE 10-continued

BAFF binding peptide sequences

| SEQUENCE | SEQ ID NO: |
|---|---|
| LPGCKWDLLIKQWVCDPL | 514 |
| SADCYFDILTKSDVCTSS | 515 |
| SDDCMYDQLTRMFICSNL | 516 |
| DLNCKYDELTYKEWCQFN | 517 |
| FHDCKYDLLTRQMVCHGL | 518 |
| RNHCFWDHLLKQDICPSP | 519 |
| ANQCWWDSLTKKNVCEFF | 520 |
| YKGRQQMWDILTRSWVVSL | 521 |
| QQDVGLWWDILTRAWMPNI | 522 |
| QQNAQRVWDLLIRTWVYPQ | 523 |
| GWNEAWWDELTKIWVLEQQ | 524 |
| RITCDTWDSLIKKCVPQQS | 525 |
| GAIMQQFWDSLTKTWLRQS | 526 |
| WLHSGWWDPLTKHWLQQKV | 527 |
| SEWFFWFDPLTRAQQLKFR | 528 |
| GVWFWWFDPLTKQWTQQAG | 529 |
| MQQCKGYYDILTKWCVTNG | 530 |
| LWSKEVWDILTKSWVSQQA | 531 |
| KAAGWWFDWLTKVWVPAP | 532 |
| AYQQTWFWDSLTRLWLSTT | 533 |
| SGQQHFWWDLLTRSWTPST | 534 |
| LGVGQQKWDPLTKQWVSRG | 535 |
| VGKMCQQWDPLIKRTVCVG | 536 |
| CRQGAKFDLLTKQCLLGR | 537 |
| GQAIRHWDVLTKQWVDSQQ | 538 |
| RGPCGSWDLLTKHCLDSQQ | 539 |
| WQWKQQQWDLLTKQMVWVG | 540 |
| PITICRKDLLTKQVVCLD | 541 |
| KTCNGKWDLLTKQCLQQQA | 542 |
| KCLKGKWDLLTKQCVTEV | 543 |
| RCWNGKWDLLTKQCIHPW | 544 |
| NRDMRKWDPLIKQWIVRP | 545 |
| QQAAAATWDLLTKQWLVPP | 546 |
| PEGGPKWDPLTKQQFLPPV | 547 |
| QQTPQQKKWDLLTKQWFTRN | 548 |
| IGSPCKWDLLTKQMICQQT | 549 |
| CTAAGKWDLLTKQCIQQEK | 550 |
| VSQCMKWDLLTKQCLQQGW | 551 |
| VWGTWKWDLLTKQYLPPQQ | 552 |
| GWWEMKWDLLTKQWYRPQQ | 553 |
| TAQQVSKWDLLTKQWLPLA | 554 |
| QLWGTKWDLLTKQYIQQIM | 555 |
| WATSQKWDLLTKQWVQQNM | 556 |
| QQRQCAKWDLLTKQCVLFY | 557 |
| KTTDCKWDLLTKQRICQQV | 558 |
| LLCQQGKWDLLTKQCLKLR | 559 |
| LMWFWKWDLLTKQLVPTF | 560 |
| QQTWAWKWDLLTKQWIGPM | 561 |
| NKELLKWDLLTKQCRGRS | 562 |
| GQQKDLKWDLLTKQYVRQS | 563 |
| PKPCQQKWDLLTKQCLGSV | 564 |
| GQIGWKWDLLTKQWIQQTR | 565 |
| VWLDWKWDLLTKQWIHPQQ | 566 |
| QQEWEYKWDLLTKQWGWLR | 567 |
| HWDSWKWDLLTKQWVVQQA | 568 |
| TRPLQQKWDLLTKQWLRVG | 569 |
| SDQWQQKWDLLTKQWFWDV | 570 |
| QQQTFMKWDLLTKQWIRRH | 571 |
| QQGECRKWDLLTKQCFPGQ | 572 |
| GQQMGWRWDPLIKMCLGPS | 573 |
| QQLDGCKWDLLTKQKVCIP | 574 |
| HGYWQQKWDLLTKQWVSSE | 575 |
| HQQGQCGWDLLTRIYLPCH | 576 |
| LHKACKWDLLTKQCWPMQQ | 577 |
| GPPGSVWDLLTKIWIQQTG | 578 |
| ITQQDWRFDTLTRLWLPLR | 579 |
| QQGGFAAWDVLTKMWITVP | 580 |
| GHGTPWWDALTRIWILGV | 581 |
| VWPWQQKWDLLTKQFVFQD | 582 |
| WQQWSWKWDLLTRQYISSS | 583 |
| NQQTLWKWDLLTKQFITYM | 584 |
| PVYQQGWWDTLTKLYIWDG | 585 |
| WLDGGWRDPLIKRSVQQLG | 586 |
| GHQQQFKWDLLTKQWVQSN | 587 |
| QQRVGQFWDVLTKMFITGS | 588 |
| QQAQGWSYDALIKTWIRWP | 589 |

TABLE 10-continued

BAFF binding peptide sequences

| SEQUENCE | SEQ ID NO: |
|---|---|
| GWMHWKWDPLTKQQALPWM | 590 |
| GHPTYKWDLLTKQWILQQM | 591 |
| WNNWSLWDPLTKLWLQQQN | 592 |
| WQWGWKWDLLTKQWVQQQ | 593 |
| GQMGWRWDPLTKMWLGTS | 594 |

In addition to peptides and polypeptides having amino acid sequences set forth in Tables 5-10, polypeptides that can be useful in accordance with the invention include the Ang-2 binding polypeptide having amino acid sequence SEQ ID NO: 612:

```
                                              SEQ ID NO: 612
Met Asp Lys Thr His Thr Cys Pro Pro Cys Pro Ala Pro Glu Leu Leu Gly Gly Pro

Ser Val Phe Leu Phe Pro Pro Lys Pro Lys Asp Thr Leu Met Ile Ser Arg Thr Pro

Glu Val Thr Cys Val Val Val Asp Val Ser His Glu Asp Pro Glu Val Lys Phe Asn

Trp Tyr Val Asp Gly Val Glu Val His Asn Ala Lys Thr Lys Pro Arg Glu Glu Gln

Tyr Asn Ser Thr Tyr Arg Val Val Ser Val Leu Thr Val Leu His Gln Asp Trp Leu

Asn Gly Lys Glu Tyr Lys Cys Lys Val Ser Asn Lys Ala Leu Pro Ala Pro Ile Glu

Lys Thr Ile Ser Lys Ala Lys Gly Gln Pro Arg Glu Pro Gln Val Tyr Thr Leu Pro

Pro Ser Arg Asp Glu Leu Gly Gly Gln Glu Glu Cys Glu Trp Asp Pro Trp Thr Cys

Glu His Met Gly Gly Thr Lys Asn Gln Val Ser Leu Thr Cys Leu Val Lys Gly Phe

Tyr Pro Ser Asp Ile Ala Val Glu Trp Glu Ser Asn Gly Gln Pro Glu Asn Asn Tyr

Lys Thr Thr Pro Pro Val Leu Asp Ser Asp Gly Ser Phe Phe Leu Tyr Ser Lys Leu

Thr Val Asp Lys Ser Arg Trp Gln Gln Gly Asn Val Phe Ser Cys Ser Val Met His

Glu Ala Leu His Asn His Tyr Thr Gln Lys Ser Leu Ser Leu Ser Pro Gly Lys//;
```

And the myostatin binding polypeptide having amino acid sequence SEQ ID NO: 613:

```
                                              SEQ ID NO: 613
Met Asp Lys Thr His Thr Cys Pro Pro Cys Pro Ala Pro Glu Leu Leu

Gly Gly Pro Ser Val Phe Leu Phe Pro Pro Lys Pro Lys Asp Thr Leu

Met Ile Ser Arg Thr Pro Glu Val Thr Cys Val Val Val Asp Val Ser

His Glu Asp Pro Glu Val Lys Phe Asn Trp Tyr Val Asp Gly Val Glu

Val His Asn Ala Lys Thr Lys Pro Arg Glu Glu Gln Tyr Asn Ser Thr

Tyr Arg Val Val Ser Val Leu Thr Val Leu His Gln Asp Trp Leu Asn

Gly Lys Glu Tyr Lys Cys Lys Val Ser Asn Lys Ala Leu Pro Ala Pro

Ile Glu Lys Thr Ile Ser Lys Ala Lys Gly Gln Pro Arg Glu Pro Gln

Val Tyr Thr Leu Pro Pro Ser Arg Asp Glu Leu Gly Gly Leu Ala Asp

His Gly Gln Cys Ile Arg Trp Pro Trp Met Cys Pro Pro Glu Gly Trp

Glu Gly Gly Thr Lys Asn Gln Val Ser Leu Thr Cys Leu Val Lys Gly

Phe Tyr Pro Ser Asp Ile Ala Val Glu Trp Glu Ser Asn Gly Gln Pro

Glu Asn Asn Tyr Lys Thr Thr Pro Pro Val Leu Asp Ser Asp Gly Ser

Phe Phe Leu Tyr Ser Lys Leu Thr Val Asp Lys Ser Arg Trp Gln Gln
```

Gly Asn Val Phe Ser Cys Ser Val Met His Glu Ala Leu His Asn His

Tyr Thr Gln Lys Ser Leu Ser Leu Ser Pro Gly Lys//;

And the EPO-mimetic polypeptide having amino acid sequence SEQ ID NO: 614:

SEQ ID NO: 614
Met Asp Lys Thr His Thr Cys Pro Pro Cys Pro Ala Pro Glu Leu Leu

Gly Gly Pro Ser Val Phe Leu Phe Pro Pro Lys Pro Lys Asp Thr Leu

Met Ile Ser Arg Thr Pro Glu Val Thr Cys Val Val Val Asp Val Ser

His Glu Asp Pro Glu Val Lys Phe Asn Trp Tyr Val Asp Gly Val Glu

Val His Asn Ala Lys Thr Lys Pro Arg Glu Glu Gln Tyr Asn Ser Thr

Tyr Arg Val Val Ser Val Leu Thr Val Leu His Gln Asp Trp Leu Asn

Gly Lys Glu Tyr Lys Cys Lys Val Ser Asn Lys Ala Leu Pro Ala Pro

Ile Glu Lys Thr Ile Ser Lys Ala Lys Gly Gln Pro Arg Glu Pro Gln

Val Tyr Thr Leu Pro Pro Ser Arg Asp Glu Leu Gly Gly Gly Gly Thr

Tyr Ser Cys His Phe Gly Pro Leu Thr Trp Val Cys Lys Pro Gln Gly

Gly Gly Gly Thr Lys Asn Gln Val Ser Leu Thr Cys Leu Val Lys Gly

Phe Tyr Pro Ser Asp Ile Ala Val Glu Trp Glu Ser Asn Gly Gln Pro

Glu Asn Asn Tyr Lys Thr Thr Pro Pro Val Leu Asp Ser Asp Gly Ser

Phe Phe Leu Tyr Ser Lys Leu Thr Val Asp Lys Ser Arg Trp Gln Gln

Gly Asn Val Phe Ser Cys Ser Val Met His Glu Ala Leu His Asn His Tyr Thr Gln

Lys Ser Leu Ser Leu Ser Pro Gly Lys//;

And the TPO-mimetic polypeptide having amino acid sequence SEQ ID NO: 615:

SEQ ID NO: 615
Met Asp Lys Thr His Thr Cys Pro Pro Cys Pro Ala Pro Glu Leu Leu

Gly Gly Pro Ser Val Phe Leu Phe Pro Pro Lys Pro Lys Asp Thr Leu

Met Ile Ser Arg Thr Pro Glu Val Thr Cys Val Val Val Asp Val Ser

His Glu Asp Pro Glu Val Lys Phe Asn Trp Tyr Val Asp Gly Val Glu

Val His Asn Ala Lys Thr Lys Pro Arg Glu Glu Gln Tyr Asn Ser Thr

Tyr Arg Val Val Ser Val Leu Thr Val Leu His Gln Asp Trp Leu Asn

Gly Lys Glu Tyr Lys Cys Lys Val Ser Asn Lys Ala Leu Pro Ala Pro

Ile Glu Lys Thr Ile Ser Lys Ala Lys Gly Gln Pro Arg Glu Pro Gln

Val Tyr Thr Leu Pro Pro Ser Arg Asp Glu Leu Gly Gly Ile Glu Gly

Pro Thr Leu Arg Gln Trp Leu Ala Ala Arg Ala Gly Gly Thr Lys Asn

Gln Val Ser Leu Thr Cys Leu Val Lys Gly Phe Tyr Pro Ser Asp Ile

Ala Val Glu Trp Glu Ser Asn Gly Gln Pro Glu Asn Asn Tyr Lys Thr

Thr Pro Pro Val Leu Asp Ser Asp Gly Ser Phe Phe Leu Tyr Ser Lys

Leu Thr Val Asp Lys Ser Arg Trp Gln Gln Gly Asn Val Phe Ser Cys

Ser Val Met His Glu Ala Leu His Asn His Tyr Thr Gln Lys Ser Leu

Ser Leu Ser Pro Gly Lys//.

Pharmaceutically acceptable polymers. The invention further embraces molecules covalently modified to include one or more water soluble polymer attachments. Pharmaceutically acceptable polymers useful in accordance with the present invention include, polyethylene glycol, polyoxyethylene glycol, or polypropylene glycol, as described U.S. Pat. Nos. 4,640,835; 4,496,689; 4,301,144; 4,670,417; 4,791,192; and 4,179,337. Still other useful polymers known in the art include, but are not limited to, monomethoxy-polyethylene glycol, dextran, cellulose, or other carbohydrate based polymers (e.g., hydroxypropyl cellulose, hydroxypropyl methylcellulose, hydroxyethyl cellulose), poly-(N-vinyl pyrrolidone)-polyethylene glycol, propylene glycol homopolymers, a polypropylene oxide/ethylene oxide co-polymer, polyoxyethylated polyols (e.g., glycerol) polyvinyl alcohol, polylactic acid, polyglycolic acid, copolymers of ethylene glycol and propylene glycol, carboxymethyl cellulose, dextran, polyvinyl pyrrolidone and polyproline, hyaluronic acid, poly-1,3-dioxolane and poly-1,3,6-tioxocane, pectin, starch, gelatin, as well as mixtures of any of these polymers.

A preferred polymer is polyethylene glycol (PEG). The PEG group may be of any convenient molecular weight and may be linear or branched. The average molecular weight of the PEG will preferably range from about 2 kiloDalton ("kD") to about 100 kD, more preferably from about 5 kDa to about 50 kDa, most preferably from about 5 kD to about 20 kD. The PEG groups will generally be attached to the compounds of the invention via acylation or reductive alkylation through a reactive group on the PEG moiety (e.g., an aldehyde, maleimide, amino, thiol, or ester group) to a reactive group on the inventive compound (e.g., an aldehyde, amino, thiol or ester group).

Covalent conjugation of proteins and peptides with poly(ethylene glycol) (PEG) has been widely recognized as an approach to significantly extend the in vivo circulating half-lives of therapeutic proteins. PEGylation achieves this effect predominately by retarding renal clearance, since the PEG moiety adds considerable hydrodynamic radius to the protein. (Zalipsky, S., et al., Use of functionalized poly(ethylene glycol)s for modification of polypeptides., in poly(ethylene glycol) chemistry: Biotechnical and biomedical applications., J. M. Harris, Ed., Plenum Press: New York., 347-370 (1992)). Additional benefits often conferred by PEGylation of proteins and peptides include increased solubility, resistance to proteolytic degradation, and reduced immunogenicity of the therapeutic polypeptide. The merits of protein PEGylation are evidenced by the commercialization of several PEGylated proteins including PEG-Adenosine deaminase (Adagen™/Enzon Corp.), PEG-L-asparaginase (Oncaspar™/Enzon Corp.), PEG-Interferon α-2b (PEG-Intron™/Schering/Enzon), PEG-Interferon α-2a (PEGASYS™/Roche) and PEG-G-CSF (Neulasta™/Amgen) as well as many others in clinical trials.

Briefly, the PEG groups are generally attached to the peptide portion of the composition of the invention via acylation or reductive alkylation through a reactive group on the PEG moiety (e.g., an aldehyde, amino, thiol, or ester group) to a reactive group on the inventive compound (e.g., an aldehyde, amino, or ester group).

A useful strategy for the PEGylation of synthetic peptides consists of combining, through forming a conjugate linkage in solution, a polypeptide or peptide and a PEG moiety, each bearing a special functionality that is mutually reactive toward the other. The polypeptides or peptides can be easily prepared with conventional solid phase synthesis. The polypeptides or peptides are "preactivated" with an appropriate functional group at a specific site. The precursors are purified and fully characterized prior to reacting with the PEG moiety. Ligation of the polypeptide or peptide with PEG usually takes place in aqueous phase and can be easily monitored by reverse phase analytical HPLC. The PEGylated polypeptides or peptides can be easily purified by preparative HPLC and characterized by analytical HPLC, amino acid analysis and laser desorption mass spectrometry.

PEG is a well-known, water soluble polymer that is commercially available or can be prepared by ring-opening polymerization of ethylene glycol according to methods well known in the art (Sandler and Karo, Polymer Synthesis, Academic Press, New York, Vol. 3, pages 138-161). In the present application, the term "PEG" is used broadly to encompass any polyethylene glycol molecule, in mono-, bi-, or polyfunctional form, without regard to size or to modification at an end of the PEG, and can be represented by the formula:

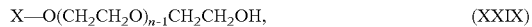
$$X-O(CH_2CH_2O)_{n-1}CH_2CH_2OH, \quad (XXIX)$$

where n is 20 to 2300 and X is H or a terminal modification, e.g., a $C_{1-4}$ alkyl.

In some useful embodiments, a PEG used in the invention terminates on one end with hydroxy or methoxy, i.e., X is H or $CH_3$ ("methoxy PEG"). It is noted that the other end of the PEG, which is shown in formula (II) terminating in OH, covalently attaches to an activating moiety via an ether oxygen bond, an amine linkage, or amide linkage. When used in a chemical structure, the term "PEG" includes the formula (II) above without the hydrogen of the hydroxyl group shown, leaving the oxygen available to react with a free carbon atom of a linker to form an ether bond. More specifically, in order to conjugate PEG to a peptide, the peptide must be reacted with PEG in an "activated" form. Activated PEG can be represented by the formula:

$$(PEG)-(A) \quad (XXX)$$

where PEG (defined supra) covalently attaches to a carbon atom of the activation moiety (A) to form an ether bond, an amine linkage, or amide linkage, and (A) contains a reactive group which can react with an amino, imino, or thiol group on an amino acid residue of a polypeptide, peptide or a linker moiety covalently attached to the peptide portion.

Techniques for the preparation of activated PEG and its conjugation to biologically active peptides are well known in the art. (E.g., see U.S. Pat. Nos. 5,643,575, 5,919,455, 5,932,462, and 5,990,237; Thompson et al., PEGylation of polypeptides, EP 0575545 B1; Petit, Site specific protein modification, U.S. Pat. Nos. 6,451,986, and 6,548,644; S. Herman et al., Poly(ethylene glycol) with reactive endgroups: I. Modification of proteins, J. Bioactive Compatible Polymers, 10:145-187 (1995); Y. Lu et al., Pegylated peptides III: Solid-phase synthesis with PEGylating reagents of varying molecular weight: synthesis of multiply PEGylated peptides, Reactive Polymers, 22:221-229 (1994); A. M. Felix et al., PEGylated Peptides IV: Enhanced biological activity of site-directed PEGylated GRF analogs, Int. J. Peptide Protein Res., 46:253-264 (1995); A. M. Felix, Site-specific poly(ethylene glycol)ylation of peptides, ACS Symposium Series 680(poly (ethylene glycol)): 218-238 (1997); Y. Ikeda et al., Polyethylene glycol derivatives, their modified peptides, methods for producing them and use of the modified peptides, EP 0473084 B1; G. E. Means et al., Selected techniques for the modification of protein side chains, in: Chemical modification of proteins, Holden Day, Inc., 219 (1971)).

Activated PEG, such as PEG-aldehydes or PEG-aldehyde hydrates, can be chemically synthesized by known means or obtained from commercial sources, e.g., Shearwater Polymers, (Huntsville, Ala.) or Enzon, Inc. (Piscataway, N.J.).

An example of a useful activated PEG for purposes of the present invention is a PEG-aldehyde compound (e.g., a methoxy PEG-aldehyde), such as PEG-propionaldehyde, which is commercially available from Shearwater Polymers (Huntsville, Al). PEG-propionaldehyde is represented by the formula PEG-CH$_2$CH$_2$CHO. (See, e.g., U.S. Pat. No. 5,252,714). Other examples of useful activated PEG are PEG acetaldehyde hydrate and PEG bis aldehyde hydrate, which latter yields a bifunctionally activated structure. (See, e.g., Bentley et al., Poly(ethylene glycol) aldehyde hydrates and related polymers and applications in modifying amines, U.S. Pat. No. 5,990,237).

Another useful activated PEG for generating PEG-conjugated polypeptides or peptides of the present invention is a PEG-maleimide compound, such as, but not limited to, a methoxy PEG-maleimide, such as maleimido monomethoxy PEG, are particularly useful for generating the PEG-conjugated peptides of the invention. (E.g., Shen, N-maleimidyl polymer derivatives, U.S. Pat. No. 6,602,498; C. Delgado et al., The uses and properties of PEG-linked proteins., Crit. Rev. Therap. Drug Carrier Systems, 9:249-304 (1992); S. Zalipsky et al., Use of functionalized poly(ethylene glycol)s for modification of polypeptides, in: Poly(ethylene glycol) chemistry: Biotechnical and biomedical applications (J. M. Harris, Editor, Plenum Press: New York, 347-370 (1992); S. Herman et al., Poly(ethylene glycol) with reactive endgroups: I. Modification of proteins, J. Bioactive Compatible Polymers, 10:145-187 (1995); P. J. Shadle et al., Conjugation of polymer to colony stimulating factor-1, U.S. Pat. No. 4,847,325; G. Shaw et al., Cysteine added variants IL-3 and chemical modifications thereof, U.S. Pat. No. 5,166,322 and EP 0469074 B1; G. Shaw et al., Cysteine added variants of EPO and chemical modifications thereof, EP 0668353 A1; G. Shaw et al., Cysteine added variants G-CSF and chemical modifications thereof, EP 0668354 A1; N. V. Katre et al., Interleukin-2 muteins and polymer conjugation thereof, U.S. Pat. No. 5,206,344; R. J. Goodson and N. V. Katre, Site-directed pegylation of recombinant interleukin-2 at its glycosylation site, Biotechnology, 8:343-346 (1990)).

A poly(ethylene glycol) vinyl sulfone is another useful activated PEG for generating the PEG-conjugated peptides of the present invention by conjugation at thiolated amino acid residues, e.g., at C residues. (E.g., M. Morpurgo et al., Preparation and characterization of poly(ethylene glycol) vinyl sulfone, Bioconj. Chem., 7:363-368 (1996); see also Harris, Functionalization of polyethylene glycol for formation of active sulfone-terminated PEG derivatives for binding to proteins and biologically compatible materials, U.S. Pat. Nos. 5,446,090; 5,739,208; 5,900,461; 6,610,281 and 6,894,025; and Harris, Water soluble active sulfones of poly(ethylene glycol), WO 95/13312 A1).

Another activated form of PEG that is useful in accordance with the present invention, is a PEG-N-hydroxysuccinimide ester compound, for example, methoxy PEG-N-hydroxysuccinimidyl (NHS) ester.

Heterobifunctionally activated forms of PEG are also useful. (See, e.g., Thompson et al., PEGylation reagents and biologically active compounds formed therewith, U.S. Pat. No. 6,552,170).

Typically, a polypeptide or peptide of interest is reacted by known chemical techniques with an activated PEG compound, such as but not limited to, a thiol-activated PEG compound, a diol-activated PEG compound, a PEG-hydrazide compound, a PEG-oxyamine compound, or a PEG-bromoacetyl compound. (See, e.g., S. Herman, Poly(ethylene glycol) with Reactive Endgroups: I. Modification of Proteins, J. Bioactive and Compatible Polymers, 10:145-187 (1995); S. Zalipsky, Chemistry of Polyethylene Glycol Conjugates with Biologically Active Molecules, Advanced Drug Delivery Reviews, 16:157-182 (1995); R. Greenwald et al., Poly(ethylene glycol) conjugated drugs and prodrugs: a comprehensive review, Critical Reviews in Therapeutic Drug Carrier Systems, 17:101-161 (2000)).

Polysaccharide polymers are another type of water soluble polymer which may be used for protein modification. Dextrans are polysaccharide polymers comprised of individual subunits of glucose predominantly linked by al-6 linkages The dextran itself is available in many molecular weight ranges, and is readily available in molecular weights from about 1 kD to about 70 kD. Dextran is a suitable water soluble polymer for use in the present invention by itself or in combination with a different additional functional moiety (e.g., Fc). See, for example, WO 96/11953 and WO 96/05309. The use of dextran conjugated to therapeutic or diagnostic immunoglobulins has been reported; see, for example, European Patent Publication No. 0 315 456, which is hereby incorporated by reference. Dextran of about 1 kD to about 20 kD is preferred when dextran is used in accordance with the present invention.

Linkers. Any "linker" group is optional. When present, its chemical structure is not critical, since it serves primarily as a spacer, which can be useful in optimizing pharamcologial activity of some embodiments of the inventive composition. The linker is preferably made up of amino acids linked together by peptide bonds. As stated herein above, the linker moiety, if present, can be independently the same or different from any other linker, or linkers, that may be present in the inventive composition. For example, an "(L)$_c$" can represent the same linker moiety as, or a different linker moiety from, any other "(L)$_c$" or any "(L)$_d$", "(L)$_e$", or "(L)$_f$", in accordance with the invention. The linker is preferably made up of amino acids linked together by peptide bonds. Thus, in some embodiments, the linker is made up of from 1 to about 30 amino acids linked by peptide bonds, wherein the amino acids are selected from the 20 naturally occurring amino acids. Some of these amino acids may be glycosylated, as is well understood by those in the art. For example, a useful linker sequence constituting a sialylation site is X$_1$X$_2$NX$_4$X$_5$G (SEQ ID NO: 619), wherein X$_1$, X$_2$,X$_4$ and X$_5$ are each independently any amino acid residue.

In a more preferred embodiment, the 1 to 30 amino acids are selected from glycine, alanine, proline, asparagine, glutamine, and lysine. Even more preferably, a linker is made up of a majority of amino acids that are sterically unhindered, such as glycine and alanine. Thus, preferred linkers include polyglycines (particularly (Gly)4, (Gly)5), poly(Gly-Ala), and polyalanines Other preferred linkers are those identified herein as "L5" (GGGGS; SEQ ID NO: 620), "L10" (GGGGSGGGGS; SEQ ID NO: 621), "L25" GGGGSGGGGSGGGGSGGGGSGGGGS; SEQ ID NO: 622) and any linkers used in the working examples hereinafter. The linkers described herein, however, are exemplary; linkers within the scope of this invention can be much longer and can include other residues. Thus, preferred linkers are polyglycines (particularly (Gly)$_4$, (Gly)$_5$), poly(Gly-Ala), and polyalanines. Other specific examples of linkers are:

| | |
|---|---|
| (Gly)$_3$Lys(Gly)$_4$; | (SEQ ID NO: 595) |
| (Gly)$_3$AsnGlySer(Gly)$_2$; | (SEQ ID NO: 596) |
| (Gly)$_3$Cys(Gly)$_4$; and | (SEQ ID NO: 597) |
| GlyProAsnGlyGly. | (SEQ ID NO: 598) |

To explain the above nomenclature, for example, (Gly)$_3$Lys(Gly)$_4$ means Gly-Gly-Gly-Lys-Gly-Gly-Gly-Gly. Combinations of Gly and Ala are also preferred. The linkers shown here are exemplary; linkers within the scope of this invention may be much longer and may include other residues.

In some embodiments of the compositions of this invention, which comprise a peptide linker moiety (L), acidic residues, for example, glutamate or aspartate residues, are placed in the amino acid sequence of the linker moiety (L). Examples include the following peptide linker sequences:

```
GGEGGG;              (SEQ ID NO: 623)

GGEEEGGG;            (SEQ ID NO: 624)

GEEEG;               (SEQ ID NO: 625)

GEEE;                (SEQ ID NO: 626)

GGDGGG;              (SEQ ID NO: 627)

GGDDDGG;             (SEQ ID NO: 628)

GDDDG;               (SEQ ID NO: 629)

GDDD;                (SEQ ID NO: 630)

GGGGSDDSDEGSDGEDGGGGS;  (SEQ ID NO: 631)

WEWEW;               (SEQ ID NO: 632)

FEFEF;               (SEQ ID NO: 633)

EEEWWW;              (SEQ ID NO: 634)

EEEFFF;              (SEQ ID NO: 635)

WWEEEWW;             (SEQ ID NO: 636)
or

FFEEEFF.             (SEQ ID NO: 637)
```

In other embodiments, the linker constitutes a phosphorylation site, e.g., $X_1X_2YX_3X_4G$ (SEQ ID NO: 638), wherein $X_1$, $X_2$, $X_3$ and $X_4$ are each independently any amino acid residue; $X_1X_2SX_3X_4G$ (SEQ ID NO: 639), wherein $X_1$, $X_2$, $X_3$ and $X_4$ are each independently any amino acid residue; or $X_1X_2TX_3X_4G$ (SEQ ID NO: 640), wherein $X_1$, $X_2$, $X_3$ and $X_4$ are each independently any amino acid residue.

Non-peptide linkers are also possible. For example, alkyl linkers such as —NH—$(CH_2)_s$—C(O)—, wherein s=2-20 could be used. These alkyl linkers may further be substituted by any non-sterically hindering group such as lower alkyl (e.g., $C_1$-$C_6$) lower acyl, halogen (e.g., Cl, Br), CN, $NH_2$, phenyl, etc. An exemplary non-peptide linker is a PEG linker,

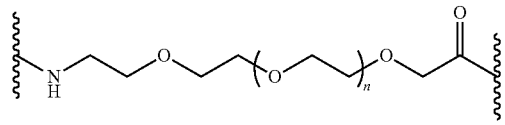

(XXXI)

wherein n is such that the linker has a molecular weight of 100 to 5000 kD, preferably 100 to 500 kD. The peptide linkers may be altered to form derivatives in the same manner as described above.

Derivatives. The compositions of matter of the present invention also encompass "derivatives" that include polypeptide or peptide portions bearing modifications other than, or in addition to, insertions, deletions, or substitutions of amino acid residues. Preferably, the modifications are covalent in nature, and include for example, chemical bonding with polymers, lipids, other organic, and inorganic moieties. Derivatives of the invention may be prepared to increase circulating half-life of a molecule; to improve targeting capacity for the molecule to desired cells, tissues, or organs; to improve the solubility or absorption of a molecule; or to eliminate or attenuate any undesirable side-effect of a molecule.

Exemplary derivatives include compounds in which:

1. The compound or some portion thereof is cyclic. For example, the peptide portion may be modified to contain two or more Cys residues (e.g., in the linker), which could cyclize by disulfide bond formation.

2. The compound is cross-linked or is rendered capable of cross-linking between molecules. For example, the peptide portion may be modified to contain one Cys residue and thereby be able to form an intermolecular disulfide bond with a like molecule. The compound may also be cross-linked through its C-terminus, as in the molecule shown below.

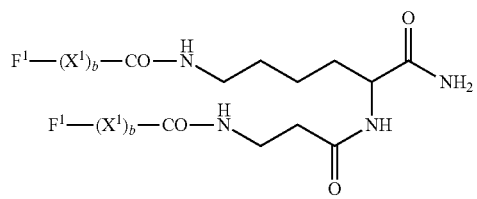

(XXXII)

3. One or more peptidyl [—C(O)NR—] linkages (bonds) is replaced by a non-peptidyl linkage. Exemplary non-peptidyl linkages are —$CH_2$-carbamate [—$CH_2$—OC(O)NR—], phosphonate, —$CH_2$-sulfonamide [—$CH_2$—S(O)$_2$NR—], urea [—NHC(O)NH—], —$CH_2$-secondary amine, and alkylated peptide [—C(O)NR$^6$— wherein R$^6$ is lower alkyl].

4. The N-terminus is derivatized. Typically, the N-terminus may be acylated or modified to a substituted amine. Exemplary N-terminal derivative groups include —NRR$^1$ (other than —NH$_2$), —NRC(O)R$^1$, —NRC(O)OR$^1$, —NRS(O)$_2$R$^1$, —NHC(O)NHR$^1$, succinimide, or benzyloxycarbonyl-NH— (CBZ—NH—), wherein R and R$^1$ are each independently hydrogen or lower alkyl and wherein the phenyl ring may be substituted with 1 to 3 substituents selected from the group consisting of $C_1$-$C_4$ alkyl, $C_1$-$C_4$ alkoxy, chloro, and bromo.

5. The free C-terminus is derivatized. Typically, the C-terminus is esterified or amidated. For example, one may use methods described in the art to add (NH—$CH_2$—$CH_2$—$NH_2$)$_2$ to compounds of this invention. Likewise, one may use methods described in the art to add —$NH_2$ to compounds of this invention. Exemplary C-terminal derivative groups include, for example, —C(O)R$^2$ wherein R$^2$ is lower alkoxy or —NR$^3$R$^4$ wherein R$^3$ and R$^4$ are independently hydrogen or $C_1$-$C_8$ alkyl (preferably $C_1$-$C_4$ alkyl).

6. A disulfide bond is replaced with another, preferably more stable, cross-linking moiety (e.g., an alkylene). See, e.g., Bhatnagar et al. (1996), *J. Med. Chem.* 39: 3814-9; Alberts et al. (1993) *Thirteenth Am. Pep. Symp.*, 357-9.

7. One or more individual amino acid residues is modified. Various derivatizing agents are known to react specifically with selected side chains or terminal residues, as described in detail below.

Lysinyl residues and amino terminal residues may be reacted with succinic or other carboxylic acid anhydrides, which reverse the charge of the lysinyl residues. Other suitable reagents for derivatizing alpha-amino-containing residues include imidoesters such as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues may be modified by reaction with any one or combination of several conventional reagents, including phenylglyoxal, 2,3-butanedione, 1,2-cyclohexanedione, and ninhydrin. Derivatization of arginyl residues requires that the reaction be performed in alkaline conditions because of the high pKa of the guanidine functional group. Furthermore, these reagents may react with the groups of lysine as well as the arginine epsilon-amino group.

Specific modification of tyrosyl residues has been studied extensively, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively.

Carboxyl side chain groups (aspartyl or glutamyl) may be selectively modified by reaction with carbodiimides (R'—N=C=N—R') such as 1-cyclohexyl-3-(2-morpholinyl-(4-ethyl) carbodiimide or 1-ethyl-3-(4-azonia-4,4-dimethylpentyl) carbodiimide. Furthermore, aspartyl and glutamyl residues may be converted to asparaginyl and glutaminyl residues by reaction with ammonium ions.

Glutaminyl and asparaginyl residues may be deamidated to the corresponding glutamyl and aspartyl residues. Alternatively, these residues are deamidated under mildly acidic conditions. Either form of these residues falls within the scope of this invention.

Cysteinyl residues can be replaced by amino acid residues or other moieties either to eliminate disulfide bonding or, conversely, to stabilize cross-linking. See, e.g., Bhatnagar et al. (1996), *J. Med. Chem.* 39: 3814-9.

Derivatization with bifunctional agents is useful for cross-linking the peptides or their functional derivatives to a water-insoluble support matrix or to other macromolecular vehicles. Commonly used cross-linking agents include, e.g., 1,1-bis (diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl)dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Carbohydrate (oligosaccharide) groups may conveniently be attached to sites that are known to be glycosylation sites in proteins. Generally, O-linked oligosaccharides are attached to serine (Ser) or threonine (Thr) residues while N-linked oligosaccharides are attached to asparagine (Asn) residues when they are part of the sequence Asn-X-Ser/Thr, where X can be any amino acid except proline. X is preferably one of the 19 naturally occurring amino acids other than proline. The structures of N-linked and O-linked oligosaccharides and the sugar residues found in each type are different. One type of sugar that is commonly found on both is N-acetylneuraminic acid (referred to as sialic acid). Sialic acid is usually the terminal residue of both N-linked and O-linked oligosaccharides and, by virtue of its negative charge, may confer acidic properties to the glycosylated compound. Such site(s) may be incorporated in the linker of the compounds of this invention and are preferably glycosylated by a cell during recombinant production of the polypeptide compounds (e.g., in mammalian cells such as CHO, BHK, COS). However, such sites may further be glycosylated by synthetic or semi-synthetic procedures known in the art.

Other possible modifications include hydroxylation of proline and lysine, phosphorylation of hydroxyl groups of seryl or threonyl residues, oxidation of the sulfur atom in Cys, methylation of the alpha-amino groups of lysine, arginine, and histidine side chains. Creighton, *Proteins: Structure and Molecule Properties* (W. H. Freeman & Co., San Francisco), pp. 79-86 (1983).

Such derivatized moieties preferably improve one or more characteristics including anti-angiogenic activity, solubility, absorption, biological half life, and the like of the compounds. Alternatively, derivatized moieties may result in compounds that have the same, or essentially the same, characteristics and/or properties of the compound that is not derivatized. The moieties may alternatively eliminate or attenuate any undesirable side effect of the compounds and the like.

Compounds of the present invention may be changed at the DNA level, as well. The DNA sequence encoding any portion of the compound may be changed to codons more compatible with the chosen host cell. For *E. coli*, which is the preferred host cell, optimized codons are known in the art. Codons may be substituted to eliminate restriction sites or to include silent restriction sites, which may aid in processing of the DNA in the selected host cell. The vehicle, linker and peptide DNA sequences may be modified to include any of the foregoing sequence changes.

Isotope- and toxin-conjugated derivatives. Another set of useful derivatives are the above-described molecules conjugated to toxins, tracers, or radioisotopes. Such conjugation is especially useful for molecules comprising peptide sequences that bind to tumor cells or pathogens. Such molecules may be used as therapeutic agents or as an aid to surgery (e.g., radioimmunoguided surgery or RIGS) or as diagnostic agents (e.g., radioimmunodiagnostics or RID).

As therapeutic agents, these conjugated derivatives possess a number of advantages. They facilitate use of toxins and radioisotopes that would be toxic if administered without the specific binding provided by the peptide sequence. They also can reduce the side-effects that attend the use of radiation and chemotherapy by facilitating lower effective doses of the conjugation partner.

Useful conjugation partners include:
radioisotopes, such as $^{90}$Yttrium, $^{131}$Iodine, $^{225}$Actinium, and $^{213}$Bismuth;
ricin A toxin, microbially derived toxins such as *Pseudomonas* endotoxin (e.g., PE38, PE40), and the like;
partner molecules in capture systems (see below);
biotin, streptavidin (useful as either partner molecules in capture systems or as tracers, especially for diagnostic use); and
cytotoxic agents (e.g., doxorubicin).

One useful adaptation of these conjugated derivatives is use in a capture system. In such a system, the molecule of the present invention would comprise a benign capture molecule. This capture molecule would be able to specifically bind to a separate effector molecule comprising, for example, a toxin or radioisotope. Both the vehicle-conjugated molecule and the effector molecule would be administered to the patient. In such a system, the effector molecule would have a short half-life except when bound to the vehicle-conjugated capture molecule, thus minimizing any toxic side-effects. The vehicle-conjugated molecule would have a relatively long half-life but would be benign and non-toxic. The specific binding portions of both molecules can be part of a known specific binding pair (e.g., biotin, streptavidin) or can result from peptide generation methods such as those described herein.

Such conjugated derivatives may be prepared by methods known in the art. In the case of protein effector molecules (e.g., *Pseudomonas* endotoxin), such molecules can be expressed as fusion proteins from correlative DNA constructs. Radioisotope conjugated derivatives may be prepared, for example, as described for the BEXA antibody (Coulter). Derivatives comprising cytotoxic agents or microbial toxins may be prepared, for example, as described for the BR96 antibody (Bristol-Myers Squibb). Molecules employed in capture systems may be prepared, for example, as described by the patents, patent applications, and publications from NeoRx. Molecules employed for RIGS and RID may be prepared, for example, by the patents, patent applications, and publications from NeoProbe.

Preparing a peptide derivative for conjugation to a Fc domain in accordance with the present invention can be useful. Tumor cells, for example, exhibit epitopes not found on their normal counterparts. Such epitopes include, for example, different post-translational modifications resulting from their rapid proliferation. Thus, one aspect of this invention is a process comprising:
  a) selecting at least one randomized peptide that specifically binds to a target epitope; and
  b) preparing a pharmacologic agent comprising (i) at least one Fc domain monomer, (ii) at least one amino acid sequence of the selected peptide or peptides, and (iii) an effector molecule.

The target epitope is preferably a tumor-specific epitope or an epitope specific to a pathogenic organism. The effector molecule may be any of the above-noted conjugation partners and is preferably a radioisotope.

Variants. Variants of polypeptide or peptide portions of the inventive composition of matter (e.g., additional functional moiety, linker, or Fc domain portions), are also included within the scope of the present invention. Included within variants are insertional, deletional, and substitutional variants. It is understood that a particular molecule of the present invention may contain one, two or all three types of variant polypeptides or peptides. Insertional and substitutional variants may contain canonical amino acids, non-canonical amino acids (as set forth herein), or both. It is also understood that, in accordance with the present invention, polypeptide or peptide variants can be made before chemical conjugation to an Fc domain or can be designed to be expressed as part of a fusion protein with the Fc domain, as desired in various embodiments of the inventive composition of matter.

In one example, insertional variants are provided wherein one or more amino acid residues, either naturally occurring or unconventional amino acids, supplement a peptide or a polypeptide amino acid sequence. Insertions may be located at either or both termini, or may be positioned within internal regions of the amino acid sequence. Insertional variants with additional residues at either or both termini can include, for example, fusion proteins and proteins including amino acid tags or labels. Insertional variants include peptides and peptibodies wherein one or more amino acid residues are added to the peptide or polypeptide amino acid sequence, or fragment thereof.

Variants of the invention also include mature peptides and polypeptides wherein leader or signal sequences are removed, and the resulting proteins having additional amino terminal residues, which amino acids may be natural or nonnatural. Molecules of this invention (such as peptibodies) with an additional methionyl residue at amino acid position $-1$ ($Met^{-1}$-peptibody) are contemplated, as are specific binding agents with additional methionine and lysine residues at positions $-2$ and $-1$ ($Met^{-2}$-$Lys^{-1}$-) conjugated to Fc domain as additional moieties in accordance with the invention. Variants having additional Met, Met-Lys, Lys residues (or one or more basic residues, in general) are particularly useful for enhanced recombinant protein production in bacterial host cells.

The invention also embraces variants having additional amino acid residues that arise from use of specific expression systems. For example, use of commercially available vectors that express a desired polypeptide as part of glutathione-S-transferase (GST) fusion product provides the desired polypeptide having an additional glycine residue at amino acid position $-1$ after cleavage of the GST component from the desired polypeptide. Variants which result from expression in other vector systems are also contemplated, including those wherein poly-histidine tags are incorporated into the amino acid sequence, generally at the carboxy and/or amino terminus of the sequence.

Insertional variants also include fusion proteins wherein the amino and/or carboxy termini of the peptide or peptibody is fused to another polypeptide, a fragment thereof or amino acids which are not generally recognized to be part of any specific protein sequence. Examples of such fusion proteins are immunogenic polypeptides, proteins with long circulating half lives, such as immunoglobulin constant regions, marker proteins, proteins or polypeptides that facilitate purification of the desired peptide or peptibody, and polypeptide sequences that promote formation of multimeric proteins (such as leucine zipper motifs that are useful in dimer formation/stability).

This type of insertional variant generally has all or a substantial portion of the native molecule, linked at the N- or C-terminus, to all or a portion of a second polypeptide. For example, fusion proteins typically employ leader sequences from other species to permit the recombinant expression of a protein in a heterologous host. Another useful fusion protein includes the addition of an immunologically active domain, such as an antibody epitope, to facilitate purification of the fusion protein. Inclusion of a cleavage site at or near the fusion junction will facilitate removal of the extraneous polypeptide after purification. Other useful fusions include linking of functional domains, such as active sites from enzymes, glycosylation domains, cellular targeting signals or transmembrane regions.

There are various commercially available fusion protein expression systems that may be used in the present invention. Particularly useful systems include but are not limited to the glutathione-5-transferase (GST) system (Pharmacia), the maltose binding protein system (NEB, Beverley, Mass.), the FLAG system (IBI, New Haven, Conn.), and the 6×His system (Qiagen, Chatsworth, Calif.). These systems are capable of producing recombinant peptides and/or peptibodies bearing only a small number of additional amino acids, which are unlikely to significantly affect the activity of the peptide or peptibody. For example, both the FLAG system and the 6×His system add only short sequences, both of which are known to be poorly antigenic and which do not adversely affect folding of a polypeptide to its native conformation. Another N-terminal fusion that is contemplated to be useful is the fusion of a Met-Lys dipeptide at the N-terminal region of the protein or peptides. Such a fusion may produce beneficial increases in protein expression or activity.

Other fusion systems produce polypeptide hybrids where it is desirable to excise the fusion partner from the desired peptide or peptibody. In one embodiment, the fusion partner is linked to the recombinant peptibody by a peptide sequence containing a specific recognition sequence for a protease. Examples of suitable sequences are those recognized by the Tobacco Etch Virus protease (Life Technologies, Gaithersburg, Md.) or Factor Xa (New England Biolabs, Beverley, Mass.).

In some embodiments of the inventive composition of matter, fusion polypeptides comprise all or part of the molecule, in combination with truncated tissue factor (tTF). tTF is a vascular targeting agent consisting of a truncated form of a human coagulation-inducing protein that acts as a tumor blood vessel clotting agent, as described U.S. Pat. Nos. 5,877,289; 6,004,555; 6,132,729; 6,132,730; 6,156,321; and European Patent No. EP 0988056. The fusion of tTF to the anti-Ang-2 peptibody or peptide, or fragments thereof facilitates the delivery of anti-Ang-2 to target cells.

In some embodiments of the present invention, deletion variants can be useful, wherein one or more amino acid residues in a peptide or polypeptide portion of the composition of matter are removed. Deletions can be effected at one or both termini of the polypeptide or peptide portion, or from removal of one or more non-terminal residues within the amino acid sequence. Deletion variants necessarily include all fragments of a peptide or polypeptide portion of the inventive composition of matter.

In other embodiments of the present invention, substitution variants can be useful. Substitution variants include those peptides and polypeptide portions wherein one or more amino acid residues are removed and replaced with one or more alternative amino acids, which amino acids may be naturally occurring or non-naturally occurring. Substitutional variants generate peptides or polypeptides that are "similar" to the original peptide or polypeptide, in that the two have sequences with a certain percentage of amino acids that are identical. Substitution variants include substitutions of 1, 2, 3, 4, 5, 6, 7, 8, 9, 10, 15, 20, 25, 30, amino acids within a peptide or peptibody, wherein the number of substitutions may be up to ten percent or more, of the amino acids of the peptide or peptibody. The substitutions can be conservative in nature, however, the invention embraces substitutions that are also non-conservative and also includes non-canonical amino acids.

Identity and similarity of related peptides and peptibodies can be readily calculated by known methods. Such methods include, but are not limited to, those described in *Computational Molecular Biology*, Lesk, A. M., ed., Oxford University Press, New York (1988); *Biocomputing: Informatics and Genome Projects*, Smith, D. W., ed., Academic Press, New York (1993); *Computer Analysis of Sequence Data, Part 1*, Griffin, A. M., and Griffin, H. G., eds., Humana Press, N.J. (1994); *Sequence Analysis in Molecular Biology*, von Heinje, G., Academic Press (1987); *Sequence Analysis Primer*, Gribskov, M. and Devereux, J., eds., M. Stockton Press, New York (1991); and Carillo et al., *SIAM J. Applied Math.*, 48:1073 (1988).

Preferred methods to determine the relatedness or percent identity of two peptides or polypeptides, or a polypeptide and a peptide, are designed to give the largest match between the sequences tested. Methods to determine identity are described in publicly available computer programs. Preferred computer program methods to determine identity between two sequences include, but are not limited to, the GCG program package, including GAP (Devereux et al., *Nucl. Acid. Res.*, 12:387 (1984); Genetics Computer Group, University of Wisconsin, Madison, Wis., BLASTP, BLASTN, and FASTA (Altschul et al., *J. Mol. Biol.*, 215:403-410 (1990)). The BLASTX program is publicly available from the National Center for Biotechnology Information (NCBI) and other sources (*BLAST Manual*. Altschul et al. NCB/NLM/NIH Bethesda, Md. 20894; Altschul et al., supra (1990)). The well-known Smith Waterman algorithm may also be used to determine identity.

Certain alignment schemes for aligning two amino acid sequences may result in the matching of only a short region of the two sequences, and this small aligned region may have very high sequence identity even though there is no significant relationship between the two full-length sequences. Accordingly, in certain embodiments, the selected alignment method (GAP program) will result in an alignment that spans at least ten percent of the full length of the target polypeptide being compared, i.e., at least 40 contiguous amino acids where sequences of at least 400 amino acids are being compared, 30 contiguous amino acids where sequences of at least 300 to about 400 amino acids are being compared, at least 20 contiguous amino acids where sequences of 200 to about 300 amino acids are being compared, and at least 10 contiguous amino acids where sequences of about 100 to 200 amino acids are being compared.

For example, using the computer algorithm GAP (Genetics Computer Group, University of Wisconsin, Madison, Wis.), two polypeptides for which the percent sequence identity is to be determined are aligned for optimal matching of their respective amino acids (the "matched span", as determined by the algorithm). In certain embodiments, a gap opening penalty (which is typically calculated as 3× the average diagonal; the "average diagonal" is the average of the diagonal of the comparison matrix being used; the "diagonal" is the score or number assigned to each perfect amino acid match by the particular comparison matrix) and a gap extension penalty (which is usually 1/10 times the gap opening penalty), as well as a comparison matrix such as PAM 250 or BLOSUM 62 are used in conjunction with the algorithm. In certain embodiments, one may also use a standard comparison matrix in the algorithm, See Dayhoff et al., *Atlas of Protein Sequence and Structure*, 5(3)(1978) for the PAM 250 comparison matrix; and Henikoff et al., *Proc. Natl. Acad. Sci. USA*, 89:10915-10919 (1992) for the BLOSUM 62 comparison matrix.

In certain embodiments, the parameters for a polypeptide sequence comparison include the following:

Algorithm: Needleman et al., *J. Mol. Biol.*, 48:443-453 (1970);

Comparison matrix: BLOSUM 62 from Henikoff et al., supra (1992);

Gap Penalty: 12

Gap Length Penalty: 4

Threshold of Similarity: 0

The GAP program may be useful with the above parameters. In certain embodiments, the aforementioned parameters are the default parameters for polypeptide comparisons (along with no penalty for end gaps) using the GAP algorithm.

In certain embodiments, the parameters for polynucleotide molecule sequence (as opposed to an amino acid sequence) comparisons include the following:

Algorithm: Needleman et al., supra (1970);
Comparison matrix: matches=+10, mismatch=0
Gap Penalty: 50
Gap Length Penalty: 3

The GAP program may also be useful with the above parameters. The aforementioned parameters are the default parameters for polynucleotide molecule comparisons.

Other exemplary algorithms, gap opening penalties, gap extension penalties, comparison matrices, thresholds of similarity, etc. may be used, including those set forth in the Program Manual, Wisconsin Package, Version 9, September, 1997. The particular choices to be made will be apparent to those of skill in the art and will depend on the specific comparison to be made, such as DNA-to-DNA, protein-to-protein, protein-to-DNA; and additionally, whether the comparison is between given pairs of sequences (in which case GAP or BestFit are generally preferred) or between one sequence and a large database of sequences (in which case FASTA or BLASTA are preferred).

It will be appreciated that amino acid residues can be divided into classes based on their common side chain properties:

1. Neutral Hydrophobic: Alanine (Ala; A), Valine (Val; V), Leucine (Leu; L), Isoleucine (Ile; I), Proline (Pro; P), Tryptophan (Trp; W), Phenylalanine (Phe; F), and Methionine (Met, M).
2. Neutral Polar: Glycine (Gly; G); Serine (Ser; S), Threonine (Thr; T), Tyrosine (Tyr; Y), Cysteine (Cys; C), Glutamine (Glu; Q), Asparagine (Asn; N), and Norleucine.
3. Acidic: Aspartic Acid (Asp; D), Glutamic Acid (Glu; E);
4) Basic: Lysine (Lys; K), Arginine (Arg; R), Histidine (His; H).

See Lewin, B., *Genes V*, Oxford University Press (1994), p. 11.

Conservative amino acid substitutions may encompass unconventional amino acid residues, which are typically incorporated by chemical peptide synthesis rather than by synthesis in biological systems. These include, without limitation, peptidomimetics and other reversed or inverted forms of amino acid moieties. Non-conservative substitutions may involve the exchange of a member of one of these classes for a member from another class.

In making such changes, according to certain embodiments, the hydropathic index of amino acids may be considered. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is understood in the art. Kyte et al., *J. Mol. Biol.*, 157:105-131 (1982). It is known that certain amino acids may be substituted for other amino acids having a similar hydropathic index or score and still retain a similar biological activity. In making changes based upon the hydropathic index, in certain embodiments, the substitution of amino acids whose hydropathic indices are within ±2 is included. In certain embodiments, those which are within ±1 are included, and in certain embodiments, those within ±0.5 are included.

It is also understood in the art that the substitution of like amino acids can be made effectively on the basis of hydrophilicity, particularly where the biologically functional peptibody or peptide thereby created is intended for use in immunological embodiments, as in the present case. In certain embodiments, the greatest local average hydrophilicity of a protein, as governed by the hydrophilicity of its adjacent amino acids, correlates with its immunogenicity and antigenicity, i.e., with a biological property of the protein.

The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, in certain embodiments, the substitution of amino acids whose hydrophilicity values are within ±2 is included, in certain embodiments, those which are within ±1 are included, and in certain embodiments, those within ±0.5 are included. One may also identify epitopes from primary amino acid sequences on the basis of hydrophilicity. These regions are also referred to as "epitopic core regions."

Exemplary amino acid substitutions are set forth in Table 11 below.

TABLE 11

Amino Acid Substitutions

| Original Residues | Exemplary Substitutions | Preferred Substitutions |
|---|---|---|
| Ala | Val, Leu, Ile | Val |
| Arg | Lys, Gln, Asn | Lys |
| Asn | Gln, Glu, Asp | Gln |
| Asp | Glu, Gln, Asp | Glu |
| Cys | Ser, Ala | Ser |
| Gln | Asn, Glu, Asp | Asn |
| Glu | Asp, Gln, Asn | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4 Diamino-butyric Acid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

A skilled artisan will be able to determine suitable variants of useful polypeptide or peptides as set forth herein using well-known techniques. In certain embodiments, one skilled in the art may identify suitable areas of the molecule that may be changed without destroying activity by targeting regions not believed to be important for activity. In certain embodiments, one can identify residues and portions of the molecules that are conserved among similar peptides or polypeptides. In certain embodiments, one may even subject areas important for biological activity or for structure to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, one can predict the importance of amino acid residues in a protein that correspond to amino acid residues which are important for activity or structure in similar proteins. One skilled in the art may opt for chemically similar amino acid substitutions for such predicted important amino acid residues.

One skilled in the art can also analyze the three-dimensional structure and amino acid sequence in relation to that structure in similar polypeptides. In view of such information, one skilled in the art may predict the alignment of amino acid residues of an antibody with respect to its three dimensional structure. In certain embodiments, one skilled in the art may choose not to make radical changes to amino acid residues predicted to be on the surface of the protein, since such residues may be involved in important interactions with other molecules. Moreover, one skilled in the art may generate test variants containing a single amino acid substitution at each desired amino acid residue. The variants can then be screened using activity assays known to those skilled in the art. Such variants could be used to gather information about suitable variants. For example, if one discovered that a change to a particular amino acid residue resulted in destroyed, undesirably reduced, or unsuitable activity, variants with such a change may be avoided. In other words, based on information gathered from such routine experiments, one skilled in the art can readily determine the amino acids where further substitutions should be avoided either alone or in combination with other mutations.

A number of scientific publications have been devoted to the prediction of secondary structure. See Moult J., *Curr. Op. in Biotech.*, 7(4):422-427 (1996), Chou et al., *Biochemistry*, 13(2):222-245 (1974); Chou et al., *Biochemistry*, 113(2):211-222 (1974); Chou et al., *Adv. Enzymol. Relat. Areas Mol. Biol.*, 47:45-148 (1978); Chou et al., *Ann. Rev. Biochem.*, 47:251-276 and Chou et al., *Biophys. J.*, 26:367-384 (1979). Moreover, computer programs are currently available to assist with predicting secondary structure. One method of predicting secondary structure is based upon homology modeling. For example, two polypeptides or proteins that have a sequence identity of greater than 30%, or similarity greater than 40% often have similar structural topologies. The recent growth of the protein structural database (PDB) has provided enhanced predictability of secondary structure, including the potential number of folds within a polypeptide's or protein's structure. See Holm et al., *Nucl. Acid. Res.*, 27(1): 244-247 (1999). It has been suggested (Brenner et al., *Curr. Op. Struct. Biol.*, 7(3): 369-376 (1997)) that there are a limited number of folds in a given polypeptide or protein and that once a critical number of structures have been resolved, structural prediction will become dramatically more accurate.

Additional methods of predicting secondary structure include "threading" (Jones, D., *Curr. Opin. Struct. Biol.*, 7(3): 377-87 (1997); Sippl et al., *Structure*, 4(1):15-19 (1996)), "profile analysis" (Bowie et al., *Science*, 253:164-170 (1991); Gribskov et al., *Meth. Enzym.*, 183:146-159 (1990); Gribskov et al., *Proc. Nat. Acad. Sci.*, 84(13):4355-4358 (1987)), and "evolutionary linkage" (See Holm, supra (1999), and Brenner, supra (1997)).

In certain embodiments, peptibody variants include glycosylation variants wherein one or more glycosylation sites, such as a N-linked glycosylation site, has been added to the peptibody. An N-linked glycosylation site is characterized by the sequence: Asn-X-Ser or Asn-X-Thr, wherein the amino acid residue designated as X may be any amino acid residue except proline. The substitution or addition of amino acid residues to create this sequence provides a potential new site for the addition of an N-linked carbohydrate chain. Alternatively, substitutions which eliminate this sequence will remove an existing N-linked carbohydrate chain. Also provided is a rearrangement of N-linked carbohydrate chains wherein one or more N-linked glycosylation sites (typically those that are naturally occurring) are eliminated and one or more new N-linked sites are created.

Compounds of the present invention may be changed at the DNA level, as well. The DNA sequence of any portion of the compound may be changed to codons more compatible with the chosen host cell. For *E. coli*, which is the preferred host cell, optimized codons are known in the art. Codons may be substituted to eliminate restriction sites or to include silent restriction sites, which may aid in processing of the DNA in the selected host cell. The Fc domain-, linker-, polypeptide-, and/or peptide-encoding DNA sequences may be modified to include any of the foregoing sequence changes. Thus, all modifications, substitution, derivitizations, etc. discussed herein apply equally to all polypeptide or peptide portions of the inventive composition of matter.

One embodiment of the present invention includes "affinity matured" peptides and polypeptide portions, including peptibody embodiments. This procedure contemplates increasing the affinity or the bio-activity of the peptides and polypeptides using phage display or other selection technologies. Based on a consensus sequence (which is generated for a collection of related peptides), directed secondary phage display libraries can be generated in which the "core" amino acids (determined from the consensus sequence) are held constant or are biased in frequency of occurrence. Alternatively, an individual peptide sequence can be used to generate a biased, directed phage display library. Panning of such libraries can yield peptides (which can be converted to peptibodies) with enhanced binding to the target or with enhanced bio-activity.

Non-Peptide Analogs/Protein Mimetics. Furthermore, non-peptide analogs of peptides that provide a stabilized structure or lessened biodegradation, are also useful. Peptide mimetic analogs can be prepared based on a selected inhibitory peptide by replacement of one or more residues by non-peptide moieties. Preferably, the nonpeptide moieties permit the peptide to retain its natural confirmation, or stabilize a preferred, e.g., bioactive, confirmation which retains the ability to recognize and bind Ang-2. In one aspect, the resulting analog/mimetic exhibits increased binding affinity for Ang-2. One example of methods for preparation of nonpeptide mimetic analogs from peptides is described in Nachman et al., *Regul. Pept.* 57:359-370 (1995). If desired, the peptides of the invention can be modified, for instance, by glycosylation, amidation, carboxylation, or phosphorylation, or by the creation of acid addition salts, amides, esters, in particular C-terminal esters, and N-acyl derivatives of the peptides of the invention. The peptibodies also can be modified to create peptide derivatives by forming covalent or noncovalent complexes with other moieties. Covalently-bound complexes can be prepared by linking the chemical moieties to functional groups on the side chains of amino acids comprising the peptibodies, or at the N- or C-terminus.

The peptides can be conjugated to a reporter group, including, but not limited to a radiolabel, a fluorescent label, an enzyme (e.g., that catalyzes a colorimetric or fluorometric reaction), a substrate, a solid matrix, or a carrier (e.g., biotin or avidin). The invention accordingly provides a molecule comprising a peptibody molecule, wherein the molecule preferably further comprises a reporter group selected from the group consisting of a radiolabel, a fluorescent label, an enzyme, a substrate, a solid matrix, and a carrier. Such labels are well known to those of skill in the art, e.g., biotin labels are particularly contemplated. The use of such labels is well known to those of skill in the art and is described in, e.g., U.S. Pat. Nos. 3,817,837; 3,850,752; 3,996,345; and 4,277,437. Other labels that will be useful include but are not limited to radioactive labels, fluorescent labels and chemiluminescent labels. U.S. patents concerning use of such labels include, for example, U.S. Pat. Nos. 3,817,837; 3,850,752; 3,939,350; and 3,996,345. Any of the peptibodies of the present invention may comprise one, two, or more of any of these labels.

Recombinant methods. In general, the peptide or polypeptide portions of the inventive compounds of this invention (including peptides or polypeptides as additional moieties, linkers, and/or Fc domains) largely can be made in transformed host cells using recombinant DNA techniques. To do so, a recombinant DNA molecule coding for the peptide is prepared. Methods of preparing such DNA molecules are well known in the art. For instance, sequences coding for the peptides could be excised from DNA using suitable restriction enzymes. Alternatively, the DNA molecule could be synthesized using chemical synthesis techniques, such as the phosphoramidate method. Also, a combination of these techniques could be used.

Accordingly, the present invention also relates to nucleic acids, expression vectors and host cells useful in producing polypeptide compositions of the present invention. Host cells can be eukaryotic cells, with mammalian cells preferred, e.g., CHO cells and HEK293 cells. Host cells can also be prokaryotic cells, with *E. coli* cells most preferred.

The compounds of this invention largely can be made in transformed host cells using recombinant DNA techniques. To do so, a recombinant DNA molecule coding for the peptide is prepared. Methods of preparing such DNA molecules are well known in the art. For instance, sequences coding for the peptides could be excised from DNA using suitable restriction enzymes. Alternatively, the DNA molecule could be synthesized using chemical synthesis techniques, such as the phosphoramidate method. Also, a combination of these techniques could be used.

The invention also includes a vector capable of expressing the peptides in an appropriate host. The vector comprises the DNA molecule that codes for the peptides operatively linked to appropriate expression control sequences. Methods of effecting this operative linking, either before or after the DNA molecule is inserted into the vector, are well known. Expression control sequences include promoters, activators, enhancers, operators, ribosomal binding sites, start signals, stop signals, cap signals, polyadenylation signals, and other signals involved with the control of transcription or translation.

The resulting vector having the DNA molecule thereon is used to transform an appropriate host. This transformation can be performed using methods well known in the art.

Any of a large number of available and well-known host cells can be used in the practice of this invention. The selection of a particular host is dependent upon a number of factors recognized by the art. These include, for example, compatibility with the chosen expression vector, toxicity of the peptides encoded by the DNA molecule, rate of transformation, ease of recovery of the peptides, expression characteristics, bio-safety and costs. A balance of these factors must be struck with the understanding that not all host cells can be equally effective for the expression of a particular DNA sequence. Within these general guidelines, useful microbial host cells include bacteria (such as *E. coli* sp.), yeast (such as *Saccharomyces* sp.) and other fungi, insects, plants, mammalian (including human) cells in culture, or other hosts known in the art.

Next, the transformed host cell is cultured and purified. Host cells can be cultured under conventional fermentation conditions so that the desired compounds are expressed. Such fermentation conditions are well known in the art. Finally, the peptides are purified from culture by methods well known in the art.

The compounds can also be made by synthetic methods. Solid phase synthesis is the preferred technique of making individual peptides since it is the most cost-effective method of making small peptides. For example, well known solid phase synthesis techniques include the use of protecting groups, linkers, and solid phase supports, as well as specific protection and deprotection reaction conditions, linker cleavage conditions, use of scavengers, and other aspects of solid phase peptide synthesis. Suitable techniques are well known in the art. (E.g., Merrifield (1973), *Chem. Polypeptides, pp.* 335-61 (Katsoyannis and Panayotis eds.); Merrifield (1963), *J. Am. Chem. Soc.* 85: 2149; Davis et al. (1985), *Biochem. Intl.* 10: 394-414; Stewart and Young (1969), *Solid Phase Peptide Synthesis*; U.S. Pat. No. 3,941,763; Finn et al. (1976), *The Proteins* (3rd ed.) 2: 105-253; and Erickson et al. (1976), *The Proteins* (3rd ed.) 2: 257-527; "Protecting Groups in Organic Synthesis," 3rd Edition, T. W. Greene and P. G. M. Wuts, Eds., John Wiley & Sons, Inc., 1999; NovaBiochem Catalog, 2000; "Synthetic Peptides, A User's Guide," G. A. Grant, Ed., W.H. Freeman & Company, New York, N.Y., 1992; "Advanced Chemtech Handbook of Combinatorial & Solid Phase Organic Chemistry," W. D. Bennet, J. W. Christensen, L. K. Hamaker, M. L. Peterson, M. R. Rhodes, and H. H. Saneii, Eds., Advanced Chemtech, 1998; "Principles of Peptide Synthesis, 2nd ed.," M. Bodanszky, Ed., Springer-Verlag, 1993; "The Practice of Peptide Synthesis, 2nd ed.," M. Bodanszky and A. Bodanszky, Eds., Springer-Verlag, 1994; "Protecting Groups," P. J. Kocienski, Ed., Georg Thieme Verlag, Stuttgart, Germany, 1994; "Fmoc Solid Phase Peptide Synthesis, A Practical Approach," W. C. Chan and P. D. White, Eds., Oxford Press, 2000, G. B. Fields et al., Synthetic Peptides: A User's Guide, 1990, 77-183).

Whether the compositions of the present invention are prepared by synthetic or recombinant techniques, suitable protein purification techniques can also be involved, when applicable. In some embodiments of the compositions of the invention, the toxin peptide portion and/or the half-life extending portion, or any other portion, can be prepared to include a suitable isotopic label (e.g., $^{125}I$, $^{14}C$, $^{13}C$, $^{35}S$, $^{3}H$, $^{2}H$, $^{13}N$, $^{15}N$, $^{18}O$, $^{17}O$, etc.), for ease of quantification or detection.

Compounds that contain derivatized peptides or polypeptides, or which contain non-peptide groups can be synthesized by well-known organic chemistry techniques.

Uses of the Inventive Compounds

In general. The compounds of this invention have pharmacologic activity resulting from their ability to bind to proteins of interest as agonists, mimetics or antagonists of the native ligands of such proteins of interest. By way of example, the utility of a variety of specific compounds is shown in Tables 5-10. The activity of these compounds can be measured by assays known in the art.

In addition to therapeutic uses, the compounds of the present invention are useful in diagnosing diseases characterized by dysfunction of their associated protein of interest. For some of these diagnostic embodiments and for other detection (including semi-quantitative and quantitative) purposes, conjugation of the Fc domain to an immobilized substrate as an additional functional moiety, such as but not limited to, a plate surface, a chip, a bead, a matrix or a particle, can be useful. Also a moiety detectably labeled with a radioisotope, an enzyme (e.g., a peroxidase or a kinase), a biotinyl moiety, a fluorophore, or a chromophore can be useful for such puposes.

In one embodiment, a method of detecting in a biological sample a protein of interest (e.g., a receptor) that is capable of being activated comprising the steps of: (a) contacting the sample with a compound of this invention; and (b) detecting activation of the protein of interest by the compound. The biological samples include tissue specimens, intact cells, or extracts thereof. The compounds of this invention may be used as part of a kit to detect the presence of their associated proteins of interest in a biological sample. Such kits employ the compounds of the invention having an attached label to allow for detection. The compounds are useful for identifying normal or abnormal proteins of interest. For the EPO-mimetic compounds, for example, presence of abnormal protein of interest in a biological sample may be indicative of such disorders as Diamond Blackfan anemia, where it is believed that the EPO receptor is dysfunctional.

Therapeutic Uses of EPO-Mimetic Molecules

The EPO-mimetic compounds of the invention are useful for treating disorders characterized by low red blood cell levels. Included in the invention are methods of modulating the endogenous activity of an EPO receptor in a mammal, preferably methods of increasing the activity of an EPO receptor. In general, any condition treatable by erythropoietin, such as anemia, may also be treated by the EPO-mimetic compounds of the invention. These compounds are administered by an amount and route of delivery that is appropriate for the nature and severity of the condition being treated and may be ascertained by one skilled in the art. Preferably, administration is by injection, either subcutaneous, intramuscular, or intravenous.

Therapeutic Uses of TPO-Mimetic Compounds

For the TPO-mimetic compounds, one can utilize such standard assays as those described in WO95/26746 entitled "Compositions and Methods for Stimulating Megakaryocyte Growth and Differentiation." The conditions to be treated are generally those that involve an existing megakaryocyte/platelet deficiency or an expected megakaryocyte/platelet deficiency (e.g., because of planned surgery or platelet donation). Such conditions will usually be the result of a deficiency (temporary or permanent) of active Mpl ligand in vivo. The generic term for platelet deficiency is thrombocytopenia, and hence the methods and compositions of the present invention are generally available for treating thrombocytopenia in patients in need thereof.

Thrombocytopenia (platelet deficiencies) may be present for various reasons, including chemotherapy and other therapy with a variety of drugs, radiation therapy, surgery, accidental blood loss, and other specific disease conditions. Exemplary specific disease conditions that involve thrombocytopenia and may be treated in accordance with this invention are: aplastic anemia, idiopathic thrombocytopenia, metastatic tumors which result in thrombocytopenia, systemic lupus erythematosus, splenomegaly, Fanconi's syndrome, vitamin B12 deficiency, folic acid deficiency, May-Hegglin anomaly, Wiskott-Aldrich syndrome, and paroxysmal nocturnal hemoglobinuria. Also, certain treatments for AIDS result in thrombocytopenia (e.g., AZT). Certain wound healing disorders might also benefit from an increase in platelet numbers.

With regard to anticipated platelet deficiencies, e.g., due to future surgery, a compound of the present invention could be administered several days to several hours prior to the need for platelets. With regard to acute situations, e.g., accidental and massive blood loss, a compound of this invention could be administered along with blood or purified platelets.

The TPO-mimetic compounds of this invention may also be useful in stimulating certain cell types other than megakaryocytes if such cells are found to express Mpl receptor. Conditions associated with such cells that express the Mpl receptor, which are responsive to stimulation by the Mpl ligand, are also within the scope of this invention.

The TPO-mimetic compounds of this invention may be used in any situation in which production of platelets or platelet precursor cells is desired, or in which stimulation of the c-Mpl receptor is desired. Thus, for example, the compounds of this invention may be used to treat any condition in a mammal wherein there is a need of platelets, megakaryocytes, and the like. Such conditions are described in detail in the following exemplary sources: WO95/26746; WO95/21919; WO95/18858; WO95/21920 and are incorporated herein.

The TPO-mimetic compounds of this invention may also be useful in maintaining the viability or storage life of platelets and/or megakaryocytes and related cells. Accordingly, it could be useful to include an effective amount of one or more such compounds in a composition containing such cells.

Therapeutic Uses of Ang-2 Binding Molecules

Agents that modulate Ang-2 binding activity, or other cellular activity, may be used in combination with other therapeutic agents to enhance their therapeutic effects or decrease potential side effects.

In one aspect, the present invention provides reagents and methods useful for treating diseases and conditions characterized by undesirable or aberrant levels of Ang-2 activity in a cell. These diseases include cancers, and other hyperproliferative conditions, such as hyperplasia, psoriasis, contact dermatitis, immunological disorders, and infertility.

The present invention also provides methods of treating cancer in an animal, including humans, comprising administering to the animal an effective amount of a specific binding agent, such as a peptibody, that inhibits or decreases Ang-2 activity. The invention is further directed to methods of inhibiting cancer cell growth, including processes of cellular proliferation, invasiveness, and metastasis in biological systems. Methods include use of a compound of the invention as an inhibitor of cancer cell growth. Preferably, the methods are employed to inhibit or reduce cancer cell growth, invasiveness, metastasis, or tumor incidence in living animals, such as mammals. Methods of the invention are also readily adaptable for use in assay systems, e.g., assaying cancer cell growth and properties thereof, as well as identifying compounds that affect cancer cell growth.

The cancers treatable by methods of the present invention preferably occur in mammals. Mammals include, for example, humans and other primates, as well as pet or companion animals such as dogs and cats, laboratory animals such as rats, mice and rabbits, and farm animals such as horses, pigs, sheep, and cattle.

Tumors or neoplasms include growths of tissue cells in which the multiplication of the cells is uncontrolled and progressive. Some such growths are benign, but others are termed malignant and may lead to death of the organism. Malignant neoplasms or cancers are distinguished from benign growths in that, in addition to exhibiting aggressive cellular proliferation, they may invade surrounding tissues and metastasize. Moreover, malignant neoplasms are characterized in that they show a greater loss of differentiation (greater dedifferentiation), and of their organization relative to one another and their surrounding tissues. This property is also called "anaplasia."

Neoplasms treatable by the present invention also include solid tumors, i.e., carcinomas and sarcomas. Carcinomas include those malignant neoplasms derived from epithelial cells that infiltrate (invade) the surrounding tissues and give rise to metastases. Adenocarcinomas are carcinomas derived from glandular tissue, or which form recognizable glandular structures. Another broad category or cancers includes sarcomas, which are tumors whose cells are embedded in a fibrillar or homogeneous substance like embryonic connective tissue. The invention also enables treatment of cancers of the myeloid or lymphoid systems, including leukemias, lymphomas and other cancers that typically do not present as a tumor mass, but are distributed in the vascular or lymphoreticular systems.

The ang-2 binding molecules of this invention are thus useful for the treatment of a wide variety of cancers, including solid tumors and leukemias. Types of cancer or tumor cells amenable to treatment according to the invention include, for example, ACTH-producing tumor; acute lymphocytic leukemia; acute nonlymphocytic leukemia; adenoma; cancer of the adrenal cortex; adenocarcinoma of the breast, prostate, and colon; ameloblastoma; apudoma; bladder cancer; brain cancer; branchioma; breast cancer; all forms of bronchogenic carcinoma of the lung; carcinoid heart disease; carcinoma (e.g., Walker, basal cell, basosquamous, Brown-Pearce, ductal, Ehrlich tumor, Krebs 2, merkel cell, mucinous, non-small cell lung, oat cell, papillary, scirrhous, bronchiolar, bronchogenic, squamous cell, and transitional cell); malignant carcinoid syndrome; immunoproliferative small lung cell carcinoma; cementoma; cervical cancer; chondroblastoma; chondroma; chondrosarcoma; choristoma; chronic lymphocytic leukemia; chronic myelocytic leukemia; colorectal cancer; chordoma; craniopharyngioma; cutaneous T-cell lymphoma; dysgerminoma; endometrial cancer; esophageal cancer; Ewing's sarcoma; fibroma; fibrosarcoma; gallbladder cancer; giant cell tumors; glioma; hairy cell leukemia; hamartoma; head and neck cancer; hepatoma; histiocytic disorders; histiocytosis; Hodgkin's lymphoma; Kaposi's sarcoma; kidney cancer; lipoma; liposarcoma; liver cancer; lung cancer (small and non-small cell); malignant peritoneal effusion; malignant pleural effusion; melanoma; mesenchymoma; mesonephroma; mesothelioma; multiple myeloma; myosarcoma; myxoma; myxosarcoma; neuroblastoma; non-Hodgkin's lymphoma; odontoma; osteoma; osteosarcoma; ovarian cancer; ovarian (germ cell) cancer; pancreatic cancer; papilloma; penile cancer; plasmacytoma; prostate cancer; reticuloendotheliosis; retinoblastoma; skin cancer; soft tissue sarcoma; squamous cell carcinomas; stomach cancer; teratoma; testicular cancer; thymoma; thyroid cancer; trophoblastic neoplasms; uterine cancer; vaginal cancer; cancer of the vulva; Wilms' tumor.

Further, the following types of cancers may also be treated: cholangioma; cholesteatoma; cyclindroma; cystadenocarcinoma; cystadenoma; granulosa cell tumor; gynandroblastoma; hidradenoma; islet cell tumor; Leydig cell tumor; papilloma; Sertoli cell tumor; theca cell tumor; leiomyoma; leiomyosarcoma; myoblastoma; myoma; myosarcoma; rhabdomyoma; rhabdomyosarcoma; ependymoma; ganglioneuroma; glioma; medulloblastoma; meningioma; neurilemmoma; neuroblastoma; neuroepithelioma; neurofibroma; neuroma; paraganglioma; paraganglioma nonchromaffin; angiokeratoma; angiolymphoid hyperplasia with eosinophilia; angioma sclerosing; angiomatosis; glomangioma; hemangioendothelioma; hemangioma; hemangiopericytoma; hemangiosarcoma; lymphangioma; lymphangiomyoma; lymphangiosarcoma; pinealoma; carcinosarcoma; chondrosarcoma; cystosarcoma phyllodes; fibrosarcoma; hemangiosarcoma; leiomyosarcoma; leukosarcoma; liposarcoma; lymphangiosarcoma; myosarcoma; myxosarcoma; ovarian carcinoma; rhabdomyosarcoma; sarcoma; neoplasms; nerofibromatosis; and cervical dysplasia.

Therapeutic Uses of NGF Binding Molecules

The NGF binding molecules may be used in the prevention or treatment of NGF-related diseases and disorders. Such indications include but are not limited to pain (including, but not limited to, inflammatory pain and associated hyperalgesia and allodynia, neuropathic pain and associated hyperalgesia and allodynia, diabetic neuropathy pain, causalgia, sympathetically maintained pain, deafferentation syndromes, acute pain, tension headache, migraine, dental pain, pain from trauma, surgical pain, pain resulting from amputation or abscess, causalgia, demyelinating diseases, and trigeminal neuralgia). The peptides and modified peptides of the invention have therapeutic value for the prevention or treatment of other diseases linked to NGF as a causative agent, including, but not limited to, asthma, urge incontinence (i.e., hyperactive bladder), psoriasis, cancer (especially, pancreatic cancer and melanoma), chronic alcoholism, stroke, thalamic pain syndrome, diabetes, acquired immune deficiency syndrome ("AIDS"), toxins and chemotherapy, general headache, migraine, cluster headache, mixed-vascular and non-vascular syndromes, general inflammation, arthritis, rheumatic diseases, lupus, osteoarthritis, inflammatory bowel disorders, inflammatory eye disorders, inflammatory or unstable bladder disorders, psoriasis, skin complaints with inflammatory components, sunburn, carditis, dermatitis, myositis, neuritis, collagen vascular diseases, chronic inflammatory conditions, asthma, epithelial tissue damage or dysfunction, herpes simplex, disturbances of visceral motility at respiratory, genitourinary, gastrointestinal or vascular regions, wounds, burns, allergic skin reactions, pruritis, vitiligo, general gastrointestinal disorders, colitis, gastric ulceration, duodenal ulcers, vasomotor or allergic rhinitis, or bronchial disorders.

Therapeutic Uses of Myostatin Binding Molecules

The myostatin binding agents of the present invention bind to myostatin and block or inhibit myostatin signaling within targeted cells. The present invention provides methods and reagents for reducing the amount or activity of myostatin in an animal by administering an effective dosage of one or more myostatin binding agents to the animal. In one aspect, the present invention provides methods and reagents for treating myostatin-related disorders in an animal comprising administering an effective dosage of one or more binding agents to the animal. These myostatin-related disorders include but are not limited to various forms of muscle wasting, as well as metabolic disorders such as diabetes and related disorders, and bone degenerative diseases such as osteoporosis.

As shown in the Example 8 of U.S. Ser. No. 10/742,379, exemplary peptibodies of the present invention dramatically increases lean muscle mass in the CD1 nu/nu mouse model. This in vivo activity correlates to the in vitro binding and inhibitory activity described below for the same peptibodies.

Muscle wasting disorders include dystrophies such as Duchenne's muscular dystrophy, progressive muscular dystrophy, Becker's type muscular dystrophy, Dejerine-Landouzy muscular dystrophy, Erb's muscular dystrophy, and infantile neuroaxonal muscular dystrophy. For example, blocking myostatin through use of antibodies in vivo improved the dystrophic phenotype of the mdx mouse model of Duchenne muscular dystrophy (Bogdanovich et al. (2002), *Nature* 420: 28). Use of an exemplary peptibody increases lean muscle mass and increases the ratio of lean muscle to fat in mdx mouse models as described in Example 9 below.

Additional muscle wasting disorders arise from chronic disease such as amyotrophic lateral sclerosis, congestive obstructive pulmonary disease, cancer, AIDS, renal failure, and rheumatoid arthritis. For example, cachexia or muscle wasting and loss of body weight was induced in athymic nude mice by a systemically administered myostatin (Zimmers et al., supra). In another example, serum and intramuscular concentrations of myostatin-immunoreactive protein was found to be increased in men exhibiting AIDS-related muscle wasting and was inversely related to fat-free mass (Gonzalez-Cadavid et al. (1998), *PNAS USA* 95: 14938-14943). Additional conditions resulting in muscle wasting may arise from inactivity due to disability such as confinement in a wheelchair, prolonged bedrest due to stroke, illness, bone fracture or trauma, and muscular atrophy in a microgravity environment (space flight). For example, plasma myostatin immunoreactive protein was found to increase after prolonged bedrest (Zachwieja et al. *J Gravit Physiol.* 6(2):11 (1999). It was also found that the muscles of rats exposed to a microgravity environment during a space shuttle flight expressed an increased amount of myostatin compared with the muscles of rats which were not exposed (Lalani et al. (2000), *J. Endocrin.* 167(3):417-28).

In addition, age-related increases in fat to muscle ratios, and age-related muscular atrophy appear to be related to myostatin. For example, the average serum myostatin-immunoreactive protein increased with age in groups of young (19-35 yr old), middle-aged (36-75 yr old), and elderly (76-92 yr old) men and women, while the average muscle mass and fat-free mass declined with age in these groups (Yarasheski et al. *J Nutr Aging* 6(5):343-8 (2002)). It has also been shown that myostatin gene knockout in mice increased myogenesis and decreased adipogenesis (Lin et al. (2002), *Biochem Biophys Res Commun* 291(3):701-6, resulting in adults with increased muscle mass and decreased fat accumulation and leptin secretion. Exemplary molecules improve the lean muscle mass to fat ratio in aged mdx mice as shown below.

In addition, myostatin has now been found to be expressed at low levels in heart muscle and expression is upregulated after cardiomyocytes after infarct (Sharma et al. (1999), *J Cell Physiol.* 180(1):1-9). Therefore, reducing myostatin levels in the heart muscle may improve recovery of heart muscle after infarct.

Myostatin also appears to influence metabolic disorders including type 2 diabetes, noninsulin-dependent diabetes mellitus, hyperglycemia, and obesity. For example, lack of myostatin has been shown to improve the obese and diabetic phenotypes of two mouse models (Yen et al. *supra*). In addition, increasing muscle mass by reducing myostatin levels may improve bone strength and reduce osteoporosis and other degenerative bone diseases. It has been found, for example, that myostatin-deficient mice showed increased mineral content and density of the mouse humerus and increased mineral content of both trabecular and cortical bone at the regions where the muscles attach, as well as increased muscle mass (Hamrick et al. (2002), *Calcif Tissue Int* 71(1): 63-8). In the present invention, an exemplary peptibody increases the lean muscle mass to fat ratio in mdx mouse models as shown below.

The present invention also provides methods and reagents for increasing muscle mass in food animals by administering an effective dosage of the myostatin binding agent to the animal. Since the mature C-terminal myostatin polypeptide is identical in all species tested, myostatin binding agents would be expected to be effective for increasing muscle mass and reducing fat in any agriculturally important species including cattle, chicken, turkeys, and pigs.

The myostatin-binding molecules of the present invention may be used alone or in combination with other therapeutic agents to enhance their therapeutic effects or decrease potential side effects. The molecules of the present invention possess one or more desirable but unexpected combination of properties to improve the therapeutic value of the agents. These properties include increased activity, increased solubility, reduced degradation, increased half-life, reduced toxicity, and reduced immunogenicity. Thus the molecules of the present invention are useful for extended treatment regimes. In addition, the properties of hydrophilicity and hydrophobicity of the compounds of the invention are well balanced, thereby enhancing their utility for both in vitro and especially in vivo uses. Specifically, compounds of the invention have an appropriate degree of solubility in aqueous media that permits absorption and bioavailability in the body, while also having a degree of solubility in lipids that permits the compounds to traverse the cell membrane to a putative site of action, such as a particular muscle mass.

The myostatin-binding molecules of the present invention are useful for treating a "subject" or any animal, including humans, when administered in an effective dosages in a suitable composition.

In addition, the mystatin-binding molecules of the present invention are useful for detecting and quantitating myostatin in a number of assays. These assays are described in detail in U.S. Ser. No. 10/742,379.

In general, the myostatin-binding molecules of the present invention are useful as capture agents to bind and immobilize myostatin in a variety of assays, similar to those described, for example, in Asai, ed., *Methods in Cell Biology*, 37, *Antibodies in Cell Biology*, Academic Press, Inc., New York (1993). The myostatin-binding molecule may be labeled in some manner or may react with a third molecule such as an anti-binding molecule antibody which is labeled to enable myostatin to be detected and quantitated. For example, a myostatin-binding molecule or a third molecule can be modified with a detectable moiety, such as biotin, which can then be bound by a fourth molecule, such as enzyme-labeled streptavidin, or other proteins. (Akerstrom (1985), *J Immunol* 135:2589; Chaubert (1997), *Mod Pathol* 10:585).

Throughout any particular assay, incubation and/or washing steps may be required after each combination of reagents. Incubation steps can vary from about 5 seconds to several hours, preferably from about 5 minutes to about 24 hours. However, the incubation time will depend upon the assay format, volume of solution, concentrations, and the like. Usually, the assays will be carried out at ambient temperature, although they can be conducted over a range of temperatures.

Therapeutic uses of BAFF-binding molecules. Baff-Binding molecules of this invention may be particularly useful in treatment of B-cell mediated autoimmune diseases. In particular, they may be useful in treating, preventing, ameliorating, diagnosing or prognosing lupus, including systemic lupus erythematosus (SLE), and lupus-associated diseases and conditions. Other preferred indications include B-cell mediated cancers, including B-cell lymphoma.

The compounds of this invention can also be used to treat inflammatory conditions of the joints. Inflammatory conditions of a joint are chronic joint diseases that afflict and disable, to varying degrees, millions of people worldwide. Rheumatoid arthritis is a disease of articular joints in which the cartilage and bone are slowly eroded away by a proliferative, invasive connective tissue called pannus, which is derived from the synovial membrane. The disease may involve peri-articular structures such as bursae, tendon sheaths and tendons as well as extra-articular tissues such as the subcutis, cardiovascular system, lungs, spleen, lymph nodes, skeletal muscles, nervous system (central and peripheral) and eyes (Silberberg (1985), Anderson's Pathology, Kissane (ed.), II:1828). Osteoarthritis is a common joint disease characterized by degenerative changes in articular cartilage and reactive proliferation of bone and cartilage around the joint. Osteoarthritis is a cell-mediated active process that may result from the inappropriate response of chondrocytes to catabolic and anabolic stimuli. Changes in some matrix molecules of articular cartilage reportedly occur in early osteoarthritis (Thonar et al. (1993), Rheumatic disease clinics of North America, Moskowitz (ed.), 19:635-657 and Shinmei et al. (1992), *Arthritis Rheum.*, 35:1304-1308). TALL-1, TALL-1R and modulators thereof are believed to be useful in the treatment of these and related conditions.

BAFF-binding molecules may also be useful in treatment of a number of additional diseases and disorders, including acute pancreatitis; ALS; Alzheimer's disease; asthma; atherosclerosis; autoimmune hemolytic anemia; cancer, particularly cancers related to B cells; cachexia/anorexia; chronic fatigue syndrome; cirrhosis (e.g., primary biliary cirrhosis); diabetes (e.g., insulin diabetes); fever; glomerulonephritis, including IgA glomerulonephritis and primary glomerulonephritis; Goodpasture's syndrome; Guillain-Barre syndrome; graft versus host disease; Hashimoto's thyroiditis; hemorrhagic shock; hyperalgesia; inflammatory bowel disease; inflammatory conditions of a joint, including osteoarthritis, psoriatic arthritis and rheumatoid arthritis; inflammatory conditions resulting from strain, sprain, cartilage damage, trauma, orthopedic surgery, infection or other disease processes; insulin-dependent diabetes mellitus; ischemic injury, including cerebral ischemia (e.g., brain injury as a result of trauma, epilepsy, hemorrhage or stroke, each of which may lead to neurodegeneration); learning impairment; lung diseases (e.g., ARDS); lupus, particularly systemic lupus erythematosus (SLE); multiple myeloma; multiple sclerosis; Myasthenia gravis; myelogenous (e.g., AML and CML) and other leukemias; myopathies (e.g., muscle protein metabolism, esp. in sepsis); neurotoxicity (e.g., as induced by HIV); osteoporosis; pain; Parkinson's disease; Pemphigus; polymyositis/dermatomyositis; pulmonary inflammation, including autoimmune pulmonary inflammation; pre-term labor; psoriasis; Reiter's disease; reperfusion injury; septic shock; side effects from radiation therapy; Sjogren's syndrome; sleep disturbance; temporal mandibular joint disease; thrombocytopenia, including idiopathic thrombocytopenia and autoimmune neonatal thrombocytopenia; tumor metastasis; uveitis; and vasculitis.

Combination Therapy. The therapeutic methods, compositions and compounds of the present invention may also be employed, alone or in combination with other cytokines, soluble Mpl receptor, hematopoietic factors, interleukins, growth factors or antibodies in the treatment of disease states characterized by other symptoms as well as platelet deficiencies. It is anticipated that the inventive compound will prove useful in treating some forms of thrombocytopenia in combination with general stimulators of hematopoiesis, such as IL-3 or GM-CSF. Other megakaryocytic stimulatory factors, i.e., meg-CSF, stem cell factor (SCF), leukemia inhibitory factor (LIF), oncostatin M (OSM), or other molecules with megakaryocyte stimulating activity may also be employed with Mpl ligand. Additional exemplary cytokines or hematopoietic factors for such co-administration include IL-1 alpha, IL-1 beta, IL-2, IL-3, IL-4, IL-5, IL-6, IL-11, colony stimulating factor-1 (CSF-1), SCF, GM-CSF, granulocyte colony stimulating factor (G-CSF), EPO, interferon-alpha (IFN-alpha), consensus interferon, IFN-beta, or IFN-gamma. It may further be useful to administer, either simultaneously or sequentially, an effective amount of a soluble mammalian Mpl receptor, which appears to have an effect of causing megakaryocytes to fragment into platelets once the megakaryocytes have reached mature form. Thus, administration of an inventive compound (to enhance the number of mature megakaryocytes) followed by administration of the soluble Mpl receptor (to inactivate the ligand and allow the mature megakaryocytes to produce platelets) is expected to be a particularly effective means of stimulating platelet production. The dosage recited above would be adjusted to compensate for such additional components in the therapeutic composition. Progress of the treated patient can be monitored by conventional methods.

In cases where the inventive compounds are added to compositions of platelets and/or megakaryocytes and related cells, the amount to be included will generally be ascertained experimentally by techniques and assays known in the art. An exemplary range of amounts is 0.1 µg-1 mg inventive compound per $10^6$ cells.

Therapeutics incorporating toxin peptides. Some embodiments of the inventive composition of matter incorporate toxin peptides as additional functional moieties, which toxin peptides can have pharmacologic activity resulting from the ability to bind to ion channels of interest as agonists, mimetics or antagonists of the native ligands of such ion channels of interest. Consequently such embodiments of the inventive composition of matter can have utility in the treatment of pathologies associated with ion channels. Heritable diseases that have a known linkage to ion channels ("channelopathies") cover various fields of medicine, some of which include neurology, nephrology, myology and cardiology. A list of inherited disorders attributed to ion channels (channel types in parentheses) includes:

cystic fibrosis ($Cl^-$ channel; CFTR),
Dent's disease (proteinuria and hypercalciuria; $Cl^-$ channel; CLCN5),
osteopetrosis ($Cl^-$ channel; CLCN7),
familial hyperinsulinemia (SUR1; KCNJ11; K channel),
diabetes (KATP/SUR channel),
Andersen syndrome (KCNJ2, Kir2.1 K channel),
Bartter syndrome (KCNJ1; Kir1.1/ROMK; K channel),
hereditary hearing loss (KCNQ4; K channel),
hereditary hypertension (Liddle's syndrome; SCNN1; epithelial Na channel),
dilated cardiomyopathy (SUR2, K channel),
long-QT syndrome or cardiac arrhythmias (cardiac potassium and sodium channels),
Thymothy syndrome (CACNA1C, Cav1.2),
myasthenic syndromes (CHRNA,CHRNB,CNRNE; nAChR), and a variety of other myopathies,
hyperkalemic periodic paralysis (Na and K channels),
epilepsy ($Na^+$ and $K^+$ channels),
hemiplegic migraine (CACNA1A, Cav2.1 $Ca^{2+}$ channel and ATP1A2),
central core disease (RYR1, RyR1; $Ca^{2+}$ channel), and
paramyotonia and myotonia ($Na^+$, $Cl^-$ channels)

See L. J. Ptacek and Y-H Fu (2004), *Arch. Neurol.* 61: 166-8; B. A. Niemeyer et al. (2001), *EMBO reports* 21: 568-73; F. Lehmann-Horn and K. Jurkat-Rott (1999), *Physiol. Rev.* 79: 1317-72. Although the foregoing list concerned disorders of inherited origin, molecules targeting the channels cited in these disorders can also be useful in treating related disorders of other, or indeterminate, origin.

In addition to the aforementioned disorders, evidence has also been provided supporting ion channels as targets for treatment of:

sickle cell anemia (IKCa1)—in sickle cell anemia, water loss from erythrocytes leads to hemoglobin polymerization and subsequent hemolysis and vascular obstruction. The water loss is consequent to potassium efflux through the so-called Gardos channel i.e., IKCa1. Therefore, block of IKCa1 is a potential therapeutic treatment for sickle cell anemia.

glaucoma (BKCa),—in glaucoma the intraocular pressure is too high leading to optic nerve damage, abnormal eye function and possibly blindness. Block of BKCa potassium channels can reduce intraocular fluid secretion and increase smooth muscle contraction, possibly leading to lower intraocular pressure and neuroprotection in the eye.

multiple sclerosis (Kv, KCa),
psoriasis (Kv, KCa),
arthritis (Kv, KCa),
asthma (KCa, Kv),
allergy(KCa, Kv),
COPD (KCa, Kv, Ca),
allergic rhinitis (KCa, Kv),
pulmonary fibrosis,
lupus (IKCa1, Kv),
transplantation, GvHD (KCa, Kv),
inflammatory bone resorption (KCa, Kv),
periodontal disease (KCa, Kv), diabetes, type I (Kv),—type I diabetes is an autoimmune disease that is characterized by abnormal glucose, protein and lipid metabolism and is associated with insulin deficiency or resistance. In this disease, Kv1.3-expressing T-lymphocytes attack and destroy pancreatic islets leading to loss of beta-cells. Block of Kv1.3 decreases inflammatory cytokines. In addition block of Kv1.3 facilitates the translocation of GLUT4 to the plasma membrane, thereby increasing insulin sensitivity.

obesity (Kv),—Kv1.3 appears to play a critical role in controlling energy homeostasis and in protecting against diet-induced obesity. Consequently, Kv1.3 blockers could increase metabolic rate, leading to greater energy utilization and decreased body weight.

restenosis (KCa, $Ca^{2+}$),—proliferation and migration of vascular smooth muscle cells can lead to neointimal thickening and vascular restenosis. Excessive neointimal vascular smooth muscle cell proliferation is associated with elevated expression of IKCa1. Therefore, block of IKCa1 could represent a therapeutic strategy to prevent restenosis after angioplasty.

ischaemia (KCa, $Ca^{2+}$),—in neuronal or cardiac ischemia, depolarization of cell membranes leads to opening of voltage-gated sodium and calcium channels. In turn this can lead to calcium overload, which is cytotoxic. Block of voltage-gated sodium and/or calcium channels can reduce calcium overload and provide cytoprotective effects. In addition, due to their critical role in controlling and stabilizing cell membrane potential, modulators of voltage- and calcium-activated potassium channels can also act to reduce calcium overload and protect cells.

renal incontinence (KCa), renal incontinence is associated with overactive bladder smooth muscle cells. Calcium-activated potassium channels are expressed in bladder smooth muscle cells, where they control the membrane potential and indirectly control the force and frequency of cell contraction. Openers of calcium-activated potassium channels therefore provide a mechanism to dampen electrical and contractile activity in bladder, leading to reduced urge to urinate.

osteoporosis (Kv), pain, including migraine ($Na_v$, TRP [transient receptor potential channels], P2X, $Ca^{2+}$), N-type voltage-gated calcium channels are key regulators of nociceptive neurotransmission in the spinal cord. Ziconotide, a peptide blocker of N-type calcium channels reduces nociceptive neurotransmission and is approved worldwide for the symptomatic alleviation of severe chronic pain in humans. Novel blockers of nociceptor-specific N-type calcium channels would be improved analgesics with reduced side-effect profiles.

hypertension ($Ca^{2+}$),—L-type and T-type voltage-gated calcium channels are expressed in vascular smooth muscle cells where they control excitation-contraction coupling and cellular proliferation. In particular, T-type calcium channel activity has been linked to neointima formation during hypertension. Blockers of L-type and T-type calcium channels are useful for the clinical treatment of hypertension because they reduce calcium influx and inhibit smooth muscle cell contraction.

wound healing, cell migration serves a key role in wound healing. Intracellular calcium gradients have been implicated as important regulators of cellular migration machinery in keratinocytes and fibroblasts. In addition, ion flux across cell membranes is associated with cell volume changes. By controlling cell volume, ion channels contribute to the intracellular environment that is required for operation of the cellular migration machinery. In particular, IKCa1 appears to be required universally for cell migration. In addition, Kv1.3, Kv3.1, NMDA receptors and N-type calcium channels are associated with the migration of lymphocytes and neurons.

stroke,
Alzheimer's,
Parkenson's Disease (nACHR, Nav)
Bipolar Disorder (Nav, Cav)

cancer, many potassium channel genes are amplified and protein subunits are upregulated in many cancerous condition. Consistent with a pathophysiological role for potassium channel upregulation, potassium channel blockers have been shown to suppress proliferation of uterine cancer cells and hepatocarcinoma cells, presumably through inhibition of calcium influx and effects on calcium-dependent gene expression.

a variety of neurological, cardiovascular, metabolic and autoimmune diseases.

Both agonists and antagonists of ion channels can achieve therapeutic benefit. Therapeutic benefits can result, for example, from antagonizing Kv1.3, IKCa1, SKCa, BKCa, N-type or T-type $Ca^{2+}$ channels and the like. Small molecule and peptide antagonists of these channels have been shown to possess utility in vitro and in vivo.

The diseases and pharmacologically active additional moieties described herein are merely exemplary and in no way limit the range of inventive pharmacologically active compounds and compositions that can be prepared using the inventive method or the diseases and disorders that can be treated with the benefit of the present invention.

Pharmaceutical Compositions

In General. The present invention also provides pharmaceutical compositions comprising the inventive composition of matter and a pharmaceutically acceptable carrier. Such pharmaceutical compositions can be configured for administration to a patient by a wide variety of delivery routes, e.g., an intravascular delivery route such as by injection or infusion, subcutaneous, intramuscular, intraperitoneal, epidural, or intrathecal delivery routes, or for oral, enteral, pulmonary (e.g., inhalant), intranasal, transmucosal (e.g., sublingual administration), transdermal or other delivery routes and/or forms of administration known in the art. The inventive pharmaceutical compositions may be prepared in liquid form, or may be in dried powder form, such as lyophilized form. For oral or enteral use, the pharmaceutical compositions can be configured, for example, as tablets, troches, lozenges, aqueous or oily suspensions, dispersible powders or granules, emulsions, hard or soft capsules, syrups, elixirs or enteral formulas.

In the practice of this invention the "pharmaceutically acceptable carrier" is any physiologically tolerated substance known to those of ordinary skill in the art useful in formulating pharmaceutical compositions, including, any pharmaceutically acceptable diluents, excipients, dispersants, binders, fillers, glidants, anti-frictional agents, compression aids, tablet-disintegrating agents (disintegrants), suspending agents, lubricants, flavorants, odorants, sweeteners, permeation or penetration enhancers, preservatives, surfactants, solubilizers, emulsifiers, thickeners, adjuvants, dyes, coatings, encapsulating material(s), and/or other additives singly or in combination. Such pharmaceutical compositions can include diluents of various buffer content (e.g., Tris-HCl, acetate, phosphate), pH and ionic strength; additives such as detergents and solubilizing agents (e.g., Tween® 80, Polysorbate 80), anti-oxidants (e.g., ascorbic acid, sodium metabisulfite), preservatives (e.g., Thimersol®, benzyl alcohol) and bulking substances (e.g., lactose, mannitol); incorporation of the material into particulate preparations of polymeric compounds such as polylactic acid, polyglycolic acid, etc. or into liposomes. Hyaluronic acid can also be used, and this can have the effect of promoting sustained duration in the circulation. Such compositions can influence the physical state, stability, rate of in vivo release, and rate of in vivo clearance of the present proteins and derivatives. See, e.g., *Remington's Pharmaceutical Sciences*, 18th Ed. (1990, Mack Publishing Co., Easton, Pa. 18042) pages 1435-1712, which are herein incorporated by reference in their entirety. The compositions can be prepared in liquid form, or can be in dried powder, such as lyophilized form. Implantable sustained release formulations are also useful, as are transdermal or transmucosal formulations. Additionally (or alternatively), the present invention provides compositions for use in any of the various slow or sustained release formulations or microparticle formulations known to the skilled artisan, for example, sustained release microparticle formulations, which can be administered via pulmonary, intranasal, or subcutaneous delivery routes.

One can dilute the inventive compositions or increase the volume of the pharmaceutical compositions of the invention with an inert material. Such diluents can include carbohydrates, especially, mannitol, a-lactose, anhydrous lactose, cellulose, sucrose, modified dextrans and starch. Certain inorganic salts may also be used as fillers, including calcium triphosphate, magnesium carbonate and sodium chloride. Some commercially available diluents are Fast-Flo, Emdex, STA-Rx 1500, Emcompress and Avicell.

A variety of conventional thickeners are useful in creams, ointments, suppository and gel configurations of the pharmaceutical composition, such as, but not limited to, alginate, xanthan gum, or petrolatum, may also be employed in such configurations of the pharmaceutical composition of the present invention. A permeation or penetration enhancer, such as polyethylene glycol monolaurate, dimethyl sulfoxide, N-vinyl-2-pyrrolidone, N-(2-hydroxyethyl)-pyrrolidone, or 3-hydroxy-N-methyl-2-pyrrolidone can also be employed. Useful techniques for producing hydrogel matrices are known. (E.g., Feijen, Biodegradable hydrogel matrices for the controlled release of pharmacologically active agents, U.S. Pat. No. 4,925,677; Shah et al., Biodegradable pH/thermosensitive hydrogels for sustained delivery of biologically active agents, WO 00/38651 A1). Such biodegradable gel matrices can be formed, for example, by crosslinking a proteinaceous component and a polysaccharide or mucopolysaccharide component, then loading with the inventive composition of matter to be delivered.

Liquid pharmaceutical compositions of the present invention that are sterile solutions or suspensions can be administered to a patient by injection, for example, intramuscularly, intrathecally, epidurally, intravascularly (e.g., intravenously or intraarterially), intraperitoneally or subcutaneously. (See, e.g., Goldenberg et al., Suspensions for the sustained release of proteins, U.S. Pat. No. 6,245,740 and WO 00/38652 A1). Sterile solutions can also be administered by intravenous infusion. The inventive composition can be included in a sterile solid pharmaceutical composition, such as a lyophilized powder, which can be dissolved or suspended at a convenient time before administration to a patient using sterile water, saline, buffered saline or other appropriate sterile injectable medium.

Implantable sustained release formulations are also useful embodiments of the inventive pharmaceutical compositions. For example, the pharmaceutically acceptable carrier, being a biodegradable matrix implanted within the body or under the skin of a human or non-human vertebrate, can be a hydrogel similar to those described above. Alternatively, it may be formed from a poly-alpha-amino acid component. (Sidman, Biodegradable, implantable drug delivery device, and process for preparing and using same, U.S. Pat. No. 4,351,337). Other techniques for making implants for delivery of drugs are also known and useful in accordance with the present invention.

In powder forms, the pharmaceutically acceptable carrier is a finely divided solid, which is in admixture with finely divided active ingredient(s), including the inventive composition. For example, in some embodiments, a powder form is useful when the pharmaceutical composition is configured as an inhalant. (See, e.g., Zeng et al., Method of preparing dry powder inhalation compositions, WO 2004/017918; Trunk et al., Salts of the CGRP antagonist BIBN4096 and inhalable powdered medicaments containing them, U.S. Pat. No. 6,900,317).

One can dilute or increase the volume of the compound of the invention with an inert material. These diluents could include carbohydrates, especially mannitol, a-lactose, anhydrous lactose, cellulose, sucrose, modified dextrans and starch. Certain inorganic salts can also be used as fillers including calcium triphosphate, magnesium carbonate and sodium chloride. Some commercially available diluents are Fast-Flo™, Emdex™, STA-Rx™ 1500, Emcompress™ and Avicell™.

Disintegrants can be included in the formulation of the pharmaceutical composition into a solid dosage form. Materials used as disintegrants include but are not limited to starch including the commercial disintegrant based on starch, Explotab™. Sodium starch glycolate, Amberlite™, sodium carboxymethylcellulose, ultramylopectin, sodium alginate, gelatin, orange peel, acid carboxymethyl cellulose, natural sponge and bentonite can all be used. Insoluble cationic exchange resin is another form of disintegrant. Powdered gums can be used as disintegrants and as binders and these can include powdered gums such as agar, Karaya or tragacanth. Alginic acid and its sodium salt are also useful as disintegrants.

Binders can be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An antifrictional agent can be included in the formulation of the therapeutic to prevent sticking during the formulation process. Lubricants can be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants can also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants can include starch, talc, pyrogenic silica and hydrated silicoaluminate.

To aid dissolution of the compound of this invention into the aqueous environment a surfactant might be added as a wetting agent. Surfactants can include anionic detergents such as sodium lauryl sulfate, dioctyl sodium sulfosuccinate and dioctyl sodium sulfonate. Cationic detergents might be used and could include benzalkonium chloride or benzethonium chloride. The list of potential nonionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the protein or derivative either alone or as a mixture in different ratios.

Oral dosage forms. Also useful are oral dosage forms of the inventive compositionss. If necessary, the composition can be chemically modified so that oral delivery is efficacious. Generally, the chemical modification contemplated is the attachment of at least one moiety to the molecule itself, where said moiety permits (a) inhibition of proteolysis; and (b) uptake into the blood stream from the stomach or intestine. Also desired is the increase in overall stability of the compound and increase in circulation time in the body. Moieties useful as covalently attached half-life extending moieties in this invention can also be used for this purpose. Examples of such moieties include: PEG, copolymers of ethylene glycol and propylene glycol, carboxymethyl cellulose, dextran, polyvinyl alcohol, polyvinyl pyrrolidone and polyproline. See, for example, Abuchowski and Davis (1981), *Soluble Polymer-Enzyme Adducts, Enzymes as Drugs* (Hocenberg and Roberts, eds.), Wiley-Interscience, New York, N.Y., pp 367-83; Newmark, et al. (1982), *J. Appl. Biochem.* 4:185-9. Other polymers that could be used are poly-1,3-dioxolane and poly-1,3,6-tioxocane. Preferred for pharmaceutical usage, as indicated above, are PEG moieties.

For oral delivery dosage forms, it is also possible to use a salt of a modified aliphatic amino acid, such as sodium N-(8-[2-hydroxybenzoyl]amino) caprylate (SNAC), as a carrier to enhance absorption of the therapeutic compounds of this invention. The clinical efficacy of a heparin formulation using SNAC has been demonstrated in a Phase II trial conducted by Emisphere Technologies. See U.S. Pat. No. 5,792,451, "Oral drug delivery composition and methods."

In one embodiment, the pharmaceutically acceptable carrier can be a liquid and the pharmaceutical composition is prepared in the form of a solution, suspension, emulsion, syrup, elixir or pressurized composition. The active ingredient(s) (e.g., the inventive composition of matter) can be dissolved, diluted or suspended in a pharmaceutically acceptable liquid carrier such as water, an organic solvent, a mixture of both, or pharmaceutically acceptable oils or fats. The liquid carrier can contain other suitable pharmaceutical additives such as detergents and/or solubilizers (e.g., Tween 80, Polysorbate 80), emulsifiers, buffers at appropriate pH (e.g., Tris-HCl, acetate, phosphate), adjuvants, anti-oxidants (e.g., ascorbic acid, sodium metabisulfite), preservatives (e.g., Thimersol, benzyl alcohol), sweeteners, flavoring agents, suspending agents, thickening agents, bulking substances (e.g., lactose, mannitol), colors, viscosity regulators, stabilizers, electrolytes, osmolutes or osmo-regulators. Additives can also be included in the formulation to enhance uptake of the inventive composition. Additives potentially having this property are for instance the fatty acids oleic acid, linoleic acid and linolenic acid.

Useful are oral solid dosage forms, which are described generally in *Remington's Pharmaceutical Sciences* (1990), supra, in Chapter 89, which is hereby incorporated by reference in its entirety. Solid dosage forms include tablets, capsules, pills, troches or lozenges, cachets or pellets. Also, liposomal or proteinoid encapsulation can be used to formulate the present compositions (as, for example, proteinoid microspheres reported in U.S. Pat. No. 4,925,673). Liposomal encapsulation can be used and the liposomes can be derivatized with various polymers (e.g., U.S. Pat. No. 5,013,556). A description of possible solid dosage forms for the therapeutic is given in Marshall, K., *Modern Pharmaceutics* (1979), edited by G. S. Banker and C. T. Rhodes, in Chapter 10, which is hereby incorporated by reference in its entirety. In general, the formulation will include the inventive compound, and inert ingredients that allow for protection against the stomach environment, and release of the biologically active material in the intestine.

The composition of this invention can be included in the formulation as fine multiparticulates in the form of granules or pellets of particle size about 1 mm. The formulation of the material for capsule administration could also be as a powder, lightly compressed plugs or even as tablets. The therapeutic could be prepared by compression.

Colorants and flavoring agents can all be included. For example, the protein (or derivative) can be formulated (such as by liposome or microsphere encapsulation) and then further contained within an edible product, such as a refrigerated beverage containing colorants and flavoring agents.

In tablet form, the active ingredient(s) are mixed with a pharmaceutically acceptable carrier having the necessary compression properties in suitable proportions and compacted in the shape and size desired. The powders and tablets preferably contain up to 99% of the active ingredient(s). Suitable solid carriers include, for example, calcium phosphate, magnesium stearate, talc, sugars, lactose, dextrin, starch, gelatin, cellulose, polyvinylpyrrolidine, low melting waxes and ion exchange resins.

Controlled release formulation can be desirable. The composition of this invention could be incorporated into an inert matrix that permits release by either diffusion or leaching mechanisms e.g., gums. Slowly degenerating matrices can also be incorporated into the formulation, e.g., alginates, polysaccharides. Another form of a controlled release of the compositions of this invention is by a method based on the Oros™ therapeutic system (Alza Corp.), i.e., the drug is enclosed in a semipermeable membrane which allows water to enter and push drug out through a single small opening due to osmotic effects. Some enteric coatings also have a delayed release effect.

Other coatings can be used for the formulation. These include a variety of sugars that could be applied in a coating pan. The therapeutic agent could also be given in a film-coated tablet and the materials used in this instance are divided into 2 groups. The first are the nonenteric materials and include methylcellulose, ethyl cellulose, hydroxyethyl cellulose, methylhydroxy-ethyl cellulose, hydroxypropyl cellulose, hydroxypropyl-methyl cellulose, sodium carboxymethyl cellulose, providone and the polyethylene glycols. The second group consists of the enteric materials that are commonly esters of phthalic acid.

A mix of materials might be used to provide the optimum film coating. Film coating can be carried out in a pan coater or in a fluidized bed or by compression coating.

Pulmonary delivery forms. Pulmonary delivery of the inventive compositions is also useful. The protein (or derivative) is delivered to the lungs of a mammal while inhaling and traverses across the lung epithelial lining to the blood stream. (Other reports of this include Adjei et al., *Pharma. Res.* (1990) 7: 565-9; Adjei et al. (1990), *Internatl. J. Pharmaceutics* 63: 135-44 (leuprolide acetate); Braquet et al. (1989), *J. Cardiovasc. Pharmacol.* 13 (suppl.5): s.143-146 (endothelin-1); Hubbard et al. (1989), *Annals Int. Med.* 3: 206-12 (al-antitrypsin); Smith et al. (1989), *J. Clin. Invest.* 84: 1145-6 (a 1-proteinase); Oswein et al. (March 1990), "Aerosolization of Proteins," *Proc. Symp. Resp. Drug Delivery II*, Keystone, Colo. (recombinant human growth hormone); Debs et al. (1988), *J. Immunol.* 140: 3482-8 (interferon-γ and tumor necrosis factor α) and Platz et al., U.S. Pat. No. 5,284,656 (granulocyte colony stimulating factor). Useful in the practice of this invention are a wide range of mechanical devices designed for pulmonary delivery of therapeutic products, including but not limited to nebulizers, metered dose inhalers, and powder inhalers, all of which are familiar to those skilled in the art. Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, N.C.; and the Spinhaler powder inhaler, manufactured by Fisons Corp., Bedford, Mass. (See, e.g., Helgesson et al, Inhalation device, U.S. Pat. No. 6,892,728; McDerment et al., Dry powder inhaler, WO 02/11801 A1; Ohki et al., Inhalant medicator, U.S. Pat. No. 6,273,086).

All such devices require the use of formulations suitable for the dispensing of the inventive compound. Typically, each formulation is specific to the type of device employed and can involve the use of an appropriate propellant material, in addition to diluents, adjuvants and/or carriers useful in therapy.

The inventive compound should most advantageously be prepared in particulate form with an average particle size of less than 10 μm (or microns), most preferably 0.5 to 5 μm, for most effective delivery to the distal lung.

Pharmaceutically acceptable carriers include carbohydrates such as trehalose, mannitol, xylitol, sucrose, lactose, and sorbitol. Other ingredients for use in formulations can include DPPC, DOPE, DSPC and DOPC. Natural or synthetic surfactants can be used. PEG can be used (even apart from its use in derivatizing the protein or analog). Dextrans, such as cyclodextran, can be used. Bile salts and other related enhancers can be used. Cellulose and cellulose derivatives can be used. Amino acids can be used, such as use in a buffer formulation.

Also, the use of liposomes, microcapsules or microspheres, inclusion complexes, or other types of carriers is contemplated.

Formulations suitable for use with a nebulizer, either jet or ultrasonic, will typically comprise the inventive compound dissolved in water at a concentration of about 0.1 to 25 mg of biologically active protein per mL of solution. The formulation can also include a buffer and a simple sugar (e.g., for protein stabilization and regulation of osmotic pressure). The nebulizer formulation can also contain a surfactant, to reduce or prevent surface induced aggregation of the protein caused by atomization of the solution in forming the aerosol.

Formulations for use with a metered-dose inhaler device will generally comprise a finely divided powder containing the inventive compound suspended in a propellant with the aid of a surfactant. The propellant can be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid can also be useful as a surfactant. (See, e.g., Bäckström et al., Aerosol drug formulations containing hydrofluoroalkanes and alkyl saccharides, U.S. Pat. No. 6,932,962).

Formulations for dispensing from a powder inhaler device will comprise a finely divided dry powder containing the inventive compound and can also include a bulking agent, such as lactose, sorbitol, sucrose, mannitol, trehalose, or xylitol in amounts which facilitate dispersal of the powder from the device, e.g., 50 to 90% by weight of the formulation.

Nasal delivery forms. In accordance with the present invention, intranasal delivery of the inventive composition of matter and/or pharmaceutical compositions is also useful, which allows passage thereof to the blood stream directly after administration to the inside of the nose, without the necessity for deposition of the product in the lung. Formulations suitable for intransal administration include those with dextran or cyclodextran, and intranasal delivery devices are known. (See, e.g, Freezer, Inhaler, U.S. Pat. No. 4,083,368).

Transdermal and transmucosal (e.g., buccal) delivery forms). In some embodiments, the inventive composition is configured as a part of a pharmaceutically acceptable transdermal or transmucosal patch or a troche. Transdermal patch drug delivery systems, for example, matrix type transdermal patches, are known and useful for practicing some embodiments of the present pharmaceutical compositions. (E.g., Chien et al., Transdermal estrogen/progestin dosage unit, system and process, U.S. Pat. Nos. 4,906,169 and 5,023,084; Cleary et al., Diffusion matrix for transdermal drug administration and transdermal drug delivery devices including same, U.S. Pat. No. 4,911,916; Teillaud et al., EVA-based transdermal matrix system for the administration of an estrogen and/or a progestogen, U.S. Pat. No. 5,605,702; Venkateshwaran et al., Transdermal drug delivery matrix for coadministering estradiol and another steroid, U.S. Pat. No. 5,783,208; Ebert et al., Methods for providing testosterone and optionally estrogen replacement therapy to women, U.S. Pat. No. 5,460,820). A variety of pharmaceutically acceptable systems for transmucosal delivery of therapeutic agents are also known in the art and are compatible with the practice of the present invention. (E.g., Heiber et al., Transmucosal delivery of macromolecular drugs, U.S. Pat. Nos. 5,346,701 and 5,516,523;

Longenecker et al., Transmembrane formulations for drug administration, U.S. Pat. No. 4,994,439).

Buccal delivery of the inventive compositions is also useful. Buccal delivery formulations are known in the art for use with peptides. For example, known tablet or patch systems configured for drug delivery through the oral mucosa (e.g., sublingual mucosa), include some embodiments that comprise an inner layer containing the drug, a permeation enhancer, such as a bile salt or fusidate, and a hydrophilic polymer, such as hydroxypropyl cellulose, hydroxypropyl methylcellulose, hydroxyethyl cellulose, dextran, pectin, polyvinyl pyrrolidone, starch, gelatin, or any number of other polymers known to be useful for this purpose. This inner layer can have one surface adapted to contact and adhere to the moist mucosal tissue of the oral cavity and can have an opposing surface adhering to an overlying non-adhesive inert layer. Optionally, such a transmucosal delivery system can be in the form of a bilayer tablet, in which the inner layer also contains additional binding agents, flavoring agents, or fillers. Some useful systems employ a non-ionic detergent along with a permeation enhancer. Transmucosal delivery devices may be in free form, such as a cream, gel, or ointment, or may comprise a determinate form such as a tablet, patch or troche. For example, delivery of the inventive composition can be via a transmucosal delivery system comprising a laminated composite of, for example, an adhesive layer, a backing layer, a permeable membrane defining a reservoir containing the inventive composition, a peel seal disc underlying the membrane, one or more heat seals, and a removable release liner. (E.g., Ebert et al., Transdermal delivery system with adhesive overlay and peel seal disc, U.S. Pat. No. 5,662,925; Chang et al., Device for administering an active agent to the skin or mucosa, U.S. Pat. Nos. 4,849,224 and 4,983,395). These examples are merely illustrative of available transmucosal drug delivery technology and are not limiting of the present invention.

Dosages. The dosage regimen involved in a method for treating the above-described conditions will be determined by the attending physician, considering various factors which modify the action of drugs, e.g. the age, condition, body weight, sex and diet of the patient, the severity of any infection, time of administration and other clinical factors. Generally, the daily regimen should be in the range of 0.1-1000 micrograms of the inventive compound per kilogram of body weight, preferably 0.1-150 micrograms per kilogram.

The following working examples are illustrative and not to be construed in any way as limiting the scope of the present invention.

EXAMPLES

Example 1 huFc(IgG1) Variants Constructed For Bacterial Expression

By way of example, four variants of human Fc domain (huFc(IgG1)) were constructed.

1) huFc(IgG1) with a Q143C mutation (at position 143 of SEQ ID NO:599; designated "Strain 13300") was made as follows. Two PCR fragments introducing the Q143C mutation were amplified from a plasmid encoding the huFc(IgG1). The first PCR fragment was amplified by the following two primers:

3430-37
GAGGAATAACATATGGACAAAACTCACA-
CATGTCCACCT (SEQ ID NO: 641), which encodes the first 8 amino acids of huFc(IgG1) plus a 15-nucleotide 5' extension including a NdeI site; and 4220-28
GGTCAGGCTGACGCAGTTCTTGGTCAG (SEQ ID NO: 642), which encodes 9 amino acids of huFc(IgG1) from the 139th to the 147th amino acid with the 143th amino acid mutated from Glutamine to Cysteine in the 3' orientation.

The second PCR fragment was amplified by the following two primers:

4220-27
CTGACCAAGAACTGCGTCAGCCTGACC (SEQ ID NO: 643), which encodes 9 amino acids of huFc(IgG1) from the 139th to the 147th amino acid with the 143th amino acid mutated from Glutamine to Cysteine in the 5' orientation.

3421-87
CCGCGGCGTCTCGAGATTATTTACCCG-
GAGACAGGGAGAGGCT (SEQ ID NO: 644), which encodes the last 8 amino acids of huFc(IgG1), a stop codon and a 15-nucleotide 3' extension including a XhoI site.

The 2 PCR fragments were again amplified with primers 3430-37 and 3421-87. The PCR product was cloned in pAMG21 vector and sequence-confirmed by DNA sequencing. The E. coli strain that harbors this plasmid is named strain 13300.

The relevant coding sequence of Strain 13300 is:

```
                                              SEQ ID NO: 645
  1 ATGGACAAAA CTCACACATG TCCACCTTGC CCAGCACCTG
    AACTCCTGGG

51 GGGACCGTCA GTTTTCCTCT TCCCCCCAAA ACCCAAGGAC
    ACCCTCATGA

101 TCTCCCGGAC CCCTGAGGTC ACATGCGTGG TGGTGGACGT
    GAGCCACGAA

151 GACCCTGAGG TCAAGTTCAA CTGGTACGTG GACGGCGTGG
    AGGTGCATAA

201 TGCCAAGACA AAGCCGCGGG AGGAGCAGTA CAACAGCACG
    TACCGTGTGG

251 TCAGCGTCCT CACCGTCCTG CACCAGGACT GGCTGAATGG
    CAAGGAGTAC

301 AAGTGCAAGG TCTCCAACAA AGCCCTCCCA GCCCCCATCG
    AGAAAACCAT

351 CTCCAAAGCC AAAGGGCAGC CCCGAGAACC ACAGGTGTAC
    ACCCTGCCCC

401 CATCCCGGGA TGAGCTGACC AAGAACTGCG TCAGCCTGAC
    CTGCCTGGTC

451 AAAGGCTTCT ATCCCAGCGA CATCGCCGTG GAGTGGGAGA
    GCAATGGGCA

501 GCCGGAGAAC AACTACAAGA CCACGCCTCC CGTGCTGGAC
    TCCGACGGCT

551 CCTTCTTCCT CTACAGCAAG CTCACCGTGG ACAAGAGCAG
    GTGGCAGCAG

601 GGGAACGTCT TCTCATGCTC CGTGATGCAT GAGGCTCTGC
    ACAACCACTA

651 CACGCAGAAG AGCCTCTCCC TGTCTCCGGG TAAATAAT//
```

The translation of this nucleotide sequence is as follows:
Strain 13300 (huFC(IgG1)Q143C):

(SEQ ID NO: 646)
```
  1 MDKTHTCPPC PAPELLGGPS VFLFPPKPKD TLMISRTPEV
    TCVVVDVSHE

51 DPEVKFNWYV DGVEVHNAKT KPREEQYNST YRVVSVLTVL
    HQDWLNGKEY

101 KCKVSNKALP APIEKTISKA KGQPREPQVY TLPPSRDELT
    KNCVSLTCLV

151 KGFYPSDIAV EWESNGQPEN NYKTTPPVLD SDGSFFLYSK
    LTVDKSRWQQ

201 GNVFSCSVMH EALHNHYTQK SLSLSPGK//.
```

2) huFc(IgG1) with a L139C mutation (at position 139 of SEQ ID NO:599; designated "Strain 13322") was made following procedures similar to those described in (1) above using the following primers and procedures. The first PCR fragment was amplified by the following two primers:
3430-37
GAGGAATAACATATGGACAAAACTCACA-CATGTCCACCT (SEQ ID NO: 641), which encodes the first 8 amino acids of huFc(IgG1) plus a 15-nucleotide 5' extension including a NdeI site and
4220-26
CTGGTTCTTGGTGCACTCATCCCGGGA (SEQ ID NO: 647), which encodes 9 amino acids of huFc(IgG1) from the 135th to the 143th amino acid with the 138th amino acid mutated from Leucine to Cysteine in the 3' orientation.
The second PCR fragment was amplified by the following two primers:
4220-25
TCCCGGGATGAGTGCACCAAGAACCAG (SEQ ID NO: 648), which encodes 9 amino acids of huFc(IgG1) from the 135th to the 143th amino acid with the 138th amino acid mutated from Leucine to Cysteine in the 5' orientation.
3421-87
CCGCGGCGTCTCGAGATTATTTACCCG-GAGACAGGGAGAGGCT (SEQ ID NO: 644), which encodes the last 8 amino acids of huFc(IgG1), a stop codon and a 15-nucleotide 3' extension including a XhoI site. The 2 PCR fragments were again amplified with primers 3430-37 and 3421-87. The PCR product was cloned in pAMG21 vector and sequenced-confirmed by DNA sequencing. The *E. coli* strain that harbors this plasmid is named strain 13322.
The relevant coding sequence of Strain 13322 is:

SEQ ID NO: 649
```
  1 ATGGACAAAA CTCACACATG TCCACCTTGC CCAGCACCTG
    AACTCCTGGG

51 GGGACCGTCA GTTTTCCTCT TCCCCCCAAA ACCCAAGGAC
    ACCCTCATGA

101 TCTCCCGGAC CCCTGAGGTC ACATGCGTGG TGGTGGACGT
    GAGCCACGAA

151 GACCCTGAGG TCAAGTTTAA CTGGTACGTG ACGGCGTGG
    AGGTGCATAA

201 TGCCAAGACA AAGCCGCGGG AGGAGCAGTA CAACAGCACG
    TACCGTGTGG

251 TCAGCGTCCT CACCGTCCTG CACCAGGACT GGCTGAATGG
    CAAGGAGTAC

301 AAGTGCAAGG TCTCCAACAA AGCCCTCCCA GCCCCCATCG
    AGAAAACCAT

351 CTCCAAAGCC AAAGGGCAGC CCCGAGAACC ACAGGTGTAC
    ACCCTGCCCC

401 CATCCCGGGA TGAGTGCACC AAGAACCAGG TCAGCCTGAC
    CTGCCTGGTC

451 AAAGGCTTCT ATCCCAGCGA CATCGCCGTG GAGTGGGAGA
    GCAATGGGCA

501 GCCGGAGAAC AACTACAAGA CCACGCCTCC CGTGCTGGAC
    TCCGACGGCT

551 CCTTCTTCCT CTACAGCAAG CTCACCGTGG ACAAGAGCAG
    GTGGCAGCAG

601 GGGAACGTCT TCTCATGCTC CGTGATGCAT GAGGCTCTGC
    ACAACCACTA

651 CACGCAGAAG AGCCTCTCCC TGTCTCCGGG TAAATAAT//.
```

The translation of this nucleotide sequence is as follows:
Strain 13322 (huFc(IgG1)L139C):

(SEQ ID NO: 650)
```
  1 MDKTHTCPPC PAPELLGGPS VFLFPPKPKD TLMISRTPEV
    TCVVVDVSHE

51 DPEVKFNWYV DGVEVHNAKT KPREEQYNST YRVVSVLTVL
    HQDWLNGKEY

101 KCKVSNKALP APIEKTISKA KGQPREPQVY TLPPSRDECT
    KNQVSLTCLV

151 KGFYPSDIAV EWESNGQPEN NYKTTPPVLD SDGSFFLYSK
    LTVDKSRWQQ

201 GNVFSCSVMH EALHNHYTQK SLSLSPGK//.
```

3) huFc(IgG1) with a S145C mutation (at position 145 of SEQ ID NO:599; designated "Strain 13323") was made following procedures similar to those described in (1) above using the following primers and procedures. The first PCR fragment was amplified by the following two primers:
3430-37
GAGGAATAACATATGGACAAAACTCACA-CATGTCCACCT (SEQ ID NO: 641) which encodes the first 8 amino acids of huFc(IgG1) plus a 15-nucleotide 5' extension including a NdeI site and
4220-30
CAGGCAGGTCAGGCAGACCTGGTTCTT (SEQ ID NO: 651), which encodes the 9 amino acids of huFc (IgG1) from the 141th to the 149th amino acid with the 145th amino acid mutated from Serine to Cysteine in the 3' orientation.
The second PCR fragment was amplified by the following two primers:
4220-29
AAGAACCAGGTCTGCCTGACCTGCCTG (SEQ ID NO: 652), which encodes the 9 amino acids of huFc (IgG1) from the 141th to the 149th amino acid with the 145th amino acid mutated from Serine to Cysteine in the 5' orientation.
3421-87
CCGCGGCGTCTCGAGATTATTTACCCG-GAGACAGGGAGAGGCT (SEQ ID NO: 644), which encodes the last 8 amino acids of huFc(IgG1), a stop codon and a 15-nucleotide 3' extension including a XhoI site. The 2 PCR fragments were again amplified with primers 3430-37 and 3421-87. The PCR product was cloned in pAMG21 vector and sequence-confirmed by DNA sequencing. The *E. coli* strain that harbors this plasmid is named strain 13323.

The relevant coding sequence of Strain 13323 is:

```
                                       SEQ ID NO: 653
  1  ATGGACAAAA CTCACACATG TCCACCTTGC CCAGCACCTG
     AACTCCTGGG

51  GGGACCGTCA GTTTTCCTCT TCCCCCCAAA ACCCAAGGAC
     ACCCTCATGA

101  TCTCCCGGAC CCCTGAGGTC ACATGCGTGG TGGTGGACGT
     GAGCCACGAA

151  GACCCTGAGG TCAAGTTCAA CTGGTACGTG GACGGCGTGG
     AGGTGCATAA

201  TGCCAAGACA AAGCCGCGGG AGGAGCAGTA CAACAGCACG
     TACCGTGTGG

251  TCAGCGTCCT CACCGTCCTG CACCAGGACT GGCTGAATGG
     CAAGGAGTAC

301  AAGTGCAAGG TCTCCAACAA AGCCCTCCCA GCCCCCATCG
     AGAAAACCAT

351  CTCCAAAGCC AAAGGGCAGC CCCGAGAACC ACAGGTGTAC
     ACCCTGCCCC

401  CATCCCGGGA TGAGCTGACC AAGAACCAGG TCTGCCTGAC
     CTGCCTGGTC

451  AAAGGCTTCT ATCCCAGCGA CATCGCCGTG GAGTGGGAGA
     GCAATGGGCA

501  GCCGGAGAAC AACTACAAGA CCACGCCTCC CGTGCTGGAC
     TCCGACGGCT

551  CCTTCTTCCT CTACAGCAAG CTCACCGTGG ACAAGAGCAG
     GTGGCAGCAG

601  GGGAACGTCT TCTCATGCTC CGTGATGCAT GAGGCTCTGC
     ACAACCACTA

651  CACGCAGAAG AGCCTCTCCC TGTCTCCGGG TAAATAAT//
```

The translation of this sequence is as follows:

Strain 13323 (huFc(IgG1)S145C):

```
                                      (SEQ ID NO: 654)
  1  MDKTHTCPPC PAPELLGGPS VFLFPPKPKD TLMISRTPEV
     TCVVVDVSHE

51  DPEVKFNWYV DGVEVHNAKT KPREEQYNST YRVVSVLTVL
     HQDWLNGKEY

101  KCKVSNKALP APIEKTISKA KGQPREPQVY TLPPSRDELT
     KNQVCLTCLV

151  KGFYPSDIAV EWESNGQPEN NYKTTPPVLD SDGSFFLYSK
     LTVDKSRWQQ

201  GNVFSCSVMH EALHNHYTQK SLSLSPGK//.
```

4) huFc(IgG1) with a S196C mutation (at position 196 of SEQ ID NO:599; designated "Strain 13324") was made following procedures similar to those described in (1) above using the following primers and procedures. The first PCR fragment was amplified by the following two primers:

3430-37
GAGGAATAACATATGGACAAAACTCACA-CATGTCCACCT (SEQ ID NO: 641), which encodes the first 8 amino acids of huFc(IgG1) plus a 15-nucleotide 5' extension including a NdeI site and 4220-32
CTGCTGCCACCTGCACTTGTCCACGGT (SEQ ID NO: 655), which encodes 9 amino acids of huFc(IgG1) from the 192th to the 200th amino acid with the 196th amino acid mutated from Serine to Cysteine in the 3' orientation.

The second PCR fragment was amplified by the following two primers:

4220-31
ACCGTGGACAAGTGCAGGTGGCAGCAG (SEQ ID NO: 656), which encodes 9 amino acids of huFc(IgG1) from the 192th to the 200th amino acid with the 196th amino acid mutated from Serine to Cysteine in the 5' orientation.

3421-87
CCGCGGCGTCTCGAGATTATTTACCCG-GAGACAGGGAGAGGCT (SEQ ID NO: 644), which encodes the last 8 amino acids of huFc(IgG1), a stop codon and a 15-nucleotide 3' extension including a XhoI site. The 2 PCR fragments were again amplified with primers 3430-37 and 3421-87. The PCR product was cloned in pAMG21 vector and sequenced-confirmed by DNA sequencing. The *E. coli* strain that harbors this plasmid is named strain 13324.

The relevant coding sequence of Strain 13324 is:

```
                                       SEQ ID NO: 657
  1  ATGGACAAAA CTCACACATG TCCACCTTGC CCAGCACCTG
     AACTCCTGGG

51  GGGACCGTCA GTTTTCCTCT TCCCCCCAAA ACCCAAGGAC
     ACCCTCATGA

101  TCTCCCGGAC CCCTGAGGTC ACATGCGTGG TGGTGGACGT
     GAGCCACGAA

151  GACCCTGAGG TCAAGTTCAA CTGGTACGTG GACGGCGTGG
     AGGTGCATAA

201  TGCCAAGACA AAGCCGCGGG AGGAGCAGTA CAACAGCACG
     TACCGTGTGG

251  TCAGCGTCCT CACCGTCCTG CACCAGGACT GGCTGAATGG
     CAAGGAGTAC

301  AAGTGCAAGG TCTCCAACAA AGCCCTCCCA GCCCCCATCG
     AGAAAACCAT

351  CTCCAAAGCC AAAGGGCAGC CCCGAGAACC ACAGGTGTAC
     ACCCTGCCCC

401  CATCCCGGGA TGAGCTGACC AAGAACCAGG TCAGCCTGAC
     CTGCCTGGTC

451  AAAGGCTTCT ATCCCAGCGA CATCGCCGTG GAGTGGGAGA
     GCAATGGGCA

501  GCCGGAGAAC AACTACAAGA CCACGCCTCC CGTGCTGGAC
     TCCGACGGCT

551  CCTTCTTCCT CTACAGCAAG CTCACCGTGG ACAAGTGCAG
     GTGGCAGCAG

601  GGGAACGTCT TCTCATGCTC CGTGATGCAT GAGGCTCTGC
     ACAACCACTA

651  CACGCAGAAG AGCCTCTCCC TGTCTCCGGG TAAATAAT//
```

The translation of this nucleotide sequence is as follows:
Strain 13324 (huFC(IgG1)S196C):

(SEQ ID NO: 658)
```
  1  MDKTHTCPPC PAPELLGGPS VFLFPPKPKD TLMISRTPEV
     TCVVVDVSHE

51  DPEVKFNWYV DGVEVHNAKT KPREEQYNST YRVVSVLTVL
     HQDWLNGKEY

101  KCKVSNKALP APIEKTISKA KGQPREPQVY TLPPSRDELT
     KNQVSLTCLV

151  KGFYPSDIAV EWESNGQPEN NYKTTPPVLD SDGSFFLYSK
     LTVDKCRWQQ

201  GNVFSCSVMH EALHNHYTQK SLSLSPGK//.
```

Example 2

Purification of Fc-Cysteine Analogs

The cDNA clones constructed as described in Example 1 hereinabove: Strain 13300 (huFc(IgG1)Q143C), Strain 13322 (huFc(IgG1)L139C), Strain 13323 (huFc(IgG1)S145C) and Strain 13324 (huFc(IgG1)S196C) were transformed in *E. coli* and expressed in inclusion bodies. Cell pastes from each strain were resuspended in 10 ml water/g paste, lysed by three passages through a microfluidizer and the insoluble inclusion body (IB) fraction was collected by centrifugation. The IBs were subsequently washed with 1% deoxycholate, centrifuged and washed again with water. The final pellet of deoxycholate washed inclusion bodies (DWIBs) was weighed and frozen at −80° C.

The frozen DWIBs, from each clone, were then thawed and resuspended in 1 ml water/g DWIBs, then solubilized and reduced by the addition of 9 ml of 8 M buffered Gdn-HCl, 11 mM DTT. The solubilization proceeded at room temperature, with stirring, for 1 hour.

Each huFc-cysteine analog was then refolded by rapid dilution (20-fold) of the solubilized DWIBs into a refolding buffer consisting of 2 M Urea, 150 mM Arginine, 50 mM Tris, 1 mM Cysteine, 3 mM Cystamine, pH 8.5. The refolding reaction was allowed to proceed for 48-72 hours with gentle stirring at 4° C.

Purification of the huFc-cysteine analogs began affinity column chromatography using MAb Select resin (GE Healthcare, Piscataway, N.J.). Briefly, the refold reaction was clarified by centrifugation followed by 0.45 micron filtration. The filtered refold was then loaded to a MAb select column pre-equilibrated in PBS. After loading, the column was further washed with 3 column volumes PBS, then eluted with 0.1 N acetic acid. The protein fraction that was acid eluted from the MAb Select column was immediately dialyzed into 10 mM NaOAc, 50 mM NaCl, pH 5.0.

Additional purification was achieved by cation exchange chromatography using SP Sepharose HP resin (GE Healthcare, Piscataway, N.J.). Briefly, after dialysis, the MAb Select eluted pool was loaded to the ion exchange column, pre-equilibrated in 10 mM NaOAc, 50 mM NaCl, pH 5.0, washed with 3 column volumes of equilibration buffer, then eluted with a linear 50-500 mM NaCl gradient. The eluted peaks were evaluated by SDS-PAGE and the peaks containing protein of approximately 51 kD were pooled and concentrated. The concentrated pools were then dialyzed into PBS and concentrations determined spectrascopically using calculated extinction coefficients.

The final pools were analyzed by SDS-PAGE, SEC-HPLC, RP-HPLC and LC-MS. FIG. 5 shows the purity by SDS-PAGE gel of the 4 purified huFc-cysteine analogs. FIG. 6 shows the purity of clone 13324 huFCS196C by SEC-HPLC. FIG. 7 shows the purity and mass determinations of clone 13324 huFc(S196C) by LC-MS. Additional mass observed is consistent with cystamine adducts carried over from the refold reaction. The observed mass differential disappears when the samples are reduced prior to LC-MS analyses, further indicating a mixed disulphide adduct is present.

Example 3

Conjugation of Polyethylene Glycol (PEG) to Fc-Cysteine Analogs

The huFc (S196C) analog, clone #13324, was selected as representative of the huFc-cysteine analogs produced, as described in Example 2 herein above, for the purpose of developing a site-selective conjugation process for the Fc-cysteine analogs. Since the LC-MS analyses of the purified huFc-cysteine analogs indicated the presence of mixed disulphides with low molecular weight adducts, a limited reduction step was undertaken prior to conjugation. This was followed by thiol specific PEGylation to assess the degree and site-selectivity of conjugation at the engineered cysteine.

Briefly, the huFc (S196C) analog described in Example 2 was partially reduced by titrating ris(2-carboxyethylphosphine) hydrochloride (TCEP) from 0-5 molar excess stoichiometries relative to the concentration of engineered cysteine. The reduction reaction was incubated 2 hours, at room temperature, in 50 mM sodium phosphate, 5 mM EDTA, pH 6.0 at a protein concentration of 1 mg/ml. TCEP and reduced adduct were removed by gel filtration using disposable Zebra desalt spin columns (Pierce, Rockford, Ill.) equilibrated in 50 mM sodium phosphate, 5 mM EDTA, pH 6.0. The reduced protein eluted from the gel filtration was then reacted with 20 kD mPEG-maleimide (Nektar Inc., Huntsville, Ala.) in a 2-fold molar excess over the engineered cysteine concentration. The PEGylation reaction was allowed to proceed overnight, at room temperature. The extent of modification was determined by SDS-PAGE (FIG. 8A and FIG. 8B) and by SEC-HPLC (FIG. 9A-B).

Next, the PEGylation reaction was scaled up using a 1:1.25 molar ratio of engineered cysteine to TCEP and the PEG-huFc(S196C) analog was purified by cation exchange chromatography. Purification was achieved with an SP Sepharose HP column (GE Healthcare, Piscataway, N.J.) equilibrated in 20 mM sodium acetate, pH 4.0 and was eluted with a linear 0-0.5 M sodium chloride gradient. The eluted peaks were evaluated by SDS-PAGE and SEC-LS and were pooled and concentrated based on size. FIG. 9A-B shows the SEC-LS result identifying the isolated PEG-huFc(S196C) conjugate, demonstrating a mass consistent with two 20 kD PEG molecules conjugated to one Fc dimer (~53 kD). Subsequent peptide mapping confirmed Cys196 as the site of PEGylation in this pool.

Abbreviations

Abbreviations used throughout this specification are as defined below, unless otherwise defined in specific circumstances.

Ac acetyl (used to refer to acetylated residues)
AcBpa acetylated p-benzoyl-L-phenylalanine
ADCC antibody-dependent cellular cytotoxicity
Aib aminoisobutyric acid
bA beta-alanine
Bpa p-benzoyl-L-phenylalanine
BrAc bromoacetyl (BrCH$_2$C(O))
BSA Bovine serum albumin Bzl Benzyl
Cap Caproic acid
CTL Cytotoxic T lymphocytes
CTLA4 Cytotoxic T lymphocyte antigen 4
DARC Duffy blood group antigen receptor
DCC Dicylcohexylcarbodiimide
Dde 1-(4,4-dimethyl-2,6-dioxo-cyclohexylidene)ethyl
EDTA ethylene diamine tetraacetic acid
EMP Erythropoietin-mimetic peptide
ESI-MS Electron spray ionization mass spectrometry
EPO Erythropoietin
Fmoc fluorenylmethoxycarbonyl
G-CSF Granulocyte colony stimulating factor
GH Growth hormone
HCT hematocrit
HGB hemoglobin
hGH Human growth hormone
HOBt 1-Hydroxybenzotriazole
HPLC high performance liquid chromatography
IL interleukin
IL-R interleukin receptor
IL-1R interleukin-1 receptor
IL-1ra interleukin-1 receptor antagonist
Lau Laurie acid
LPS lipopolysaccharide
LYMPH lymphocytes
MALDI-MS Matrix-assisted laser desorption ionization mass spectrometry
Me methyl
MeO methoxy
MHC major histocompatibility complex
MMP matrix metalloproteinase
MMPI matrix metalloproteinase inhibitor
1-Nap 1-napthylalanine
NEUT neutrophils
NGF nerve growth factor
Nle norleucine
NMP N-methyl-2-pyrrolidinone
PAGE polyacrylamide gel electrophoresis
PBS Phosphate-buffered saline
Pbf 2,2,4,6,7-pendamethyldihydrobenzofuran-5-sulfonyl
PCR polymerase chain reaction
Pec pipecolic acid
PEG Poly(ethylene glycol)
pGlu pyroglutamic acid
Pic picolinic acid
PLT platelets
pY phosphotyrosine
PTFE polytetrafluoroethylene
RBC red blood cells
RBS ribosome binding site
RP-HPLC reversed phase HPLC
RT room temperature (25° C.)
Sar sarcosine
SDS sodium dodecyl sulfate
STK serine-threonine kinases
t-Boc tert-Butoxycarbonyl
tBu tert-Butyl
TGF tissue growth factor
THF thymic humoral factor
TK tyrosine kinase
TMP Thrombopoietin-mimetic peptide
TNF Tissue necrosis factor
TPO Thrombopoietin
TRAIL TNF-related apoptosis-inducing ligand
Trt trityl
UK urokinase
UKR urokinase receptor
VEGF vascular endothelial cell growth factor
VIP vasocative inteinal peptide
WBC white blood cells

---

What is claimed is:

1. A composition of matter of the formula

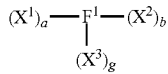

wherein:

$F^1$ is a monomer of the monomeric or multimeric Fc domain;

$X^1$ is covalently bound to the N-terminus of $F^1$ through the α-amino site of $F^1$;

$X^2$ is covalently bound to the C-terminus of $F^1$ through the α-carboxy site of $F^1$;

$X^3$ is covalently bound to the one or more specifically selected internal conjugation site(s) in $F^1$ through the side chain of an amino acid residue selected from the group consisting of D46, S48, H49, E50, E53, K55, D61, G62, Q76, K107, K121, G122, Q123, R136, D137, T140, K141, N142, N170, K173, S181, G183, D194, K195, R197, and Q199, relative to reference sequence SEQ ID NO: 599, or, if g>1, any combination of these members;

$X^1$, $X^2$, and $X^3$ are each independently selected from $-(L^1)_c-P^0$, $-(L^1)_c-P^1$, $-(L^1)_c-P^1-(L^2)_d-P^2$, $-(L^1)_c-P^1-(L^2)_d-P^2-(L^3)_e-P^3$, and $-(L^1)_c-P^1-(L^2)_d-P^2-(L^3)_e-P^3-(L^4)_f-P^4$;

$P^0$, $P^1$, $P^2$, $P^3$, and $P^4$ are each independently selected from the group consisting of:
 i) a pharmaceutically acceptable polymer or dextran;
 ii) a pharmacologically active polypeptide, peptide, peptidomimetic, or non-peptide organic moiety;
 iii) a radioisotope, an enzyme, a biotinyl moiety, a fluorophore, or a chromophore; and
 iv) an immobilized substrate, provided that in a chain comprising more than one additional functional moieties, the immobilized substrate is the moiety most distal from $F^1$, and there can be no more than one immobilized substrate in the chain;

$L^1$, $L^2$, $L^3$, and $L^4$ are each independently linkers;

a, b, c, d, e, and f are each independently 0 or 1; and g is 1, 2, 3, or 4.

2. The composition of matter of claim 1, wherein the Fc domain comprises an IgG Fc domain.

3. The composition of matter of claim 1, wherein the Fc domain comprises an IgG1 Fc domain.

4. The composition of matter of claim 3, wherein the IgG1 Fc domain comprises SEQ ID NO:600 or SEQ ID NO: 603.

5. The composition of matter of claim 1, wherein a =0 and b=1, or a=1 and b=0, or a=1 and b=1, or a=0 and b=0.

6. The composition of matter of claim 1, wherein $X^3$ comprises polyethylene glycol (PEG).

7. The composition of matter of claim 1, wherein $X^3$ has the structure $-(L^1)_c-P^1$ or $-(L^1)_c-P^1-(L^2)_d-P^2$.

8. The composition of matter of claim 1, wherein g=1 or 2.

9. The composition of matter of claim 1, wherein the pharmacologically active peptide is a toxin peptide and/or comprises a cyclic peptide.

10. The composition of matter of claim 1, wherein $P^0$, $P^1$, $P^2$, $P^3$, or $P^4$ is a non-peptide organic moiety.

11. The composition of matter of claim 1, wherein $P^0$, $P^1$, $P^2$, $P^3$, or $P^4$ is a radioisotope, an enzyme, a biotinyl moiety, a fluorophore, or a chromophore.

12. The composition of matter of claim 1, wherein $P^0$, $P^1$, $P^2$, $P^3$, or $P^4$ is selected from the group consisting of an immobilized substrate, a half-life extending moiety, a polymer, and polyethylene glycol.

13. The composition of matter of claim 12, wherein the half-life extending moiety is a polyethylene glycol, a copolymer of ethylene glycol, a polypropylene glycol, a copolymer of propylene glycol, a carboxymethylcellulose, a polyvinyl pyrrolidone, a poly-1,3-dioxolane, a poly-1,3,6-trioxane, an ethylene maleic anhydride copolymer, a polyaminoacid, a dextran n-vinyl pyrrolidone, a poly n-vinyl pyrrolidone, a propylene glycol homopolymer, a propylene oxide polymer, an ethylene oxide polymer, a polyoxyethylated polyol, a polyvinyl alcohol, a linear or branched glycosylated chain, a polyacetal, a long chain fatty acid, a long chain hydrophobic aliphatic group, an immunoglobulin $F_c$ domain, an albumin, a transthyretin, or a thyroxine-binding globulin; or a combination of any of these members.

14. The composition of matter of claim 1, wherein any of $X^1$, $X^2$, or $X^3$ comprises a B cell activating factor (BAFF) binding peptide or polypeptide.

15. The composition of matter of claim 14, wherein the BAFF binding peptide or polypeptide comprises the amino acid sequence of SEQ ID NO:514.

16. A pharmaceutical composition, comprising the composition of matter of claim 1, and a pharmaceutically acceptable carrier.

17. The composition of matter of claim 1, wherein:
(a) the composition of matter is an antibody modified so that it comprises at least one $X^3$ additional functional moiety covalently bound to the Fc domain of the antibody through one or more specifically selected internal conjugation site(s) in the Fc domain through the side chain of an amino acid residue selected from the group consisting of D46, S48, H49, E50, E53, K55, D61, G62, Q76, K107, K121, G122, Q123, R136, D137, T140, K141, N142, N170, K173, S181, G183, D194, K195, R197, and Q199, relative to reference sequence SEQ ID NO: 599, or, if there is more than one $X^3$, any combination of these members;
(b) $X^3$ is selected from $-(L^1)_c-P^0$, $-(L^1)_c-P^1$, $-(L^1)_c-P^1-(L^2)_d-P^2$, $-(L^1)_c-P^1-(L^2)_d-P^2-(L^3)_e-P^3$, and $-(L^1)_c-P^1-(L^2)_d-P^2-(L^3)_e-P^3-(L^4)_f-P^4$;
$P^0$, $P^1$, $P^2$, $P^3$, and $P^4$ are each independently selected from the group consisting of:
 i) a pharmaceutically acceptable polymer or dextran;
 ii) a pharmacologically active polypeptide, peptide, peptidomimetic, or non-peptide organic moiety;
 iii) a radioisotope, an enzyme, a biotinyl moiety, a fluorophore, or a chromophore; and
 iv) an immobilized substrate, provided that in a chain comprising more than one additional functional moieties, the immobilized substrate is the moiety most distal from the Fc domain, and there can be no more than one immobilized substrate in the chain;
$L^1$, $L^2$, $L^3$, and $L^4$ are each independently linkers;
c, d, e, and f are each independently 0 or 1.

18. A pharmaceutical composition, comprising the composition of matter of claim 1, and a pharmaceutically acceptable carrier.

19. A pharmaceutical composition, comprising the composition of matter of claim 17, and a pharmaceutically acceptable carrier.

20. The composition of matter of claim 17, comprising a B cell activating factor (BAFF) binding peptide or polypeptide.

21. The composition of matter of claim 20, wherein the BAFF binding peptide or polypeptide comprises the amino acid sequence of SEQ ID NO: 514.

* * * * *

SEQUENCE LISTING

```
<160> NUMBER OF SEQ ID NOS: 658

<210> SEQ ID NO 1
<211> LENGTH: 14
<212> TYPE: PRT
<213> ORGANISM: Artificial Sequence
<220> FEATURE:
<223> OTHER INFORMATION: EPO-mimetic peptide sequence
<220> FEATURE:
<221> NAME/KEY: MISC_FEATURE
<222> LOCATION: (2)..(2)
<223> OTHER INFORMATION: Xaa is any amino acid
<220> FEATURE:
<221> NAME/KEY: MISC_FEATURE
<222> LOCATION: (4)..(5)
<223> OTHER INFORMATION: Xaa is any amino acid
<220> FEATURE:
<221> NAME/KEY: MISC_FEATURE
<222> LOCATION: (8)..(8)
<223> OTHER INFORMATION: Xaa is any amino acid
<220> FEATURE:
<221> NAME/KEY: MISC_FEATURE
<222> LOCATION: (11)..(11)
<223> OTHER INFORMATION: Xaa is any amino acid
<220> FEATURE:
<221> NAME/KEY: MISC_FEATURE
<222> LOCATION: (13)..(13)
<223> OTHER INFORMATION: Xaa is any amino acid

<400> SEQUENCE: 1

Tyr Xaa Cys Xaa Xaa Gly Pro Xaa Thr Trp Xaa Cys Xaa Pro
1               5                   10
```

```
<210> SEQ ID NO 2
<211> LENGTH: 20
<212> TYPE: PRT
<213> ORGANISM: Artificial Sequence
<220> FEATURE:
<223> OTHER INFORMATION: EPO-mimetic peptide sequence

<400> SEQUENCE: 2

Gly Gly Thr Tyr Ser Cys His Phe Gly Pro Leu Thr Trp Val Cys Lys
1               5                   10                  15

Pro Gln Gly Gly
            20

<210> SEQ ID NO 3
<211> LENGTH: 20
<212> TYPE: PRT
<213> ORGANISM: Artificial Sequence
<220> FEATURE:
<223> OTHER INFORMATION: EPO-mimetic peptide sequence

<400> SEQUENCE: 3

Gly Gly Asp Tyr His Cys Arg Met Gly Pro Leu Thr Trp Val Cys Lys
1               5                   10                  15

Pro Leu Gly Gly
            20

<210> SEQ ID NO 4
<211> LENGTH: 20
<212> TYPE: PRT
<213> ORGANISM: Artificial Sequence
<220> FEATURE:
<223> OTHER INFORMATION: EPO-mimetic peptide sequence

<400> SEQUENCE: 4

Gly Gly Val Tyr Ala Cys Arg Met Gly Pro Ile Thr Trp Val Cys Ser
1               5                   10                  15

Pro Leu Gly Gly
            20

<210> SEQ ID NO 5
<211> LENGTH: 20
<212> TYPE: PRT
<213> ORGANISM: Artificial Sequence
<220> FEATURE:
<223> OTHER INFORMATION: EPO-mimetic peptide sequence

<400> SEQUENCE: 5

Val Gly Asn Tyr Met Cys His Phe Gly Pro Ile Thr Trp Val Cys Arg
1               5                   10                  15

Pro Gly Gly Gly
            20

<210> SEQ ID NO 6
<211> LENGTH: 20
<212> TYPE: PRT
<213> ORGANISM: Artificial Sequence
<220> FEATURE:
<223> OTHER INFORMATION: EPO-mimetic peptide sequence

<400> SEQUENCE: 6

Gly Gly Leu Tyr Leu Cys Arg Phe Gly Pro Val Thr Trp Asp Cys Gly
1               5                   10                  15

Tyr Lys Gly Gly
```

```
                         20

<210> SEQ ID NO 7
<211> LENGTH: 23
<212> TYPE: PRT
<213> ORGANISM: Artificial Sequence
<220> FEATURE:
<223> OTHER INFORMATION: EPO-mimetic peptide sequence

<400> SEQUENCE: 7

Gly Gly Thr Tyr Ser Cys His Phe Gly Pro Leu Thr Trp Val Cys Lys
1               5                   10                  15

Pro Gln Gly Gly Ser Ser Lys
            20

<210> SEQ ID NO 8
<211> LENGTH: 19
<212> TYPE: PRT
<213> ORGANISM: Artificial Sequence
<220> FEATURE:
<223> OTHER INFORMATION: EPO-mimetic peptide sequence

<400> SEQUENCE: 8

Gly Gly Thr Tyr Ser Cys His Gly Pro Leu Thr Trp Val Cys Lys Pro
1               5                   10                  15

Gln Gly Gly

<210> SEQ ID NO 9
<211> LENGTH: 19
<212> TYPE: PRT
<213> ORGANISM: Artificial Sequence
<220> FEATURE:
<223> OTHER INFORMATION: EPO-mimetic peptide sequence

<400> SEQUENCE: 9

Val Gly Asn Tyr Met Ala His Met Gly Pro Ile Thr Trp Val Cys Arg
1               5                   10                  15

Pro Gly Gly

<210> SEQ ID NO 10
<211> LENGTH: 18
<212> TYPE: PRT
<213> ORGANISM: Artificial Sequence
<220> FEATURE:
<223> OTHER INFORMATION: EPO-mimetic peptide sequence

<400> SEQUENCE: 10

Gly Gly Pro His His Val Tyr Ala Cys Arg Met Gly Pro Leu Thr Trp
1               5                   10                  15

Ile Cys

<210> SEQ ID NO 11
<211> LENGTH: 18
<212> TYPE: PRT
<213> ORGANISM: Artificial Sequence
<220> FEATURE:
<223> OTHER INFORMATION: EPO-mimetic peptide sequence

<400> SEQUENCE: 11

Gly Gly Thr Tyr Ser Cys His Phe Gly Pro Leu Thr Trp Val Cys Lys
1               5                   10                  15

Pro Gln
```

<210> SEQ ID NO 12
<211> LENGTH: 20
<212> TYPE: PRT
<213> ORGANISM: Artificial Sequence
<220> FEATURE:
<223> OTHER INFORMATION: EPO-mimetic peptide sequence

<400> SEQUENCE: 12

Gly Gly Leu Tyr Ala Cys His Met Gly Pro Met Thr Trp Val Cys Gln
1               5                   10                  15

Pro Leu Arg Gly
            20

<210> SEQ ID NO 13
<211> LENGTH: 22
<212> TYPE: PRT
<213> ORGANISM: Artificial Sequence
<220> FEATURE:
<223> OTHER INFORMATION: EPO-mimetic peptide sequence

<400> SEQUENCE: 13

Thr Ile Ala Gln Tyr Ile Cys Tyr Met Gly Pro Glu Thr Trp Glu Cys
1               5                   10                  15

Arg Pro Ser Pro Lys Ala
            20

<210> SEQ ID NO 14
<211> LENGTH: 13
<212> TYPE: PRT
<213> ORGANISM: Artificial Sequence
<220> FEATURE:
<223> OTHER INFORMATION: EPO-mimetic peptide sequence

<400> SEQUENCE: 14

Tyr Ser Cys His Phe Gly Pro Leu Thr Trp Val Cys Lys
1               5                   10

<210> SEQ ID NO 15
<211> LENGTH: 11
<212> TYPE: PRT
<213> ORGANISM: Artificial Sequence
<220> FEATURE:
<223> OTHER INFORMATION: EPO-mimetic peptide sequence

<400> SEQUENCE: 15

Tyr Cys His Phe Gly Pro Leu Thr Trp Val Cys
1               5                   10

<210> SEQ ID NO 16
<211> LENGTH: 20
<212> TYPE: PRT
<213> ORGANISM: Artificial Sequence
<220> FEATURE:
<223> OTHER INFORMATION: EPO-mimetic peptide sequence

<400> SEQUENCE: 16

Gly Gly Leu Tyr Leu Cys Arg Phe Gly Pro Val Thr Trp Asp Cys Gly
1               5                   10                  15

Tyr Lys Gly Gly
            20

<210> SEQ ID NO 17
<211> LENGTH: 20
<212> TYPE: PRT
<213> ORGANISM: Artificial Sequence
<220> FEATURE:

<223> OTHER INFORMATION: EPO-mimetic peptide sequence

<400> SEQUENCE: 17

Gly Gly Thr Tyr Ser Cys His Phe Gly Pro Leu Thr Trp Val Cys Lys
1               5                   10                  15
Pro Gln Gly Gly
            20

<210> SEQ ID NO 18
<211> LENGTH: 20
<212> TYPE: PRT
<213> ORGANISM: Artificial Sequence
<220> FEATURE:
<223> OTHER INFORMATION: EPO-mimetic peptide sequence

<400> SEQUENCE: 18

Gly Gly Asp Tyr His Cys Arg Met Gly Pro Leu Thr Trp Val Cys Lys
1               5                   10                  15
Pro Leu Gly Gly
            20

<210> SEQ ID NO 19
<211> LENGTH: 20
<212> TYPE: PRT
<213> ORGANISM: Artificial Sequence
<220> FEATURE:
<223> OTHER INFORMATION: EPO-mimetic peptide sequence

<400> SEQUENCE: 19

Val Gly Asn Tyr Met Cys His Phe Gly Pro Ile Thr Trp Val Cys Arg
1               5                   10                  15
Pro Gly Gly Gly
            20

<210> SEQ ID NO 20
<211> LENGTH: 20
<212> TYPE: PRT
<213> ORGANISM: Artificial Sequence
<220> FEATURE:
<223> OTHER INFORMATION: EPO-mimetic peptide sequence

<400> SEQUENCE: 20

Gly Gly Val Tyr Ala Cys Arg Met Gly Pro Ile Thr Trp Val Cys Ser
1               5                   10                  15
Pro Leu Gly Gly
            20

<210> SEQ ID NO 21
<211> LENGTH: 19
<212> TYPE: PRT
<213> ORGANISM: Artificial Sequence
<220> FEATURE:
<223> OTHER INFORMATION: EPO-mimetic peptide sequence

<400> SEQUENCE: 21

Val Gly Asn Tyr Met Ala His Met Gly Pro Ile Thr Trp Val Cys Arg
1               5                   10                  15
Pro Gly Gly

<210> SEQ ID NO 22
<211> LENGTH: 18
<212> TYPE: PRT
<213> ORGANISM: Artificial Sequence
<220> FEATURE:

```
<223> OTHER INFORMATION: EPO-mimetic peptide sequence

<400> SEQUENCE: 22

Gly Gly Thr Tyr Ser Cys His Phe Gly Pro Leu Thr Trp Val Cys Lys
1               5                   10                  15
Pro Gln

<210> SEQ ID NO 23
<211> LENGTH: 20
<212> TYPE: PRT
<213> ORGANISM: Artificial Sequence
<220> FEATURE:
<223> OTHER INFORMATION: EPO-mimetic peptide sequence

<400> SEQUENCE: 23

Gly Gly Leu Tyr Ala Cys His Met Gly Pro Met Thr Trp Val Cys Gln
1               5                   10                  15
Pro Leu Arg Gly
            20

<210> SEQ ID NO 24
<211> LENGTH: 22
<212> TYPE: PRT
<213> ORGANISM: Artificial Sequence
<220> FEATURE:
<223> OTHER INFORMATION: EPO-mimetic peptide sequence

<400> SEQUENCE: 24

Thr Ile Ala Gln Tyr Ile Cys Tyr Met Gly Pro Glu Thr Trp Glu Cys
1               5                   10                  15
Arg Pro Ser Pro Lys Ala
            20

<210> SEQ ID NO 25
<211> LENGTH: 13
<212> TYPE: PRT
<213> ORGANISM: Artificial Sequence
<220> FEATURE:
<223> OTHER INFORMATION: EPO-mimetic peptide sequence

<400> SEQUENCE: 25

Tyr Ser Cys His Phe Gly Pro Leu Thr Trp Val Cys Lys
1               5                   10

<210> SEQ ID NO 26
<211> LENGTH: 11
<212> TYPE: PRT
<213> ORGANISM: Artificial Sequence
<220> FEATURE:
<223> OTHER INFORMATION: EPO-mimetic peptide sequence

<400> SEQUENCE: 26

Tyr Cys His Phe Gly Pro Leu Thr Trp Val Cys
1               5                   10

<210> SEQ ID NO 27
<211> LENGTH: 12
<212> TYPE: PRT
<213> ORGANISM: Artificial Sequence
<220> FEATURE:
<223> OTHER INFORMATION: EPO-mimetic peptide sequence

<400> SEQUENCE: 27

Ser Cys His Phe Gly Pro Leu Thr Trp Val Cys Lys
1               5                   10
```

```
<210> SEQ ID NO 28
<211> LENGTH: 14
<212> TYPE: PRT
<213> ORGANISM: Artificial Sequence
<220> FEATURE:
<223> OTHER INFORMATION: TPO-mimetic peptide sequences

<400> SEQUENCE: 28

Ile Glu Gly Pro Thr Leu Arg Gln Trp Leu Ala Ala Arg Ala
1               5                   10

<210> SEQ ID NO 29
<211> LENGTH: 14
<212> TYPE: PRT
<213> ORGANISM: Artificial Sequence
<220> FEATURE:
<223> OTHER INFORMATION: TPO-mimetic peptide sequences

<400> SEQUENCE: 29

Ile Glu Gly Pro Thr Leu Arg Gln Trp Leu Ala Ala Lys Ala
1               5                   10

<210> SEQ ID NO 30
<211> LENGTH: 14
<212> TYPE: PRT
<213> ORGANISM: Artificial Sequence
<220> FEATURE:
<223> OTHER INFORMATION: TPO-mimetic peptide sequences

<400> SEQUENCE: 30

Ile Glu Gly Pro Thr Leu Arg Glu Trp Leu Ala Ala Arg Ala
1               5                   10

<210> SEQ ID NO 31
<211> LENGTH: 6
<212> TYPE: PRT
<213> ORGANISM: Artificial Sequence
<220> FEATURE:
<223> OTHER INFORMATION: TPO-mimetic peptide sequences

<400> SEQUENCE: 31

Thr Leu Arg Glu Trp Leu
1               5

<210> SEQ ID NO 32
<211> LENGTH: 10
<212> TYPE: PRT
<213> ORGANISM: Artificial Sequence
<220> FEATURE:
<223> OTHER INFORMATION: TPO-mimetic peptide sequences

<400> SEQUENCE: 32

Gly Arg Val Arg Asp Gln Val Ala Gly Trp
1               5                   10

<210> SEQ ID NO 33
<211> LENGTH: 10
<212> TYPE: PRT
<213> ORGANISM: Artificial Sequence
<220> FEATURE:
<223> OTHER INFORMATION: TPO-mimetic peptide sequences

<400> SEQUENCE: 33

Gly Arg Val Lys Asp Gln Ile Ala Gln Leu
1               5                   10
```

<210> SEQ ID NO 34
<211> LENGTH: 10
<212> TYPE: PRT
<213> ORGANISM: Artificial Sequence
<220> FEATURE:
<223> OTHER INFORMATION: TPO-mimetic peptide sequences

<400> SEQUENCE: 34

Gly Val Arg Asp Gln Val Ser Trp Ala Leu
1               5                   10

<210> SEQ ID NO 35
<211> LENGTH: 10
<212> TYPE: PRT
<213> ORGANISM: Artificial Sequence
<220> FEATURE:
<223> OTHER INFORMATION: TPO-mimetic peptide sequences

<400> SEQUENCE: 35

Glu Ser Val Arg Glu Gln Val Met Lys Tyr
1               5                   10

<210> SEQ ID NO 36
<211> LENGTH: 10
<212> TYPE: PRT
<213> ORGANISM: Artificial Sequence
<220> FEATURE:
<223> OTHER INFORMATION: TPO-mimetic peptide sequences

<400> SEQUENCE: 36

Ser Val Arg Ser Gln Ile Ser Ala Ser Leu
1               5                   10

<210> SEQ ID NO 37
<211> LENGTH: 10
<212> TYPE: PRT
<213> ORGANISM: Artificial Sequence
<220> FEATURE:
<223> OTHER INFORMATION: TPO-mimetic peptide sequences

<400> SEQUENCE: 37

Gly Val Arg Glu Thr Val Tyr Arg His Met
1               5                   10

<210> SEQ ID NO 38
<211> LENGTH: 11
<212> TYPE: PRT
<213> ORGANISM: Artificial Sequence
<220> FEATURE:
<223> OTHER INFORMATION: TPO-mimetic peptide sequences

<400> SEQUENCE: 38

Gly Val Arg Glu Val Ile Val Met His Met Leu
1               5                   10

<210> SEQ ID NO 39
<211> LENGTH: 11
<212> TYPE: PRT
<213> ORGANISM: Artificial Sequence
<220> FEATURE:
<223> OTHER INFORMATION: TPO-mimetic peptide sequences

<400> SEQUENCE: 39

Gly Arg Val Arg Asp Gln Ile Trp Ala Ala Leu
1               5                   10

```
<210> SEQ ID NO 40
<211> LENGTH: 11
<212> TYPE: PRT
<213> ORGANISM: Artificial Sequence
<220> FEATURE:
<223> OTHER INFORMATION: TPO-mimetic peptide sequences

<400> SEQUENCE: 40

Ala Gly Val Arg Asp Gln Ile Leu Ile Trp Leu
1               5                   10

<210> SEQ ID NO 41
<211> LENGTH: 11
<212> TYPE: PRT
<213> ORGANISM: Artificial Sequence
<220> FEATURE:
<223> OTHER INFORMATION: TPO-mimetic peptide sequences

<400> SEQUENCE: 41

Gly Arg Val Arg Asp Gln Ile Met Leu Ser Leu
1               5                   10

<210> SEQ ID NO 42
<211> LENGTH: 10
<212> TYPE: PRT
<213> ORGANISM: Artificial Sequence
<220> FEATURE:
<223> OTHER INFORMATION: TPO-mimetic peptide sequences

<400> SEQUENCE: 42

Cys Thr Leu Arg Gln Trp Leu Gln Gly Cys
1               5                   10

<210> SEQ ID NO 43
<211> LENGTH: 10
<212> TYPE: PRT
<213> ORGANISM: Artificial Sequence
<220> FEATURE:
<223> OTHER INFORMATION: TPO-mimetic peptide sequences

<400> SEQUENCE: 43

Cys Thr Leu Gln Glu Phe Leu Glu Gly Cys
1               5                   10

<210> SEQ ID NO 44
<211> LENGTH: 10
<212> TYPE: PRT
<213> ORGANISM: Artificial Sequence
<220> FEATURE:
<223> OTHER INFORMATION: TPO-mimetic peptide sequences

<400> SEQUENCE: 44

Cys Thr Arg Thr Glu Trp Leu His Gly Cys
1               5                   10

<210> SEQ ID NO 45
<211> LENGTH: 12
<212> TYPE: PRT
<213> ORGANISM: Artificial Sequence
<220> FEATURE:
<223> OTHER INFORMATION: TPO-mimetic peptide sequences

<400> SEQUENCE: 45

Cys Thr Leu Arg Glu Trp Leu His Gly Gly Phe Cys
1               5                   10

<210> SEQ ID NO 46
```

```
<211> LENGTH: 12
<212> TYPE: PRT
<213> ORGANISM: Artificial Sequence
<220> FEATURE:
<223> OTHER INFORMATION: TPO-mimetic peptide sequences

<400> SEQUENCE: 46

Cys Thr Leu Arg Glu Trp Val Phe Ala Gly Leu Cys
1               5                   10

<210> SEQ ID NO 47
<211> LENGTH: 13
<212> TYPE: PRT
<213> ORGANISM: Artificial Sequence
<220> FEATURE:
<223> OTHER INFORMATION: TPO-mimetic peptide sequences

<400> SEQUENCE: 47

Cys Thr Leu Arg Gln Trp Leu Ile Leu Leu Gly Met Cys
1               5                   10

<210> SEQ ID NO 48
<211> LENGTH: 14
<212> TYPE: PRT
<213> ORGANISM: Artificial Sequence
<220> FEATURE:
<223> OTHER INFORMATION: TPO-mimetic peptide sequences

<400> SEQUENCE: 48

Cys Thr Leu Ala Glu Phe Leu Ala Ser Gly Val Glu Gln Cys
1               5                   10

<210> SEQ ID NO 49
<211> LENGTH: 14
<212> TYPE: PRT
<213> ORGANISM: Artificial Sequence
<220> FEATURE:
<223> OTHER INFORMATION: TPO-mimetic peptide sequences

<400> SEQUENCE: 49

Cys Ser Leu Gln Glu Phe Leu Ser His Gly Gly Tyr Val Cys
1               5                   10

<210> SEQ ID NO 50
<211> LENGTH: 14
<212> TYPE: PRT
<213> ORGANISM: Artificial Sequence
<220> FEATURE:
<223> OTHER INFORMATION: TPO-mimetic peptide sequences

<400> SEQUENCE: 50

Cys Thr Leu Arg Glu Phe Leu Asp Pro Thr Thr Ala Val Cys
1               5                   10

<210> SEQ ID NO 51
<211> LENGTH: 14
<212> TYPE: PRT
<213> ORGANISM: Artificial Sequence
<220> FEATURE:
<223> OTHER INFORMATION: TPO-mimetic peptide sequences

<400> SEQUENCE: 51

Cys Thr Leu Lys Glu Trp Leu Val Ser His Glu Val Trp Cys
1               5                   10

<210> SEQ ID NO 52
<211> LENGTH: 10
```

```
<212> TYPE: PRT
<213> ORGANISM: Artificial Sequence
<220> FEATURE:
<223> OTHER INFORMATION: TPO-mimetic peptide sequences

<400> SEQUENCE: 52

Arg Glu Gly Pro Thr Leu Arg Gln Trp Met
1               5                   10

<210> SEQ ID NO 53
<211> LENGTH: 10
<212> TYPE: PRT
<213> ORGANISM: Artificial Sequence
<220> FEATURE:
<223> OTHER INFORMATION: TPO-mimetic peptide sequences

<400> SEQUENCE: 53

Glu Gly Pro Thr Leu Arg Gln Trp Leu Ala
1               5                   10

<210> SEQ ID NO 54
<211> LENGTH: 10
<212> TYPE: PRT
<213> ORGANISM: Artificial Sequence
<220> FEATURE:
<223> OTHER INFORMATION: TPO-mimetic peptide sequences

<400> SEQUENCE: 54

Glu Arg Gly Pro Phe Trp Ala Lys Ala Cys
1               5                   10

<210> SEQ ID NO 55
<211> LENGTH: 10
<212> TYPE: PRT
<213> ORGANISM: Artificial Sequence
<220> FEATURE:
<223> OTHER INFORMATION: TPO-mimetic peptide sequences

<400> SEQUENCE: 55

Arg Glu Gly Pro Arg Cys Val Met Trp Met
1               5                   10

<210> SEQ ID NO 56
<211> LENGTH: 14
<212> TYPE: PRT
<213> ORGANISM: Artificial Sequence
<220> FEATURE:
<223> OTHER INFORMATION: TPO-mimetic peptide sequences

<400> SEQUENCE: 56

Cys Gly Thr Glu Gly Pro Thr Leu Ser Thr Trp Leu Asp Cys
1               5                   10

<210> SEQ ID NO 57
<211> LENGTH: 14
<212> TYPE: PRT
<213> ORGANISM: Artificial Sequence
<220> FEATURE:
<223> OTHER INFORMATION: EPO-mimetic peptide sequences

<400> SEQUENCE: 57

Cys Glu Gln Asp Gly Pro Thr Leu Leu Glu Trp Leu Lys Cys
1               5                   10

<210> SEQ ID NO 58
<211> LENGTH: 14
<212> TYPE: PRT
```

<213> ORGANISM: Artificial Sequence
<220> FEATURE:
<223> OTHER INFORMATION: TPO-mimetic peptide sequences

<400> SEQUENCE: 58

Cys Glu Leu Val Gly Pro Ser Leu Met Ser Trp Leu Thr Cys
1               5                   10

<210> SEQ ID NO 59
<211> LENGTH: 14
<212> TYPE: PRT
<213> ORGANISM: Artificial Sequence
<220> FEATURE:
<223> OTHER INFORMATION: TPO-mimetic peptide sequences

<400> SEQUENCE: 59

Cys Leu Thr Gly Pro Phe Val Thr Gln Trp Leu Tyr Glu Cys
1               5                   10

<210> SEQ ID NO 60
<211> LENGTH: 14
<212> TYPE: PRT
<213> ORGANISM: Artificial Sequence
<220> FEATURE:
<223> OTHER INFORMATION: TPO-mimetic peptide sequences

<400> SEQUENCE: 60

Cys Arg Ala Gly Pro Thr Leu Leu Glu Trp Leu Thr Leu Cys
1               5                   10

<210> SEQ ID NO 61
<211> LENGTH: 14
<212> TYPE: PRT
<213> ORGANISM: Artificial Sequence
<220> FEATURE:
<223> OTHER INFORMATION: TPO-mimetic peptide sequences

<400> SEQUENCE: 61

Cys Ala Asp Gly Pro Thr Leu Arg Glu Trp Ile Ser Phe Cys
1               5                   10

<210> SEQ ID NO 62
<211> LENGTH: 16
<212> TYPE: PRT
<213> ORGANISM: Artificial Sequence
<220> FEATURE:
<223> OTHER INFORMATION: TPO-mimetic peptide sequences

<400> SEQUENCE: 62

Gly Gly Cys Thr Leu Arg Glu Trp Leu His Gly Gly Phe Cys Gly Gly
1               5                   10                  15

<210> SEQ ID NO 63
<211> LENGTH: 18
<212> TYPE: PRT
<213> ORGANISM: Artificial Sequence
<220> FEATURE:
<223> OTHER INFORMATION: TPO-mimetic peptide sequences

<400> SEQUENCE: 63

Gly Gly Cys Ala Asp Gly Pro Thr Leu Arg Glu Trp Ile Ser Phe Cys
1               5                   10                  15

Gly Gly

<210> SEQ ID NO 64
<211> LENGTH: 19

```
<212> TYPE: PRT
<213> ORGANISM: Artificial Sequence
<220> FEATURE:
<223> OTHER INFORMATION: TPO-mimetic peptide sequences

<400> SEQUENCE: 64

Gly Asn Ala Asp Gly Pro Thr Leu Arg Gln Trp Leu Glu Gly Arg Arg
1               5                   10                  15

Pro Lys Asn

<210> SEQ ID NO 65
<211> LENGTH: 19
<212> TYPE: PRT
<213> ORGANISM: Artificial Sequence
<220> FEATURE:
<223> OTHER INFORMATION: TPO-mimetic peptide sequences

<400> SEQUENCE: 65

Leu Ala Ile Glu Gly Pro Thr Leu Arg Gln Trp Leu His Gly Asn Gly
1               5                   10                  15

Arg Asp Thr

<210> SEQ ID NO 66
<211> LENGTH: 19
<212> TYPE: PRT
<213> ORGANISM: Artificial Sequence
<220> FEATURE:
<223> OTHER INFORMATION: TPO-mimetic peptide sequences

<400> SEQUENCE: 66

His Gly Arg Val Gly Pro Thr Leu Arg Glu Trp Lys Thr Gln Val Ala
1               5                   10                  15

Thr Lys Lys

<210> SEQ ID NO 67
<211> LENGTH: 18
<212> TYPE: PRT
<213> ORGANISM: Artificial Sequence
<220> FEATURE:
<223> OTHER INFORMATION: TPO-mimetic peptide sequences

<400> SEQUENCE: 67

Thr Ile Lys Gly Pro Thr Leu Arg Gln Trp Leu Lys Ser Arg Glu His
1               5                   10                  15

Thr Ser

<210> SEQ ID NO 68
<211> LENGTH: 18
<212> TYPE: PRT
<213> ORGANISM: Artificial Sequence
<220> FEATURE:
<223> OTHER INFORMATION: TPO-mimetic peptide sequences

<400> SEQUENCE: 68

Ile Ser Asp Gly Pro Thr Leu Lys Glu Trp Leu Ser Val Thr Arg Gly
1               5                   10                  15

Ala Ser

<210> SEQ ID NO 69
<211> LENGTH: 18
<212> TYPE: PRT
<213> ORGANISM: Artificial Sequence
<220> FEATURE:
<223> OTHER INFORMATION: TPO-mimetic peptide sequences
```

<400> SEQUENCE: 69

Ser Ile Glu Gly Pro Thr Leu Arg Glu Trp Leu Thr Ser Arg Thr Pro
1               5                   10                  15

His Ser

<210> SEQ ID NO 70
<211> LENGTH: 18
<212> TYPE: PRT
<213> ORGANISM: Artificial Sequence
<220> FEATURE:
<223> OTHER INFORMATION: TPO-mimetic peptide sequences

<400> SEQUENCE: 70

Gly Ala Arg Glu Gly Pro Thr Leu Arg Gln Trp Leu Glu Trp Val Arg
1               5                   10                  15

Val Gly

<210> SEQ ID NO 71
<211> LENGTH: 18
<212> TYPE: PRT
<213> ORGANISM: Artificial Sequence
<220> FEATURE:
<223> OTHER INFORMATION: TPO-mimetic peptide sequences

<400> SEQUENCE: 71

Arg Asp Leu Asp Gly Pro Thr Leu Arg Gln Trp Leu Pro Leu Pro Ser
1               5                   10                  15

Val Gln

<210> SEQ ID NO 72
<211> LENGTH: 18
<212> TYPE: PRT
<213> ORGANISM: Artificial Sequence
<220> FEATURE:
<223> OTHER INFORMATION: TPO-mimetic peptide sequences

<400> SEQUENCE: 72

Ala Leu Arg Asp Gly Pro Thr Leu Lys Gln Trp Leu Glu Tyr Arg Arg
1               5                   10                  15

Gln Ala

<210> SEQ ID NO 73
<211> LENGTH: 18
<212> TYPE: PRT
<213> ORGANISM: Artificial Sequence
<220> FEATURE:
<223> OTHER INFORMATION: TPO-mimetic peptide sequences

<400> SEQUENCE: 73

Ala Arg Gln Glu Gly Pro Thr Leu Lys Glu Trp Leu Phe Trp Val Arg
1               5                   10                  15

Met Gly

<210> SEQ ID NO 74
<211> LENGTH: 18
<212> TYPE: PRT
<213> ORGANISM: Artificial Sequence
<220> FEATURE:
<223> OTHER INFORMATION: TPO-mimetic peptide sequences

<400> SEQUENCE: 74

Glu Ala Leu Leu Gly Pro Thr Leu Arg Glu Trp Leu Ala Trp Arg Arg

```
1               5                   10                  15

Ala Gln

<210> SEQ ID NO 75
<211> LENGTH: 18
<212> TYPE: PRT
<213> ORGANISM: Artificial Sequence
<220> FEATURE:
<223> OTHER INFORMATION: TPO-mimetic peptide sequence

<400> SEQUENCE: 75

Met Ala Arg Asp Gly Pro Thr Leu Arg Glu Trp Leu Arg Thr Tyr Arg
1               5                   10                  15

Met Met

<210> SEQ ID NO 76
<211> LENGTH: 18
<212> TYPE: PRT
<213> ORGANISM: Artificial Sequence
<220> FEATURE:
<223> OTHER INFORMATION: TPO-mimetic peptide sequence

<400> SEQUENCE: 76

Trp Met Pro Glu Gly Pro Thr Leu Lys Gln Trp Leu Phe His Gly Arg
1               5                   10                  15

Gly Gln

<210> SEQ ID NO 77
<211> LENGTH: 18
<212> TYPE: PRT
<213> ORGANISM: Artificial Sequence
<220> FEATURE:
<223> OTHER INFORMATION: TPO-mimetic peptide sequence

<400> SEQUENCE: 77

His Ile Arg Glu Gly Pro Thr Leu Arg Gln Trp Leu Val Ala Leu Arg
1               5                   10                  15

Met Val

<210> SEQ ID NO 78
<211> LENGTH: 18
<212> TYPE: PRT
<213> ORGANISM: Artificial Sequence
<220> FEATURE:
<223> OTHER INFORMATION: TPO-mimetic peptide sequence

<400> SEQUENCE: 78

Gln Leu Gly His Gly Pro Thr Leu Arg Gln Trp Leu Ser Trp Tyr Arg
1               5                   10                  15

Gly Met

<210> SEQ ID NO 79
<211> LENGTH: 18
<212> TYPE: PRT
<213> ORGANISM: Artificial Sequence
<220> FEATURE:
<223> OTHER INFORMATION: TPO-mimetic peptide sequence

<400> SEQUENCE: 79

Glu Leu Arg Gln Gly Pro Thr Leu His Glu Trp Leu Gln His Leu Ala
1               5                   10                  15

Ser Lys
```

```
<210> SEQ ID NO 80
<211> LENGTH: 18
<212> TYPE: PRT
<213> ORGANISM: Artificial Sequence
<220> FEATURE:
<223> OTHER INFORMATION: TPO-mimetic peptide sequence

<400> SEQUENCE: 80

Val Gly Ile Glu Gly Pro Thr Leu Arg Gln Trp Leu Ala Gln Arg Leu
1               5                   10                  15

Asn Pro

<210> SEQ ID NO 81
<211> LENGTH: 18
<212> TYPE: PRT
<213> ORGANISM: Artificial Sequence
<220> FEATURE:
<223> OTHER INFORMATION: TPO-mimetic peptide sequence

<400> SEQUENCE: 81

Trp Ser Arg Asp Gly Pro Thr Leu Arg Glu Trp Leu Ala Trp Arg Ala
1               5                   10                  15

Val Gly

<210> SEQ ID NO 82
<211> LENGTH: 18
<212> TYPE: PRT
<213> ORGANISM: Artificial Sequence
<220> FEATURE:
<223> OTHER INFORMATION: TPO-mimetic peptide sequence

<400> SEQUENCE: 82

Ala Val Pro Gln Gly Pro Thr Leu Lys Gln Trp Leu Leu Trp Arg Arg
1               5                   10                  15

Cys Ala

<210> SEQ ID NO 83
<211> LENGTH: 18
<212> TYPE: PRT
<213> ORGANISM: Artificial Sequence
<220> FEATURE:
<223> OTHER INFORMATION: TPO-mimetic peptide sequence

<400> SEQUENCE: 83

Arg Ile Arg Glu Gly Pro Thr Leu Lys Glu Trp Leu Ala Gln Arg Arg
1               5                   10                  15

Gly Phe

<210> SEQ ID NO 84
<211> LENGTH: 18
<212> TYPE: PRT
<213> ORGANISM: Artificial Sequence
<220> FEATURE:
<223> OTHER INFORMATION: TPO-mimetic peptide sequence

<400> SEQUENCE: 84

Arg Phe Ala Glu Gly Pro Thr Leu Arg Glu Trp Leu Glu Gln Arg Lys
1               5                   10                  15

Leu Val

<210> SEQ ID NO 85
<211> LENGTH: 18
<212> TYPE: PRT
```

```
<213> ORGANISM: Artificial Sequence
<220> FEATURE:
<223> OTHER INFORMATION: TPO-mimetic peptide sequence

<400> SEQUENCE: 85

Asp Arg Phe Gln Gly Pro Thr Leu Arg Glu Trp Leu Ala Ala Ile Arg
1               5                   10                  15

Ser Val

<210> SEQ ID NO 86
<211> LENGTH: 18
<212> TYPE: PRT
<213> ORGANISM: Artificial Sequence
<220> FEATURE:
<223> OTHER INFORMATION: TPO-mimetic peptide sequence

<400> SEQUENCE: 86

Ala Gly Arg Glu Gly Pro Thr Leu Arg Glu Trp Leu Asn Met Arg Val
1               5                   10                  15

Trp Gln

<210> SEQ ID NO 87
<211> LENGTH: 18
<212> TYPE: PRT
<213> ORGANISM: Artificial Sequence
<220> FEATURE:
<223> OTHER INFORMATION: TPO-mimetic peptide sequence

<400> SEQUENCE: 87

Ala Leu Gln Glu Gly Pro Thr Leu Arg Gln Trp Leu Gly Trp Gly Gln
1               5                   10                  15

Trp Gly

<210> SEQ ID NO 88
<211> LENGTH: 18
<212> TYPE: PRT
<213> ORGANISM: Artificial Sequence
<220> FEATURE:
<223> OTHER INFORMATION: TPO-mimetic peptide sequence

<400> SEQUENCE: 88

Tyr Cys Asp Glu Gly Pro Thr Leu Lys Gln Trp Leu Val Cys Leu Gly
1               5                   10                  15

Leu Gln

<210> SEQ ID NO 89
<211> LENGTH: 18
<212> TYPE: PRT
<213> ORGANISM: Artificial Sequence
<220> FEATURE:
<223> OTHER INFORMATION: TPO-mimetic peptide sequence

<400> SEQUENCE: 89

Trp Cys Lys Glu Gly Pro Thr Leu Arg Glu Trp Leu Arg Trp Gly Phe
1               5                   10                  15

Leu Cys

<210> SEQ ID NO 90
<211> LENGTH: 18
<212> TYPE: PRT
<213> ORGANISM: Artificial Sequence
<220> FEATURE:
<223> OTHER INFORMATION: TPO-mimetic peptide sequence
```

```
<400> SEQUENCE: 90

Cys Ser Ser Gly Gly Pro Thr Leu Arg Glu Trp Leu Gln Cys Arg Arg
1               5                   10                  15

Met Gln

<210> SEQ ID NO 91
<211> LENGTH: 18
<212> TYPE: PRT
<213> ORGANISM: Artificial Sequence
<220> FEATURE:
<223> OTHER INFORMATION: TPO-mimetic peptide sequence

<400> SEQUENCE: 91

Cys Ser Trp Gly Gly Pro Thr Leu Lys Gln Trp Leu Gln Cys Val Arg
1               5                   10                  15

Ala Lys

<210> SEQ ID NO 92
<211> LENGTH: 18
<212> TYPE: PRT
<213> ORGANISM: Artificial Sequence
<220> FEATURE:
<223> OTHER INFORMATION: TPO-mimetic peptide sequence

<400> SEQUENCE: 92

Cys Gln Leu Gly Gly Pro Thr Leu Arg Glu Trp Leu Ala Cys Arg Leu
1               5                   10                  15

Gly Ala

<210> SEQ ID NO 93
<211> LENGTH: 18
<212> TYPE: PRT
<213> ORGANISM: Artificial Sequence
<220> FEATURE:
<223> OTHER INFORMATION: TPO-mimetic peptide sequence

<400> SEQUENCE: 93

Cys Trp Glu Gly Gly Pro Thr Leu Lys Glu Trp Leu Gln Cys Leu Val
1               5                   10                  15

Glu Arg

<210> SEQ ID NO 94
<211> LENGTH: 18
<212> TYPE: PRT
<213> ORGANISM: Artificial Sequence
<220> FEATURE:
<223> OTHER INFORMATION: TPO-mimetic peptide sequence

<400> SEQUENCE: 94

Cys Arg Gly Gly Gly Pro Thr Leu His Gln Trp Leu Ser Cys Phe Arg
1               5                   10                  15

Trp Gln

<210> SEQ ID NO 95
<211> LENGTH: 18
<212> TYPE: PRT
<213> ORGANISM: Artificial Sequence
<220> FEATURE:
<223> OTHER INFORMATION: TPO-mimetic peptide sequence

<400> SEQUENCE: 95

Cys Arg Asp Gly Gly Pro Thr Leu Arg Gln Trp Leu Ala Cys Leu Gln
1               5                   10                  15
```

```
Gln Lys

<210> SEQ ID NO 96
<211> LENGTH: 18
<212> TYPE: PRT
<213> ORGANISM: Artificial Sequence
<220> FEATURE:
<223> OTHER INFORMATION: TPO-mimetic peptide sequence

<400> SEQUENCE: 96

Glu Leu Arg Ser Gly Pro Thr Leu Lys Glu Trp Leu Val Trp Arg Leu
1               5                   10                  15

Ala Gln

<210> SEQ ID NO 97
<211> LENGTH: 18
<212> TYPE: PRT
<213> ORGANISM: Artificial Sequence
<220> FEATURE:
<223> OTHER INFORMATION: TPO-mimetic peptide sequence

<400> SEQUENCE: 97

Gly Cys Arg Ser Gly Pro Thr Leu Arg Glu Trp Leu Ala Cys Arg Glu
1               5                   10                  15

Val Gln

<210> SEQ ID NO 98
<211> LENGTH: 18
<212> TYPE: PRT
<213> ORGANISM: Artificial Sequence
<220> FEATURE:
<223> OTHER INFORMATION: TPO-mimetic peptide sequence

<400> SEQUENCE: 98

Thr Cys Glu Gln Gly Pro Thr Leu Arg Gln Trp Leu Leu Cys Arg Gln
1               5                   10                  15

Gly Arg

<210> SEQ ID NO 99
<211> LENGTH: 22
<212> TYPE: PRT
<213> ORGANISM: Artificial Sequence
<220> FEATURE:
<223> OTHER INFORMATION: TPO-mimetic peptide sequence

<400> SEQUENCE: 99

Gln Gly Tyr Cys Asp Glu Gly Pro Thr Leu Lys Gln Trp Leu Val Cys
1               5                   10                  15

Leu Gly Leu Gln His Ser
            20

<210> SEQ ID NO 100
<211> LENGTH: 5
<212> TYPE: PRT
<213> ORGANISM: Artificial Sequence
<220> FEATURE:
<223> OTHER INFORMATION: Ang-2 binding peptide sequence

<400> SEQUENCE: 100

Trp Asp Pro Trp Thr
1               5

<210> SEQ ID NO 101
```

```
<211> LENGTH: 6
<212> TYPE: PRT
<213> ORGANISM: Artificial Sequence
<220> FEATURE:
<223> OTHER INFORMATION: Ang-2 binding peptide sequence

<400> SEQUENCE: 101

Trp Asp Pro Trp Thr Cys
1               5

<210> SEQ ID NO 102
<211> LENGTH: 7
<212> TYPE: PRT
<213> ORGANISM: Artificial Sequence
<220> FEATURE:
<223> OTHER INFORMATION: Ang-2 binding peptide sequence
<220> FEATURE:
<221> NAME/KEY: MISC_FEATURE
<222> LOCATION: (2)..(2)
<223> OTHER INFORMATION: Xaa in position 2 is an acidic or neutral polar
      amino acid residue

<400> SEQUENCE: 102

Cys Xaa Trp Asp Pro Trp Thr
1               5

<210> SEQ ID NO 103
<211> LENGTH: 8
<212> TYPE: PRT
<213> ORGANISM: Artificial Sequence
<220> FEATURE:
<223> OTHER INFORMATION: Ang-2 binding peptide sequence
<220> FEATURE:
<221> NAME/KEY: MISC_FEATURE
<222> LOCATION: (2)..(2)
<223> OTHER INFORMATION: Xaa in position 2 is an acidic or neutral polar
      amino acid residue

<400> SEQUENCE: 103

Cys Xaa Trp Asp Pro Trp Thr Cys
1               5

<210> SEQ ID NO 104
<211> LENGTH: 20
<212> TYPE: PRT
<213> ORGANISM: Artificial Sequence
<220> FEATURE:
<223> OTHER INFORMATION: Ang-2 binding peptide sequence

<400> SEQUENCE: 104

Pro Ile Arg Gln Glu Glu Cys Asp Trp Asp Pro Trp Thr Cys Glu His
1               5                   10                  15

Met Trp Glu Val
            20

<210> SEQ ID NO 105
<211> LENGTH: 20
<212> TYPE: PRT
<213> ORGANISM: Artificial Sequence
<220> FEATURE:
<223> OTHER INFORMATION: Ang-2 binding peptide sequence

<400> SEQUENCE: 105

Thr Asn Ile Gln Glu Glu Cys Glu Trp Asp Pro Trp Thr Cys Asp His
1               5                   10                  15

Met Pro Gly Lys
            20
```

<210> SEQ ID NO 106
<211> LENGTH: 20
<212> TYPE: PRT
<213> ORGANISM: Artificial Sequence
<220> FEATURE:
<223> OTHER INFORMATION: Ang-2 binding peptide sequence

<400> SEQUENCE: 106

Trp Tyr Glu Gln Asp Ala Cys Glu Trp Asp Pro Trp Thr Cys Glu His
1               5                   10                  15

Met Ala Glu Val
            20

<210> SEQ ID NO 107
<211> LENGTH: 20
<212> TYPE: PRT
<213> ORGANISM: Artificial Sequence
<220> FEATURE:
<223> OTHER INFORMATION: Ang-2 binding peptide sequence

<400> SEQUENCE: 107

Asn Arg Leu Gln Glu Val Cys Glu Trp Asp Pro Trp Thr Cys Glu His
1               5                   10                  15

Met Glu Asn Val
            20

<210> SEQ ID NO 108
<211> LENGTH: 20
<212> TYPE: PRT
<213> ORGANISM: Artificial Sequence
<220> FEATURE:
<223> OTHER INFORMATION: Ang-2 binding peptide sequence

<400> SEQUENCE: 108

Ala Ala Thr Gln Glu Glu Cys Glu Trp Asp Pro Trp Thr Cys Glu His
1               5                   10                  15

Met Pro Arg Ser
            20

<210> SEQ ID NO 109
<211> LENGTH: 20
<212> TYPE: PRT
<213> ORGANISM: Artificial Sequence
<220> FEATURE:
<223> OTHER INFORMATION: Ang-2 binding peptide sequence

<400> SEQUENCE: 109

Leu Arg His Gln Glu Gly Cys Glu Trp Asp Pro Trp Thr Cys Glu His
1               5                   10                  15

Met Phe Asp Trp
            20

<210> SEQ ID NO 110
<211> LENGTH: 20
<212> TYPE: PRT
<213> ORGANISM: Artificial Sequence
<220> FEATURE:
<223> OTHER INFORMATION: Ang-2 binding peptide sequence

<400> SEQUENCE: 110

Val Pro Arg Gln Lys Asp Cys Glu Trp Asp Pro Trp Thr Cys Glu His
1               5                   10                  15

Met Tyr Val Gly
            20

<210> SEQ ID NO 111
<211> LENGTH: 20
<212> TYPE: PRT
<213> ORGANISM: Artificial Sequence
<220> FEATURE:
<223> OTHER INFORMATION: Ang-2 binding peptide sequence

<400> SEQUENCE: 111

Ser Ile Ser His Glu Glu Cys Glu Trp Asp Pro Trp Thr Cys Glu His
1               5                   10                  15

Met Gln Val Gly
            20

<210> SEQ ID NO 112
<211> LENGTH: 20
<212> TYPE: PRT
<213> ORGANISM: Artificial Sequence
<220> FEATURE:
<223> OTHER INFORMATION: Ang-2 binding peptide sequence

<400> SEQUENCE: 112

Trp Ala Ala Gln Glu Glu Cys Glu Trp Asp Pro Trp Thr Cys Glu His
1               5                   10                  15

Met Gly Arg Met
            20

<210> SEQ ID NO 113
<211> LENGTH: 20
<212> TYPE: PRT
<213> ORGANISM: Artificial Sequence
<220> FEATURE:
<223> OTHER INFORMATION: Ang-2 binding peptide sequence

<400> SEQUENCE: 113

Thr Trp Pro Gln Asp Lys Cys Glu Trp Asp Pro Trp Thr Cys Glu His
1               5                   10                  15

Met Gly Ser Thr
            20

<210> SEQ ID NO 114
<211> LENGTH: 20
<212> TYPE: PRT
<213> ORGANISM: Artificial Sequence
<220> FEATURE:
<223> OTHER INFORMATION: Ang-2 binding peptide sequence

<400> SEQUENCE: 114

Gly His Ser Gln Glu Glu Cys Gly Trp Asp Pro Trp Thr Cys Glu His
1               5                   10                  15

Met Gly Thr Ser
            20

<210> SEQ ID NO 115
<211> LENGTH: 20
<212> TYPE: PRT
<213> ORGANISM: Artificial Sequence
<220> FEATURE:
<223> OTHER INFORMATION: Ang-2 binding peptide sequence

<400> SEQUENCE: 115

Gln His Trp Gln Glu Glu Cys Glu Trp Asp Pro Trp Thr Cys Asp His
1               5                   10                  15

Met Pro Ser Lys

```
            20

<210> SEQ ID NO 116
<211> LENGTH: 20
<212> TYPE: PRT
<213> ORGANISM: Artificial Sequence
<220> FEATURE:
<223> OTHER INFORMATION: Ang-2 binding peptide sequence

<400> SEQUENCE: 116

Asn Val Arg Gln Glu Lys Cys Glu Trp Asp Pro Trp Thr Cys Glu His
1               5                   10                  15

Met Pro Val Arg
            20

<210> SEQ ID NO 117
<211> LENGTH: 20
<212> TYPE: PRT
<213> ORGANISM: Artificial Sequence
<220> FEATURE:
<223> OTHER INFORMATION: Ang-2 binding peptide sequence

<400> SEQUENCE: 117

Lys Ser Gly Gln Val Glu Cys Asn Trp Asp Pro Trp Thr Cys Glu His
1               5                   10                  15

Met Pro Arg Asn
            20

<210> SEQ ID NO 118
<211> LENGTH: 20
<212> TYPE: PRT
<213> ORGANISM: Artificial Sequence
<220> FEATURE:
<223> OTHER INFORMATION: Ang-2 binding peptide sequence

<400> SEQUENCE: 118

Val Lys Thr Gln Glu His Cys Asp Trp Asp Pro Trp Thr Cys Glu His
1               5                   10                  15

Met Arg Glu Trp
            20

<210> SEQ ID NO 119
<211> LENGTH: 20
<212> TYPE: PRT
<213> ORGANISM: Artificial Sequence
<220> FEATURE:
<223> OTHER INFORMATION: Ang-2 binding peptide sequence

<400> SEQUENCE: 119

Ala Trp Gly Gln Glu Gly Cys Asp Trp Asp Pro Trp Thr Cys Glu His
1               5                   10                  15

Met Leu Pro Met
            20

<210> SEQ ID NO 120
<211> LENGTH: 20
<212> TYPE: PRT
<213> ORGANISM: Artificial Sequence
<220> FEATURE:
<223> OTHER INFORMATION: Ang-2 binding peptide sequence

<400> SEQUENCE: 120

Pro Val Asn Gln Glu Asp Cys Glu Trp Asp Pro Trp Thr Cys Glu His
1               5                   10                  15
```

Met Pro Pro Met
            20

<210> SEQ ID NO 121
<211> LENGTH: 20
<212> TYPE: PRT
<213> ORGANISM: Artificial Sequence
<220> FEATURE:
<223> OTHER INFORMATION: Ang-2 binding peptide sequence

<400> SEQUENCE: 121

Arg Ala Pro Gln Glu Asp Cys Glu Trp Asp Pro Trp Thr Cys Ala His
1               5                   10                  15

Met Asp Ile Lys
            20

<210> SEQ ID NO 122
<211> LENGTH: 20
<212> TYPE: PRT
<213> ORGANISM: Artificial Sequence
<220> FEATURE:
<223> OTHER INFORMATION: Ang-2 binding peptide sequence

<400> SEQUENCE: 122

His Gly Gln Asn Met Glu Cys Glu Trp Asp Pro Trp Thr Cys Glu His
1               5                   10                  15

Met Phe Arg Tyr
            20

<210> SEQ ID NO 123
<211> LENGTH: 20
<212> TYPE: PRT
<213> ORGANISM: Artificial Sequence
<220> FEATURE:
<223> OTHER INFORMATION: Ang-2 binding peptide sequence

<400> SEQUENCE: 123

Pro Arg Leu Gln Glu Glu Cys Val Trp Asp Pro Trp Thr Cys Glu His
1               5                   10                  15

Met Pro Leu Arg
            20

<210> SEQ ID NO 124
<211> LENGTH: 20
<212> TYPE: PRT
<213> ORGANISM: Artificial Sequence
<220> FEATURE:
<223> OTHER INFORMATION: Ang-2 binding peptide sequence

<400> SEQUENCE: 124

Arg Thr Thr Gln Glu Lys Cys Glu Trp Asp Pro Trp Thr Cys Glu His
1               5                   10                  15

Met Glu Ser Gln
            20

<210> SEQ ID NO 125
<211> LENGTH: 20
<212> TYPE: PRT
<213> ORGANISM: Artificial Sequence
<220> FEATURE:
<223> OTHER INFORMATION: Ang-2 binding peptide sequence

<400> SEQUENCE: 125

Gln Thr Ser Gln Glu Asp Cys Val Trp Asp Pro Trp Thr Cys Asp His
1               5                   10                  15

```
Met Val Ser Ser
            20

<210> SEQ ID NO 126
<211> LENGTH: 20
<212> TYPE: PRT
<213> ORGANISM: Artificial Sequence
<220> FEATURE:
<223> OTHER INFORMATION: Ang-2 binding peptide sequence

<400> SEQUENCE: 126

Gln Val Ile Gly Arg Pro Cys Glu Trp Asp Pro Trp Thr Cys Glu His
1               5                   10                  15

Leu Glu Gly Leu
            20

<210> SEQ ID NO 127
<211> LENGTH: 20
<212> TYPE: PRT
<213> ORGANISM: Artificial Sequence
<220> FEATURE:
<223> OTHER INFORMATION: Ang-2 binding peptide sequence

<400> SEQUENCE: 127

Trp Ala Gln Gln Glu Glu Cys Ala Trp Asp Pro Trp Thr Cys Asp His
1               5                   10                  15

Met Val Gly Leu
            20

<210> SEQ ID NO 128
<211> LENGTH: 20
<212> TYPE: PRT
<213> ORGANISM: Artificial Sequence
<220> FEATURE:
<223> OTHER INFORMATION: Ang-2 binding peptide sequence

<400> SEQUENCE: 128

Leu Pro Gly Gln Glu Asp Cys Glu Trp Asp Pro Trp Thr Cys Glu His
1               5                   10                  15

Met Val Arg Ser
            20

<210> SEQ ID NO 129
<211> LENGTH: 20
<212> TYPE: PRT
<213> ORGANISM: Artificial Sequence
<220> FEATURE:
<223> OTHER INFORMATION: Ang-2 binding peptide sequence

<400> SEQUENCE: 129

Pro Met Asn Gln Val Glu Cys Asp Trp Asp Pro Trp Thr Cys Glu His
1               5                   10                  15

Met Pro Arg Ser
            20

<210> SEQ ID NO 130
<211> LENGTH: 20
<212> TYPE: PRT
<213> ORGANISM: Artificial Sequence
<220> FEATURE:
<223> OTHER INFORMATION: Ang-2 binding peptide sequence

<400> SEQUENCE: 130

Phe Gly Trp Ser His Gly Cys Glu Trp Asp Pro Trp Thr Cys Glu His
```

```
1               5                   10                  15

Met Gly Ser Thr
            20

<210> SEQ ID NO 131
<211> LENGTH: 20
<212> TYPE: PRT
<213> ORGANISM: Artificial Sequence
<220> FEATURE:
<223> OTHER INFORMATION: Ang-2 binding peptide sequence

<400> SEQUENCE: 131

Lys Ser Thr Gln Asp Asp Cys Asp Trp Asp Pro Trp Thr Cys Glu His
1               5                   10                  15

Met Val Gly Pro
            20

<210> SEQ ID NO 132
<211> LENGTH: 20
<212> TYPE: PRT
<213> ORGANISM: Artificial Sequence
<220> FEATURE:
<223> OTHER INFORMATION: Ang-2 binding peptide sequence

<400> SEQUENCE: 132

Gly Pro Arg Ile Ser Thr Cys Gln Trp Asp Pro Trp Thr Cys Glu His
1               5                   10                  15

Met Asp Gln Leu
            20

<210> SEQ ID NO 133
<211> LENGTH: 20
<212> TYPE: PRT
<213> ORGANISM: Artificial Sequence
<220> FEATURE:
<223> OTHER INFORMATION: Ang-2 binding peptide sequence

<400> SEQUENCE: 133

Ser Thr Ile Gly Asp Met Cys Glu Trp Asp Pro Trp Thr Cys Ala His
1               5                   10                  15

Met Gln Val Asp
            20

<210> SEQ ID NO 134
<211> LENGTH: 20
<212> TYPE: PRT
<213> ORGANISM: Artificial Sequence
<220> FEATURE:
<223> OTHER INFORMATION: Ang-2 binding peptide sequence

<400> SEQUENCE: 134

Val Leu Gly Gly Gln Gly Cys Glu Trp Asp Pro Trp Thr Cys Arg Leu
1               5                   10                  15

Leu Gln Gly Trp
            20

<210> SEQ ID NO 135
<211> LENGTH: 20
<212> TYPE: PRT
<213> ORGANISM: Artificial Sequence
<220> FEATURE:
<223> OTHER INFORMATION: Ang-2 binding peptide sequence

<400> SEQUENCE: 135
```

```
Val Leu Gly Gly Gln Gly Cys Gln Trp Asp Pro Trp Thr Cys Ser His
1               5                   10                  15

Leu Glu Asp Gly
            20
```

<210> SEQ ID NO 136
<211> LENGTH: 20
<212> TYPE: PRT
<213> ORGANISM: Artificial Sequence
<220> FEATURE:
<223> OTHER INFORMATION: Ang-2 binding peptide sequence

<400> SEQUENCE: 136

```
Thr Thr Ile Gly Ser Met Cys Glu Trp Asp Pro Trp Thr Cys Ala His
1               5                   10                  15

Met Gln Gly Gly
            20
```

<210> SEQ ID NO 137
<211> LENGTH: 20
<212> TYPE: PRT
<213> ORGANISM: Artificial Sequence
<220> FEATURE:
<223> OTHER INFORMATION: Ang-2 binding peptide sequence

<400> SEQUENCE: 137

```
Thr Lys Gly Lys Ser Val Cys Gln Trp Asp Pro Trp Thr Cys Ser His
1               5                   10                  15

Met Gln Ser Gly
            20
```

<210> SEQ ID NO 138
<211> LENGTH: 20
<212> TYPE: PRT
<213> ORGANISM: Artificial Sequence
<220> FEATURE:
<223> OTHER INFORMATION: Ang-2 binding peptide sequence

<400> SEQUENCE: 138

```
Thr Thr Ile Gly Ser Met Cys Gln Trp Asp Pro Trp Thr Cys Ala His
1               5                   10                  15

Met Gln Gly Gly
            20
```

<210> SEQ ID NO 139
<211> LENGTH: 20
<212> TYPE: PRT
<213> ORGANISM: Artificial Sequence
<220> FEATURE:
<223> OTHER INFORMATION: Ang-2 binding peptide sequence

<400> SEQUENCE: 139

```
Trp Val Asn Glu Val Val Cys Glu Trp Asp Pro Trp Thr Cys Asn His
1               5                   10                  15

Trp Asp Thr Pro
            20
```

<210> SEQ ID NO 140
<211> LENGTH: 20
<212> TYPE: PRT
<213> ORGANISM: Artificial Sequence
<220> FEATURE:
<223> OTHER INFORMATION: Ang-2 binding peptide sequence

<400> SEQUENCE: 140

```
Val Val Gln Val Gly Met Cys Gln Trp Asp Pro Trp Thr Cys Lys His
1               5                   10                  15

Met Arg Leu Gln
            20

<210> SEQ ID NO 141
<211> LENGTH: 20
<212> TYPE: PRT
<213> ORGANISM: Artificial Sequence
<220> FEATURE:
<223> OTHER INFORMATION: Ang-2 binding peptide sequence

<400> SEQUENCE: 141

Ala Val Gly Ser Gln Thr Cys Glu Trp Asp Pro Trp Thr Cys Ala His
1               5                   10                  15

Leu Val Glu Val
            20

<210> SEQ ID NO 142
<211> LENGTH: 20
<212> TYPE: PRT
<213> ORGANISM: Artificial Sequence
<220> FEATURE:
<223> OTHER INFORMATION: Ang-2 binding peptide sequence

<400> SEQUENCE: 142

Gln Gly Met Lys Met Phe Cys Glu Trp Asp Pro Trp Thr Cys Ala His
1               5                   10                  15

Ile Val Tyr Arg
            20

<210> SEQ ID NO 143
<211> LENGTH: 20
<212> TYPE: PRT
<213> ORGANISM: Artificial Sequence
<220> FEATURE:
<223> OTHER INFORMATION: Ang-2 binding peptide sequence

<400> SEQUENCE: 143

Thr Thr Ile Gly Ser Met Cys Gln Trp Asp Pro Trp Thr Cys Glu His
1               5                   10                  15

Met Gln Gly Gly
            20

<210> SEQ ID NO 144
<211> LENGTH: 20
<212> TYPE: PRT
<213> ORGANISM: Artificial Sequence
<220> FEATURE:
<223> OTHER INFORMATION: Ang-2 binding peptide sequence

<400> SEQUENCE: 144

Thr Ser Gln Arg Val Gly Cys Glu Trp Asp Pro Trp Thr Cys Gln His
1               5                   10                  15

Leu Thr Tyr Thr
            20

<210> SEQ ID NO 145
<211> LENGTH: 20
<212> TYPE: PRT
<213> ORGANISM: Artificial Sequence
<220> FEATURE:
<223> OTHER INFORMATION: Ang-2 binding peptide sequence
```

```
<400> SEQUENCE: 145

Gln Trp Ser Trp Pro Pro Cys Glu Trp Asp Pro Trp Thr Cys Gln Thr
1               5                   10                  15

Val Trp Pro Ser
            20

<210> SEQ ID NO 146
<211> LENGTH: 20
<212> TYPE: PRT
<213> ORGANISM: Artificial Sequence
<220> FEATURE:
<223> OTHER INFORMATION: Ang-2 binding peptide sequence

<400> SEQUENCE: 146

Gly Thr Ser Pro Ser Phe Cys Gln Trp Asp Pro Trp Thr Cys Ser His
1               5                   10                  15

Met Val Gln Gly
            20

<210> SEQ ID NO 147
<211> LENGTH: 14
<212> TYPE: PRT
<213> ORGANISM: Artificial Sequence
<220> FEATURE:
<223> OTHER INFORMATION: Ang-2 binding peptide sequence

<400> SEQUENCE: 147

Gln Glu Glu Cys Glu Trp Asp Pro Trp Thr Cys Glu His Met
1               5                   10

<210> SEQ ID NO 148
<211> LENGTH: 22
<212> TYPE: PRT
<213> ORGANISM: Artificial Sequence
<220> FEATURE:
<223> OTHER INFORMATION: Ang-2 binding peptide sequence

<400> SEQUENCE: 148

Gln Asn Tyr Lys Pro Leu Asp Glu Leu Asp Ala Thr Leu Tyr Glu His
1               5                   10                  15

Phe Ile Phe His Tyr Thr
            20

<210> SEQ ID NO 149
<211> LENGTH: 22
<212> TYPE: PRT
<213> ORGANISM: Artificial Sequence
<220> FEATURE:
<223> OTHER INFORMATION: Ang-2 binding peptide sequence

<400> SEQUENCE: 149

Leu Asn Phe Thr Pro Leu Asp Glu Leu Glu Gln Thr Leu Tyr Glu Gln
1               5                   10                  15

Trp Thr Leu Gln Gln Ser
            20

<210> SEQ ID NO 150
<211> LENGTH: 22
<212> TYPE: PRT
<213> ORGANISM: Artificial Sequence
<220> FEATURE:
<223> OTHER INFORMATION: Ang-2 binding peptide sequence

<400> SEQUENCE: 150
```

Thr Lys Phe Asn Pro Leu Asp Glu Leu Glu Gln Thr Leu Tyr Glu Gln
1               5                   10                  15

Trp Thr Leu Gln His Gln
            20

<210> SEQ ID NO 151
<211> LENGTH: 22
<212> TYPE: PRT
<213> ORGANISM: Artificial Sequence
<220> FEATURE:
<223> OTHER INFORMATION: Ang-2 binding peptide sequence

<400> SEQUENCE: 151

Val Lys Phe Lys Pro Leu Asp Ala Leu Glu Gln Thr Leu Tyr Glu His
1               5                   10                  15

Trp Met Phe Gln Gln Ala
            20

<210> SEQ ID NO 152
<211> LENGTH: 22
<212> TYPE: PRT
<213> ORGANISM: Artificial Sequence
<220> FEATURE:
<223> OTHER INFORMATION: Ang-2 binding peptide sequence

<400> SEQUENCE: 152

Val Lys Tyr Lys Pro Leu Asp Glu Leu Asp Glu Ile Leu Tyr Glu Gln
1               5                   10                  15

Gln Thr Phe Gln Glu Arg
            20

<210> SEQ ID NO 153
<211> LENGTH: 22
<212> TYPE: PRT
<213> ORGANISM: Artificial Sequence
<220> FEATURE:
<223> OTHER INFORMATION: Ang-2 binding peptide sequence

<400> SEQUENCE: 153

Thr Asn Phe Met Pro Met Asp Asp Leu Glu Gln Arg Leu Tyr Glu Gln
1               5                   10                  15

Phe Ile Leu Gln Gln Gly
            20

<210> SEQ ID NO 154
<211> LENGTH: 22
<212> TYPE: PRT
<213> ORGANISM: Artificial Sequence
<220> FEATURE:
<223> OTHER INFORMATION: Ang-2 binding peptide sequence

<400> SEQUENCE: 154

Ser Lys Phe Lys Pro Leu Asp Glu Leu Glu Gln Thr Leu Tyr Glu Gln
1               5                   10                  15

Trp Thr Leu Gln His Ala
            20

<210> SEQ ID NO 155
<211> LENGTH: 22
<212> TYPE: PRT
<213> ORGANISM: Artificial Sequence
<220> FEATURE:
<223> OTHER INFORMATION: Ang-2 binding peptide sequence

<400> SEQUENCE: 155

-continued

Gln Lys Phe Gln Pro Leu Asp Glu Leu Glu Gln Thr Leu Tyr Glu Gln
1               5                   10                  15

Phe Met Leu Gln Gln Ala
            20

<210> SEQ ID NO 156
<211> LENGTH: 22
<212> TYPE: PRT
<213> ORGANISM: Artificial Sequence
<220> FEATURE:
<223> OTHER INFORMATION: Ang-2 binding peptide sequence

<400> SEQUENCE: 156

Gln Asn Phe Lys Pro Met Asp Glu Leu Glu Asp Thr Leu Tyr Lys Gln
1               5                   10                  15

Phe Leu Phe Gln His Ser
            20

<210> SEQ ID NO 157
<211> LENGTH: 22
<212> TYPE: PRT
<213> ORGANISM: Artificial Sequence
<220> FEATURE:
<223> OTHER INFORMATION: Ang-2 binding peptide sequence

<400> SEQUENCE: 157

Tyr Lys Phe Thr Pro Leu Asp Asp Leu Glu Gln Thr Leu Tyr Glu Gln
1               5                   10                  15

Trp Thr Leu Gln His Val
            20

<210> SEQ ID NO 158
<211> LENGTH: 22
<212> TYPE: PRT
<213> ORGANISM: Artificial Sequence
<220> FEATURE:
<223> OTHER INFORMATION: Ang-2 binding peptide sequence

<400> SEQUENCE: 158

Gln Glu Tyr Glu Pro Leu Asp Glu Leu Asp Glu Thr Leu Tyr Asn Gln
1               5                   10                  15

Trp Met Phe His Gln Arg
            20

<210> SEQ ID NO 159
<211> LENGTH: 22
<212> TYPE: PRT
<213> ORGANISM: Artificial Sequence
<220> FEATURE:
<223> OTHER INFORMATION: Ang-2 binding peptide sequence

<400> SEQUENCE: 159

Ser Asn Phe Met Pro Leu Asp Glu Leu Glu Gln Thr Leu Tyr Glu Gln
1               5                   10                  15

Phe Met Leu Gln His Gln
            20

<210> SEQ ID NO 160
<211> LENGTH: 22
<212> TYPE: PRT
<213> ORGANISM: Artificial Sequence
<220> FEATURE:
<223> OTHER INFORMATION: Ang-2 binding peptide sequence

```
<400> SEQUENCE: 160

Gln Lys Tyr Gln Pro Leu Asp Glu Leu Asp Lys Thr Leu Tyr Asp Gln
1               5                   10                  15

Phe Met Leu Gln Gln Gly
            20

<210> SEQ ID NO 161
<211> LENGTH: 22
<212> TYPE: PRT
<213> ORGANISM: Artificial Sequence
<220> FEATURE:
<223> OTHER INFORMATION: Ang-2 binding peptide sequence

<400> SEQUENCE: 161

Gln Lys Phe Gln Pro Leu Asp Glu Leu Glu Glu Thr Leu Tyr Lys Gln
1               5                   10                  15

Trp Thr Leu Gln Gln Arg
            20

<210> SEQ ID NO 162
<211> LENGTH: 22
<212> TYPE: PRT
<213> ORGANISM: Artificial Sequence
<220> FEATURE:
<223> OTHER INFORMATION: Ang-2 binding peptide sequence

<400> SEQUENCE: 162

Val Lys Tyr Lys Pro Leu Asp Glu Leu Asp Glu Trp Leu Tyr His Gln
1               5                   10                  15

Phe Thr Leu His His Gln
            20

<210> SEQ ID NO 163
<211> LENGTH: 22
<212> TYPE: PRT
<213> ORGANISM: Artificial Sequence
<220> FEATURE:
<223> OTHER INFORMATION: Ang-2 binding peptide sequence

<400> SEQUENCE: 163

Gln Lys Phe Met Pro Leu Asp Glu Leu Asp Glu Ile Leu Tyr Glu Gln
1               5                   10                  15

Phe Met Phe Gln Gln Ser
            20

<210> SEQ ID NO 164
<211> LENGTH: 22
<212> TYPE: PRT
<213> ORGANISM: Artificial Sequence
<220> FEATURE:
<223> OTHER INFORMATION: Ang-2 binding peptide sequence

<400> SEQUENCE: 164

Gln Thr Phe Gln Pro Leu Asp Asp Leu Glu Glu Tyr Leu Tyr Glu Gln
1               5                   10                  15

Trp Ile Arg Arg Tyr His
            20

<210> SEQ ID NO 165
<211> LENGTH: 22
<212> TYPE: PRT
<213> ORGANISM: Artificial Sequence
<220> FEATURE:
<223> OTHER INFORMATION: Ang-2 binding peptide sequence
```

<400> SEQUENCE: 165

Glu Asp Tyr Met Pro Leu Asp Ala Leu Asp Ala Gln Leu Tyr Glu Gln
1               5                   10                  15

Phe Ile Leu Leu His Gly
            20

<210> SEQ ID NO 166
<211> LENGTH: 22
<212> TYPE: PRT
<213> ORGANISM: Artificial Sequence
<220> FEATURE:
<223> OTHER INFORMATION: Ang-2 binding peptide sequence

<400> SEQUENCE: 166

His Thr Phe Gln Pro Leu Asp Glu Leu Glu Glu Thr Leu Tyr Tyr Gln
1               5                   10                  15

Trp Leu Tyr Asp Gln Leu
            20

<210> SEQ ID NO 167
<211> LENGTH: 22
<212> TYPE: PRT
<213> ORGANISM: Artificial Sequence
<220> FEATURE:
<223> OTHER INFORMATION: Ang-2 binding peptide sequence

<400> SEQUENCE: 167

Tyr Lys Phe Asn Pro Met Asp Glu Leu Glu Gln Thr Leu Tyr Glu Glu
1               5                   10                  15

Phe Leu Phe Gln His Ala
            20

<210> SEQ ID NO 168
<211> LENGTH: 22
<212> TYPE: PRT
<213> ORGANISM: Artificial Sequence
<220> FEATURE:
<223> OTHER INFORMATION: Ang-2 binding peptide sequence

<400> SEQUENCE: 168

Thr Asn Tyr Lys Pro Leu Asp Glu Leu Asp Ala Thr Leu Tyr Glu His
1               5                   10                  15

Trp Ile Leu Gln His Ser
            20

<210> SEQ ID NO 169
<211> LENGTH: 22
<212> TYPE: PRT
<213> ORGANISM: Artificial Sequence
<220> FEATURE:
<223> OTHER INFORMATION: Ang-2 binding peptide sequence

<400> SEQUENCE: 169

Gln Lys Phe Lys Pro Leu Asp Glu Leu Glu Gln Thr Leu Tyr Glu Gln
1               5                   10                  15

Trp Thr Leu Gln Gln Arg
            20

<210> SEQ ID NO 170
<211> LENGTH: 22
<212> TYPE: PRT
<213> ORGANISM: Artificial Sequence
<220> FEATURE:

<223> OTHER INFORMATION: Ang-2 binding peptide sequence

<400> SEQUENCE: 170

Thr Lys Phe Gln Pro Leu Asp Glu Leu Asp Gln Thr Leu Tyr Glu Gln
1               5                   10                  15

Trp Thr Leu Gln Gln Arg
            20

<210> SEQ ID NO 171
<211> LENGTH: 22
<212> TYPE: PRT
<213> ORGANISM: Artificial Sequence
<220> FEATURE:
<223> OTHER INFORMATION: Ang-2 binding peptide sequence

<400> SEQUENCE: 171

Thr Asn Phe Gln Pro Leu Asp Glu Leu Asp Gln Thr Leu Tyr Glu Gln
1               5                   10                  15

Trp Thr Leu Gln Gln Arg
            20

<210> SEQ ID NO 172
<211> LENGTH: 20
<212> TYPE: PRT
<213> ORGANISM: Artificial Sequence
<220> FEATURE:
<223> OTHER INFORMATION: Ang-2 binding peptide sequence

<400> SEQUENCE: 172

Lys Phe Asn Pro Leu Asp Glu Leu Glu Glu Thr Leu Tyr Glu Gln Phe
1               5                   10                  15

Thr Phe Gln Gln
            20

<210> SEQ ID NO 173
<211> LENGTH: 20
<212> TYPE: PRT
<213> ORGANISM: Artificial Sequence
<220> FEATURE:
<223> OTHER INFORMATION: Ang-2 binding peptide sequence

<400> SEQUENCE: 173

Ala Gly Gly Met Arg Pro Tyr Asp Gly Met Leu Gly Trp Pro Asn Tyr
1               5                   10                  15

Asp Val Gln Ala
            20

<210> SEQ ID NO 174
<211> LENGTH: 20
<212> TYPE: PRT
<213> ORGANISM: Artificial Sequence
<220> FEATURE:
<223> OTHER INFORMATION: Ang-2 binding peptide sequence

<400> SEQUENCE: 174

Gln Thr Trp Asp Asp Pro Cys Met His Ile Leu Gly Pro Val Thr Trp
1               5                   10                  15

Arg Arg Cys Ile
            20

<210> SEQ ID NO 175
<211> LENGTH: 20
<212> TYPE: PRT
<213> ORGANISM: Artificial Sequence

```
<220> FEATURE:
<223> OTHER INFORMATION: Ang-2 binding peptide sequence

<400> SEQUENCE: 175

Ala Pro Gly Gln Arg Pro Tyr Asp Gly Met Leu Gly Trp Pro Thr Tyr
1               5                   10                  15

Gln Arg Ile Val
            20

<210> SEQ ID NO 176
<211> LENGTH: 20
<212> TYPE: PRT
<213> ORGANISM: Artificial Sequence
<220> FEATURE:
<223> OTHER INFORMATION: Ang-2 binding peptide sequence

<400> SEQUENCE: 176

Ser Gly Gln Leu Arg Pro Cys Glu Glu Ile Phe Gly Cys Gly Thr Gln
1               5                   10                  15

Asn Leu Ala Leu
            20

<210> SEQ ID NO 177
<211> LENGTH: 20
<212> TYPE: PRT
<213> ORGANISM: Artificial Sequence
<220> FEATURE:
<223> OTHER INFORMATION: Ang-2 binding peptide sequence

<400> SEQUENCE: 177

Phe Gly Asp Lys Arg Pro Leu Glu Cys Met Phe Gly Gly Pro Ile Gln
1               5                   10                  15

Leu Cys Pro Arg
            20

<210> SEQ ID NO 178
<211> LENGTH: 20
<212> TYPE: PRT
<213> ORGANISM: Artificial Sequence
<220> FEATURE:
<223> OTHER INFORMATION: Ang-2 binding peptide sequence

<400> SEQUENCE: 178

Gly Gln Asp Leu Arg Pro Cys Glu Asp Met Phe Gly Cys Gly Thr Lys
1               5                   10                  15

Asp Trp Tyr Gly
            20

<210> SEQ ID NO 179
<211> LENGTH: 14
<212> TYPE: PRT
<213> ORGANISM: Artificial Sequence
<220> FEATURE:
<223> OTHER INFORMATION: Ang-2 binding peptide sequence

<400> SEQUENCE: 179

Lys Arg Pro Cys Glu Glu Ile Phe Gly Gly Cys Thr Tyr Gln
1               5                   10

<210> SEQ ID NO 180
<211> LENGTH: 20
<212> TYPE: PRT
<213> ORGANISM: Artificial Sequence
<220> FEATURE:
<223> OTHER INFORMATION: Ang-2 binding peptide sequence
```

<400> SEQUENCE: 180

Gly Phe Glu Tyr Cys Asp Gly Met Glu Asp Pro Phe Thr Phe Gly Cys
1               5                   10                  15

Asp Lys Gln Thr
            20

<210> SEQ ID NO 181
<211> LENGTH: 20
<212> TYPE: PRT
<213> ORGANISM: Artificial Sequence
<220> FEATURE:
<223> OTHER INFORMATION: Ang-2 binding peptide sequence

<400> SEQUENCE: 181

Lys Leu Glu Tyr Cys Asp Gly Met Glu Asp Pro Phe Thr Gln Gly Cys
1               5                   10                  15

Asp Asn Gln Ser
            20

<210> SEQ ID NO 182
<211> LENGTH: 20
<212> TYPE: PRT
<213> ORGANISM: Artificial Sequence
<220> FEATURE:
<223> OTHER INFORMATION: Ang-2 binding peptide sequence

<400> SEQUENCE: 182

Leu Gln Glu Trp Cys Glu Gly Val Glu Asp Pro Phe Thr Phe Gly Cys
1               5                   10                  15

Glu Lys Gln Arg
            20

<210> SEQ ID NO 183
<211> LENGTH: 20
<212> TYPE: PRT
<213> ORGANISM: Artificial Sequence
<220> FEATURE:
<223> OTHER INFORMATION: Ang-2 binding peptide sequence

<400> SEQUENCE: 183

Ala Gln Asp Tyr Cys Glu Gly Met Glu Asp Pro Phe Thr Phe Gly Cys
1               5                   10                  15

Glu Met Gln Lys
            20

<210> SEQ ID NO 184
<211> LENGTH: 20
<212> TYPE: PRT
<213> ORGANISM: Artificial Sequence
<220> FEATURE:
<223> OTHER INFORMATION: Ang-2 binding peptide sequence

<400> SEQUENCE: 184

Leu Leu Asp Tyr Cys Glu Gly Val Gln Asp Pro Phe Thr Phe Gly Cys
1               5                   10                  15

Glu Asn Leu Asp
            20

<210> SEQ ID NO 185
<211> LENGTH: 20
<212> TYPE: PRT
<213> ORGANISM: Artificial Sequence
<220> FEATURE:

```
<223> OTHER INFORMATION: Ang-2 binding peptide sequence

<400> SEQUENCE: 185

His Gln Glu Tyr Cys Glu Gly Met Glu Asp Pro Phe Thr Phe Gly Cys
1               5                   10                  15

Glu Tyr Gln Gly
            20

<210> SEQ ID NO 186
<211> LENGTH: 20
<212> TYPE: PRT
<213> ORGANISM: Artificial Sequence
<220> FEATURE:
<223> OTHER INFORMATION: Ang-2 binding peptide sequence

<400> SEQUENCE: 186

Met Leu Asp Tyr Cys Glu Gly Met Asp Asp Pro Phe Thr Phe Gly Cys
1               5                   10                  15

Asp Lys Gln Met
            20

<210> SEQ ID NO 187
<211> LENGTH: 20
<212> TYPE: PRT
<213> ORGANISM: Artificial Sequence
<220> FEATURE:
<223> OTHER INFORMATION: Ang-2 binding peptide sequence

<400> SEQUENCE: 187

Leu Gln Asp Tyr Cys Glu Gly Val Glu Asp Pro Phe Thr Phe Gly Cys
1               5                   10                  15

Glu Asn Gln Arg
            20

<210> SEQ ID NO 188
<211> LENGTH: 20
<212> TYPE: PRT
<213> ORGANISM: Artificial Sequence
<220> FEATURE:
<223> OTHER INFORMATION: Ang-2 binding peptide sequence

<400> SEQUENCE: 188

Leu Gln Asp Tyr Cys Glu Gly Val Glu Asp Pro Phe Thr Phe Gly Cys
1               5                   10                  15

Glu Lys Gln Arg
            20

<210> SEQ ID NO 189
<211> LENGTH: 18
<212> TYPE: PRT
<213> ORGANISM: Artificial Sequence
<220> FEATURE:
<223> OTHER INFORMATION: Ang-2 binding peptide sequence

<400> SEQUENCE: 189

Phe Asp Tyr Cys Glu Gly Val Glu Asp Pro Phe Thr Phe Gly Cys Asp
1               5                   10                  15

Asn His

<210> SEQ ID NO 190
<211> LENGTH: 20
<212> TYPE: PRT
<213> ORGANISM: Artificial Sequence
<220> FEATURE:
```

```
<223> OTHER INFORMATION: NGF-Binding Peptide Sequences

<400> SEQUENCE: 190

Thr Gly Tyr Thr Glu Tyr Thr Glu Glu Trp Pro Met Gly Phe Gly Tyr
1               5                   10                  15

Gln Trp Ser Phe
            20

<210> SEQ ID NO 191
<211> LENGTH: 20
<212> TYPE: PRT
<213> ORGANISM: Artificial Sequence
<220> FEATURE:
<223> OTHER INFORMATION: NGF-Binding Peptide Sequences

<400> SEQUENCE: 191

Thr Asp Trp Leu Ser Asp Phe Pro Phe Tyr Glu Gln Tyr Phe Gly Leu
1               5                   10                  15

Met Pro Pro Gly
            20

<210> SEQ ID NO 192
<211> LENGTH: 20
<212> TYPE: PRT
<213> ORGANISM: Artificial Sequence
<220> FEATURE:
<223> OTHER INFORMATION: NGF-Binding Peptide Sequences

<400> SEQUENCE: 192

Phe Met Arg Phe Pro Asn Pro Trp Lys Leu Val Glu Pro Pro Gln Gly
1               5                   10                  15

Trp Tyr Tyr Gly
            20

<210> SEQ ID NO 193
<211> LENGTH: 20
<212> TYPE: PRT
<213> ORGANISM: Artificial Sequence
<220> FEATURE:
<223> OTHER INFORMATION: NGF-Binding Peptide Sequences

<400> SEQUENCE: 193

Val Val Lys Ala Pro His Phe Glu Phe Leu Ala Pro Pro His Phe His
1               5                   10                  15

Glu Phe Pro Phe
            20

<210> SEQ ID NO 194
<211> LENGTH: 20
<212> TYPE: PRT
<213> ORGANISM: Artificial Sequence
<220> FEATURE:
<223> OTHER INFORMATION: NGF-Binding Peptide Sequences

<400> SEQUENCE: 194

Phe Ser Tyr Ile Trp Ile Asp Glu Thr Pro Ser Asn Ile Asp Arg Tyr
1               5                   10                  15

Met Leu Trp Leu
            20

<210> SEQ ID NO 195
<211> LENGTH: 20
<212> TYPE: PRT
<213> ORGANISM: Artificial Sequence
```

```
<220> FEATURE:
<223> OTHER INFORMATION: NGF-Binding Peptide Sequences

<400> SEQUENCE: 195

Val Asn Phe Pro Lys Val Pro Glu Asp Val Glu Pro Trp Pro Trp Ser
1               5                   10                  15

Leu Lys Leu Tyr
            20

<210> SEQ ID NO 196
<211> LENGTH: 20
<212> TYPE: PRT
<213> ORGANISM: Artificial Sequence
<220> FEATURE:
<223> OTHER INFORMATION: NGF-Binding Peptide Sequences

<400> SEQUENCE: 196

Thr Trp His Pro Lys Thr Tyr Glu Glu Phe Ala Leu Pro Phe Phe Val
1               5                   10                  15

Pro Glu Ala Pro
            20

<210> SEQ ID NO 197
<211> LENGTH: 20
<212> TYPE: PRT
<213> ORGANISM: Artificial Sequence
<220> FEATURE:
<223> OTHER INFORMATION: NGF-Binding Peptide Sequences

<400> SEQUENCE: 197

Trp His Phe Gly Thr Pro Tyr Ile Gln Gln Gln Pro Gly Val Tyr Trp
1               5                   10                  15

Leu Gln Ala Pro
            20

<210> SEQ ID NO 198
<211> LENGTH: 20
<212> TYPE: PRT
<213> ORGANISM: Artificial Sequence
<220> FEATURE:
<223> OTHER INFORMATION: NGF-Binding Peptide Sequences

<400> SEQUENCE: 198

Val Trp Asn Tyr Gly Pro Phe Phe Met Asn Phe Pro Asp Ser Thr Tyr
1               5                   10                  15

Phe Leu His Glu
            20

<210> SEQ ID NO 199
<211> LENGTH: 20
<212> TYPE: PRT
<213> ORGANISM: Artificial Sequence
<220> FEATURE:
<223> OTHER INFORMATION: NGF-Binding Peptide Sequences

<400> SEQUENCE: 199

Trp Arg Ile His Ser Lys Pro Leu Asp Tyr Ser His Val Trp Phe Phe
1               5                   10                  15

Pro Ala Asp Phe
            20

<210> SEQ ID NO 200
<211> LENGTH: 20
<212> TYPE: PRT
```

```
<213> ORGANISM: Artificial Sequence
<220> FEATURE:
<223> OTHER INFORMATION: NGF-Binding Peptide Sequences

<400> SEQUENCE: 200

Phe Trp Asp Gly Asn Gln Pro Pro Asp Ile Leu Val Asp Trp Pro Trp
1               5                   10                  15

Asn Pro Pro Val
            20

<210> SEQ ID NO 201
<211> LENGTH: 20
<212> TYPE: PRT
<213> ORGANISM: Artificial Sequence
<220> FEATURE:
<223> OTHER INFORMATION: NGF-Binding Peptide Sequences

<400> SEQUENCE: 201

Phe Tyr Ser Leu Glu Trp Leu Lys Asp His Ser Glu Phe Phe Gln Thr
1               5                   10                  15

Val Thr Glu Trp
            20

<210> SEQ ID NO 202
<211> LENGTH: 20
<212> TYPE: PRT
<213> ORGANISM: Artificial Sequence
<220> FEATURE:
<223> OTHER INFORMATION: NGF-Binding Peptide Sequences

<400> SEQUENCE: 202

Gln Phe Met Glu Leu Leu Lys Phe Phe Asn Ser Pro Gly Asp Ser Ser
1               5                   10                  15

His His Phe Leu
            20

<210> SEQ ID NO 203
<211> LENGTH: 20
<212> TYPE: PRT
<213> ORGANISM: Artificial Sequence
<220> FEATURE:
<223> OTHER INFORMATION: NGF-Binding Peptide Sequences

<400> SEQUENCE: 203

Thr Asn Val Asp Trp Ile Ser Asn Asn Trp Glu His Met Lys Ser Phe
1               5                   10                  15

Phe Thr Glu Asp
            20

<210> SEQ ID NO 204
<211> LENGTH: 20
<212> TYPE: PRT
<213> ORGANISM: Artificial Sequence
<220> FEATURE:
<223> OTHER INFORMATION: NGF-Binding Peptide Sequences

<400> SEQUENCE: 204

Pro Asn Glu Lys Pro Tyr Gln Met Gln Ser Trp Phe Pro Pro Asp Trp
1               5                   10                  15

Pro Val Pro Tyr
            20

<210> SEQ ID NO 205
<211> LENGTH: 20
```

```
<212> TYPE: PRT
<213> ORGANISM: Artificial Sequence
<220> FEATURE:
<223> OTHER INFORMATION: NGF-Binding Peptide Sequences

<400> SEQUENCE: 205

Trp Ser His Thr Glu Trp Val Pro Gln Val Trp Trp Lys Pro Pro Asn
1               5                   10                  15

His Phe Tyr Val
            20

<210> SEQ ID NO 206
<211> LENGTH: 20
<212> TYPE: PRT
<213> ORGANISM: Artificial Sequence
<220> FEATURE:
<223> OTHER INFORMATION: NGF-Binding Peptide Sequences

<400> SEQUENCE: 206

Trp Gly Glu Trp Ile Asn Asp Ala Gln Val His Met His Glu Gly Phe
1               5                   10                  15

Ile Ser Glu Ser
            20

<210> SEQ ID NO 207
<211> LENGTH: 20
<212> TYPE: PRT
<213> ORGANISM: Artificial Sequence
<220> FEATURE:
<223> OTHER INFORMATION: NGF-Binding Peptide Sequences

<400> SEQUENCE: 207

Val Pro Trp Glu His Asp His Asp Leu Trp Glu Ile Ile Ser Gln Asp
1               5                   10                  15

Trp His Ile Ala
            20

<210> SEQ ID NO 208
<211> LENGTH: 20
<212> TYPE: PRT
<213> ORGANISM: Artificial Sequence
<220> FEATURE:
<223> OTHER INFORMATION: NGF-Binding Peptide Sequences

<400> SEQUENCE: 208

Val Leu His Leu Gln Asp Pro Arg Gly Trp Ser Asn Phe Pro Pro Gly
1               5                   10                  15

Val Leu Glu Leu
            20

<210> SEQ ID NO 209
<211> LENGTH: 14
<212> TYPE: PRT
<213> ORGANISM: Artificial Sequence
<220> FEATURE:
<223> OTHER INFORMATION: NGF-Binding Peptide Sequences

<400> SEQUENCE: 209

Ile His Gly Cys Trp Phe Thr Glu Glu Gly Cys Val Trp Gln
1               5                   10

<210> SEQ ID NO 210
<211> LENGTH: 14
<212> TYPE: PRT
<213> ORGANISM: Artificial Sequence
```

```
<220> FEATURE:
<223> OTHER INFORMATION: NGF-Binding Peptide Sequences

<400> SEQUENCE: 210

Tyr Met Gln Cys Gln Phe Ala Arg Asp Gly Cys Pro Gln Trp
1               5                   10

<210> SEQ ID NO 211
<211> LENGTH: 14
<212> TYPE: PRT
<213> ORGANISM: Artificial Sequence
<220> FEATURE:
<223> OTHER INFORMATION: NGF-Binding Peptide Sequences

<400> SEQUENCE: 211

Lys Leu Gln Cys Gln Tyr Ser Glu Ser Gly Cys Pro Thr Ile
1               5                   10

<210> SEQ ID NO 212
<211> LENGTH: 14
<212> TYPE: PRT
<213> ORGANISM: Artificial Sequence
<220> FEATURE:
<223> OTHER INFORMATION: NGF-Binding Peptide Sequences

<400> SEQUENCE: 212

Phe Leu Gln Cys Glu Ile Ser Gly Gly Ala Cys Pro Ala Pro
1               5                   10

<210> SEQ ID NO 213
<211> LENGTH: 14
<212> TYPE: PRT
<213> ORGANISM: Artificial Sequence
<220> FEATURE:
<223> OTHER INFORMATION: NGF-Binding Peptide Sequences

<400> SEQUENCE: 213

Lys Leu Gln Cys Glu Phe Ser Thr Ser Gly Cys Pro Asp Leu
1               5                   10

<210> SEQ ID NO 214
<211> LENGTH: 14
<212> TYPE: PRT
<213> ORGANISM: Artificial Sequence
<220> FEATURE:
<223> OTHER INFORMATION: NGF-Binding Peptide Sequences

<400> SEQUENCE: 214

Lys Leu Gln Cys Glu Phe Ser Thr Gln Gly Cys Pro Asp Leu
1               5                   10

<210> SEQ ID NO 215
<211> LENGTH: 14
<212> TYPE: PRT
<213> ORGANISM: Artificial Sequence
<220> FEATURE:
<223> OTHER INFORMATION: NGF-Binding Peptide Sequences

<400> SEQUENCE: 215

Lys Leu Gln Cys Glu Phe Ser Thr Ser Gly Cys Pro Trp Leu
1               5                   10

<210> SEQ ID NO 216
<211> LENGTH: 14
<212> TYPE: PRT
<213> ORGANISM: Artificial Sequence
<220> FEATURE:
```

<223> OTHER INFORMATION: NGF-Binding Peptide Sequences

<400> SEQUENCE: 216

Ile Gln Gly Cys Trp Phe Thr Glu Glu Gly Cys Pro Trp Gln
1               5                   10

<210> SEQ ID NO 217
<211> LENGTH: 18
<212> TYPE: PRT
<213> ORGANISM: Artificial Sequence
<220> FEATURE:
<223> OTHER INFORMATION: NGF-Binding Peptide Sequences

<400> SEQUENCE: 217

Ser Phe Asp Cys Asp Asn Pro Trp Gly His Val Leu Gln Ser Cys Phe
1               5                   10                  15

Gly Phe

<210> SEQ ID NO 218
<211> LENGTH: 18
<212> TYPE: PRT
<213> ORGANISM: Artificial Sequence
<220> FEATURE:
<223> OTHER INFORMATION: NGF-Binding Peptide Sequences

<400> SEQUENCE: 218

Ser Phe Asp Cys Asp Asn Pro Trp Gly His Lys Leu Gln Ser Cys Phe
1               5                   10                  15

Gly Phe

<210> SEQ ID NO 219
<211> LENGTH: 14
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 219

Lys Asp Leu Cys Ala Met Trp His Trp Met Cys Lys Pro Pro
1               5                   10

<210> SEQ ID NO 220
<211> LENGTH: 14
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 220

Lys Asp Leu Cys Lys Met Trp Lys Trp Met Cys Lys Pro Pro
1               5                   10

<210> SEQ ID NO 221
<211> LENGTH: 14
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 221

Lys Asp Leu Cys Lys Met Trp His Trp Met Cys Lys Pro Lys
1               5                   10

<210> SEQ ID NO 222
<211> LENGTH: 14
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 222

Trp Tyr Pro Cys Tyr Glu Phe His Phe Trp Cys Tyr Asp Leu
1               5                   10

<210> SEQ ID NO 223
<211> LENGTH: 14
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 223

Trp Tyr Pro Cys Tyr Glu Gly His Phe Trp Cys Tyr Asp Leu
1               5                   10

<210> SEQ ID NO 224
<211> LENGTH: 14
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 224

Ile Phe Gly Cys Lys Trp Trp Asp Val Gln Cys Tyr Gln Phe
1               5                   10

<210> SEQ ID NO 225
<211> LENGTH: 14
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 225

Ile Phe Gly Cys Lys Trp Trp Asp Val Asp Cys Tyr Gln Phe
1               5                   10

<210> SEQ ID NO 226
<211> LENGTH: 14
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 226

Ala Asp Trp Cys Val Ser Pro Asn Trp Phe Cys Met Val Met
1               5                   10

<210> SEQ ID NO 227
<211> LENGTH: 14
<212> TYPE: PRT
<213> ORGANISM: Artificial Sequence
<220> FEATURE:
<223> OTHER INFORMATION: Myostatin binding peptide or polypeptide
      sequence

```
<400> SEQUENCE: 227

His Lys Phe Cys Pro Trp Trp Ala Leu Phe Cys Trp Asp Phe
1               5                   10

<210> SEQ ID NO 228
<211> LENGTH: 14
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 228

Lys Asp Leu Cys Lys Met Trp His Trp Met Cys Lys Pro Pro
1               5                   10

<210> SEQ ID NO 229
<211> LENGTH: 14
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 229

Ile Asp Lys Cys Ala Ile Trp Gly Trp Met Cys Pro Pro Leu
1               5                   10

<210> SEQ ID NO 230
<211> LENGTH: 14
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 230

Trp Tyr Pro Cys Gly Glu Phe Gly Met Trp Cys Leu Asn Val
1               5                   10

<210> SEQ ID NO 231
<211> LENGTH: 11
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 231

Trp Phe Thr Cys Leu Trp Asn Cys Asp Asn Glu
1               5                   10

<210> SEQ ID NO 232
<211> LENGTH: 14
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 232

His Thr Pro Cys Pro Trp Phe Ala Pro Leu Cys Val Glu Trp
1               5                   10

<210> SEQ ID NO 233
<211> LENGTH: 14
<212> TYPE: PRT
```

```
<213> ORGANISM: Artificial Sequence
<220> FEATURE:
<223> OTHER INFORMATION: Myostatin binding peptide or polypeptide
      sequence

<400> SEQUENCE: 233

Lys Glu Trp Cys Trp Arg Trp Lys Trp Met Cys Lys Pro Glu
1               5                   10

<210> SEQ ID NO 234
<211> LENGTH: 14
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 234

Phe Glu Thr Cys Pro Ser Trp Ala Tyr Phe Cys Leu Asp Ile
1               5                   10

<210> SEQ ID NO 235
<211> LENGTH: 14
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 235

Ala Tyr Lys Cys Glu Ala Asn Asp Trp Gly Cys Trp Trp Leu
1               5                   10

<210> SEQ ID NO 236
<211> LENGTH: 14
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 236

Asn Ser Trp Cys Glu Asp Gln Trp His Arg Cys Trp Trp Leu
1               5                   10

<210> SEQ ID NO 237
<211> LENGTH: 14
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 237

Trp Ser Ala Cys Tyr Ala Gly His Phe Trp Cys Tyr Asp Leu
1               5                   10

<210> SEQ ID NO 238
<211> LENGTH: 14
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 238

Ala Asn Trp Cys Val Ser Pro Asn Trp Phe Cys Met Val Met
1               5                   10
```

```
<210> SEQ ID NO 239
<211> LENGTH: 14
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 239

Trp Thr Glu Cys Tyr Gln Gln Glu Phe Trp Cys Trp Asn Leu
1               5                   10

<210> SEQ ID NO 240
<211> LENGTH: 14
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 240

Glu Asn Thr Cys Glu Arg Trp Lys Trp Met Cys Pro Pro Lys
1               5                   10

<210> SEQ ID NO 241
<211> LENGTH: 14
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 241

Trp Leu Pro Cys His Gln Glu Gly Phe Trp Cys Met Asn Phe
1               5                   10

<210> SEQ ID NO 242
<211> LENGTH: 14
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 242

Ser Thr Met Cys Ser Gln Trp His Trp Met Cys Asn Pro Phe
1               5                   10

<210> SEQ ID NO 243
<211> LENGTH: 14
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 243

Ile Phe Gly Cys His Trp Trp Asp Val Asp Cys Tyr Gln Phe
1               5                   10

<210> SEQ ID NO 244
<211> LENGTH: 14
<212> TYPE: PRT
<213> ORGANISM: Artificial Sequence
<220> FEATURE:
<223> OTHER INFORMATION: Myostatin binding peptide or polypeptide
      sequence
```

-continued

<400> SEQUENCE: 244

Ile Tyr Gly Cys Lys Trp Trp Asp Ile Gln Cys Tyr Asp Ile
1               5                   10

<210> SEQ ID NO 245
<211> LENGTH: 14
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 245

Pro Asp Trp Cys Ile Asp Pro Asp Trp Trp Cys Lys Phe Trp
1               5                   10

<210> SEQ ID NO 246
<211> LENGTH: 14
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 246

Gln Gly His Cys Thr Arg Trp Pro Trp Met Cys Pro Pro Tyr
1               5                   10

<210> SEQ ID NO 247
<211> LENGTH: 14
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 247

Trp Gln Glu Cys Tyr Arg Glu Gly Phe Trp Cys Leu Gln Thr
1               5                   10

<210> SEQ ID NO 248
<211> LENGTH: 14
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 248

Trp Phe Asp Cys Tyr Gly Pro Gly Phe Lys Cys Trp Ser Pro
1               5                   10

<210> SEQ ID NO 249
<211> LENGTH: 14
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 249

Gly Val Arg Cys Pro Lys Gly His Leu Trp Cys Leu Tyr Pro
1               5                   10

<210> SEQ ID NO 250
<211> LENGTH: 14

```
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 250

His Trp Ala Cys Gly Tyr Trp Pro Trp Ser Cys Lys Trp Val
1               5                   10

<210> SEQ ID NO 251
<211> LENGTH: 14
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 251

Gly Pro Ala Cys His Ser Pro Trp Trp Cys Val Phe Gly
1               5                   10

<210> SEQ ID NO 252
<211> LENGTH: 14
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 252

Thr Thr Trp Cys Ile Ser Pro Met Trp Phe Cys Ser Gln Gln
1               5                   10

<210> SEQ ID NO 253
<211> LENGTH: 14
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 253

His Lys Phe Cys Pro Pro Trp Ala Ile Phe Cys Trp Asp Phe
1               5                   10

<210> SEQ ID NO 254
<211> LENGTH: 14
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 254

Pro Asp Trp Cys Val Ser Pro Arg Trp Tyr Cys Asn Met Trp
1               5                   10

<210> SEQ ID NO 255
<211> LENGTH: 14
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 255

Val Trp Lys Cys His Trp Phe Gly Met Asp Cys Glu Pro Thr
```

<210> SEQ ID NO 256
<211> LENGTH: 14
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 256

Lys Lys His Cys Gln Ile Trp Thr Trp Met Cys Ala Pro Lys
1               5                   10

<210> SEQ ID NO 257
<211> LENGTH: 14
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 257

Trp Phe Gln Cys Gly Ser Thr Leu Phe Trp Cys Tyr Asn Leu
1               5                   10

<210> SEQ ID NO 258
<211> LENGTH: 14
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 258

Trp Ser Pro Cys Tyr Asp His Tyr Phe Tyr Cys Tyr Thr Ile
1               5                   10

<210> SEQ ID NO 259
<211> LENGTH: 14
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 259

Ser Trp Met Cys Gly Phe Phe Lys Glu Val Cys Met Trp Val
1               5                   10

<210> SEQ ID NO 260
<211> LENGTH: 14
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 260

Glu Met Leu Cys Met Ile His Pro Val Phe Cys Asn Pro His
1               5                   10

<210> SEQ ID NO 261
<211> LENGTH: 14
<212> TYPE: PRT
<213> ORGANISM: Artificial Sequence
<220> FEATURE:
<223> OTHER INFORMATION: Myostatin binding peptide or polypeptide sequence

<400> SEQUENCE: 261

Leu Lys Thr Cys Asn Leu Trp Pro Trp Met Cys Pro Pro Leu
1               5                   10

<210> SEQ ID NO 262
<211> LENGTH: 14
<212> TYPE: PRT
<213> ORGANISM: Artificial Sequence
<220> FEATURE:
<223> OTHER INFORMATION: Myostatin binding peptide or polypeptide
       sequence

<400> SEQUENCE: 262

Val Val Gly Cys Lys Trp Tyr Glu Ala Trp Cys Tyr Asn Lys
1               5                   10

<210> SEQ ID NO 263
<211> LENGTH: 14
<212> TYPE: PRT
<213> ORGANISM: Artificial Sequence
<220> FEATURE:
<223> OTHER INFORMATION: Myostatin binding peptide or polypeptide
       sequence

<400> SEQUENCE: 263

Pro Ile His Cys Thr Gln Trp Ala Trp Met Cys Pro Pro Thr
1               5                   10

<210> SEQ ID NO 264
<211> LENGTH: 14
<212> TYPE: PRT
<213> ORGANISM: Artificial Sequence
<220> FEATURE:
<223> OTHER INFORMATION: Myostatin binding peptide or polypeptide
       sequence

<400> SEQUENCE: 264

Asp Ser Asn Cys Pro Trp Tyr Phe Leu Ser Cys Val Ile Phe
1               5                   10

<210> SEQ ID NO 265
<211> LENGTH: 14
<212> TYPE: PRT
<213> ORGANISM: Artificial Sequence
<220> FEATURE:
<223> OTHER INFORMATION: Myostatin binding peptide or polypeptide
       sequence

<400> SEQUENCE: 265

His Ile Trp Cys Asn Leu Ala Met Met Lys Cys Val Glu Met
1               5                   10

<210> SEQ ID NO 266
<211> LENGTH: 14
<212> TYPE: PRT
<213> ORGANISM: Artificial Sequence
<220> FEATURE:
<223> OTHER INFORMATION: Myostatin binding peptide or polypeptide
       sequence

<400> SEQUENCE: 266

Asn Leu Gln Cys Ile Tyr Phe Leu Gly Lys Cys Ile Tyr Phe
1               5                   10

<210> SEQ ID NO 267

```
<211> LENGTH: 14
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 267

Ala Trp Arg Cys Met Trp Phe Ser Asp Val Cys Thr Pro Gly
1               5                   10

<210> SEQ ID NO 268
<211> LENGTH: 14
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 268

Trp Phe Arg Cys Phe Leu Asp Ala Asp Trp Cys Thr Ser Val
1               5                   10

<210> SEQ ID NO 269
<211> LENGTH: 14
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 269

Glu Lys Ile Cys Gln Met Trp Ser Trp Met Cys Ala Pro Pro
1               5                   10

<210> SEQ ID NO 270
<211> LENGTH: 14
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 270

Trp Phe Tyr Cys His Leu Asn Lys Ser Glu Cys Thr Glu Pro
1               5                   10

<210> SEQ ID NO 271
<211> LENGTH: 14
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 271

Phe Trp Arg Cys Ala Ile Gly Ile Asp Lys Cys Lys Arg Val
1               5                   10

<210> SEQ ID NO 272
<211> LENGTH: 14
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 272
```

```
Asn Leu Gly Cys Lys Trp Tyr Glu Val Trp Cys Phe Thr Tyr
1               5                   10
```

<210> SEQ ID NO 273
<211> LENGTH: 14
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 273

```
Ile Asp Leu Cys Asn Met Trp Asp Gly Met Cys Tyr Pro Pro
1               5                   10
```

<210> SEQ ID NO 274
<211> LENGTH: 14
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 274

```
Glu Met Pro Cys Asn Ile Trp Gly Trp Met Cys Pro Pro Val
1               5                   10
```

<210> SEQ ID NO 275
<211> LENGTH: 18
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 275

```
Trp Phe Arg Cys Val Leu Thr Gly Ile Val Asp Trp Ser Glu Cys Phe
1               5                   10                  15

Gly Leu
```

<210> SEQ ID NO 276
<211> LENGTH: 18
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 276

```
Gly Phe Ser Cys Thr Phe Gly Leu Asp Glu Phe Tyr Val Asp Cys Ser
1               5                   10                  15

Pro Phe
```

<210> SEQ ID NO 277
<211> LENGTH: 18
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 277

```
Leu Pro Trp Cys His Asp Gln Val Asn Ala Asp Trp Gly Phe Cys Met
1               5                   10                  15

Leu Trp
```

<210> SEQ ID NO 278
<211> LENGTH: 18
<212> TYPE: PRT
<213> ORGANISM: Artificial Sequence
<220> FEATURE:
<223> OTHER INFORMATION: Myostatin binding peptide or polypeptide sequence

<400> SEQUENCE: 278

Tyr Pro Thr Cys Ser Glu Lys Phe Trp Ile Tyr Gly Gln Thr Cys Val
1               5                   10                  15

Leu Trp

<210> SEQ ID NO 279
<211> LENGTH: 18
<212> TYPE: PRT
<213> ORGANISM: Artificial Sequence
<220> FEATURE:
<223> OTHER INFORMATION: Myostatin binding peptide or polypeptide sequence

<400> SEQUENCE: 279

Leu Gly Pro Cys Pro Ile His His Gly Pro Trp Pro Gln Tyr Cys Val
1               5                   10                  15

Tyr Trp

<210> SEQ ID NO 280
<211> LENGTH: 18
<212> TYPE: PRT
<213> ORGANISM: Artificial Sequence
<220> FEATURE:
<223> OTHER INFORMATION: Myostatin binding peptide or polypeptide sequence

<400> SEQUENCE: 280

Pro Phe Pro Cys Glu Thr His Gln Ile Ser Trp Leu Gly His Cys Leu
1               5                   10                  15

Ser Phe

<210> SEQ ID NO 281
<211> LENGTH: 18
<212> TYPE: PRT
<213> ORGANISM: Artificial Sequence
<220> FEATURE:
<223> OTHER INFORMATION: Myostatin binding peptide or polypeptide sequence

<400> SEQUENCE: 281

His Trp Gly Cys Glu Asp Leu Met Trp Ser Trp His Pro Leu Cys Arg
1               5                   10                  15

Arg Pro

<210> SEQ ID NO 282
<211> LENGTH: 18
<212> TYPE: PRT
<213> ORGANISM: Artificial Sequence
<220> FEATURE:
<223> OTHER INFORMATION: Myostatin binding peptide or polypeptide sequence

<400> SEQUENCE: 282

Leu Pro Leu Cys Asp Ala Asp Met Met Pro Thr Ile Gly Phe Cys Val
1               5                   10                  15

Ala Tyr

<210> SEQ ID NO 283
<211> LENGTH: 18
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 283

Ser His Trp Cys Glu Thr Thr Phe Trp Met Asn Tyr Ala Lys Cys Val
1               5                   10                  15

His Ala

<210> SEQ ID NO 284
<211> LENGTH: 18
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 284

Leu Pro Lys Cys Thr His Val Pro Phe Asp Gln Gly Gly Phe Cys Leu
1               5                   10                  15

Trp Tyr

<210> SEQ ID NO 285
<211> LENGTH: 18
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 285

Phe Ser Ser Cys Trp Ser Pro Val Ser Arg Gln Asp Met Phe Cys Val
1               5                   10                  15

Phe Tyr

<210> SEQ ID NO 286
<211> LENGTH: 17
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 286

Ser His Lys Cys Glu Tyr Ser Gly Trp Leu Gln Pro Leu Cys Tyr Arg
1               5                   10                  15

Pro

<210> SEQ ID NO 287
<211> LENGTH: 18
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 287

Pro Trp Trp Cys Gln Asp Asn Tyr Val Gln His Met Leu His Cys Asp
1               5                   10                  15

Ser Pro

<210> SEQ ID NO 288
<211> LENGTH: 18
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 288

Trp Phe Arg Cys Met Leu Met Asn Ser Phe Asp Ala Phe Gln Cys Val
1               5                   10                  15

Ser Tyr

<210> SEQ ID NO 289
<211> LENGTH: 18
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 289

Pro Asp Ala Cys Arg Asp Gln Pro Trp Tyr Met Phe Met Gly Cys Met
1               5                   10                  15

Leu Gly

<210> SEQ ID NO 290
<211> LENGTH: 14
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 290

Phe Leu Ala Cys Phe Val Glu Phe Glu Leu Cys Phe Asp Ser
1               5                   10

<210> SEQ ID NO 291
<211> LENGTH: 18
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 291

Ser Ala Tyr Cys Ile Ile Thr Glu Ser Asp Pro Tyr Val Leu Cys Val
1               5                   10                  15

Pro Leu

<210> SEQ ID NO 292
<211> LENGTH: 18
<212> TYPE: PRT
<213> ORGANISM: Artificial Sequence
<220> FEATURE:

<223> OTHER INFORMATION: Myostatin binding peptide or polypeptide
      sequence

<400> SEQUENCE: 292

Pro Ser Ile Cys Glu Ser Tyr Ser Thr Met Trp Leu Pro Met Cys Gln
1               5                   10                  15

His Asn

<210> SEQ ID NO 293
<211> LENGTH: 18
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 293

Trp Leu Asp Cys His Asp Asp Ser Trp Ala Trp Thr Lys Met Cys Arg
1               5                   10                  15

Ser His

<210> SEQ ID NO 294
<211> LENGTH: 18
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 294

Tyr Leu Asn Cys Val Met Met Asn Thr Ser Pro Phe Val Glu Cys Val
1               5                   10                  15

Phe Asn

<210> SEQ ID NO 295
<211> LENGTH: 18
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 295

Tyr Pro Trp Cys Asp Gly Phe Met Ile Gln Gln Gly Ile Thr Cys Met
1               5                   10                  15

Phe Tyr

<210> SEQ ID NO 296
<211> LENGTH: 18
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 296

Phe Asp Tyr Cys Thr Trp Leu Asn Gly Phe Lys Asp Trp Lys Cys Trp
1               5                   10                  15

Ser Arg

<210> SEQ ID NO 297
<211> LENGTH: 18
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 297

Leu Pro Leu Cys Asn Leu Lys Glu Ile Ser His Val Gln Ala Cys Val

```
1               5                   10                  15

Leu Phe

<210> SEQ ID NO 298
<211> LENGTH: 18
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 298

Ser Pro Glu Cys Ala Phe Ala Arg Trp Leu Gly Ile Glu Gln Cys Gln
1               5                   10                  15

Arg Asp

<210> SEQ ID NO 299
<211> LENGTH: 18
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 299

Tyr Pro Gln Cys Phe Asn Leu His Leu Leu Glu Trp Thr Glu Cys Asp
1               5                   10                  15

Trp Phe

<210> SEQ ID NO 300
<211> LENGTH: 18
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 300

Arg Trp Arg Cys Glu Ile Tyr Asp Ser Glu Phe Leu Pro Lys Cys Trp
1               5                   10                  15

Phe Phe

<210> SEQ ID NO 301
<211> LENGTH: 14
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 301

Leu Val Gly Cys Asp Asn Val Trp His Arg Cys Lys Leu Phe
1               5                   10

<210> SEQ ID NO 302
<211> LENGTH: 18
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 302

Ala Gly Trp Cys His Val Trp Gly Glu Met Phe Gly Met Gly Cys Ser
1               5                   10                  15
```

Ala Leu

<210> SEQ ID NO 303
<211> LENGTH: 18
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 303

His His Glu Cys Glu Trp Met Ala Arg Trp Met Ser Leu Asp Cys Val
1               5                   10                  15

Gly Leu

<210> SEQ ID NO 304
<211> LENGTH: 18
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 304

Phe Pro Met Cys Gly Ile Ala Gly Met Lys Asp Phe Asp Phe Cys Val
1               5                   10                  15

Trp Tyr

<210> SEQ ID NO 305
<211> LENGTH: 18
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 305

Arg Asp Asp Cys Thr Phe Trp Pro Glu Trp Leu Trp Lys Leu Cys Glu
1               5                   10                  15

Arg Pro

<210> SEQ ID NO 306
<211> LENGTH: 18
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 306

Tyr Asn Phe Cys Ser Tyr Leu Phe Gly Val Ser Lys Glu Ala Cys Gln
1               5                   10                  15

Leu Pro

<210> SEQ ID NO 307
<211> LENGTH: 18
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 307

Ala His Trp Cys Glu Gln Gly Pro Trp Arg Tyr Gly Asn Ile Cys Met

```
1               5                   10                  15

Ala Tyr

<210> SEQ ID NO 308
<211> LENGTH: 18
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 308

Asn Leu Val Cys Gly Lys Ile Ser Ala Trp Gly Asp Glu Ala Cys Ala
1               5                   10                  15

Arg Ala

<210> SEQ ID NO 309
<211> LENGTH: 18
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 309

His Asn Val Cys Thr Ile Met Gly Pro Ser Met Lys Trp Phe Cys Trp
1               5                   10                  15

Asn Asp

<210> SEQ ID NO 310
<211> LENGTH: 18
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 310

Asn Asp Leu Cys Ala Met Trp Gly Trp Arg Asn Thr Ile Trp Cys Gln
1               5                   10                  15

Asn Ser

<210> SEQ ID NO 311
<211> LENGTH: 18
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 311

Pro Pro Phe Cys Gln Asn Asp Asn Asp Met Leu Gln Ser Leu Cys Lys
1               5                   10                  15

Leu Leu

<210> SEQ ID NO 312
<211> LENGTH: 18
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 312
```

```
Trp Tyr Asp Cys Asn Val Pro Asn Glu Leu Leu Ser Gly Leu Cys Arg
1               5                   10                  15

Leu Phe

<210> SEQ ID NO 313
<211> LENGTH: 18
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 313

Tyr Gly Asp Cys Asp Gln Asn His Trp Met Trp Pro Phe Thr Cys Leu
1               5                   10                  15

Ser Leu

<210> SEQ ID NO 314
<211> LENGTH: 18
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 314

Gly Trp Met Cys His Phe Asp Leu His Asp Trp Gly Ala Thr Cys Gln
1               5                   10                  15

Pro Asp

<210> SEQ ID NO 315
<211> LENGTH: 18
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 315

Tyr Phe His Cys Met Phe Gly Gly His Glu Phe Glu Val His Cys Glu
1               5                   10                  15

Ser Phe

<210> SEQ ID NO 316
<211> LENGTH: 12
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 316

Ala Tyr Trp Cys Trp His Gly Gln Cys Val Arg Phe
1               5                   10

<210> SEQ ID NO 317
<211> LENGTH: 19
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 317

Ser Glu His Trp Thr Phe Thr Asp Trp Asp Gly Asn Glu Trp Trp Val
```

-continued

```
<210> SEQ ID NO 318
<211> LENGTH: 20
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 318

Met Glu Met Leu Asp Ser Leu Phe Glu Leu Leu Lys Asp Met Val Pro
1               5                   10                  15

Ile Ser Lys Ala
            20

<210> SEQ ID NO 319
<211> LENGTH: 19
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 319

Ser Pro Pro Glu Glu Ala Leu Met Glu Trp Leu Gly Trp Gln Tyr Gly
1               5                   10                  15

Lys Phe Thr

<210> SEQ ID NO 320
<211> LENGTH: 20
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 320

Ser Pro Glu Asn Leu Leu Asn Asp Leu Tyr Ile Leu Met Thr Lys Gln
1               5                   10                  15

Glu Trp Tyr Gly
            20

<210> SEQ ID NO 321
<211> LENGTH: 20
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 321

Phe His Trp Glu Glu Gly Ile Pro Phe His Val Val Thr Pro Tyr Ser
1               5                   10                  15

Tyr Asp Arg Met
            20

<210> SEQ ID NO 322
<211> LENGTH: 19
<212> TYPE: PRT
<213> ORGANISM: Artificial Sequence
<220> FEATURE:
<223> OTHER INFORMATION: Myostatin binding peptide or polypeptide
      sequence
```

Arg Pro Phe

<400> SEQUENCE: 322

Lys Arg Leu Leu Glu Gln Phe Met Asn Asp Leu Ala Glu Leu Val Ser
1               5                   10                  15

Gly His Ser

<210> SEQ ID NO 323
<211> LENGTH: 20
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 323

Asp Thr Arg Asp Ala Leu Phe Gln Glu Phe Tyr Glu Phe Val Arg Ser
1               5                   10                  15

Arg Leu Val Ile
            20

<210> SEQ ID NO 324
<211> LENGTH: 20
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 324

Arg Met Ser Ala Ala Pro Arg Pro Leu Thr Tyr Arg Asp Ile Met Asp
1               5                   10                  15

Gln Tyr Trp His
            20

<210> SEQ ID NO 325
<211> LENGTH: 20
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 325

Asn Asp Lys Ala His Phe Phe Glu Met Phe Met Phe Asp Val His Asn
1               5                   10                  15

Phe Val Glu Ser
            20

<210> SEQ ID NO 326
<211> LENGTH: 20
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 326

Gln Thr Gln Ala Gln Lys Ile Asp Gly Leu Trp Glu Leu Leu Gln Ser
1               5                   10                  15

Ile Arg Asn Gln
            20

<210> SEQ ID NO 327
<211> LENGTH: 18

```
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 327

Met Leu Ser Glu Phe Glu Glu Phe Leu Gly Asn Leu Val His Arg Gln
1               5                   10                  15

Glu Ala

<210> SEQ ID NO 328
<211> LENGTH: 20
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 328

Tyr Thr Pro Lys Met Gly Ser Glu Trp Thr Ser Phe Trp His Asn Arg
1               5                   10                  15

Ile His Tyr Leu
            20

<210> SEQ ID NO 329
<211> LENGTH: 20
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 329

Leu Asn Asp Thr Leu Leu Arg Glu Leu Lys Met Val Leu Asn Ser Leu
1               5                   10                  15

Ser Asp Met Lys
            20

<210> SEQ ID NO 330
<211> LENGTH: 20
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 330

Phe Asp Val Glu Arg Asp Leu Met Arg Trp Leu Glu Gly Phe Met Gln
1               5                   10                  15

Ser Ala Ala Thr
            20

<210> SEQ ID NO 331
<211> LENGTH: 20
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 331

His His Gly Trp Asn Tyr Leu Arg Lys Gly Ser Ala Pro Gln Trp Phe
1               5                   10                  15

Glu Ala Trp Val
```

```
            20

<210> SEQ ID NO 332
<211> LENGTH: 20
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 332

Val Glu Ser Leu His Gln Leu Gln Met Trp Leu Asp Gln Lys Leu Ala
1               5                   10                  15

Ser Gly Pro His
            20

<210> SEQ ID NO 333
<211> LENGTH: 18
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 333

Arg Ala Thr Leu Leu Lys Asp Phe Trp Gln Leu Val Glu Gly Tyr Gly
1               5                   10                  15

Asp Asn

<210> SEQ ID NO 334
<211> LENGTH: 16
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 334

Glu Glu Leu Leu Arg Glu Phe Tyr Arg Phe Val Ser Ala Phe Asp Tyr
1               5                   10                  15

<210> SEQ ID NO 335
<211> LENGTH: 20
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 335

Gly Leu Leu Asp Glu Phe Ser His Phe Ile Ala Glu Gln Phe Tyr Gln
1               5                   10                  15

Met Pro Gly Gly
            20

<210> SEQ ID NO 336
<211> LENGTH: 20
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 336

Tyr Arg Glu Met Ser Met Leu Glu Gly Leu Leu Asp Val Leu Glu Arg
1               5                   10                  15
```

```
Leu Gln His Tyr
            20

<210> SEQ ID NO 337
<211> LENGTH: 20
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 337

His Asn Ser Ser Gln Met Leu Leu Ser Glu Leu Ile Met Leu Val Gly
1               5                   10                  15

Ser Met Met Gln
            20

<210> SEQ ID NO 338
<211> LENGTH: 20
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 338

Trp Arg Glu His Phe Leu Asn Ser Asp Tyr Ile Arg Asp Lys Leu Ile
1               5                   10                  15

Ala Ile Asp Gly
            20

<210> SEQ ID NO 339
<211> LENGTH: 19
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 339

Gln Phe Pro Phe Tyr Val Phe Asp Asp Leu Pro Ala Gln Leu Glu Tyr
1               5                   10                  15

Trp Ile Ala

<210> SEQ ID NO 340
<211> LENGTH: 20
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 340

Glu Phe Phe His Trp Leu His Asn His Arg Ser Glu Val Asn His Trp
1               5                   10                  15

Leu Asp Met Asn
            20

<210> SEQ ID NO 341
<211> LENGTH: 19
<212> TYPE: PRT
<213> ORGANISM: Artificial Sequence
<220> FEATURE:
<223> OTHER INFORMATION: Myostatin binding peptide or polypeptide
      sequence
```

-continued

<400> SEQUENCE: 341

Glu Ala Leu Phe Gln Asn Phe Phe Arg Asp Val Leu Thr Leu Ser Glu
1               5                   10                  15

Arg Glu Tyr

<210> SEQ ID NO 342
<211> LENGTH: 20
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 342

Gln Tyr Trp Glu Gln Gln Trp Met Thr Tyr Phe Arg Glu Asn Gly Leu
1               5                   10                  15

His Val Gln Tyr
            20

<210> SEQ ID NO 343
<211> LENGTH: 20
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 343

Asn Gln Arg Met Met Leu Glu Asp Leu Trp Arg Ile Met Thr Pro Met
1               5                   10                  15

Phe Gly Arg Ser
            20

<210> SEQ ID NO 344
<211> LENGTH: 20
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 344

Phe Leu Asp Glu Leu Lys Ala Glu Leu Ser Arg His Tyr Ala Leu Asp
1               5                   10                  15

Asp Leu Asp Glu
            20

<210> SEQ ID NO 345
<211> LENGTH: 20
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 345

Gly Lys Leu Ile Glu Gly Leu Leu Asn Glu Leu Met Gln Leu Glu Thr
1               5                   10                  15

Phe Met Pro Asp
            20

<210> SEQ ID NO 346
<211> LENGTH: 15

```
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 346

Ile Leu Leu Leu Asp Glu Tyr Lys Lys Asp Trp Lys Ser Trp Phe
1               5                   10                  15

<210> SEQ ID NO 347
<211> LENGTH: 50
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 347

Gln Gly His Cys Thr Arg Trp Pro Trp Met Cys Pro Pro Tyr Gly Ser
1               5                   10                  15

Gly Ser Ala Thr Gly Gly Ser Gly Ser Thr Ala Ser Ser Gly Ser Gly
            20                  25                  30

Ser Ala Thr Gly Gln Gly His Cys Thr Arg Trp Pro Trp Met Cys Pro
        35                  40                  45

Pro Tyr
    50

<210> SEQ ID NO 348
<211> LENGTH: 43
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 348

Trp Tyr Pro Cys Tyr Glu Gly His Phe Trp Cys Tyr Asp Leu Gly Ser
1               5                   10                  15

Gly Ser Thr Ala Ser Ser Gly Ser Gly Ser Ala Thr Gly Trp Tyr Pro
            20                  25                  30

Cys Tyr Glu Gly His Phe Trp Cys Tyr Asp Leu
        35                  40

<210> SEQ ID NO 349
<211> LENGTH: 50
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 349

His Thr Pro Cys Pro Trp Phe Ala Pro Leu Cys Val Glu Trp Gly Ser
1               5                   10                  15

Gly Ser Ala Thr Gly Gly Ser Gly Ser Thr Ala Ser Ser Gly Ser Gly
            20                  25                  30

Ser Ala Thr Gly His Thr Pro Cys Pro Trp Phe Ala Pro Leu Cys Val
        35                  40                  45

Glu Trp
    50

<210> SEQ ID NO 350
```

```
<211> LENGTH: 50
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 350

Pro Asp Trp Cys Ile Asp Pro Asp Trp Trp Cys Lys Phe Trp Gly Ser
1               5                   10                  15

Gly Ser Ala Thr Gly Gly Ser Gly Ser Thr Ala Ser Ser Gly Ser Gly
            20                  25                  30

Ser Ala Thr Gly Pro Asp Trp Cys Ile Asp Pro Asp Trp Trp Cys Lys
        35                  40                  45

Phe Trp
    50

<210> SEQ ID NO 351
<211> LENGTH: 50
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 351

Ala Asn Trp Cys Val Ser Pro Asn Trp Phe Cys Met Val Met Gly Ser
1               5                   10                  15

Gly Ser Ala Thr Gly Gly Ser Gly Ser Thr Ala Ser Ser Gly Ser Gly
            20                  25                  30

Ser Ala Thr Gly Ala Asn Trp Cys Val Ser Pro Asn Trp Phe Cys Met
        35                  40                  45

Val Met
    50

<210> SEQ ID NO 352
<211> LENGTH: 50
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 352

Pro Asp Trp Cys Ile Asp Pro Asp Trp Trp Cys Lys Phe Trp Gly Ser
1               5                   10                  15

Gly Ser Ala Thr Gly Gly Ser Gly Ser Thr Ala Ser Ser Gly Ser Gly
            20                  25                  30

Ser Ala Thr Gly Pro Asp Trp Cys Ile Asp Pro Asp Trp Trp Cys Lys
        35                  40                  45

Phe Trp
    50

<210> SEQ ID NO 353
<211> LENGTH: 50
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 353

His Trp Ala Cys Gly Tyr Trp Pro Trp Ser Cys Lys Trp Val Gly Ser
```

```
1               5                   10                  15
Gly Ser Ala Thr Gly Gly Ser Gly Ser Thr Ala Ser Ser Gly Ser Gly
                20                  25                  30
Ser Ala Thr Gly His Trp Ala Cys Gly Tyr Trp Pro Trp Ser Cys Lys
        35                  40                  45
Trp Val
    50

<210> SEQ ID NO 354
<211> LENGTH: 50
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 354

Lys Lys His Cys Gln Ile Trp Thr Trp Met Cys Ala Pro Lys Gly Ser
1               5                   10                  15
Gly Ser Ala Thr Gly Gly Ser Gly Ser Thr Ala Ser Ser Gly Ser Gly
                20                  25                  30
Ser Ala Thr Gly Gln Gly His Cys Thr Arg Trp Pro Trp Met Cys Pro
        35                  40                  45
Pro Tyr
    50

<210> SEQ ID NO 355
<211> LENGTH: 50
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 355

Gln Gly His Cys Thr Arg Trp Pro Trp Met Cys Pro Pro Tyr Gly Ser
1               5                   10                  15
Gly Ser Ala Thr Gly Gly Ser Gly Ser Thr Ala Ser Ser Gly Ser Gly
                20                  25                  30
Ser Ala Thr Gly Lys Lys His Cys Gln Ile Trp Thr Trp Met Cys Ala
        35                  40                  45
Pro Lys
    50

<210> SEQ ID NO 356
<211> LENGTH: 50
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 356

Lys Lys His Cys Gln Ile Trp Thr Trp Met Cys Ala Pro Lys Gly Ser
1               5                   10                  15
Gly Ser Ala Thr Gly Gly Ser Gly Ser Thr Ala Ser Ser Gly Ser Gly
                20                  25                  30
Ser Ala Thr Gly Gln Gly His Cys Thr Arg Trp Pro Trp Met Cys Pro
        35                  40                  45
Pro Tyr
    50
```

<210> SEQ ID NO 357
<211> LENGTH: 36
<212> TYPE: PRT
<213> ORGANISM: Artificial Sequence
<220> FEATURE:
<223> OTHER INFORMATION: Myostatin binding peptide or polypeptide sequence

<400> SEQUENCE: 357

Lys Lys His Cys Gln Ile Trp Thr Trp Met Cys Ala Pro Lys Gly Gly
 1               5                  10                  15

Gly Gly Gly Gly Gly Gly Gln Gly His Cys Thr Arg Trp Pro Trp Met
            20                  25                  30

Cys Pro Pro Tyr
        35

<210> SEQ ID NO 358
<211> LENGTH: 34
<212> TYPE: PRT
<213> ORGANISM: Artificial Sequence
<220> FEATURE:
<223> OTHER INFORMATION: Myostatin binding peptide or polypeptide sequence

<400> SEQUENCE: 358

Gln Gly His Cys Thr Arg Trp Pro Trp Met Cys Pro Pro Tyr Gly Gly
 1               5                  10                  15

Gly Gly Gly Gly Lys Lys His Cys Gln Ile Trp Thr Trp Met Cys Ala
            20                  25                  30

Pro Lys

<210> SEQ ID NO 359
<211> LENGTH: 20
<212> TYPE: PRT
<213> ORGANISM: Artificial Sequence
<220> FEATURE:
<223> OTHER INFORMATION: Myostatin binding peptide or polypeptide sequence

<400> SEQUENCE: 359

Val Ala Leu His Gly Gln Cys Thr Arg Trp Pro Trp Met Cys Pro Pro
 1               5                  10                  15

Gln Arg Glu Gly
            20

<210> SEQ ID NO 360
<211> LENGTH: 20
<212> TYPE: PRT
<213> ORGANISM: Artificial Sequence
<220> FEATURE:
<223> OTHER INFORMATION: Myostatin binding peptide or polypeptide sequence

<400> SEQUENCE: 360

Tyr Pro Glu Gln Gly Leu Cys Thr Arg Trp Pro Trp Met Cys Pro Pro
 1               5                  10                  15

Gln Thr Leu Ala
            20

<210> SEQ ID NO 361
<211> LENGTH: 20
<212> TYPE: PRT
<213> ORGANISM: Artificial Sequence

```
<220> FEATURE:
<223> OTHER INFORMATION: Myostatin binding peptide or polypeptide
      sequence

<400> SEQUENCE: 361

Gly Leu Asn Gln Gly His Cys Thr Arg Trp Pro Trp Met Cys Pro Pro
1               5                   10                  15

Gln Asp Ser Asn
            20

<210> SEQ ID NO 362
<211> LENGTH: 20
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 362

Met Ile Thr Gln Gly Gln Cys Thr Arg Trp Pro Trp Met Cys Pro Pro
1               5                   10                  15

Gln Pro Ser Gly
            20

<210> SEQ ID NO 363
<211> LENGTH: 20
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 363

Ala Gly Ala Gln Glu His Cys Thr Arg Trp Pro Trp Met Cys Ala Pro
1               5                   10                  15

Asn Asp Trp Ile
            20

<210> SEQ ID NO 364
<211> LENGTH: 20
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 364

Gly Val Asn Gln Gly Gln Cys Thr Arg Trp Arg Trp Met Cys Pro Pro
1               5                   10                  15

Asn Gly Trp Glu
            20

<210> SEQ ID NO 365
<211> LENGTH: 20
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 365

Leu Ala Asp His Gly Gln Cys Ile Arg Trp Pro Trp Met Cys Pro Pro
1               5                   10                  15

Glu Gly Trp Glu
            20
```

<210> SEQ ID NO 366
<211> LENGTH: 20
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 366

Ile Leu Glu Gln Ala Gln Cys Thr Arg Trp Pro Trp Met Cys Pro Pro
1               5                   10                  15

Gln Arg Gly Gly
            20

<210> SEQ ID NO 367
<211> LENGTH: 20
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 367

Thr Gln Thr His Ala Gln Cys Thr Arg Trp Pro Trp Met Cys Pro Pro
1               5                   10                  15

Gln Trp Glu Gly
            20

<210> SEQ ID NO 368
<211> LENGTH: 20
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 368

Val Val Thr Gln Gly His Cys Thr Leu Trp Pro Trp Met Cys Pro Pro
1               5                   10                  15

Gln Arg Trp Arg
            20

<210> SEQ ID NO 369
<211> LENGTH: 20
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 369

Ile Tyr Pro His Asp Gln Cys Thr Arg Trp Pro Trp Met Cys Pro Pro
1               5                   10                  15

Gln Pro Tyr Pro
            20

<210> SEQ ID NO 370
<211> LENGTH: 20
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 370

Ser Tyr Trp Gln Gly Gln Cys Thr Arg Trp Pro Trp Met Cys Pro Pro
1               5                   10                  15

Gln Trp Arg Gly
            20

<210> SEQ ID NO 371
<211> LENGTH: 20
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 371

Met Trp Gln Gln Gly His Cys Thr Arg Trp Pro Trp Met Cys Pro Pro
1               5                   10                  15

Gln Gly Trp Gly
            20

<210> SEQ ID NO 372
<211> LENGTH: 20
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 372

Glu Phe Thr Gln Trp His Cys Thr Arg Trp Pro Trp Met Cys Pro Pro
1               5                   10                  15

Gln Arg Ser Gln
            20

<210> SEQ ID NO 373
<211> LENGTH: 20
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 373

Leu Asp Asp Gln Trp Gln Cys Thr Arg Trp Pro Trp Met Cys Pro Pro
1               5                   10                  15

Gln Gly Phe Ser
            20

<210> SEQ ID NO 374
<211> LENGTH: 20
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 374

Tyr Gln Thr Gln Gly Leu Cys Thr Arg Trp Pro Trp Met Cys Pro Pro
1               5                   10                  15

Gln Ser Gln Arg
            20

<210> SEQ ID NO 375
<211> LENGTH: 20
<212> TYPE: PRT

<213> ORGANISM: Artificial Sequence
<220> FEATURE:
<223> OTHER INFORMATION: Myostatin binding peptide or polypeptide
      sequence

<400> SEQUENCE: 375

Glu Ser Asn Gln Gly Gln Cys Thr Arg Trp Pro Trp Met Cys Pro Pro
1               5                   10                  15

Gln Gly Gly Trp
            20

<210> SEQ ID NO 376
<211> LENGTH: 20
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 376

Trp Thr Asp Arg Gly Pro Cys Thr Arg Trp Pro Trp Met Cys Pro Pro
1               5                   10                  15

Gln Ala Asn Gly
            20

<210> SEQ ID NO 377
<211> LENGTH: 20
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 377

Val Gly Thr Gln Gly Gln Cys Thr Arg Trp Pro Trp Met Cys Pro Pro
1               5                   10                  15

Tyr Glu Thr Gly
            20

<210> SEQ ID NO 378
<211> LENGTH: 20
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 378

Pro Tyr Glu Gln Gly Lys Cys Thr Arg Trp Pro Trp Met Cys Pro Pro
1               5                   10                  15

Tyr Glu Val Glu
            20

<210> SEQ ID NO 379
<211> LENGTH: 20
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 379

Ser Glu Tyr Gln Gly Leu Cys Thr Arg Trp Pro Trp Met Cys Pro Pro
1               5                   10                  15

Gln Gly Trp Lys

20

<210> SEQ ID NO 380
<211> LENGTH: 20
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 380

Thr Phe Ser Gln Gly His Cys Thr Arg Trp Pro Trp Met Cys Pro Pro
1               5                   10                  15

Gln Gly Trp Gly
            20

<210> SEQ ID NO 381
<211> LENGTH: 20
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 381

Pro Gly Ala His Asp His Cys Thr Arg Trp Pro Trp Met Cys Pro Pro
1               5                   10                  15

Gln Ser Arg Tyr
            20

<210> SEQ ID NO 382
<211> LENGTH: 20
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 382

Val Ala Glu Glu Trp His Cys Arg Arg Trp Pro Trp Met Cys Pro Pro
1               5                   10                  15

Gln Asp Trp Arg
            20

<210> SEQ ID NO 383
<211> LENGTH: 20
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 383

Val Gly Thr Gln Gly His Cys Thr Arg Trp Pro Trp Met Cys Pro Pro
1               5                   10                  15

Gln Pro Ala Gly
            20

<210> SEQ ID NO 384
<211> LENGTH: 20
<212> TYPE: PRT
<213> ORGANISM: Artificial Sequence
<220> FEATURE:
<223> OTHER INFORMATION: Myostatin binding peptide or polypeptide
      sequence

```
<400> SEQUENCE: 384

Glu Glu Asp Gln Ala His Cys Arg Ser Trp Pro Trp Met Cys Pro Pro
1               5                   10                  15

Gln Gly Trp Val
            20

<210> SEQ ID NO 385
<211> LENGTH: 20
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 385

Ala Asp Thr Gln Gly His Cys Thr Arg Trp Pro Trp Met Cys Pro Pro
1               5                   10                  15

Gln His Trp Phe
            20

<210> SEQ ID NO 386
<211> LENGTH: 20
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 386

Ser Gly Pro Gln Gly His Cys Thr Arg Trp Pro Trp Met Cys Ala Pro
1               5                   10                  15

Gln Gly Trp Phe
            20

<210> SEQ ID NO 387
<211> LENGTH: 20
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 387

Thr Leu Val Gln Gly His Cys Thr Arg Trp Pro Trp Met Cys Pro Pro
1               5                   10                  15

Gln Arg Trp Val
            20

<210> SEQ ID NO 388
<211> LENGTH: 20
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 388

Gly Met Ala His Gly Lys Cys Thr Arg Trp Ala Trp Met Cys Pro Pro
1               5                   10                  15

Gln Ser Trp Lys
            20

<210> SEQ ID NO 389
<211> LENGTH: 20
```

```
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 389

Glu Leu Tyr His Gly Gln Cys Thr Arg Trp Pro Trp Met Cys Pro Pro
1               5                   10                  15

Gln Ser Trp Ala
            20

<210> SEQ ID NO 390
<211> LENGTH: 20
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 390

Val Ala Asp His Gly His Cys Thr Arg Trp Pro Trp Met Cys Pro Pro
1               5                   10                  15

Gln Gly Trp Gly
            20

<210> SEQ ID NO 391
<211> LENGTH: 20
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 391

Pro Glu Ser Gln Gly His Cys Thr Arg Trp Pro Trp Met Cys Pro Pro
1               5                   10                  15

Gln Gly Trp Gly
            20

<210> SEQ ID NO 392
<211> LENGTH: 20
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 392

Ile Pro Ala His Gly His Cys Thr Arg Trp Pro Trp Met Cys Pro Pro
1               5                   10                  15

Gln Arg Trp Arg
            20

<210> SEQ ID NO 393
<211> LENGTH: 20
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 393

Phe Thr Val His Gly His Cys Thr Arg Trp Pro Trp Met Cys Pro Pro
1               5                   10                  15
```

Tyr Gly Trp Val
        20

<210> SEQ ID NO 394
<211> LENGTH: 20
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 394

Pro Asp Phe Pro Gly His Cys Thr Arg Trp Arg Trp Met Cys Pro Pro
1               5                   10                  15

Gln Gly Trp Glu
        20

<210> SEQ ID NO 395
<211> LENGTH: 20
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 395

Gln Leu Trp Gln Gly Pro Cys Thr Gln Trp Pro Trp Met Cys Pro Pro
1               5                   10                  15

Lys Gly Arg Tyr
        20

<210> SEQ ID NO 396
<211> LENGTH: 20
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 396

His Ala Asn Asp Gly His Cys Thr Arg Trp Gln Trp Met Cys Pro Pro
1               5                   10                  15

Gln Trp Gly Gly
        20

<210> SEQ ID NO 397
<211> LENGTH: 20
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 397

Glu Thr Asp His Gly Leu Cys Thr Arg Trp Pro Trp Met Cys Pro Pro
1               5                   10                  15

Tyr Gly Ala Arg
        20

<210> SEQ ID NO 398
<211> LENGTH: 20
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 398

Gly Thr Trp Gln Gly Leu Cys Thr Arg Trp Pro Trp Met Cys Pro Pro
1               5                   10                  15

Gln Gly Trp Gln
            20

<210> SEQ ID NO 399
<211> LENGTH: 20
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 399

Val Ala Thr Gln Gly Gln Cys Thr Arg Trp Pro Trp Met Cys Pro Pro
1               5                   10                  15

Gln Gly Trp Gly
            20

<210> SEQ ID NO 400
<211> LENGTH: 20
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 400

Val Ala Thr Gln Gly Gln Cys Thr Arg Trp Pro Trp Met Cys Pro Pro
1               5                   10                  15

Gln Arg Trp Gly
            20

<210> SEQ ID NO 401
<211> LENGTH: 20
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 401

Gln Arg Glu Trp Tyr Pro Cys Tyr Gly Gly His Leu Trp Cys Tyr Asp
1               5                   10                  15

Leu His Lys Ala
            20

<210> SEQ ID NO 402
<211> LENGTH: 20
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 402

Ile Ser Ala Trp Tyr Ser Cys Tyr Ala Gly His Phe Trp Cys Trp Asp
1               5                   10                  15

Leu Lys Gln Lys
            20

<210> SEQ ID NO 403

-continued

```
<211> LENGTH: 20
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 403

Trp Thr Gly Trp Tyr Gln Cys Tyr Gly Gly His Leu Trp Cys Tyr Asp
1               5                   10                  15

Leu Arg Arg Lys
            20

<210> SEQ ID NO 404
<211> LENGTH: 20
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 404

Lys Thr Phe Trp Tyr Pro Cys Tyr Asp Gly His Phe Trp Cys Tyr Asn
1               5                   10                  15

Leu Lys Ser Ser
            20

<210> SEQ ID NO 405
<211> LENGTH: 20
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 405

Glu Ser Arg Trp Tyr Pro Cys Tyr Glu Gly His Leu Trp Cys Phe Asp
1               5                   10                  15

Leu Thr Glu Thr
            20

<210> SEQ ID NO 406
<211> LENGTH: 20
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 406

Met Glu Met Leu Asp Ser Leu Phe Glu Leu Leu Lys Asp Met Val Pro
1               5                   10                  15

Ile Ser Lys Ala
            20

<210> SEQ ID NO 407
<211> LENGTH: 22
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 407

Arg Met Glu Met Leu Glu Ser Leu Leu Glu Leu Leu Lys Glu Ile Val
1               5                   10                  15
```

```
Pro Met Ser Lys Ala Gly
            20

<210> SEQ ID NO 408
<211> LENGTH: 22
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 408

Arg Met Glu Met Leu Glu Ser Leu Leu Glu Leu Leu Lys Glu Ile Val
1               5                   10                  15

Pro Met Ser Lys Ala Arg
            20

<210> SEQ ID NO 409
<211> LENGTH: 22
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 409

Arg Met Glu Met Leu Glu Ser Leu Leu Glu Leu Leu Lys Asp Ile Val
1               5                   10                  15

Pro Met Ser Lys Pro Ser
            20

<210> SEQ ID NO 410
<211> LENGTH: 22
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 410

Gly Met Glu Met Leu Glu Ser Leu Phe Glu Leu Leu Gln Glu Ile Val
1               5                   10                  15

Pro Met Ser Lys Ala Pro
            20

<210> SEQ ID NO 411
<211> LENGTH: 22
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 411

Arg Met Glu Met Leu Glu Ser Leu Leu Glu Leu Leu Lys Asp Ile Val
1               5                   10                  15

Pro Ile Ser Asn Pro Pro
            20

<210> SEQ ID NO 412
<211> LENGTH: 22
<212> TYPE: PRT
<213> ORGANISM: Artificial Sequence
<220> FEATURE:
<223> OTHER INFORMATION: Myostatin binding peptide or polypeptide
``` sequence

<400> SEQUENCE: 412

Arg Ile Glu Met Leu Glu Ser Leu Leu Glu Leu Leu Gln Glu Ile Val
1               5                   10                  15

Pro Ile Ser Lys Ala Glu
            20

<210> SEQ ID NO 413
<211> LENGTH: 22
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 413

Arg Met Glu Met Leu Gln Ser Leu Leu Glu Leu Leu Lys Asp Ile Val
1               5                   10                  15

Pro Met Ser Asn Ala Arg
            20

<210> SEQ ID NO 414
<211> LENGTH: 22
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 414

Arg Met Glu Met Leu Glu Ser Leu Leu Glu Leu Leu Lys Glu Ile Val
1               5                   10                  15

Pro Thr Ser Asn Gly Thr
            20

<210> SEQ ID NO 415
<211> LENGTH: 22
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 415

Arg Met Glu Met Leu Glu Ser Leu Phe Glu Leu Leu Lys Glu Ile Val
1               5                   10                  15

Pro Met Ser Lys Ala Gly
            20

<210> SEQ ID NO 416
<211> LENGTH: 22
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 416

Arg Met Glu Met Leu Gly Ser Leu Leu Glu Leu Leu Lys Glu Ile Val
1               5                   10                  15

Pro Met Ser Lys Ala Arg
            20

```
<210> SEQ ID NO 417
<211> LENGTH: 22
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 417

Gln Met Glu Leu Leu Asp Ser Leu Phe Glu Leu Leu Lys Glu Ile Val
1               5                   10                  15

Pro Lys Ser Gln Pro Ala
            20

<210> SEQ ID NO 418
<211> LENGTH: 22
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 418

Arg Met Glu Met Leu Asp Ser Leu Leu Glu Leu Leu Lys Glu Ile Val
1               5                   10                  15

Pro Met Ser Asn Ala Arg
            20

<210> SEQ ID NO 419
<211> LENGTH: 22
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 419

Arg Met Glu Met Leu Glu Ser Leu Leu Glu Leu Leu His Glu Ile Val
1               5                   10                  15

Pro Met Ser Gln Ala Gly
            20

<210> SEQ ID NO 420
<211> LENGTH: 22
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 420

Gln Met Glu Met Leu Glu Ser Leu Leu Gln Leu Leu Lys Glu Ile Val
1               5                   10                  15

Pro Met Ser Lys Ala Ser
            20

<210> SEQ ID NO 421
<211> LENGTH: 22
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 421

Arg Met Glu Met Leu Asp Ser Leu Leu Glu Leu Leu Lys Asp Met Val
```

```
1               5                   10                  15

Pro Met Thr Thr Gly Ala
            20

<210> SEQ ID NO 422
<211> LENGTH: 22
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 422

Arg Ile Glu Met Leu Glu Ser Leu Leu Glu Leu Leu Lys Asp Met Val
1               5                   10                  15

Pro Met Ala Asn Ala Ser
            20

<210> SEQ ID NO 423
<211> LENGTH: 22
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 423

Arg Met Glu Met Leu Glu Ser Leu Leu Gln Leu Leu Asn Glu Ile Val
1               5                   10                  15

Pro Met Ser Arg Ala Arg
            20

<210> SEQ ID NO 424
<211> LENGTH: 22
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 424

Arg Met Glu Met Leu Glu Ser Leu Phe Asp Leu Leu Lys Glu Leu Val
1               5                   10                  15

Pro Met Ser Lys Gly Val
            20

<210> SEQ ID NO 425
<211> LENGTH: 22
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 425

Arg Ile Glu Met Leu Glu Ser Leu Leu Glu Leu Leu Lys Asp Ile Val
1               5                   10                  15

Pro Ile Gln Lys Ala Arg
            20

<210> SEQ ID NO 426
<211> LENGTH: 22
<212> TYPE: PRT
<213> ORGANISM: Artificial Sequence
<220> FEATURE:
```

```
<223> OTHER INFORMATION: Myostatin binding peptide or polypeptide
      sequence

<400> SEQUENCE: 426

Arg Met Glu Leu Leu Glu Ser Leu Phe Glu Leu Leu Lys Asp Met Val
 1               5                  10                  15

Pro Met Ser Asp Ser Ser
             20

<210> SEQ ID NO 427
<211> LENGTH: 22
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 427

Arg Met Glu Met Leu Glu Ser Leu Leu Glu Val Leu Gln Glu Ile Val
 1               5                  10                  15

Pro Arg Ala Lys Gly Ala
             20

<210> SEQ ID NO 428
<211> LENGTH: 22
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 428

Arg Met Glu Met Leu Asp Ser Leu Leu Gln Leu Leu Asn Glu Ile Val
 1               5                  10                  15

Pro Met Ser His Ala Arg
             20

<210> SEQ ID NO 429
<211> LENGTH: 22
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 429

Arg Met Glu Met Leu Glu Ser Leu Leu Glu Leu Leu Lys Asp Ile Val
 1               5                  10                  15

Pro Met Ser Asn Ala Gly
             20

<210> SEQ ID NO 430
<211> LENGTH: 22
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 430

Arg Met Glu Met Leu Gln Ser Leu Phe Glu Leu Leu Lys Gly Met Val
 1               5                  10                  15

Pro Ile Ser Lys Ala Gly
             20
```

<210> SEQ ID NO 431
<211> LENGTH: 22
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 431

Arg Met Glu Met Leu Glu Ser Leu Leu Glu Leu Leu Lys Glu Ile Val
1               5                   10                  15

Pro Asn Ser Thr Ala Ala
            20

<210> SEQ ID NO 432
<211> LENGTH: 22
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 432

Arg Met Glu Met Leu Gln Ser Leu Leu Glu Leu Leu Lys Glu Ile Val
1               5                   10                  15

Pro Ile Ser Lys Ala Gly
            20

<210> SEQ ID NO 433
<211> LENGTH: 22
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 433

Arg Ile Glu Met Leu Asp Ser Leu Leu Glu Leu Leu Asn Glu Leu Val
1               5                   10                  15

Pro Met Ser Lys Ala Arg
            20

<210> SEQ ID NO 434
<211> LENGTH: 20
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 434

His His Gly Trp Asn Tyr Leu Arg Lys Gly Ser Ala Pro Gln Trp Phe
1               5                   10                  15

Glu Ala Trp Val
            20

<210> SEQ ID NO 435
<211> LENGTH: 22
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 435

```
Gln Val Glu Ser Leu Gln Gln Leu Leu Met Trp Leu Asp Gln Lys Leu
1               5                   10                  15

Ala Ser Gly Pro Gln Gly
            20

<210> SEQ ID NO 436
<211> LENGTH: 22
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 436

Arg Met Glu Leu Leu Glu Ser Leu Phe Glu Leu Leu Lys Glu Met Val
1               5                   10                  15

Pro Arg Ser Lys Ala Val
            20

<210> SEQ ID NO 437
<211> LENGTH: 22
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 437

Gln Ala Val Ser Leu Gln His Leu Leu Met Trp Leu Asp Gln Lys Leu
1               5                   10                  15

Ala Ser Gly Pro Gln His
            20

<210> SEQ ID NO 438
<211> LENGTH: 22
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 438

Asp Glu Asp Ser Leu Gln Gln Leu Leu Met Trp Leu Asp Gln Lys Leu
1               5                   10                  15

Ala Ser Gly Pro Gln Leu
            20

<210> SEQ ID NO 439
<211> LENGTH: 22
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 439

Pro Val Ala Ser Leu Gln Gln Leu Leu Ile Trp Leu Asp Gln Lys Leu
1               5                   10                  15

Ala Gln Gly Pro His Ala
            20

<210> SEQ ID NO 440
<211> LENGTH: 22
<212> TYPE: PRT
<213> ORGANISM: Artificial Sequence
```

```
<220> FEATURE:
<223> OTHER INFORMATION: Myostatin binding peptide or polypeptide
      sequence

<400> SEQUENCE: 440

Glu Val Asp Glu Leu Gln Gln Leu Leu Asn Trp Leu Asp His Lys Leu
1               5                   10                  15

Ala Ser Gly Pro Leu Gln
            20

<210> SEQ ID NO 441
<211> LENGTH: 22
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 441

Asp Val Glu Ser Leu Glu Gln Leu Leu Met Trp Leu Asp His Gln Leu
1               5                   10                  15

Ala Ser Gly Pro His Gly
            20

<210> SEQ ID NO 442
<211> LENGTH: 22
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 442

Gln Val Asp Ser Leu Gln Gln Val Leu Leu Trp Leu Glu His Lys Leu
1               5                   10                  15

Ala Leu Gly Pro Gln Val
            20

<210> SEQ ID NO 443
<211> LENGTH: 22
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 443

Gly Asp Glu Ser Leu Gln His Leu Leu Met Trp Leu Glu Gln Lys Leu
1               5                   10                  15

Ala Leu Gly Pro His Gly
            20

<210> SEQ ID NO 444
<211> LENGTH: 22
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 444

Gln Ile Glu Met Leu Glu Ser Leu Leu Asp Leu Leu Arg Asp Met Val
1               5                   10                  15

Pro Met Ser Asn Ala Phe
            20
```

<210> SEQ ID NO 445
<211> LENGTH: 22
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 445

Glu Val Asp Ser Leu Gln Gln Leu Leu Met Trp Leu Asp Gln Lys Leu
1               5                   10                  15

Ala Ser Gly Pro Gln Ala
            20

<210> SEQ ID NO 446
<211> LENGTH: 22
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 446

Glu Asp Glu Ser Leu Gln Gln Leu Leu Ile Tyr Leu Asp Lys Met Leu
1               5                   10                  15

Ser Ser Gly Pro Gln Val
            20

<210> SEQ ID NO 447
<211> LENGTH: 22
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 447

Ala Met Asp Gln Leu His Gln Leu Leu Ile Trp Leu Asp His Lys Leu
1               5                   10                  15

Ala Ser Gly Pro Gln Ala
            20

<210> SEQ ID NO 448
<211> LENGTH: 22
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 448

Arg Ile Glu Met Leu Glu Ser Leu Leu Glu Leu Leu Asp Glu Ile Ala
1               5                   10                  15

Leu Ile Pro Lys Ala Trp
            20

<210> SEQ ID NO 449
<211> LENGTH: 22
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 449

```
Glu Val Val Ser Leu Gln His Leu Leu Met Trp Leu Glu His Lys Leu
1               5                   10                  15

Ala Ser Gly Pro Asp Gly
            20
```

<210> SEQ ID NO 450
<211> LENGTH: 22
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 450

```
Gly Gly Glu Ser Leu Gln Gln Leu Leu Met Trp Leu Asp Gln Gln Leu
1               5                   10                  15

Ala Ser Gly Pro Gln Arg
            20
```

<210> SEQ ID NO 451
<211> LENGTH: 22
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 451

```
Gly Val Glu Ser Leu Gln Gln Leu Leu Ile Phe Leu Asp His Met Leu
1               5                   10                  15

Val Ser Gly Pro His Asp
            20
```

<210> SEQ ID NO 452
<211> LENGTH: 22
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 452

```
Asn Val Glu Ser Leu Glu His Leu Met Met Trp Leu Glu Arg Leu Leu
1               5                   10                  15

Ala Ser Gly Pro Tyr Ala
            20
```

<210> SEQ ID NO 453
<211> LENGTH: 22
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 453

```
Gln Val Asp Ser Leu Gln Gln Leu Leu Ile Trp Leu Asp His Gln Leu
1               5                   10                  15

Ala Ser Gly Pro Lys Arg
            20
```

<210> SEQ ID NO 454
<211> LENGTH: 22
<212> TYPE: PRT

<213> ORGANISM: Artificial Sequence
<220> FEATURE:
<223> OTHER INFORMATION: Myostatin binding peptide or polypeptide
      sequence

<400> SEQUENCE: 454

Glu Val Glu Ser Leu Gln Gln Leu Leu Met Trp Leu Glu His Lys Leu
1               5                   10                  15

Ala Gln Gly Pro Gln Gly
            20

<210> SEQ ID NO 455
<211> LENGTH: 22
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 455

Glu Val Asp Ser Leu Gln Gln Leu Leu Met Trp Leu Asp Gln Lys Leu
1               5                   10                  15

Ala Ser Gly Pro His Ala
            20

<210> SEQ ID NO 456
<211> LENGTH: 22
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 456

Glu Val Asp Ser Leu Gln Gln Leu Leu Met Trp Leu Asp Gln Gln Leu
1               5                   10                  15

Ala Ser Gly Pro Gln Lys
            20

<210> SEQ ID NO 457
<211> LENGTH: 22
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 457

Gly Val Glu Gln Leu Pro Gln Leu Leu Met Trp Leu Glu Gln Lys Leu
1               5                   10                  15

Ala Ser Gly Pro Gln Arg
            20

<210> SEQ ID NO 458
<211> LENGTH: 22
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 458

Gly Glu Asp Ser Leu Gln Gln Leu Leu Met Trp Leu Asp Gln Gln Leu
1               5                   10                  15

Ala Ala Gly Pro Gln Val

<210> SEQ ID NO 459
<211> LENGTH: 22
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 459

Ala Asp Asp Ser Leu Gln Gln Leu Leu Met Trp Leu Asp Arg Lys Leu
1               5                   10                  15

Ala Ser Gly Pro His Val
            20

<210> SEQ ID NO 460
<211> LENGTH: 22
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 460

Pro Val Asp Ser Leu Gln Gln Leu Leu Ile Trp Leu Asp Gln Lys Leu
1               5                   10                  15

Ala Ser Gly Pro Gln Gly
            20

<210> SEQ ID NO 461
<211> LENGTH: 18
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 461

Arg Ala Thr Leu Leu Lys Asp Phe Trp Gln Leu Val Glu Gly Tyr Gly
1               5                   10                  15

Asp Asn

<210> SEQ ID NO 462
<211> LENGTH: 22
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 462

Asp Trp Arg Ala Thr Leu Leu Lys Glu Phe Trp Gln Leu Val Glu Gly
1               5                   10                  15

Leu Gly Asp Asn Leu Val
            20

<210> SEQ ID NO 463
<211> LENGTH: 22
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 463

```
Gln Ser Arg Ala Thr Leu Leu Lys Glu Phe Trp Gln Leu Val Glu Gly
1               5                   10                  15

Leu Gly Asp Lys Gln Ala
            20
```

<210> SEQ ID NO 464
<211> LENGTH: 22
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 464

```
Asp Gly Arg Ala Thr Leu Leu Thr Glu Phe Trp Gln Leu Val Gln Gly
1               5                   10                  15

Leu Gly Gln Lys Glu Ala
            20
```

<210> SEQ ID NO 465
<211> LENGTH: 22
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 465

```
Leu Ala Arg Ala Thr Leu Leu Lys Glu Phe Trp Gln Leu Val Glu Gly
1               5                   10                  15

Leu Gly Glu Lys Val Val
            20
```

<210> SEQ ID NO 466
<211> LENGTH: 22
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 466

```
Gly Ser Arg Asp Thr Leu Leu Lys Glu Phe Trp Gln Leu Val Val Gly
1               5                   10                  15

Leu Gly Asp Met Gln Thr
            20
```

<210> SEQ ID NO 467
<211> LENGTH: 22
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 467

```
Asp Ala Arg Ala Thr Leu Leu Lys Glu Phe Trp Gln Leu Val Asp Ala
1               5                   10                  15

Tyr Gly Asp Arg Met Val
            20
```

<210> SEQ ID NO 468
<211> LENGTH: 22
<212> TYPE: PRT

<213> ORGANISM: Artificial Sequence
<220> FEATURE:
<223> OTHER INFORMATION: Myostatin binding peptide or polypeptide
      sequence

<400> SEQUENCE: 468

Asn Asp Arg Ala Gln Leu Leu Arg Asp Phe Trp Gln Leu Val Asp Gly
1               5                   10                  15

Leu Gly Val Lys Ser Trp
            20

<210> SEQ ID NO 469
<211> LENGTH: 22
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 469

Gly Val Arg Glu Thr Leu Leu Tyr Glu Leu Trp Tyr Leu Leu Lys Gly
1               5                   10                  15

Leu Gly Ala Asn Gln Gly
            20

<210> SEQ ID NO 470
<211> LENGTH: 22
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 470

Gln Ala Arg Ala Thr Leu Leu Lys Glu Phe Cys Gln Leu Val Gly Cys
1               5                   10                  15

Gln Gly Asp Lys Leu Ser
            20

<210> SEQ ID NO 471
<211> LENGTH: 22
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 471

Gln Glu Arg Ala Thr Leu Leu Lys Glu Phe Trp Gln Leu Val Ala Gly
1               5                   10                  15

Leu Gly Gln Asn Met Arg
            20

<210> SEQ ID NO 472
<211> LENGTH: 22
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 472

Ser Gly Arg Ala Thr Leu Leu Lys Glu Phe Trp Gln Leu Val Gln Gly
1               5                   10                  15

Leu Gly Glu Tyr Arg Trp

20

<210> SEQ ID NO 473
<211> LENGTH: 22
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 473

Thr Met Arg Ala Thr Leu Leu Lys Glu Phe Trp Leu Phe Val Asp Gly
1               5                   10                  15

Gln Arg Glu Met Gln Trp
            20

<210> SEQ ID NO 474
<211> LENGTH: 22
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 474

Gly Glu Arg Ala Thr Leu Leu Asn Asp Phe Trp Gln Leu Val Asp Gly
1               5                   10                  15

Gln Gly Asp Asn Thr Gly
            20

<210> SEQ ID NO 475
<211> LENGTH: 22
<212> TYPE: PRT
<213> ORGANISM: Artificial Sequence
<220> FEATURE:
<223> OTHER INFORMATION: Myostatin binding peptide or polypeptide sequence

<400> SEQUENCE: 475

Asp Glu Arg Glu Thr Leu Leu Lys Glu Phe Trp Gln Leu Val His Gly
1 5 10 15

Trp Gly Asp Asn Val Ala
20

<210> SEQ ID NO 476
<211> LENGTH: 22
<212> TYPE: PRT
<213> ORGANISM: Artificial Sequence
<220> FEATURE:
<223> OTHER INFORMATION: Myostatin binding peptide or polypeptide sequence

<400> SEQUENCE: 476

Gly Gly Arg Ala Thr Leu Leu Lys Glu Leu Trp Gln Leu Leu Glu Gly
1 5 10 15

Gln Gly Ala Asn Leu Val
20

<210> SEQ ID NO 477
<211> LENGTH: 22
<212> TYPE: PRT
<213> ORGANISM: Artificial Sequence
<220> FEATURE:
<223> OTHER INFORMATION: Myostatin binding peptide or polypeptide sequence

```
<400> SEQUENCE: 477

Thr Ala Arg Ala Thr Leu Leu Asn Glu Leu Val Gln Leu Val Lys Gly
1               5                   10                  15

Tyr Gly Asp Lys Leu Val
            20

<210> SEQ ID NO 478
<211> LENGTH: 22
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 478

Gly Met Arg Ala Thr Leu Leu Gln Glu Phe Trp Gln Leu Val Gly Gly
1               5                   10                  15

Gln Gly Asp Asn Trp Met
            20

<210> SEQ ID NO 479
<211> LENGTH: 22
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 479

Ser Thr Arg Ala Thr Leu Leu Asn Asp Leu Trp Gln Leu Met Lys Gly
1               5                   10                  15

Trp Ala Glu Asp Arg Gly
            20

<210> SEQ ID NO 480
<211> LENGTH: 22
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 480

Ser Glu Arg Ala Thr Leu Leu Lys Glu Leu Trp Gln Leu Val Gly Gly
1               5                   10                  15

Trp Gly Asp Asn Phe Gly
            20

<210> SEQ ID NO 481
<211> LENGTH: 22
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 481

Val Gly Arg Ala Thr Leu Leu Lys Glu Phe Trp Gln Leu Val Glu Gly
1               5                   10                  15

Leu Val Gly Gln Ser Arg
            20

<210> SEQ ID NO 482
<211> LENGTH: 22
```

```
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 482

Glu Ile Arg Ala Thr Leu Leu Lys Glu Phe Trp Gln Leu Val Asp Glu
1               5                   10                  15

Trp Arg Glu Gln Pro Asn
            20

<210> SEQ ID NO 483
<211> LENGTH: 22
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 483

Gln Leu Arg Ala Thr Leu Leu Lys Glu Phe Leu Gln Leu Val His Gly
1               5                   10                  15

Leu Gly Glu Thr Asp Ser
            20

<210> SEQ ID NO 484
<211> LENGTH: 22
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 484

Thr Gln Arg Ala Thr Leu Leu Lys Glu Phe Trp Gln Leu Ile Glu Gly
1               5                   10                  15

Leu Gly Gly Lys His Val
            20

<210> SEQ ID NO 485
<211> LENGTH: 22
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 485

His Tyr Arg Ala Thr Leu Leu Lys Glu Phe Trp Gln Leu Val Asp Gly
1               5                   10                  15

Leu Arg Glu Gln Gly Val
            20

<210> SEQ ID NO 486
<211> LENGTH: 22
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 486

Gln Ser Arg Val Thr Leu Leu Arg Glu Phe Trp Gln Leu Val Glu Ser
1               5                   10                  15
```

Tyr Arg Pro Ile Val Asn
            20

<210> SEQ ID NO 487
<211> LENGTH: 22
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 487

Leu Ser Arg Ala Thr Leu Leu Asn Glu Phe Trp Gln Phe Val Asp Gly
1               5                   10                  15

Gln Arg Asp Lys Arg Met
            20

<210> SEQ ID NO 488
<211> LENGTH: 22
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 488

Trp Asp Arg Ala Thr Leu Leu Asn Asp Phe Trp His Leu Met Glu Glu
1               5                   10                  15

Leu Ser Gln Lys Pro Gly
            20

<210> SEQ ID NO 489
<211> LENGTH: 22
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 489

Gln Glu Arg Ala Thr Leu Leu Lys Glu Phe Trp Arg Met Val Glu Gly
1               5                   10                  15

Leu Gly Lys Asn Arg Gly
            20

<210> SEQ ID NO 490
<211> LENGTH: 22
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 490

Asn Glu Arg Ala Thr Leu Leu Arg Glu Phe Trp Gln Leu Val Gly Gly
1               5                   10                  15

Tyr Gly Val Asn Gln Arg
            20

<210> SEQ ID NO 491
<211> LENGTH: 20
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 491

Tyr Arg Glu Met Ser Met Leu Glu Gly Leu Leu Asp Val Leu Glu Arg
1               5                   10                  15

Leu Gln His Tyr
            20

<210> SEQ ID NO 492
<211> LENGTH: 22
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 492

His Gln Arg Asp Met Ser Met Leu Trp Glu Leu Leu Asp Val Leu Asp
1               5                   10                  15

Gly Leu Arg Gln Tyr Ser
            20

<210> SEQ ID NO 493
<211> LENGTH: 22
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 493

Thr Gln Arg Asp Met Ser Met Leu Asp Gly Leu Leu Glu Val Leu Asp
1               5                   10                  15

Gln Leu Arg Gln Gln Arg
            20

<210> SEQ ID NO 494
<211> LENGTH: 22
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 494

Thr Ser Arg Asp Met Ser Leu Leu Trp Glu Leu Leu Glu Glu Leu Asp
1               5                   10                  15

Arg Leu Gly His Gln Arg
            20

<210> SEQ ID NO 495
<211> LENGTH: 22
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 495

Met Gln His Asp Met Ser Met Leu Tyr Gly Leu Val Glu Leu Leu Glu
1               5                   10                  15

Ser Leu Gly His Gln Ile
            20

<210> SEQ ID NO 496

```
<211> LENGTH: 22
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 496

Trp Asn Arg Asp Met Arg Met Leu Glu Ser Leu Phe Glu Val Leu Asp
1               5                   10                  15

Gly Leu Arg Gln Gln Val
            20

<210> SEQ ID NO 497
<211> LENGTH: 22
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 497

Gly Tyr Arg Asp Met Ser Met Leu Glu Gly Leu Leu Ala Val Leu Asp
1               5                   10                  15

Arg Leu Gly Pro Gln Leu
            20

<210> SEQ ID NO 498
<211> LENGTH: 22
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 498

Thr Gln Arg Asp Met Ser Met Leu Glu Gly Leu Leu Glu Val Leu Asp
1               5                   10                  15

Arg Leu Gly Gln Gln Arg
            20

<210> SEQ ID NO 499
<211> LENGTH: 22
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 499

Trp Tyr Arg Asp Met Ser Met Leu Glu Gly Leu Leu Glu Val Leu Asp
1               5                   10                  15

Arg Leu Gly Gln Gln Arg
            20

<210> SEQ ID NO 500
<211> LENGTH: 20
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 500

His Asn Ser Ser Gln Met Leu Leu Ser Glu Leu Ile Met Leu Val Gly
1               5                   10                  15
```

Ser Met Met Gln
            20

<210> SEQ ID NO 501
<211> LENGTH: 22
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 501

Thr Gln Asn Ser Arg Gln Met Leu Leu Ser Asp Phe Met Met Leu Val
1               5                   10                  15

Gly Ser Met Ile Gln Gly
            20

<210> SEQ ID NO 502
<211> LENGTH: 22
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 502

Met Gln Thr Ser Arg His Ile Leu Leu Ser Glu Phe Met Met Leu Val
1               5                   10                  15

Gly Ser Ile Met His Gly
            20

<210> SEQ ID NO 503
<211> LENGTH: 22
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 503

His Asp Asn Ser Arg Gln Met Leu Leu Ser Asp Leu Leu His Leu Val
1               5                   10                  15

Gly Thr Met Ile Gln Gly
            20

<210> SEQ ID NO 504
<211> LENGTH: 22
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 504

Met Glu Asn Ser Arg Gln Asn Leu Leu Arg Glu Leu Ile Met Leu Val
1               5                   10                  15

Gly Asn Met Ser His Gln
            20

<210> SEQ ID NO 505
<211> LENGTH: 22
<212> TYPE: PRT
<213> ORGANISM: Artificial Sequence
<220> FEATURE:
<223> OTHER INFORMATION: Myostatin binding peptide or polypeptide sequence

<400> SEQUENCE: 505

Gln Asp Thr Ser Arg His Met Leu Leu Arg Glu Phe Met Met Leu Val
1               5                   10                  15

Gly Glu Met Ile Gln Gly
            20

<210> SEQ ID NO 506
<211> LENGTH: 22
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 506

Asp Gln Asn Ser Arg Gln Met Leu Leu Ser Asp Leu Met Ile Leu Val
1               5                   10                  15

Gly Ser Met Ile Gln Gly
            20

<210> SEQ ID NO 507
<211> LENGTH: 20
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 507

Glu Phe Phe His Trp Leu His Asn His Arg Ser Glu Val Asn His Trp
1               5                   10                  15

Leu Asp Met Asn
            20

<210> SEQ ID NO 508
<211> LENGTH: 22
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 508

Asn Val Phe Phe Gln Trp Val Gln Lys His Gly Arg Val Val Tyr Gln
1               5                   10                  15

Trp Leu Asp Ile Asn Val
            20

<210> SEQ ID NO 509
<211> LENGTH: 22
<212> TYPE: PRT
<213> ORGANISM: Artificial Sequence
<220> FEATURE:
<223> OTHER INFORMATION: Myostatin binding peptide or polypeptide
      sequence

<400> SEQUENCE: 509

Phe Asp Phe Leu Gln Trp Leu Gln Asn His Arg Ser Glu Val Glu His
1               5                   10                  15

Trp Leu Val Met Asp Val
            20

```
<210> SEQ ID NO 510
<211> LENGTH: 14
<212> TYPE: PRT
<213> ORGANISM: Artificial Sequence
<220> FEATURE:
<223> OTHER INFORMATION: BAFF binding peptide sequence

<400> SEQUENCE: 510

Pro Gly Thr Cys Phe Pro Phe Pro Trp Glu Cys Thr His Ala
1               5                   10

<210> SEQ ID NO 511
<211> LENGTH: 14
<212> TYPE: PRT
<213> ORGANISM: Artificial Sequence
<220> FEATURE:
<223> OTHER INFORMATION: BAFF binding peptide sequence

<400> SEQUENCE: 511

Trp Gly Ala Cys Trp Pro Phe Pro Trp Glu Cys Phe Lys Glu
1               5                   10

<210> SEQ ID NO 512
<211> LENGTH: 14
<212> TYPE: PRT
<213> ORGANISM: Artificial Sequence
<220> FEATURE:
<223> OTHER INFORMATION: BAFF binding peptide sequence

<400> SEQUENCE: 512

Val Pro Phe Cys Asp Leu Leu Thr Lys His Cys Phe Glu Ala
1               5                   10

<210> SEQ ID NO 513
<211> LENGTH: 18
<212> TYPE: PRT
<213> ORGANISM: Artificial Sequence
<220> FEATURE:
<223> OTHER INFORMATION: BAFF binding peptide sequence

<400> SEQUENCE: 513

Gly Ser Arg Cys Lys Tyr Lys Trp Asp Val Leu Thr Lys Gln Cys Phe
1               5                   10                  15

His His

<210> SEQ ID NO 514
<211> LENGTH: 18
<212> TYPE: PRT
<213> ORGANISM: Artificial Sequence
<220> FEATURE:
<223> OTHER INFORMATION: BAFF binding peptide sequence

<400> SEQUENCE: 514

Leu Pro Gly Cys Lys Trp Asp Leu Leu Ile Lys Gln Trp Val Cys Asp
1               5                   10                  15

Pro Leu

<210> SEQ ID NO 515
<211> LENGTH: 18
<212> TYPE: PRT
<213> ORGANISM: Artificial Sequence
<220> FEATURE:
<223> OTHER INFORMATION: BAFF binding peptide sequence

<400> SEQUENCE: 515

Ser Ala Asp Cys Tyr Phe Asp Ile Leu Thr Lys Ser Asp Val Cys Thr
```

```
1               5                  10                 15

Ser Ser

<210> SEQ ID NO 516
<211> LENGTH: 18
<212> TYPE: PRT
<213> ORGANISM: Artificial Sequence
<220> FEATURE:
<223> OTHER INFORMATION: BAFF binding peptide sequence

<400> SEQUENCE: 516

Ser Asp Asp Cys Met Tyr Asp Gln Leu Thr Arg Met Phe Ile Cys Ser
1               5                  10                 15

Asn Leu

<210> SEQ ID NO 517
<211> LENGTH: 18
<212> TYPE: PRT
<213> ORGANISM: Artificial Sequence
<220> FEATURE:
<223> OTHER INFORMATION: BAFF binding peptide sequence

<400> SEQUENCE: 517

Asp Leu Asn Cys Lys Tyr Asp Glu Leu Thr Tyr Lys Glu Trp Cys Gln
1               5                  10                 15

Phe Asn

<210> SEQ ID NO 518
<211> LENGTH: 18
<212> TYPE: PRT
<213> ORGANISM: Artificial Sequence
<220> FEATURE:
<223> OTHER INFORMATION: BAFF binding peptide sequence

<400> SEQUENCE: 518

Phe His Asp Cys Lys Tyr Asp Leu Leu Thr Arg Gln Met Val Cys His
1               5                  10                 15

Gly Leu

<210> SEQ ID NO 519
<211> LENGTH: 18
<212> TYPE: PRT
<213> ORGANISM: Artificial Sequence
<220> FEATURE:
<223> OTHER INFORMATION: BAFF binding peptide sequence

<400> SEQUENCE: 519

Arg Asn His Cys Phe Trp Asp His Leu Leu Lys Gln Asp Ile Cys Pro
1               5                  10                 15

Ser Pro

<210> SEQ ID NO 520
<211> LENGTH: 18
<212> TYPE: PRT
<213> ORGANISM: Artificial Sequence
<220> FEATURE:
<223> OTHER INFORMATION: BAFF binding peptide sequence

<400> SEQUENCE: 520

Ala Asn Gln Cys Trp Trp Asp Ser Leu Thr Lys Lys Asn Val Cys Glu
1               5                  10                 15

Phe Phe
```

<210> SEQ ID NO 521
<211> LENGTH: 19
<212> TYPE: PRT
<213> ORGANISM: Artificial Sequence
<220> FEATURE:
<223> OTHER INFORMATION: BAFF binding peptide sequence

<400> SEQUENCE: 521

Tyr Lys Gly Arg Gln Gln Met Trp Asp Ile Leu Thr Arg Ser Trp Val
1               5                   10                  15

Val Ser Leu

<210> SEQ ID NO 522
<211> LENGTH: 19
<212> TYPE: PRT
<213> ORGANISM: Artificial Sequence
<220> FEATURE:
<223> OTHER INFORMATION: BAFF binding peptide sequence

<400> SEQUENCE: 522

Gln Gln Asp Val Gly Leu Trp Trp Asp Ile Leu Thr Arg Ala Trp Met
1               5                   10                  15

Pro Asn Ile

<210> SEQ ID NO 523
<211> LENGTH: 19
<212> TYPE: PRT
<213> ORGANISM: Artificial Sequence
<220> FEATURE:
<223> OTHER INFORMATION: BAFF binding peptide sequence

<400> SEQUENCE: 523

Gln Gln Asn Ala Gln Arg Val Trp Asp Leu Leu Ile Arg Thr Trp Val
1               5                   10                  15

Tyr Pro Gln

<210> SEQ ID NO 524
<211> LENGTH: 19
<212> TYPE: PRT
<213> ORGANISM: Artificial Sequence
<220> FEATURE:
<223> OTHER INFORMATION: BAFF binding peptide sequence

<400> SEQUENCE: 524

Gly Trp Asn Glu Ala Trp Trp Asp Glu Leu Thr Lys Ile Trp Val Leu
1               5                   10                  15

Glu Gln Gln

<210> SEQ ID NO 525
<211> LENGTH: 19
<212> TYPE: PRT
<213> ORGANISM: Artificial Sequence
<220> FEATURE:
<223> OTHER INFORMATION: BAFF binding peptide sequence

<400> SEQUENCE: 525

Arg Ile Thr Cys Asp Thr Trp Asp Ser Leu Ile Lys Lys Cys Val Pro
1               5                   10                  15

Gln Gln Ser

<210> SEQ ID NO 526
<211> LENGTH: 19
<212> TYPE: PRT

<213> ORGANISM: Artificial Sequence
<220> FEATURE:
<223> OTHER INFORMATION: BAFF binding peptide sequence

<400> SEQUENCE: 526

Gly Ala Ile Met Gln Gln Phe Trp Asp Ser Leu Thr Lys Thr Trp Leu
1               5                   10                  15

Arg Gln Ser

<210> SEQ ID NO 527
<211> LENGTH: 19
<212> TYPE: PRT
<213> ORGANISM: Artificial Sequence
<220> FEATURE:
<223> OTHER INFORMATION: BAFF binding peptide sequence

<400> SEQUENCE: 527

Trp Leu His Ser Gly Trp Trp Asp Pro Leu Thr Lys His Trp Leu Gln
1               5                   10                  15

Gln Lys Val

<210> SEQ ID NO 528
<211> LENGTH: 19
<212> TYPE: PRT
<213> ORGANISM: Artificial Sequence
<220> FEATURE:
<223> OTHER INFORMATION: BAFF binding peptide sequence

<400> SEQUENCE: 528

Ser Glu Trp Phe Phe Trp Phe Asp Pro Leu Thr Arg Ala Gln Gln Leu
1               5                   10                  15

Lys Phe Arg

<210> SEQ ID NO 529
<211> LENGTH: 19
<212> TYPE: PRT
<213> ORGANISM: Artificial Sequence
<220> FEATURE:
<223> OTHER INFORMATION: BAFF binding peptide sequence

<400> SEQUENCE: 529

Gly Val Trp Phe Trp Trp Phe Asp Pro Leu Thr Lys Gln Trp Thr Gln
1               5                   10                  15

Gln Ala Gly

<210> SEQ ID NO 530
<211> LENGTH: 19
<212> TYPE: PRT
<213> ORGANISM: Artificial Sequence
<220> FEATURE:
<223> OTHER INFORMATION: BAFF binding peptide sequence

<400> SEQUENCE: 530

Met Gln Gln Cys Lys Gly Tyr Tyr Asp Ile Leu Thr Lys Trp Cys Val
1               5                   10                  15

Thr Asn Gly

<210> SEQ ID NO 531
<211> LENGTH: 19
<212> TYPE: PRT
<213> ORGANISM: Artificial Sequence
<220> FEATURE:
<223> OTHER INFORMATION: BAFF binding peptide sequence

```
<400> SEQUENCE: 531

Leu Trp Ser Lys Glu Val Trp Asp Ile Leu Thr Lys Ser Trp Val Ser
1               5                   10                  15

Gln Gln Ala

<210> SEQ ID NO 532
<211> LENGTH: 18
<212> TYPE: PRT
<213> ORGANISM: Artificial Sequence
<220> FEATURE:
<223> OTHER INFORMATION: BAFF binding peptide sequence

<400> SEQUENCE: 532

Lys Ala Ala Gly Trp Trp Phe Asp Trp Leu Thr Lys Val Trp Val Pro
1               5                   10                  15

Ala Pro

<210> SEQ ID NO 533
<211> LENGTH: 19
<212> TYPE: PRT
<213> ORGANISM: Artificial Sequence
<220> FEATURE:
<223> OTHER INFORMATION: BAFF binding peptide sequence

<400> SEQUENCE: 533

Ala Tyr Gln Gln Thr Trp Phe Trp Asp Ser Leu Thr Arg Leu Trp Leu
1               5                   10                  15

Ser Thr Thr

<210> SEQ ID NO 534
<211> LENGTH: 19
<212> TYPE: PRT
<213> ORGANISM: Artificial Sequence
<220> FEATURE:
<223> OTHER INFORMATION: BAFF binding peptide sequence

<400> SEQUENCE: 534

Ser Gly Gln Gln His Phe Trp Trp Asp Leu Leu Thr Arg Ser Trp Thr
1               5                   10                  15

Pro Ser Thr

<210> SEQ ID NO 535
<211> LENGTH: 19
<212> TYPE: PRT
<213> ORGANISM: Artificial Sequence
<220> FEATURE:
<223> OTHER INFORMATION: BAFF binding peptide sequence

<400> SEQUENCE: 535

Leu Gly Val Gly Gln Gln Lys Trp Asp Pro Leu Thr Lys Gln Trp Val
1               5                   10                  15

Ser Arg Gly

<210> SEQ ID NO 536
<211> LENGTH: 19
<212> TYPE: PRT
<213> ORGANISM: Artificial Sequence
<220> FEATURE:
<223> OTHER INFORMATION: BAFF binding peptide sequence

<400> SEQUENCE: 536

Val Gly Lys Met Cys Gln Gln Trp Asp Pro Leu Ile Lys Arg Thr Val
1               5                   10                  15
```

Cys Val Gly

<210> SEQ ID NO 537
<211> LENGTH: 18
<212> TYPE: PRT
<213> ORGANISM: Artificial Sequence
<220> FEATURE:
<223> OTHER INFORMATION: BAFF binding peptide sequence

<400> SEQUENCE: 537

Cys Arg Gln Gly Ala Lys Phe Asp Leu Leu Thr Lys Gln Cys Leu Leu
1               5                   10                  15

Gly Arg

<210> SEQ ID NO 538
<211> LENGTH: 19
<212> TYPE: PRT
<213> ORGANISM: Artificial Sequence
<220> FEATURE:
<223> OTHER INFORMATION: BAFF binding peptide sequence

<400> SEQUENCE: 538

Gly Gln Ala Ile Arg His Trp Asp Val Leu Thr Lys Gln Trp Val Asp
1               5                   10                  15

Ser Gln Gln

<210> SEQ ID NO 539
<211> LENGTH: 19
<212> TYPE: PRT
<213> ORGANISM: Artificial Sequence
<220> FEATURE:
<223> OTHER INFORMATION: BAFF binding peptide sequence

<400> SEQUENCE: 539

Arg Gly Pro Cys Gly Ser Trp Asp Leu Leu Thr Lys His Cys Leu Asp
1               5                   10                  15

Ser Gln Gln

<210> SEQ ID NO 540
<211> LENGTH: 19
<212> TYPE: PRT
<213> ORGANISM: Artificial Sequence
<220> FEATURE:
<223> OTHER INFORMATION: BAFF binding peptide sequence

<400> SEQUENCE: 540

Trp Gln Trp Lys Gln Gln Gln Trp Asp Leu Leu Thr Lys Gln Met Val
1               5                   10                  15

Trp Val Gly

<210> SEQ ID NO 541
<211> LENGTH: 18
<212> TYPE: PRT
<213> ORGANISM: Artificial Sequence
<220> FEATURE:
<223> OTHER INFORMATION: BAFF binding peptide sequence

<400> SEQUENCE: 541

Pro Ile Thr Ile Cys Arg Lys Asp Leu Leu Thr Lys Gln Val Val Cys
1               5                   10                  15

Leu Asp

-continued

```
<210> SEQ ID NO 542
<211> LENGTH: 19
<212> TYPE: PRT
<213> ORGANISM: Artificial Sequence
<220> FEATURE:
<223> OTHER INFORMATION: BAFF binding peptide sequence

<400> SEQUENCE: 542

Lys Thr Cys Asn Gly Lys Trp Asp Leu Leu Thr Lys Gln Cys Leu Gln
1               5                   10                  15

Gln Gln Ala

<210> SEQ ID NO 543
<211> LENGTH: 18
<212> TYPE: PRT
<213> ORGANISM: Artificial Sequence
<220> FEATURE:
<223> OTHER INFORMATION: BAFF binding peptide sequence

<400> SEQUENCE: 543

Lys Cys Leu Lys Gly Lys Trp Asp Leu Leu Thr Lys Gln Cys Val Thr
1               5                   10                  15

Glu Val

<210> SEQ ID NO 544
<211> LENGTH: 18
<212> TYPE: PRT
<213> ORGANISM: Artificial Sequence
<220> FEATURE:
<223> OTHER INFORMATION: BAFF binding peptide sequence

<400> SEQUENCE: 544

Arg Cys Trp Asn Gly Lys Trp Asp Leu Leu Thr Lys Gln Cys Ile His
1               5                   10                  15

Pro Trp

<210> SEQ ID NO 545
<211> LENGTH: 18
<212> TYPE: PRT
<213> ORGANISM: Artificial Sequence
<220> FEATURE:
<223> OTHER INFORMATION: BAFF binding peptide sequence

<400> SEQUENCE: 545

Asn Arg Asp Met Arg Lys Trp Asp Pro Leu Ile Lys Gln Trp Ile Val
1               5                   10                  15

Arg Pro

<210> SEQ ID NO 546
<211> LENGTH: 19
<212> TYPE: PRT
<213> ORGANISM: Artificial Sequence
<220> FEATURE:
<223> OTHER INFORMATION: BAFF binding peptide sequence

<400> SEQUENCE: 546

Gln Gln Ala Ala Ala Ala Thr Trp Asp Leu Leu Thr Lys Gln Trp Leu
1               5                   10                  15

Val Pro Pro

<210> SEQ ID NO 547
<211> LENGTH: 19
<212> TYPE: PRT
<213> ORGANISM: Artificial Sequence
```

<220> FEATURE:
<223> OTHER INFORMATION: BAFF binding peptide sequence

<400> SEQUENCE: 547

Pro Glu Gly Gly Pro Lys Trp Asp Pro Leu Thr Lys Gln Gln Phe Leu
1               5                   10                  15

Pro Pro Val

<210> SEQ ID NO 548
<211> LENGTH: 20
<212> TYPE: PRT
<213> ORGANISM: Artificial Sequence
<220> FEATURE:
<223> OTHER INFORMATION: BAFF binding peptide sequence

<400> SEQUENCE: 548

Gln Gln Thr Pro Gln Gln Lys Lys Trp Asp Leu Leu Thr Lys Gln Trp
1               5                   10                  15

Phe Thr Arg Asn
            20

<210> SEQ ID NO 549
<211> LENGTH: 19
<212> TYPE: PRT
<213> ORGANISM: Artificial Sequence
<220> FEATURE:
<223> OTHER INFORMATION: BAFF binding peptide sequence

<400> SEQUENCE: 549

Ile Gly Ser Pro Cys Lys Trp Asp Leu Leu Thr Lys Gln Met Ile Cys
1               5                   10                  15

Gln Gln Thr

<210> SEQ ID NO 550
<211> LENGTH: 19
<212> TYPE: PRT
<213> ORGANISM: Artificial Sequence
<220> FEATURE:
<223> OTHER INFORMATION: BAFF binding peptide sequence

<400> SEQUENCE: 550

Cys Thr Ala Ala Gly Lys Trp Asp Leu Leu Thr Lys Gln Cys Ile Gln
1               5                   10                  15

Gln Glu Lys

<210> SEQ ID NO 551
<211> LENGTH: 19
<212> TYPE: PRT
<213> ORGANISM: Artificial Sequence
<220> FEATURE:
<223> OTHER INFORMATION: BAFF binding peptide sequence

<400> SEQUENCE: 551

Val Ser Gln Cys Met Lys Trp Asp Leu Leu Thr Lys Gln Cys Leu Gln
1               5                   10                  15

Gln Gly Trp

<210> SEQ ID NO 552
<211> LENGTH: 19
<212> TYPE: PRT
<213> ORGANISM: Artificial Sequence
<220> FEATURE:
<223> OTHER INFORMATION: BAFF binding peptide sequence

```
<400> SEQUENCE: 552

Val Trp Gly Thr Trp Lys Trp Asp Leu Leu Thr Lys Gln Tyr Leu Pro
1               5                   10                  15

Pro Gln Gln

<210> SEQ ID NO 553
<211> LENGTH: 19
<212> TYPE: PRT
<213> ORGANISM: Artificial Sequence
<220> FEATURE:
<223> OTHER INFORMATION: BAFF binding peptide sequence

<400> SEQUENCE: 553

Gly Trp Trp Glu Met Lys Trp Asp Leu Leu Thr Lys Gln Trp Tyr Arg
1               5                   10                  15

Pro Gln Gln

<210> SEQ ID NO 554
<211> LENGTH: 19
<212> TYPE: PRT
<213> ORGANISM: Artificial Sequence
<220> FEATURE:
<223> OTHER INFORMATION: BAFF binding peptide sequence

<400> SEQUENCE: 554

Thr Ala Gln Gln Val Ser Lys Trp Asp Leu Thr Lys Gln Trp Leu
1               5                   10                  15

Pro Leu Ala

<210> SEQ ID NO 555
<211> LENGTH: 19
<212> TYPE: PRT
<213> ORGANISM: Artificial Sequence
<220> FEATURE:
<223> OTHER INFORMATION: BAFF binding peptide sequence

<400> SEQUENCE: 555

Gln Leu Trp Gly Thr Lys Trp Asp Leu Leu Thr Lys Gln Tyr Ile Gln
1               5                   10                  15

Gln Ile Met

<210> SEQ ID NO 556
<211> LENGTH: 19
<212> TYPE: PRT
<213> ORGANISM: Artificial Sequence
<220> FEATURE:
<223> OTHER INFORMATION: BAFF binding peptide sequence

<400> SEQUENCE: 556

Trp Ala Thr Ser Gln Lys Trp Asp Leu Leu Thr Lys Gln Trp Val Gln
1               5                   10                  15

Gln Asn Met

<210> SEQ ID NO 557
<211> LENGTH: 19
<212> TYPE: PRT
<213> ORGANISM: Artificial Sequence
<220> FEATURE:
<223> OTHER INFORMATION: BAFF binding peptide sequence

<400> SEQUENCE: 557

Gln Gln Arg Gln Cys Ala Lys Trp Asp Leu Leu Thr Lys Gln Cys Val
1               5                   10                  15
```

Leu Phe Tyr

<210> SEQ ID NO 558
<211> LENGTH: 19
<212> TYPE: PRT
<213> ORGANISM: Artificial Sequence
<220> FEATURE:
<223> OTHER INFORMATION: BAFF binding peptide sequence

<400> SEQUENCE: 558

Lys Thr Thr Asp Cys Lys Trp Asp Leu Leu Thr Lys Gln Arg Ile Cys
1               5                   10                  15

Gln Gln Val

<210> SEQ ID NO 559
<211> LENGTH: 19
<212> TYPE: PRT
<213> ORGANISM: Artificial Sequence
<220> FEATURE:
<223> OTHER INFORMATION: BAFF binding peptide sequence

<400> SEQUENCE: 559

Leu Leu Cys Gln Gln Gly Lys Trp Asp Leu Leu Thr Lys Gln Cys Leu
1               5                   10                  15

Lys Leu Arg

<210> SEQ ID NO 560
<211> LENGTH: 18
<212> TYPE: PRT
<213> ORGANISM: Artificial Sequence
<220> FEATURE:
<223> OTHER INFORMATION: BAFF binding peptide sequence

<400> SEQUENCE: 560

Leu Met Trp Phe Trp Lys Trp Asp Leu Leu Thr Lys Gln Leu Val Pro
1               5                   10                  15

Thr Phe

<210> SEQ ID NO 561
<211> LENGTH: 19
<212> TYPE: PRT
<213> ORGANISM: Artificial Sequence
<220> FEATURE:
<223> OTHER INFORMATION: BAFF binding peptide sequence

<400> SEQUENCE: 561

Gln Gln Thr Trp Ala Trp Lys Trp Asp Leu Leu Thr Lys Gln Trp Ile
1               5                   10                  15

Gly Pro Met

<210> SEQ ID NO 562
<211> LENGTH: 18
<212> TYPE: PRT
<213> ORGANISM: Artificial Sequence
<220> FEATURE:
<223> OTHER INFORMATION: BAFF binding peptide sequence

<400> SEQUENCE: 562

Asn Lys Glu Leu Leu Lys Trp Asp Leu Leu Thr Lys Gln Cys Arg Gly
1               5                   10                  15

Arg Ser

<210> SEQ ID NO 563
<211> LENGTH: 19
<212> TYPE: PRT
<213> ORGANISM: Artificial Sequence
<220> FEATURE:
<223> OTHER INFORMATION: BAFF binding peptide sequence

<400> SEQUENCE: 563

Gly Gln Gln Lys Asp Leu Lys Trp Asp Leu Leu Thr Lys Gln Tyr Val
1               5                   10                  15

Arg Gln Ser

<210> SEQ ID NO 564
<211> LENGTH: 19
<212> TYPE: PRT
<213> ORGANISM: Artificial Sequence
<220> FEATURE:
<223> OTHER INFORMATION: BAFF binding peptide sequence

<400> SEQUENCE: 564

Pro Lys Pro Cys Gln Gln Lys Trp Asp Leu Leu Thr Lys Gln Cys Leu
1               5                   10                  15

Gly Ser Val

<210> SEQ ID NO 565
<211> LENGTH: 19
<212> TYPE: PRT
<213> ORGANISM: Artificial Sequence
<220> FEATURE:
<223> OTHER INFORMATION: BAFF binding peptide sequence

<400> SEQUENCE: 565

Gly Gln Ile Gly Trp Lys Trp Asp Leu Leu Thr Lys Gln Trp Ile Gln
1               5                   10                  15

Gln Thr Arg

<210> SEQ ID NO 566
<211> LENGTH: 19
<212> TYPE: PRT
<213> ORGANISM: Artificial Sequence
<220> FEATURE:
<223> OTHER INFORMATION: BAFF binding peptide sequence

<400> SEQUENCE: 566

Val Trp Leu Asp Trp Lys Trp Asp Leu Leu Thr Lys Gln Trp Ile His
1               5                   10                  15

Pro Gln Gln

<210> SEQ ID NO 567
<211> LENGTH: 19
<212> TYPE: PRT
<213> ORGANISM: Artificial Sequence
<220> FEATURE:
<223> OTHER INFORMATION: BAFF binding peptide sequence

<400> SEQUENCE: 567

Gln Gln Glu Trp Glu Tyr Lys Trp Asp Leu Leu Thr Lys Gln Trp Gly
1               5                   10                  15

Trp Leu Arg

<210> SEQ ID NO 568
<211> LENGTH: 19
<212> TYPE: PRT
<213> ORGANISM: Artificial Sequence

```
<220> FEATURE:
<223> OTHER INFORMATION: BAFF binding peptide sequence

<400> SEQUENCE: 568

His Trp Asp Ser Trp Lys Trp Asp Leu Leu Thr Lys Gln Trp Val Val
1               5                   10                  15

Gln Gln Ala

<210> SEQ ID NO 569
<211> LENGTH: 19
<212> TYPE: PRT
<213> ORGANISM: Artificial Sequence
<220> FEATURE:
<223> OTHER INFORMATION: BAFF binding peptide sequence

<400> SEQUENCE: 569

Thr Arg Pro Leu Gln Gln Lys Trp Asp Leu Leu Thr Lys Gln Trp Leu
1               5                   10                  15

Arg Val Gly

<210> SEQ ID NO 570
<211> LENGTH: 19
<212> TYPE: PRT
<213> ORGANISM: Artificial Sequence
<220> FEATURE:
<223> OTHER INFORMATION: BAFF binding peptide sequence

<400> SEQUENCE: 570

Ser Asp Gln Trp Gln Gln Lys Trp Asp Leu Leu Thr Lys Gln Trp Phe
1               5                   10                  15

Trp Asp Val

<210> SEQ ID NO 571
<211> LENGTH: 19
<212> TYPE: PRT
<213> ORGANISM: Artificial Sequence
<220> FEATURE:
<223> OTHER INFORMATION: BAFF binding peptide sequence

<400> SEQUENCE: 571

Gln Gln Gln Thr Phe Met Lys Trp Asp Leu Leu Thr Lys Gln Trp Ile
1               5                   10                  15

Arg Arg His

<210> SEQ ID NO 572
<211> LENGTH: 19
<212> TYPE: PRT
<213> ORGANISM: Artificial Sequence
<220> FEATURE:
<223> OTHER INFORMATION: BAFF binding peptide sequence

<400> SEQUENCE: 572

Gln Gln Gly Glu Cys Arg Lys Trp Asp Leu Leu Thr Lys Gln Cys Phe
1               5                   10                  15

Pro Gly Gln

<210> SEQ ID NO 573
<211> LENGTH: 19
<212> TYPE: PRT
<213> ORGANISM: Artificial Sequence
<220> FEATURE:
<223> OTHER INFORMATION: BAFF binding peptide sequence

<400> SEQUENCE: 573
```

```
Gly Gln Gln Met Gly Trp Arg Trp Asp Pro Leu Ile Lys Met Cys Leu
1               5                   10                  15

Gly Pro Ser

<210> SEQ ID NO 574
<211> LENGTH: 19
<212> TYPE: PRT
<213> ORGANISM: Artificial Sequence
<220> FEATURE:
<223> OTHER INFORMATION: BAFF binding peptide sequence

<400> SEQUENCE: 574

Gln Gln Leu Asp Gly Cys Lys Trp Asp Leu Leu Thr Lys Gln Lys Val
1               5                   10                  15

Cys Ile Pro

<210> SEQ ID NO 575
<211> LENGTH: 19
<212> TYPE: PRT
<213> ORGANISM: Artificial Sequence
<220> FEATURE:
<223> OTHER INFORMATION: BAFF binding peptide sequence

<400> SEQUENCE: 575

His Gly Tyr Trp Gln Gln Lys Trp Asp Leu Leu Thr Lys Gln Trp Val
1               5                   10                  15

Ser Ser Glu

<210> SEQ ID NO 576
<211> LENGTH: 19
<212> TYPE: PRT
<213> ORGANISM: Artificial Sequence
<220> FEATURE:
<223> OTHER INFORMATION: BAFF binding peptide sequence

<400> SEQUENCE: 576

His Gln Gln Gly Gln Cys Gly Trp Asp Leu Leu Thr Arg Ile Tyr Leu
1               5                   10                  15

Pro Cys His

<210> SEQ ID NO 577
<211> LENGTH: 19
<212> TYPE: PRT
<213> ORGANISM: Artificial Sequence
<220> FEATURE:
<223> OTHER INFORMATION: BAFF binding peptide sequence

<400> SEQUENCE: 577

Leu His Lys Ala Cys Lys Trp Asp Leu Leu Thr Lys Gln Cys Trp Pro
1               5                   10                  15

Met Gln Gln

<210> SEQ ID NO 578
<211> LENGTH: 19
<212> TYPE: PRT
<213> ORGANISM: Artificial Sequence
<220> FEATURE:
<223> OTHER INFORMATION: BAFF binding peptide sequence

<400> SEQUENCE: 578

Gly Pro Pro Gly Ser Val Trp Asp Leu Leu Thr Lys Ile Trp Ile Gln
1               5                   10                  15
```

```
Gln Thr Gly

<210> SEQ ID NO 579
<211> LENGTH: 19
<212> TYPE: PRT
<213> ORGANISM: Artificial Sequence
<220> FEATURE:
<223> OTHER INFORMATION: BAFF binding peptide sequence

<400> SEQUENCE: 579

Ile Thr Gln Gln Asp Trp Arg Phe Asp Thr Leu Thr Arg Leu Trp Leu
1               5                   10                  15

Pro Leu Arg

<210> SEQ ID NO 580
<211> LENGTH: 19
<212> TYPE: PRT
<213> ORGANISM: Artificial Sequence
<220> FEATURE:
<223> OTHER INFORMATION: BAFF binding peptide sequence

<400> SEQUENCE: 580

Gln Gln Gly Gly Phe Ala Ala Trp Asp Val Leu Thr Lys Met Trp Ile
1               5                   10                  15

Thr Val Pro

<210> SEQ ID NO 581
<211> LENGTH: 18
<212> TYPE: PRT
<213> ORGANISM: Artificial Sequence
<220> FEATURE:
<223> OTHER INFORMATION: BAFF binding peptide sequence

<400> SEQUENCE: 581

Gly His Gly Thr Pro Trp Trp Asp Ala Leu Thr Arg Ile Trp Ile Leu
1               5                   10                  15

Gly Val

<210> SEQ ID NO 582
<211> LENGTH: 19
<212> TYPE: PRT
<213> ORGANISM: Artificial Sequence
<220> FEATURE:
<223> OTHER INFORMATION: BAFF binding peptide sequence

<400> SEQUENCE: 582

Val Trp Pro Trp Gln Gln Lys Trp Asp Leu Leu Thr Lys Gln Phe Val
1               5                   10                  15

Phe Gln Asp

<210> SEQ ID NO 583
<211> LENGTH: 19
<212> TYPE: PRT
<213> ORGANISM: Artificial Sequence
<220> FEATURE:
<223> OTHER INFORMATION: BAFF binding peptide sequence

<400> SEQUENCE: 583

Trp Gln Gln Trp Ser Trp Lys Trp Asp Leu Leu Thr Arg Gln Tyr Ile
1               5                   10                  15

Ser Ser Ser

<210> SEQ ID NO 584
```

```
<211> LENGTH: 19
<212> TYPE: PRT
<213> ORGANISM: Artificial Sequence
<220> FEATURE:
<223> OTHER INFORMATION: BAFF binding peptide sequence

<400> SEQUENCE: 584

Asn Gln Gln Thr Leu Trp Lys Trp Asp Leu Leu Thr Lys Gln Phe Ile
1               5                   10                  15

Thr Tyr Met

<210> SEQ ID NO 585
<211> LENGTH: 19
<212> TYPE: PRT
<213> ORGANISM: Artificial Sequence
<220> FEATURE:
<223> OTHER INFORMATION: BAFF binding peptide sequence

<400> SEQUENCE: 585

Pro Val Tyr Gln Gln Gly Trp Trp Asp Thr Leu Thr Lys Leu Tyr Ile
1               5                   10                  15

Trp Asp Gly

<210> SEQ ID NO 586
<211> LENGTH: 19
<212> TYPE: PRT
<213> ORGANISM: Artificial Sequence
<220> FEATURE:
<223> OTHER INFORMATION: BAFF binding peptide sequence

<400> SEQUENCE: 586

Trp Leu Asp Gly Gly Trp Arg Asp Pro Leu Ile Lys Arg Ser Val Gln
1               5                   10                  15

Gln Leu Gly

<210> SEQ ID NO 587
<211> LENGTH: 19
<212> TYPE: PRT
<213> ORGANISM: Artificial Sequence
<220> FEATURE:
<223> OTHER INFORMATION: BAFF binding peptide sequence

<400> SEQUENCE: 587

Gly His Gln Gln Gln Phe Lys Trp Asp Leu Leu Thr Lys Gln Trp Val
1               5                   10                  15

Gln Ser Asn

<210> SEQ ID NO 588
<211> LENGTH: 19
<212> TYPE: PRT
<213> ORGANISM: Artificial Sequence
<220> FEATURE:
<223> OTHER INFORMATION: BAFF binding peptide sequence

<400> SEQUENCE: 588

Gln Gln Arg Val Gly Gln Phe Trp Asp Val Leu Thr Lys Met Phe Ile
1               5                   10                  15

Thr Gly Ser

<210> SEQ ID NO 589
<211> LENGTH: 19
<212> TYPE: PRT
<213> ORGANISM: Artificial Sequence
<220> FEATURE:
```

<223> OTHER INFORMATION: BAFF binding peptide sequence

<400> SEQUENCE: 589

Gln Gln Ala Gln Gly Trp Ser Tyr Asp Ala Leu Ile Lys Thr Trp Ile
1               5                   10                  15

Arg Trp Pro

<210> SEQ ID NO 590
<211> LENGTH: 19
<212> TYPE: PRT
<213> ORGANISM: Artificial Sequence
<220> FEATURE:
<223> OTHER INFORMATION: BAFF binding peptide sequence

<400> SEQUENCE: 590

Gly Trp Met His Trp Lys Trp Asp Pro Leu Thr Lys Gln Gln Ala Leu
1               5                   10                  15

Pro Trp Met

<210> SEQ ID NO 591
<211> LENGTH: 19
<212> TYPE: PRT
<213> ORGANISM: Artificial Sequence
<220> FEATURE:
<223> OTHER INFORMATION: BAFF binding peptide sequence

<400> SEQUENCE: 591

Gly His Pro Thr Tyr Lys Trp Asp Leu Leu Thr Lys Gln Trp Ile Leu
1               5                   10                  15

Gln Gln Met

<210> SEQ ID NO 592
<211> LENGTH: 19
<212> TYPE: PRT
<213> ORGANISM: Artificial Sequence
<220> FEATURE:
<223> OTHER INFORMATION: BAFF binding peptide sequence

<400> SEQUENCE: 592

Trp Asn Asn Trp Ser Leu Trp Asp Pro Leu Thr Lys Leu Trp Leu Gln
1               5                   10                  15

Gln Gln Asn

<210> SEQ ID NO 593
<211> LENGTH: 18
<212> TYPE: PRT
<213> ORGANISM: Artificial Sequence
<220> FEATURE:
<223> OTHER INFORMATION: BAFF binding peptide sequence

<400> SEQUENCE: 593

Trp Gln Trp Gly Trp Lys Trp Asp Leu Leu Thr Lys Gln Trp Val Gln
1               5                   10                  15

Gln Gln

<210> SEQ ID NO 594
<211> LENGTH: 18
<212> TYPE: PRT
<213> ORGANISM: Artificial Sequence
<220> FEATURE:
<223> OTHER INFORMATION: BAFF binding peptide sequence

<400> SEQUENCE: 594

Gly Gln Met Gly Trp Arg Trp Asp Pro Leu Thr Lys Met Trp Leu Gly
1               5                   10                  15

Thr Ser

<210> SEQ ID NO 595
<211> LENGTH: 8
<212> TYPE: PRT
<213> ORGANISM: Artificial Sequence
<220> FEATURE:
<223> OTHER INFORMATION: Linker

<400> SEQUENCE: 595

Gly Gly Gly Lys Gly Gly Gly Gly
1               5

<210> SEQ ID NO 596
<211> LENGTH: 8
<212> TYPE: PRT
<213> ORGANISM: Artificial Sequence
<220> FEATURE:
<223> OTHER INFORMATION: Linker

<400> SEQUENCE: 596

Gly Gly Gly Asn Gly Ser Gly Gly
1               5

<210> SEQ ID NO 597
<211> LENGTH: 8
<212> TYPE: PRT
<213> ORGANISM: Artificial Sequence
<220> FEATURE:
<223> OTHER INFORMATION: Linker

<400> SEQUENCE: 597

Gly Gly Gly Cys Gly Gly Gly Gly
1               5

<210> SEQ ID NO 598
<211> LENGTH: 5
<212> TYPE: PRT
<213> ORGANISM: Artificial Sequence
<220> FEATURE:
<223> OTHER INFORMATION: Linker

<400> SEQUENCE: 598

Gly Pro Asn Gly Gly
1               5

<210> SEQ ID NO 599
<211> LENGTH: 228
<212> TYPE: PRT
<213> ORGANISM: Homo sapiens

<400> SEQUENCE: 599

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

```
Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Arg Asp Glu Leu Thr Lys Asn Gln Val
130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Lys
225

<210> SEQ ID NO 600
<211> LENGTH: 227
<212> TYPE: PRT
<213> ORGANISM: Homo sapiens

<400> SEQUENCE: 600

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
```

```
                    210                 215                 220

Pro Gly Lys
225

<210> SEQ ID NO 601
<211> LENGTH: 2
<212> TYPE: PRT
<213> ORGANISM: Homo sapiens

<400> SEQUENCE: 601

Pro Pro
1

<210> SEQ ID NO 602
<211> LENGTH: 8
<212> TYPE: PRT
<213> ORGANISM: Homo sapiens

<400> SEQUENCE: 602

Asp Val Ser His Glu Asp Pro Glu
1               5

<210> SEQ ID NO 603
<211> LENGTH: 232
<212> TYPE: PRT
<213> ORGANISM: Homo sapiens

<400> SEQUENCE: 603

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230
```

```
<210> SEQ ID NO 604
<211> LENGTH: 4
<212> TYPE: PRT
<213> ORGANISM: Homo sapiens

<400> SEQUENCE: 604

Val His Asn Ala
1

<210> SEQ ID NO 605
<211> LENGTH: 7
<212> TYPE: PRT
<213> ORGANISM: Homo sapiens

<400> SEQUENCE: 605

Glu Glu Gln Tyr Asn Ser Thr
1               5

<210> SEQ ID NO 606
<211> LENGTH: 11
<212> TYPE: PRT
<213> ORGANISM: Homo sapiens

<400> SEQUENCE: 606

Val Leu His Gln Asp Trp Leu Asn Gly Lys Glu
1               5                   10

<210> SEQ ID NO 607
<211> LENGTH: 22
<212> TYPE: PRT
<213> ORGANISM: Homo sapiens

<400> SEQUENCE: 607

Asn Lys Ala Leu Pro Ala Pro Ile Glu Lys Thr Ile Ser Lys Ala Lys
1               5                   10                  15

Gly Gln Pro Arg Glu Pro
            20

<210> SEQ ID NO 608
<211> LENGTH: 5
<212> TYPE: PRT
<213> ORGANISM: Homo sapiens

<400> SEQUENCE: 608

Asp Glu Leu Thr Lys
1               5

<210> SEQ ID NO 609
<211> LENGTH: 7
<212> TYPE: PRT
<213> ORGANISM: Homo sapiens

<400> SEQUENCE: 609

Asn Gly Gln Pro Glu Asn Asn
1               5

<210> SEQ ID NO 610
<211> LENGTH: 11
<212> TYPE: PRT
<213> ORGANISM: Homo sapiens

<400> SEQUENCE: 610

Thr Thr Pro Pro Val Leu Asp Ser Asp Gly Ser
```

<210> SEQ ID NO 611
<211> LENGTH: 9
<212> TYPE: PRT
<213> ORGANISM: Homo sapiens

<400> SEQUENCE: 611

Lys Ser Arg Trp Gln Gln Gly Asn Val
1               5

<210> SEQ ID NO 612
<211> LENGTH: 246
<212> TYPE: PRT
<213> ORGANISM: Artificial Sequence
<220> FEATURE:
<223> OTHER INFORMATION: Ang-2 binding peptide sequence

<400> SEQUENCE: 612

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Arg Asp Glu Leu Gly Gly Gln Glu Glu
    130                 135                 140

Cys Glu Trp Asp Pro Trp Thr Cys Glu His Met Gly Gly Thr Lys Asn
145                 150                 155                 160

Gln Val Ser Leu Thr Cys Leu Val Lys Gly Phe Tyr Pro Ser Asp Ile
                165                 170                 175

Ala Val Glu Tyr Glu Ser Asn Gly Gln Pro Glu Asn Asn Tyr Lys Thr
            180                 185                 190

Thr Pro Pro Val Leu Asp Ser Asp Gly Ser Phe Phe Leu Tyr Ser Lys
        195                 200                 205

Leu Thr Val Asp Lys Ser Arg Trp Gln Gln Gly Asn Val Phe Ser Cys
    210                 215                 220

Ser Val Met His Glu Ala Leu His Asn His Tyr Thr Gln Lys Ser Leu
225                 230                 235                 240

Ser Leu Ser Pro Gly Lys
                245

<210> SEQ ID NO 613
<211> LENGTH: 252
<212> TYPE: PRT
<213> ORGANISM: Artificial Sequence
<220> FEATURE:
<223> OTHER INFORMATION: Myostatin binding polypeptide sequence -continued

```
<400> SEQUENCE: 613

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Arg Asp Glu Leu Gly Gly Leu Ala Asp
    130                 135                 140

His Gly Gln Cys Ile Arg Trp Pro Trp Met Cys Pro Pro Glu Gly Trp
145                 150                 155                 160

Glu Gly Gly Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
        195                 200                 205

Phe Phe Leu Tyr Ser Lys Leu Thr Val Asp Lys Ser Arg Trp Gln Gln
    210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys
                245                 250

<210> SEQ ID NO 614
<211> LENGTH: 252
<212> TYPE: PRT
<213> ORGANISM: Artificial Sequence
<220> FEATURE:
<223> OTHER INFORMATION: EPO-mimetic polypeptide

<400> SEQUENCE: 614

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
```

```
            100                 105                 110
Ile Glu Lys Thr Ile Ser Lys Ala Lys Gly Gln Pro Arg Glu Pro Gln
            115                 120                 125
Val Tyr Thr Leu Pro Pro Ser Arg Asp Glu Leu Gly Gly Gly Gly Thr
130                 135                 140
Tyr Ser Cys His Phe Gly Pro Leu Thr Trp Val Cys Lys Pro Gln Gly
145                 150                 155                 160
Gly Gly Gly Thr Lys Asn Gln Val Ser Leu Thr Cys Leu Val Lys Gly
                165                 170                 175
Phe Tyr Pro Ser Asp Ile Ala Val Glu Trp Glu Ser Asn Gly Gln Pro
            180                 185                 190
Glu Asn Asn Tyr Lys Thr Thr Pro Pro Val Leu Asp Ser Asp Gly Ser
            195                 200                 205
Phe Phe Leu Tyr Ser Lys Leu Thr Val Asp Lys Ser Arg Trp Gln Gln
            210                 215                 220
Gly Asn Val Phe Ser Cys Ser Val Met His Glu Ala Leu His Asn His
225                 230                 235                 240
Tyr Thr Gln Lys Ser Leu Ser Leu Ser Pro Gly Lys
            245                 250

<210> SEQ ID NO 615
<211> LENGTH: 246
<212> TYPE: PRT
<213> ORGANISM: Artificial Sequence
<220> FEATURE:
<223> OTHER INFORMATION: TPO-mimetic polypeptide sequence

<400> SEQUENCE: 615

Met Asp Lys Thr His Thr Cys Pro Pro Cys Pro Ala Pro Glu Leu Leu
1               5                   10                  15
Gly Gly Pro Ser Val Phe Leu Phe Pro Pro Lys Pro Lys Asp Thr Leu
                20                  25                  30
Met Ile Ser Arg Thr Pro Glu Val Thr Cys Val Val Val Asp Val Ser
            35                  40                  45
His Glu Asp Pro Glu Val Lys Phe Asn Trp Tyr Val Asp Gly Val Glu
50                  55                  60
Val His Asn Ala Lys Thr Lys Pro Arg Glu Glu Gln Tyr Asn Ser Thr
65                  70                  75                  80
Tyr Arg Val Val Ser Val Leu Thr Val Leu His Gln Asp Trp Leu Asn
                85                  90                  95
Gly Lys Glu Tyr Lys Cys Lys Val Ser Asn Lys Ala Leu Pro Ala Pro
            100                 105                 110
Ile Glu Lys Thr Ile Ser Lys Ala Lys Gly Gln Pro Arg Glu Pro Gln
            115                 120                 125
Val Tyr Thr Leu Pro Pro Ser Arg Asp Glu Leu Gly Gly Ile Glu Gly
            130                 135                 140
Pro Thr Leu Arg Gln Trp Leu Ala Ala Arg Ala Gly Gly Thr Lys Asn
145                 150                 155                 160
Gln Val Ser Leu Thr Cys Leu Val Lys Gly Phe Tyr Pro Ser Asp Ile
                165                 170                 175
Ala Val Glu Trp Glu Ser Asn Gly Gln Pro Glu Asn Asn Tyr Lys Thr
            180                 185                 190
Thr Pro Pro Val Leu Asp Ser Asp Gly Ser Phe Phe Leu Tyr Ser Lys
            195                 200                 205
Leu Thr Val Asp Lys Ser Arg Trp Gln Gln Gly Asn Val Phe Ser Cys
```

```
                210                 215                 220
Ser Val Met His Glu Ala Leu His Asn His Tyr Thr Gln Lys Ser Leu
225                 230                 235                 240

Ser Leu Ser Pro Gly Lys
                245

<210> SEQ ID NO 616
<211> LENGTH: 14
<212> TYPE: PRT
<213> ORGANISM: Artificial Sequence
<220> FEATURE:
<223> OTHER INFORMATION: Myostatin binding peptide sequence

<400> SEQUENCE: 616

Lys Asp Lys Cys Lys Met Trp His Trp Met Cys Lys Pro Pro
1               5                   10

<210> SEQ ID NO 617
<211> LENGTH: 279
<212> TYPE: PRT
<213> ORGANISM: Artificial Sequence
<220> FEATURE:
<223> OTHER INFORMATION: sTNF-R2 sequence

<400> SEQUENCE: 617

Gln Ile Cys Asn Val Val Ala Ile Pro Gly Asn Ala Ser Met Asp Ala
1               5                   10                  15

Val Cys Thr Ser Thr Ser Pro Thr Arg Ser Met Ala Pro Gly Ala Val
                20                  25                  30

His Leu Pro Gln Pro Val Ser Thr Arg Ser Gln His Thr Gln Pro Thr
            35                  40                  45

Pro Glu Pro Ser Thr Ala Pro Ser Thr Ser Phe Leu Leu Pro Met Gly
    50                  55                  60

Pro Ser Pro Pro Ala Glu Gly Ser Thr Gly Asp Phe Ala Leu Pro Val
65                  70                  75                  80

Gly Leu Ile Val Gly Val Thr Ala Leu Gly Leu Leu Ile Ile Gly Val
                85                  90                  95

Val Asn Cys Val Ile Met Thr Gln Val Lys Lys Lys Pro Leu Cys Leu
            100                 105                 110

Gln Arg Glu Ala Lys Val Pro His Leu Pro Ala Asp Lys Ala Arg Gly
        115                 120                 125

Thr Gln Gly Pro Glu Gln Gln His Leu Leu Ile Thr Ala Pro Ser Ser
    130                 135                 140

Ser Ser Ser Ser Leu Glu Ser Ser Ala Ser Ala Leu Asp Arg Arg Ala
145                 150                 155                 160

Pro Thr Arg Asn Gln Pro Gln Ala Pro Gly Val Glu Ala Ser Gly Ala
                165                 170                 175

Gly Glu Ala Arg Ala Ser Thr Gly Ser Ser Asp Ser Ser Pro Gly Gly
            180                 185                 190

His Gly Thr Gln Val Asn Val Thr Cys Ile Val Asn Val Cys Ser Ser
        195                 200                 205

Ser Asp His Ser Ser Gln Cys Ser Ser Gln Ala Ser Ser Thr Met Gly
    210                 215                 220

Asp Thr Asp Ser Ser Pro Ser Glu Ser Pro Lys Asp Glu Gln Val Pro
225                 230                 235                 240

Phe Ser Lys Glu Glu Cys Ala Phe Arg Ser Gln Leu Glu Thr Pro Glu
                245                 250                 255
```

Thr Leu Leu Gly Ser Thr Glu Glu Lys Pro Leu Pro Leu Gly Val Pro
            260                 265                 270

Asp Ala Gly Met Lys Pro Ser
            275

<210> SEQ ID NO 618
<211> LENGTH: 467
<212> TYPE: PRT
<213> ORGANISM: Artificial Sequence
<220> FEATURE:
<223> OTHER INFORMATION: Etanercept-Fc domain fusion

<400> SEQUENCE: 618

Leu Pro Ala Gln Val Ala Phe Thr Pro Tyr Ala Pro Glu Pro Gly Ser
1               5                   10                  15

Thr Cys Arg Leu Arg Glu Tyr Tyr Asp Gln Thr Ala Gln Met Cys Cys
            20                  25                  30

Ser Lys Cys Ser Pro Gly Gln His Ala Lys Val Phe Cys Thr Lys Thr
        35                  40                  45

Ser Asp Thr Val Cys Asp Ser Cys Glu Asp Ser Thr Tyr Thr Gln Leu
    50                  55                  60

Trp Asn Trp Val Pro Glu Cys Leu Ser Cys Gly Ser Arg Cys Ser Ser
65                  70                  75                  80

Asp Gln Val Glu Thr Gln Ala Cys Thr Arg Glu Gln Asn Arg Ile Cys
                85                  90                  95

Thr Cys Arg Pro Gly Trp Tyr Cys Ala Leu Ser Lys Gln Glu Gly Cys
            100                 105                 110

Arg Leu Cys Ala Pro Leu Arg Lys Cys Arg Pro Gly Phe Gly Val Ala
        115                 120                 125

Arg Pro Gly Thr Glu Thr Ser Asp Val Val Cys Lys Pro Cys Ala Pro
130                 135                 140

Gly Thr Phe Ser Asn Thr Thr Ser Ser Thr Asp Ile Cys Arg Pro His
145                 150                 155                 160

Gln Ile Cys Asn Val Val Ala Ile Pro Gly Asn Ala Ser Met Asp Ala
                165                 170                 175

Val Cys Thr Ser Thr Ser Pro Thr Arg Ser Met Ala Pro Gly Ala Val
            180                 185                 190

His Leu Pro Gln Pro Val Ser Thr Arg Ser Gln His Thr Gln Pro Thr
        195                 200                 205

Pro Glu Pro Ser Thr Ala Pro Ser Thr Ser Phe Leu Leu Pro Met Gly
    210                 215                 220

Pro Ser Pro Pro Ala Glu Gly Ser Thr Gly Asp Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

```
Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Glu Glu Met Thr Lys Asn Gln Val Ser
370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys
465

<210> SEQ ID NO 619
<211> LENGTH: 6
<212> TYPE: PRT
<213> ORGANISM: Artificial Sequence
<220> FEATURE:
<223> OTHER INFORMATION: Linker sequence
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid

<400> SEQUENCE: 619

Xaa Xaa Asn Xaa Xaa Gly
1               5

<210> SEQ ID NO 620
<211> LENGTH: 5
<212> TYPE: PRT
<213> ORGANISM: Artificial Sequence
<220> FEATURE:
<223> OTHER INFORMATION: L5 linker sequence

<400> SEQUENCE: 620

Gly Gly Gly Gly Ser
1               5

<210> SEQ ID NO 621
<211> LENGTH: 10
<212> TYPE: PRT
<213> ORGANISM: Artificial Sequence
<220> FEATURE:
<223> OTHER INFORMATION: L10 linker sequence

<400> SEQUENCE: 621

Gly Gly Gly Gly Ser Gly Gly Gly Gly Ser
1               5                   10

<210> SEQ ID NO 622
<211> LENGTH: 25
<212> TYPE: PRT
<213> ORGANISM: Artificial Sequence
```

```
<220> FEATURE:
<223> OTHER INFORMATION: L25 linker sequence

<400> SEQUENCE: 622

Gly Gly Gly Gly Ser Gly Gly Gly Ser Gly Gly Gly Ser Gly
1               5                   10                  15

Gly Gly Ser Gly Gly Gly Gly Ser
            20                  25

<210> SEQ ID NO 623
<211> LENGTH: 6
<212> TYPE: PRT
<213> ORGANISM: Artificial Sequence
<220> FEATURE:
<223> OTHER INFORMATION: Peptide linker sequence

<400> SEQUENCE: 623

Gly Gly Glu Gly Gly Gly
1               5

<210> SEQ ID NO 624
<211> LENGTH: 8
<212> TYPE: PRT
<213> ORGANISM: Artificial Sequence
<220> FEATURE:
<223> OTHER INFORMATION: Peptide linker sequence

<400> SEQUENCE: 624

Gly Gly Glu Glu Glu Gly Gly Gly
1               5

<210> SEQ ID NO 625
<211> LENGTH: 5
<212> TYPE: PRT
<213> ORGANISM: Artificial Sequence
<220> FEATURE:
<223> OTHER INFORMATION: Peptide linker sequence

<400> SEQUENCE: 625

Gly Glu Glu Glu Gly
1               5

<210> SEQ ID NO 626
<211> LENGTH: 4
<212> TYPE: PRT
<213> ORGANISM: Artificial Sequence
<220> FEATURE:
<223> OTHER INFORMATION: Peptide linker sequence

<400> SEQUENCE: 626

Gly Glu Glu Glu
1

<210> SEQ ID NO 627
<211> LENGTH: 6
<212> TYPE: PRT
<213> ORGANISM: Artificial Sequence
<220> FEATURE:
<223> OTHER INFORMATION: Peptide linker sequence

<400> SEQUENCE: 627

Gly Gly Asp Gly Gly Gly
1               5

<210> SEQ ID NO 628
<211> LENGTH: 7
```

```
<212> TYPE: PRT
<213> ORGANISM: Artificial Sequence
<220> FEATURE:
<223> OTHER INFORMATION: Peptide linker sequence

<400> SEQUENCE: 628

Gly Gly Asp Asp Gly Gly
1               5

<210> SEQ ID NO 629
<211> LENGTH: 5
<212> TYPE: PRT
<213> ORGANISM: Artificial Sequence
<220> FEATURE:
<223> OTHER INFORMATION: Peptide linker sequence

<400> SEQUENCE: 629

Gly Asp Asp Asp Gly
1               5

<210> SEQ ID NO 630
<211> LENGTH: 4
<212> TYPE: PRT
<213> ORGANISM: Artificial Sequence
<220> FEATURE:
<223> OTHER INFORMATION: Peptide linker sequence

<400> SEQUENCE: 630

Gly Asp Asp Asp
1

<210> SEQ ID NO 631
<211> LENGTH: 21
<212> TYPE: PRT
<213> ORGANISM: Artificial Sequence
<220> FEATURE:
<223> OTHER INFORMATION: Peptide linker sequence

<400> SEQUENCE: 631

Gly Gly Gly Gly Ser Asp Asp Ser Asp Glu Gly Ser Asp Gly Glu Asp
1               5                   10                  15

Gly Gly Gly Gly Ser
            20

<210> SEQ ID NO 632
<211> LENGTH: 5
<212> TYPE: PRT
<213> ORGANISM: Artificial Sequence
<220> FEATURE:
<223> OTHER INFORMATION: Peptide linker sequence

<400> SEQUENCE: 632

Trp Glu Trp Glu Trp
1               5

<210> SEQ ID NO 633
<211> LENGTH: 5
<212> TYPE: PRT
<213> ORGANISM: Artificial Sequence
<220> FEATURE:
<223> OTHER INFORMATION: Peptide linker sequence

<400> SEQUENCE: 633

Phe Glu Phe Glu Phe
1               5
```

```
<210> SEQ ID NO 634
<211> LENGTH: 6
<212> TYPE: PRT
<213> ORGANISM: Artificial Sequence
<220> FEATURE:
<223> OTHER INFORMATION: Peptide linker sequence

<400> SEQUENCE: 634

Glu Glu Glu Trp Trp Trp
1               5

<210> SEQ ID NO 635
<211> LENGTH: 6
<212> TYPE: PRT
<213> ORGANISM: Artificial Sequence
<220> FEATURE:
<223> OTHER INFORMATION: Peptide linker sequence

<400> SEQUENCE: 635

Glu Glu Glu Phe Phe Phe
1               5

<210> SEQ ID NO 636
<211> LENGTH: 7
<212> TYPE: PRT
<213> ORGANISM: Artificial Sequence
<220> FEATURE:
<223> OTHER INFORMATION: Peptide linker sequence

<400> SEQUENCE: 636

Trp Trp Glu Glu Glu Trp Trp
1               5

<210> SEQ ID NO 637
<211> LENGTH: 7
<212> TYPE: PRT
<213> ORGANISM: Artificial Sequence
<220> FEATURE:
<223> OTHER INFORMATION: Peptide linker sequence

<400> SEQUENCE: 637

Phe Phe Glu Glu Glu Phe Phe
1               5

<210> SEQ ID NO 638
<211> LENGTH: 6
<212> TYPE: PRT
<213> ORGANISM: Artificial Sequence
<220> FEATURE:
<223> OTHER INFORMATION: Peptide linker sequence
<220> FEATURE:
<221> NAME/KEY: MISC_FEATURE
<222> LOCATION: (1)..(2)
<223> OTHER INFORMATION: Xaa are each independently any amino acid
<220> FEATURE:
<221> NAME/KEY: MISC_FEATURE
<222> LOCATION: (4)..(5)
<223> OTHER INFORMATION: Xaa are each independently any amino acid

<400> SEQUENCE: 638

Xaa Xaa Tyr Xaa Xaa Gly
1               5

<210> SEQ ID NO 639
<211> LENGTH: 6
<212> TYPE: PRT
<213> ORGANISM: Artificial Sequence
<220> FEATURE:
<223> OTHER INFORMATION: Peptide linker sequence
```

```
<220> FEATURE:
<221> NAME/KEY: MISC_FEATURE
<222> LOCATION: (1)..(2)
<223> OTHER INFORMATION: Xaa are each independently any amino acid
<220> FEATURE:
<221> NAME/KEY: MISC_FEATURE
<222> LOCATION: (4)..(5)
<223> OTHER INFORMATION: Xaa are each independently any amino acid

<400> SEQUENCE: 639

Xaa Xaa Ser Xaa Xaa Gly
1               5

<210> SEQ ID NO 640
<211> LENGTH: 6
<212> TYPE: PRT
<213> ORGANISM: Artificial Sequence
<220> FEATURE:
<223> OTHER INFORMATION: Peptide linker sequence
<220> FEATURE:
<221> NAME/KEY: MISC_FEATURE
<222> LOCATION: (1)..(2)
<223> OTHER INFORMATION: Xaa are each independently any amino acid
<220> FEATURE:
<221> NAME/KEY: MISC_FEATURE
<222> LOCATION: (4)..(5)
<223> OTHER INFORMATION: Xaa are each independently any amino acid

<400> SEQUENCE: 640

Xaa Xaa Thr Xaa Xaa Gly
1               5

<210> SEQ ID NO 641
<211> LENGTH: 39
<212> TYPE: DNA
<213> ORGANISM: Artificial Sequence
<220> FEATURE:
<223> OTHER INFORMATION: Primer sequence (3430-37)

<400> SEQUENCE: 641
gaggaataac atatggacaa aactcacaca tgtccacct                    39

<210> SEQ ID NO 642
<211> LENGTH: 27
<212> TYPE: DNA
<213> ORGANISM: Artificial Sequence
<220> FEATURE:
<223> OTHER INFORMATION: Primer sequence (4220-28)

<400> SEQUENCE: 642
ggtcaggctg acgcagttct tggtcag                                 27

<210> SEQ ID NO 643
<211> LENGTH: 27
<212> TYPE: DNA
<213> ORGANISM: Artificial Sequence
<220> FEATURE:
<223> OTHER INFORMATION: Primer sequence (4220-27)

<400> SEQUENCE: 643
ctgaccaaga actgcgtcag cctgacc                                 27

<210> SEQ ID NO 644
<211> LENGTH: 43
<212> TYPE: DNA
<213> ORGANISM: Artificial Sequence
<220> FEATURE:
<223> OTHER INFORMATION: Primer sequence (3421-87)
```

<210> SEQ ID NO 645
<211> LENGTH: 688
<212> TYPE: DNA
<213> ORGANISM: Artificial Sequence
<220> FEATURE:
<223> OTHER INFORMATION: Strain 13300 sequence
<220> FEATURE:
<221> NAME/KEY: CDS
<222> LOCATION: (1)..(687)

<400> SEQUENCE: 645

| | | | | | | | | | | | | | | | | |
|---|---|---|---|---|---|---|---|---|---|---|---|---|---|---|---|---|
| atg | gac | aaa | act | cac | aca | tgt | cca | cct | tgc | cca | gca | cct | gaa | ctc | ctg | 48 |
| Met | Asp | Lys | Thr | His | Thr | Cys | Pro | Pro | Cys | Pro | Ala | Pro | Glu | Leu | Leu | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| ggg | gga | ccg | tca | gtt | ttc | ctc | ttc | ccc | cca | aaa | ccc | aag | gac | acc | ctc | 96 |
| Gly | Gly | Pro | Ser | Val | Phe | Leu | Phe | Pro | Pro | Lys | Pro | Lys | Asp | Thr | Leu | |
| | | | 20 | | | | | 25 | | | | | 30 | | | |

| | | | | | | | | | | | | | | | | |
|---|---|---|---|---|---|---|---|---|---|---|---|---|---|---|---|---|
| atg | atc | tcc | cgg | acc | cct | gag | gtc | aca | tgc | gtg | gtg | gtg | gac | gtg | agc | 144 |
| Met | Ile | Ser | Arg | Thr | Pro | Glu | Val | Thr | Cys | Val | Val | Val | Asp | Val | Ser | |
| | | 35 | | | | | 40 | | | | | 45 | | | | |

| | | | | | | | | | | | | | | | | |
|---|---|---|---|---|---|---|---|---|---|---|---|---|---|---|---|---|
| cac | gaa | gac | cct | gag | gtc | aag | ttc | aac | tgg | tac | gtg | gac | ggc | gtg | gag | 192 |
| His | Glu | Asp | Pro | Glu | Val | Lys | Phe | Asn | Trp | Tyr | Val | Asp | Gly | Val | Glu | |
| 50 | | | | | 55 | | | | | 60 | | | | | | |

| | | | | | | | | | | | | | | | | |
|---|---|---|---|---|---|---|---|---|---|---|---|---|---|---|---|---|
| gtg | cat | aat | gcc | aag | aca | aag | ccg | cgg | gag | gag | cag | tac | aac | agc | acg | 240 |
| Val | His | Asn | Ala | Lys | Thr | Lys | Pro | Arg | Glu | Glu | Gln | Tyr | Asn | Ser | Thr | |
| 65 | | | | 70 | | | | | 75 | | | | | 80 | | |

| | | | | | | | | | | | | | | | | |
|---|---|---|---|---|---|---|---|---|---|---|---|---|---|---|---|---|
| tac | cgt | gtg | gtc | agc | gtc | ctc | acc | gtc | ctg | cac | cag | gac | tgg | ctg | aat | 288 |
| Tyr | Arg | Val | Val | Ser | Val | Leu | Thr | Val | Leu | His | Gln | Asp | Trp | Leu | Asn | |
| | | | | 85 | | | | | 90 | | | | | 95 | | |

| | | | | | | | | | | | | | | | | |
|---|---|---|---|---|---|---|---|---|---|---|---|---|---|---|---|---|
| ggc | aag | gag | tac | aag | tgc | aag | gtc | tcc | aac | aaa | gcc | ctc | cca | gcc | ccc | 336 |
| Gly | Lys | Glu | Tyr | Lys | Cys | Lys | Val | Ser | Asn | Lys | Ala | Leu | Pro | Ala | Pro | |
| | | | | 100 | | | | | 105 | | | | | 110 | | |

| | | | | | | | | | | | | | | | | |
|---|---|---|---|---|---|---|---|---|---|---|---|---|---|---|---|---|
| atc | gag | aaa | acc | atc | tcc | aaa | gcc | aaa | ggg | cag | ccc | cga | gaa | cca | cag | 384 |
| Ile | Glu | Lys | Thr | Ile | Ser | Lys | Ala | Lys | Gly | Gln | Pro | Arg | Glu | Pro | Gln | |
| | | | 115 | | | | | 120 | | | | | 125 | | | |

| | | | | | | | | | | | | | | | | |
|---|---|---|---|---|---|---|---|---|---|---|---|---|---|---|---|---|
| gtg | tac | acc | ctg | ccc | cca | tcc | cgg | gat | gag | ctg | acc | aag | aac | tgc | gtc | 432 |
| Val | Tyr | Thr | Leu | Pro | Pro | Ser | Arg | Asp | Glu | Leu | Thr | Lys | Asn | Cys | Val | |
| | | 130 | | | | | 135 | | | | | 140 | | | | |

| | | | | | | | | | | | | | | | | |
|---|---|---|---|---|---|---|---|---|---|---|---|---|---|---|---|---|
| agc | ctg | acc | tgc | ctg | gtc | aaa | ggc | ttc | tat | ccc | agc | gac | atc | gcc | gtg | 480 |
| Ser | Leu | Thr | Cys | Leu | Val | Lys | Gly | Phe | Tyr | Pro | Ser | Asp | Ile | Ala | Val | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| gag | tgg | gag | agc | aat | ggg | cag | ccg | gag | aac | aac | tac | aag | acc | acg | cct | 528 |
| Glu | Trp | Glu | Ser | Asn | Gly | Gln | Pro | Glu | Asn | Asn | Tyr | Lys | Thr | Thr | Pro | |
| | | | | 165 | | | | | 170 | | | | | 175 | | |

| | | | | | | | | | | | | | | | | |
|---|---|---|---|---|---|---|---|---|---|---|---|---|---|---|---|---|
| ccc | gtg | ctg | gac | tcc | gac | ggc | tcc | ttc | ttc | ctc | tac | agc | aag | ctc | acc | 576 |
| Pro | Val | Leu | Asp | Ser | Asp | Gly | Ser | Phe | Phe | Leu | Tyr | Ser | Lys | Leu | Thr | |
| | | | 180 | | | | | 185 | | | | | 190 | | | |

| | | | | | | | | | | | | | | | | |
|---|---|---|---|---|---|---|---|---|---|---|---|---|---|---|---|---|
| gtg | gac | aag | agc | agg | tgg | cag | cag | ggg | aac | gtc | ttc | tca | tgc | tcc | gtg | 624 |
| Val | Asp | Lys | Ser | Arg | Trp | Gln | Gln | Gly | Asn | Val | Phe | Ser | Cys | Ser | Val | |
| | | 195 | | | | | 200 | | | | | 205 | | | | |

| | | | | | | | | | | | | | | | | |
|---|---|---|---|---|---|---|---|---|---|---|---|---|---|---|---|---|
| atg | cat | gag | gct | ctg | cac | aac | cac | tac | acg | cag | aag | agc | ctc | tcc | ctg | 672 |
| Met | His | Glu | Ala | Leu | His | Asn | His | Tyr | Thr | Gln | Lys | Ser | Leu | Ser | Leu | |
| | | 210 | | | | | 215 | | | | | 220 | | | | |

| | | | | |
|---|---|---|---|---|
| tct | ccg | ggt | aaa | taa t | 688 |
| Ser | Pro | Gly | Lys | | |
| 225 | | | | | |

<210> SEQ ID NO 646

```
<211> LENGTH: 228
<212> TYPE: PRT
<213> ORGANISM: Artificial Sequence
<220> FEATURE:
<223> OTHER INFORMATION: Synthetic Construct

<400> SEQUENCE: 646

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Arg Asp Glu Leu Thr Lys Asn Cys Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Lys
225

<210> SEQ ID NO 647
<211> LENGTH: 27
<212> TYPE: DNA
<213> ORGANISM: Artificial Sequence
<220> FEATURE:
<223> OTHER INFORMATION: Primer sequence (4220-26)

<400> SEQUENCE: 647
ctggttcttg gtgcactcat cccggga                                           27

<210> SEQ ID NO 648
<211> LENGTH: 27
<212> TYPE: DNA
<213> ORGANISM: Artificial Sequence
<220> FEATURE:
<223> OTHER INFORMATION: Primer sequence (4220-25)

<400> SEQUENCE: 648
tcccgggatg agtgcaccaa gaaccag                                           27

<210> SEQ ID NO 649
```

<211> LENGTH: 688
<212> TYPE: DNA
<213> ORGANISM: Artificial Sequence
<220> FEATURE:
<223> OTHER INFORMATION: Strain 13322 sequence
<220> FEATURE:
<221> NAME/KEY: CDS
<222> LOCATION: (1)..(687)

<400> SEQUENCE: 649

```
atg gac aaa act cac aca tgt cca cct tgc cca gca cct gaa ctc ctg      48
Met Asp Lys Thr His Thr Cys Pro Pro Cys Pro Ala Pro Glu Leu Leu
1               5                  10                  15 ggg gga ccg tca gtt ttc ctc ttc ccc cca aaa ccc aag gac acc ctc      96
Gly Gly Pro Ser Val Phe Leu Phe Pro Pro Lys Pro Lys Asp Thr Leu
            20                  25                  30 atg atc tcc cgg acc cct gag gtc aca tgc gtg gtg gtg gac gtg agc     144
Met Ile Ser Arg Thr Pro Glu Val Thr Cys Val Val Val Asp Val Ser
        35                  40                  45 cac gaa gac cct gag gtc aag ttt aac tgg tac gtg gac ggc gtg gag     192
His Glu Asp Pro Glu Val Lys Phe Asn Trp Tyr Val Asp Gly Val Glu
    50                  55                  60 gtg cat aat gcc aag aca aag ccg cgg gag gag cag tac aac agc acg     240
Val His Asn Ala Lys Thr Lys Pro Arg Glu Glu Gln Tyr Asn Ser Thr
65                  70                  75                  80 tac cgt gtg gtc agc gtc ctc acc gtc ctg cac cag gac tgg ctg aat     288
Tyr Arg Val Val Ser Val Leu Thr Val Leu His Gln Asp Trp Leu Asn
                85                  90                  95 ggc aag gag tac aag tgc aag gtc tcc aac aaa gcc ctc cca gcc ccc     336
Gly Lys Glu Tyr Lys Cys Lys Val Ser Asn Lys Ala Leu Pro Ala Pro
            100                 105                 110 atc gag aaa acc atc tcc aaa gcc aaa ggg cag ccc cga gaa cca cag     384
Ile Glu Lys Thr Ile Ser Lys Ala Lys Gly Gln Pro Arg Glu Pro Gln
        115                 120                 125 gtg tac acc ctg ccc cca tcc cgg gat gag tgc acc aag aac cag gtc     432
Val Tyr Thr Leu Pro Pro Ser Arg Asp Glu Cys Thr Lys Asn Gln Val
    130                 135                 140 agc ctg acc tgc ctg gtc aaa ggc ttc tat ccc agc gac atc gcc gtg     480
Ser Leu Thr Cys Leu Val Lys Gly Phe Tyr Pro Ser Asp Ile Ala Val
145                 150                 155                 160 gag tgg gag agc aat ggg cag ccg gag aac aac tac aag acc acg cct     528
Glu Trp Glu Ser Asn Gly Gln Pro Glu Asn Asn Tyr Lys Thr Thr Pro
                165                 170                 175 ccc gtg ctg gac tcc gac ggc tcc ttc ttc ctc tac agc aag ctc acc     576
Pro Val Leu Asp Ser Asp Gly Ser Phe Phe Leu Tyr Ser Lys Leu Thr
            180                 185                 190 gtg gac aag agc agg tgg cag cag ggg aac gtc ttc tca tgc tcc gtg     624
Val Asp Lys Ser Arg Trp Gln Gln Gly Asn Val Phe Ser Cys Ser Val
        195                 200                 205 atg cat gag gct ctg cac aac cac tac acg cag aag agc ctc tcc ctg     672
Met His Glu Ala Leu His Asn His Tyr Thr Gln Lys Ser Leu Ser Leu
    210                 215                 220 tct ccg ggt aaa taa t                                               688
Ser Pro Gly Lys
225
```

<210> SEQ ID NO 650
<211> LENGTH: 228
<212> TYPE: PRT
<213> ORGANISM: Artificial Sequence
<220> FEATURE:
<223> OTHER INFORMATION: Synthetic Construct

<400> SEQUENCE: 650

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Arg Asp Glu Cys Thr Lys Asn Gln Val
130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Lys
225

<210> SEQ ID NO 651
<211> LENGTH: 27
<212> TYPE: DNA
<213> ORGANISM: Artificial Sequence
<220> FEATURE:
<223> OTHER INFORMATION: Primer sequence (4220-30)

<400> SEQUENCE: 651
caggcaggtc aggcagacct ggttctt                                           27

<210> SEQ ID NO 652
<211> LENGTH: 27
<212> TYPE: DNA
<213> ORGANISM: Artificial Sequence
<220> FEATURE:
<223> OTHER INFORMATION: Primer sequence (4220-29)

<400> SEQUENCE: 652
aagaaccagg tctgcctgac ctgcctg                                           27

<210> SEQ ID NO 653
<211> LENGTH: 688
<212> TYPE: DNA
<213> ORGANISM: Artificial Sequence
<220> FEATURE:
<223> OTHER INFORMATION: Strain 13323 sequence
<220> FEATURE:

```
<221> NAME/KEY: CDS
<222> LOCATION: (1)..(687)

<400> SEQUENCE: 653 atg gac aaa act cac aca tgt cca cct tgc cca gca cct gaa ctc ctg      48
Met Asp Lys Thr His Thr Cys Pro Pro Cys Pro Ala Pro Glu Leu Leu
1               5                   10                  15 ggg gga ccg tca gtt ttc ctc ttc ccc cca aaa ccc aag gac acc ctc      96
Gly Gly Pro Ser Val Phe Leu Phe Pro Pro Lys Pro Lys Asp Thr Leu
                20                  25                  30 atg atc tcc cgg acc cct gag gtc aca tgc gtg gtg gtg gac gtg agc     144
Met Ile Ser Arg Thr Pro Glu Val Thr Cys Val Val Val Asp Val Ser
            35                  40                  45 cac gaa gac cct gag gtc aag ttc aac tgg tac gtg gac ggc gtg gag     192
His Glu Asp Pro Glu Val Lys Phe Asn Trp Tyr Val Asp Gly Val Glu
        50                  55                  60 gtg cat aat gcc aag aca aag ccg cgg gag gag cag tac aac agc acg     240
Val His Asn Ala Lys Thr Lys Pro Arg Glu Glu Gln Tyr Asn Ser Thr
65                  70                  75                  80 tac cgt gtg gtc agc gtc ctc acc gtc ctg cac cag gac tgg ctg aat     288
Tyr Arg Val Val Ser Val Leu Thr Val Leu His Gln Asp Trp Leu Asn
                85                  90                  95 ggc aag gag tac aag tgc aag gtc tcc aac aaa gcc ctc cca gcc ccc     336
Gly Lys Glu Tyr Lys Cys Lys Val Ser Asn Lys Ala Leu Pro Ala Pro
                100                 105                 110 atc gag aaa acc atc tcc aaa gcc aaa ggg cag ccc cga gaa cca cag     384
Ile Glu Lys Thr Ile Ser Lys Ala Lys Gly Gln Pro Arg Glu Pro Gln
            115                 120                 125 gtg tac acc ctg ccc cca tcc cgg gat gag ctg acc aag aac cag gtc     432
Val Tyr Thr Leu Pro Pro Ser Arg Asp Glu Leu Thr Lys Asn Gln Val
        130                 135                 140 tgc ctg acc tgc ctg gtc aaa ggc ttc tat ccc agc gac atc gcc gtg     480
Cys Leu Thr Cys Leu Val Lys Gly Phe Tyr Pro Ser Asp Ile Ala Val
145                 150                 155                 160 gag tgg gag agc aat ggg cag ccg gag aac aac tac aag acc acg cct     528
Glu Trp Glu Ser Asn Gly Gln Pro Glu Asn Asn Tyr Lys Thr Thr Pro
                165                 170                 175 ccc gtg ctg gac tcc gac ggc tcc ttc ttc ctc tac agc aag ctc acc     576
Pro Val Leu Asp Ser Asp Gly Ser Phe Phe Leu Tyr Ser Lys Leu Thr
                180                 185                 190 gtg gac aag agc agg tgg cag cag ggg aac gtc ttc tca tgc tcc gtg     624
Val Asp Lys Ser Arg Trp Gln Gln Gly Asn Val Phe Ser Cys Ser Val
            195                 200                 205 atg cat gag gct ctg cac aac cac tac acg cag aag agc ctc tcc ctg     672
Met His Glu Ala Leu His Asn His Tyr Thr Gln Lys Ser Leu Ser Leu
        210                 215                 220 tct ccg ggt aaa taa t                                                688
Ser Pro Gly Lys
225

<210> SEQ ID NO 654
<211> LENGTH: 228
<212> TYPE: PRT
<213> ORGANISM: Artificial Sequence
<220> FEATURE:
<223> OTHER INFORMATION: Synthetic Construct

<400> SEQUENCE: 654

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
```

```
                    20                  25                  30
Met Ile Ser Arg Thr Pro Glu Val Thr Cys Val Val Asp Val Ser
                35                  40                  45

His Glu Asp Pro Glu Val Lys Phe Asn Trp Tyr Val Asp Gly Val Glu
 50                  55                  60

Val His Asn Ala Lys Thr Lys Pro Arg Glu Glu Gln Tyr Asn Ser Thr
 65                  70                  75                  80

Tyr Arg Val Val Ser Val Leu Thr Val Leu His Gln Asp Trp Leu Asn
                    85                  90                  95

Gly Lys Glu Tyr Lys Cys Lys Val Ser Asn Lys Ala Leu Pro Ala Pro
                100                 105                 110

Ile Glu Lys Thr Ile Ser Lys Ala Lys Gly Gln Pro Arg Glu Pro Gln
            115                 120                 125

Val Tyr Thr Leu Pro Pro Ser Arg Asp Glu Leu Thr Lys Asn Gln Val
        130                 135                 140

Cys Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
210                 215                 220

Ser Pro Gly Lys
225

<210> SEQ ID NO 655
<211> LENGTH: 27
<212> TYPE: DNA
<213> ORGANISM: Artificial Sequence
<220> FEATURE:
<223> OTHER INFORMATION: Primer sequence (4220-32)

<400> SEQUENCE: 655
ctgctgccac ctgcacttgt ccacggt                                        27

<210> SEQ ID NO 656
<211> LENGTH: 27
<212> TYPE: DNA
<213> ORGANISM: Artificial Sequence
<220> FEATURE:
<223> OTHER INFORMATION: Primer sequence (4220-31)

<400> SEQUENCE: 656
accgtggaca agtgcaggtg gcagcag                                        27

<210> SEQ ID NO 657
<211> LENGTH: 688
<212> TYPE: DNA
<213> ORGANISM: Artificial Sequence
<220> FEATURE:
<223> OTHER INFORMATION: Strain 13324 sequence
<220> FEATURE:
<221> NAME/KEY: CDS
<222> LOCATION: (1)..(687)

<400> SEQUENCE: 657 atg gac aaa act cac aca tgt cca cct tgc cca gca cct gaa ctc ctg    48
```

```
Met Asp Lys Thr His Thr Cys Pro Pro Cys Pro Ala Pro Glu Leu Leu
1               5                   10                  15 ggg gga ccg tca gtt ttc ctc ttc ccc cca aaa ccc aag gac acc ctc      96
Gly Gly Pro Ser Val Phe Leu Phe Pro Pro Lys Pro Lys Asp Thr Leu
            20                  25                  30 atg atc tcc cgg acc cct gag gtc aca tgc gtg gtg gtg gac gtg agc     144
Met Ile Ser Arg Thr Pro Glu Val Thr Cys Val Val Val Asp Val Ser
        35                  40                  45 cac gaa gac cct gag gtc aag ttc aac tgg tac gtg gac ggc gtg gag     192
His Glu Asp Pro Glu Val Lys Phe Asn Trp Tyr Val Asp Gly Val Glu
50                  55                  60 gtg cat aat gcc aag aca aag ccg cgg gag gag cag tac aac agc acg     240
Val His Asn Ala Lys Thr Lys Pro Arg Glu Glu Gln Tyr Asn Ser Thr
65                  70                  75                  80 tac cgt gtg gtc agc gtc ctc acc gtc ctg cac cag gac tgg ctg aat     288
Tyr Arg Val Val Ser Val Leu Thr Val Leu His Gln Asp Trp Leu Asn
                85                  90                  95 ggc aag gag tac aag tgc aag gtc tcc aac aaa gcc ctc cca gcc ccc     336
Gly Lys Glu Tyr Lys Cys Lys Val Ser Asn Lys Ala Leu Pro Ala Pro
            100                 105                 110 atc gag aaa acc atc tcc aaa gcc aaa ggg cag ccc cga gaa cca cag     384
Ile Glu Lys Thr Ile Ser Lys Ala Lys Gly Gln Pro Arg Glu Pro Gln
        115                 120                 125 gtg tac acc ctg ccc cca tcc cgg gat gag ctg acc aag aac cag gtc     432
Val Tyr Thr Leu Pro Pro Ser Arg Asp Glu Leu Thr Lys Asn Gln Val
130                 135                 140 agc ctg acc tgc ctg gtc aaa ggc ttc tat ccc agc gac atc gcc gtg     480
Ser Leu Thr Cys Leu Val Lys Gly Phe Tyr Pro Ser Asp Ile Ala Val
145                 150                 155                 160 gag tgg gag agc aat ggg cag ccg gag aac aac tac aag acc acg cct     528
Glu Trp Glu Ser Asn Gly Gln Pro Glu Asn Asn Tyr Lys Thr Thr Pro
                165                 170                 175 ccc gtg ctg gac tcc gac ggc tcc ttc ttc ctc tac agc aag ctc acc     576
Pro Val Leu Asp Ser Asp Gly Ser Phe Phe Leu Tyr Ser Lys Leu Thr
            180                 185                 190 gtg gac aag tgc agg tgg cag cag ggg aac gtc ttc tca tgc tcc gtg     624
Val Asp Lys Cys Arg Trp Gln Gln Gly Asn Val Phe Ser Cys Ser Val
        195                 200                 205 atg cat gag gct ctg cac aac cac tac acg cag aag agc ctc tcc ctg     672
Met His Glu Ala Leu His Asn His Tyr Thr Gln Lys Ser Leu Ser Leu
210                 215                 220 tct ccg ggt aaa taa t                                                688
Ser Pro Gly Lys
225

<210> SEQ ID NO 658
<211> LENGTH: 228
<212> TYPE: PRT
<213> ORGANISM: Artificial Sequence
<220> FEATURE:
<223> OTHER INFORMATION: Synthetic Construct

<400> SEQUENCE: 658

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
```

-continued

```
            50                  55                  60
Val His Asn Ala Lys Thr Lys Pro Arg Glu Glu Gln Tyr Asn Ser Thr
 65                  70                  75                  80

Tyr Arg Val Val Ser Val Leu Thr Val Leu His Gln Asp Trp Leu Asn
                 85                  90                  95

Gly Lys Glu Tyr Lys Cys Lys Val Ser Asn Lys Ala Leu Pro Ala Pro
                100                 105                 110

Ile Glu Lys Thr Ile Ser Lys Ala Lys Gly Gln Pro Arg Glu Pro Gln
            115                 120                 125

Val Tyr Thr Leu Pro Pro Ser Arg Asp Glu Leu Thr Lys Asn Gln Val
        130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Asp Lys Cys Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Lys
225
```